US012753402B2

(12) United States Patent
Yin et al.

(10) Patent No.: US 12,753,402 B2
(45) Date of Patent: Oct. 6, 2026

(54) ORTHOGONAL UBIQUITIN TRANSFER AS A METHOD TO IDENTIFY CELLULAR SUBSTRATES OF E3 UBIQUITIN LIGASES

(71) Applicants: Northwestern University, Evanston, IL (US); Georgia State University Research Foundation, Atlanta, GA (US)

(72) Inventors: Jun Yin, Atlanta, GA (US); Hiroaki Kiyokawa, Chicago, IL (US); Yiyang Wang, Atlanta, GA (US); Karan Bhuripanyo, Atlanta, GA (US); Bo Zhao, Atlanta, GA (US); Xianpeng Liu, Evanston, IL (US); Li Zhou, Atlanta, GA (US)

(73) Assignees: Northwestern University, Evanston, IL (US); Georgia State University Research Foundation, Atlanta, GA (US)

( * ) Notice: Subject to any disclaimer, the term of this patent is extended or adjusted under 35 U.S.C. 154(b) by 1234 days.

(21) Appl. No.: 16/721,345

(22) Filed: Dec. 19, 2019

(65) Prior Publication Data

US 2020/0199576 A1 Jun. 25, 2020

Related U.S. Application Data

(60) Provisional application No. 62/782,111, filed on Dec. 19, 2018.

(51) Int. Cl.
*C12N 7/00* (2006.01)
*C12N 1/16* (2006.01)
(Continued)

(52) U.S. Cl.
CPC ........... *C12N 15/1055* (2013.01); *C12N 1/16* (2013.01); *C12N 7/00* (2013.01); *C12N 15/1037* (2013.01);
(Continued)

(58) Field of Classification Search
CPC ........... C12N 15/1055; C12N 15/1037; C12N 15/1065; C12N 1/16; C12N 7/00; G01N 33/6845
(Continued)

(56) References Cited

U.S. PATENT DOCUMENTS 4,458,066 A 7/1984 Caruthers
4,683,195 A 7/1987 Mullis
(Continued)

FOREIGN PATENT DOCUMENTS

WO 1991016024 A1 10/1991
WO 1991017424 A1 11/1991

OTHER PUBLICATIONS

Tsuchiya, M., et al. "Ubiquitin ligase CHIP suppresses cancer stem cell properties in a population of breast cancer cells." Biochemical and biophysical research communications 452.4 (2014): 928-932.
(Continued)

*Primary Examiner* — Robert B Mondesi
(74) *Attorney, Agent, or Firm* — Quarles & Brady LLP

(57) ABSTRACT

Disclosed herein are compounds, compositions, and methods for identifying substrates of E3 ubiquitin ligases. The proteins, vectors, compositions, and may be utilized in methods for orthogonal ubiquitin transfer (OUT) between variant components of the ubiquitin cascade such as a variant ubiquitin (UB), a variant ubiquitin activating enzyme (E1), a variant ubiquitin-conjugating enzyme (E2), and a variant ubiquitin ligase (E3), which may include a variant HECT type, U-box type, RBR type, and/or Ring type E3
(Continued)

ligase. The variant components of the ubiquitin cascade typically include one or more mutations relative to their wild-type counterparts, such as amino acid substitutions, such that the variant components interact specifically and orthogonally with each of their variant components and do not interact with the wild-type counterpart of their variant components.

19 Claims, 44 Drawing Sheets

Specification includes a Sequence Listing.

(51) Int. Cl.
*C12N 15/10* (2006.01)
*G01N 33/68* (2006.01)

(52) U.S. Cl.
CPC ..... *C12N 15/1065* (2013.01); *G01N 33/6845* (2013.01)

(58) Field of Classification Search
USPC .......................................................... 424/94.2
See application file for complete search history.

(56) References Cited

U.S. PATENT DOCUMENTS

| | | | | |
|---|---|---|---|---|
| 4,683,202 | A | 7/1987 | Mullis | |
| 4,897,335 | A | 1/1990 | Kakimi | |
| 4,946,787 | A | 8/1990 | Eppstein | |
| 5,049,386 | A | 9/1991 | Eppstein | |
| 5,494,810 | A | 2/1996 | Barany | |
| 7,396,664 | B2 | 7/2008 | Daly | |
| 2013/0333061 | A1* | 12/2013 | Wu et al. | C12N 15/8274 |

OTHER PUBLICATIONS

Veeriah, S, et al. "Somatic mutations of the Parkinson's disease-associated gene PARK2 in glioblastoma and other human malignancies." Nature genetics 42.1 (2010): 77.
Verba K. A. et al. Atomic structure of Hsp90-Cdc37-Cdk4 reveals that Hsp90 traps and stabilizes an unfolded kinase. Science 352, 1542-1547 (2016).
Wang, Y, et al. "Identifying the ubiquitination targets of E6AP by orthogonal ubiquitin transfer." Nature communications 8.1 (2017): 1-14.
Wauer, T, et al. "Mechanism of phospho-ubiquitin-induced PARKIN activation." Nature 524.7565 (2015): 370-374.
Wenzel, D.M., et al. E2s: structurally economical and functionally replete. The Biochemical journal 433, 31-42 (2011).
Wolyniec, K. et al. E6AP ubiquitin ligase regulates PML-induced senescence in Myc-driven lymphomagenesis. Blood 120, 822-32 (2012).
Wolyniec, K., et al. The E6AP E3 ubiquitin ligase regulates the cellular response to oxidative stress. Oncogene 32, 3510-9 (2013).
Yin, J. Identifying the Substrate Proteins of E3 Ubiquitin Ligase by Orthogonal Ubiquitin Transfer (OUT). Presentation at FASEB Science Research Conference. Ubiquitin & Cell Regulation. Jun. 18, 2018.
Zhao, B. et al. Orthogonal Ubiquitin Transfer through Engineered E1-E2 Cascades for Protein Ubiquitination. Chemistry & Biology 19, 1265-77 (2012).
Zhuang, M., et al. Substrates of IAP ubiquitin ligases identified with a designed orthogonal E3 ligase, the NEDDylator. Mol Cell 49, 273-82 (2013).
Zuin, A. et al. Rpn10 monoubiquitination orchestrates the association of the ubiquilin-type DSK2 receptor with the proteasome. Biochem J 472, 353-65 (2015).
Arnst, J.L., et al. "Discovery and characterization of small molecule Rac1 inhibitors." Oncotarget 8.21 (2017): 34586.
Beaudenon, S. et al. High-level expression and purification of recombinant E1 enzyme. Methods Enzymol 398, 3-8 (2005).
Benirschke R.C., et al., Molecular basis for the association of human E4B U box ubiquitin ligase with E2-conjugating enzymes UbcH5c and Ubc4. Structure 18, 955-965 (2010).
Bhuripanyo K. et al., "Identifying the substrate protein of U-box E3s E4B and CHIP by orthogonal ubiquitin transfer," Science Advances, 2018;4:e1701393, Jan. 3, 2018, pp. 1-16.
Bishop, A, et al. "Unnatural ligands for engineered proteins: new tools for chemical genetics." Annual review of biophysics and biomolecular structure 29.1 (2000): 577-606.
Deshaies, R.J. et al. RING domain E3 ubiquitin ligases. Annu Rev Biochem 78, 399-434 (2009).
Dou, H. et al. "Essentiality of a non-RING element in priming donor ubiquitin for catalysis by a monomeric E3." Nature structural & molecular biology 20.8 (2013): 982.
Emanuele, M.J. et al. Global identification of modular cullin-RING ligase substrates. Cell 147, 459-74 (2011).
Hatakeyama S, et al., U box proteins as a new family of ubiquitin-protein ligases. J Biol Chem 276, 33111-33120 (2001).
Hatakeyama, S. et al. "U-box proteins as a new family of ubiquitin ligases." Biochemical and biophysical research communications 302.4 (2003): 635-645.
Herschko et al., The ubiquitin system. Annu. Rev. Biochem. 67, 425-479 (1998).
Hoppe T. Multiubiquitylation by E4 enzymes: 'one size' doesn't fit all. Trends Biochem Sci 30, 183-187 (2005).
Huang, L. et al. Structure of an E6AP-UbcH7 complex: insights into ubiquitination by the E2-E3 enzyme cascade. Science 286, 1321-6 (1999).
Kim, H.C., et al. Structure and function of a HECT domain ubiquitin-binding site. EMBO reports 12, 334-41 (2011).
Kim, W. et al. Systematic and quantitative assessment of the ubiquitin-modified proteome. Mol Cell 44, 325-40 (2011).
Koegl M. et al., A novel ubiquitination factor, E4, is involved in multiubiquitin chain assembly. Cell 96, 635-644 (1999).
Komander D. et al., Breaking the chains: structure and function of the deubiquitinases. Nat Rev Mol Cell Biol 10, 550-563 (2009).
Kuslansky, Y. et al. Ubiquitin ligase E6AP mediates nonproteolytic polyubiquitylation of beta-catenin independent of the E6 oncoprotein. J Gen Virol 97, 3313-3330 (2016).
Lee I. et al., Structural insights into E1-catalyzed ubiquitin activation and transfer to conjugating enzymes. Cell 134, 268-278 (2008).
Levin-Kravets O. et al., A bacterial genetic selection system for ubiquitylation cascade discovery. Nat Methods 13, 945-952 (2016).
Liu, X. et al. Orthogonal ubiquitin transfer identifies ubiquitination substrates under differential control by the two ubiquitin activating enzymes. Nat Commun 8, 14286 (2017).
Mark, K. G. et al. "Ubiquitin ligase trapping identifies an SCFSaf1 pathway targeting unprocessed vacuolar/lysosomal proteins." Molecular cell 53.1 (2014): 148-161.
Mark, K.G., et al. Isolation of ubiquitinated substrates by tandem affinity purification of E3 ligase-polyubiquitin-binding domain fusions (ligase traps). Nat Protoc 11, 291-301 (2016).
Maspero, E. et al. Structure of a ubiquitin-loaded HECT ligase reveals the molecular basis for catalytic priming. Nat Struct Mol Biol 20, 696-701 (2013).
Medvar et al., Comprehensive database of human E3 ubiquitin ligases: application to aquaporin-2 regulation. Physiol Genomics 2016; 48(7)502-512,.
Merbl, Y. et al."Large-scale detection of ubiquitination substrates using cell extracts and protein microarrays." Proceedings of the National Academy of Sciences 106.8 (2009): 2543-2548.
Morreale, FE et al. "Types of ubiquitin ligases." Cell 165.1 (2016): 248-248.
Nikolay R. et al. Dimerization of the human E3 ligase CHIP via a coiled-coil domain is essential for its activity. J Biol Chem 279, 2673-2678 (2004).
Nordquist K. A. et al. Structural and functional characterization of the monomeric U-box domain from E4B. Biochemistry 49, 347-355 (2010).

(56) References Cited

OTHER PUBLICATIONS

O'Connor, H.F. et al. Ubiquitin-Activated Interaction Traps (UBAITs) identify E3 ligase binding partners. EMBO Rep 16, 1699-712 (2015).
Ogunjimi, A.A. et al. Regulation of Smurf2 ubiquitin ligase activity by anchoring the E2 to the HECT domain. Mol Cell 19, 297-308 (2005).
Ohi M. D. et al. Structural insights into the U-box, a domain associated with multiubiquitination. Nat Struct Biol 10, 250-255 (2003).
Pal, P et al. E3 ubiquitin ligase E6AP negatively regulates adipogenesis by downregulating proadipogenic factor C/EBPalpha. PLoS One 8, e65330 (2013).
Pierce, N.W., et al. Detection of sequential polyubiquitylation on a millisecond timescale. Nature 462, 615-9 (2009).
Popovic, D., et al. Ubiquitination in disease pathogenesis and treatment. Nat Med 20, 1242-53 (2014).
Pruneda J. N. et al. Structure of an E3:E2~Ub complex reveals an allosteric mechanism shared among RING/U-box ligases. Mol. Cell 47, 933-942 (2012).
Qian S.B., et al. CHIP-mediated stress recovery by sequential ubiquitination of substrates and Hsp70. Nature 440, 551-555 (2006).
Riley, B. E., et al. "Structure and function of Parkin E3 ubiquitin ligase reveals aspects of RING and HECT ligases." Nature communications 4.1 (2013): 1-9.
Rotin, D. et al. Physiological functions of the HECT family of ubiquitin ligases. Nat Rev Mol Cell Biol 10, 398-409 (2009).
Sanada, M, et al. "Gain-of-function of mutated C-CBL tumour suppressor in myeloid neoplasms." Nature 460.7257 (2009): 904-908.
Schulman B.A. et al., Ubiquitin-like protein activation by E1 enzymes: the apex for downstream signaling pathways. Nat. Rev. Mol. Cell Biol. 10, 319-331 (2009).
Scott, D. C., et al. "Two distinct types of E3 ligases work in unison to regulate substrate ubiquitylation." Cell 166.5 (2016): 1198-1214.
Shimoji, T. et al. Identification of annexin A1 as a novel substrate for E6AP-mediated ubiquitylation. J Cell Biochem 106, 1123-35 (2009).
Solarova, Z. et al. "Hsp90 inhibitor as a sensitizer of cancer cells to different therapies." International journal of oncology 46.3 (2015): 907-926.
Spratt, D. E., et al. "RBR E3 ubiquitin ligases: new structures, new insights, new questions." Biochemical journal 458.3 (2014): 421-437.
Starita, L. M., et al. "Activity-enhancing mutations in an E3 ubiquitin ligase identified by high-throughput mutagenesis." Proceedings of the National Academy of Sciences 110.14 (2013): E1263-E1272.
Stopa, N., et al. The PRMT5 arginine methyltransferase: many roles in development, cancer and beyond. Cell Mol Life Sci 72, 2041-59 (2015).
Sun C. et al. Diverse roles of C-terminal Hsp70-interacting protein (CHIP) in tumorigenesis. J Cancer Res Clin Oncol 140, 189-197 (2014).
Tagwerker, C. et al. A tandem affinity tag for two-step purification under fully denaturing conditions: application in ubiquitin profiling and protein complex identification combined with in vivocross-linking. Molecular & cellular proteomics : MCP 5, 737-48 (2006).
Trempe, J-F, et al. "Structure of parkin reveals mechanisms for ubiquitin ligase activation." Science 340.6139 (2013): 1451-1455.

* cited by examiner

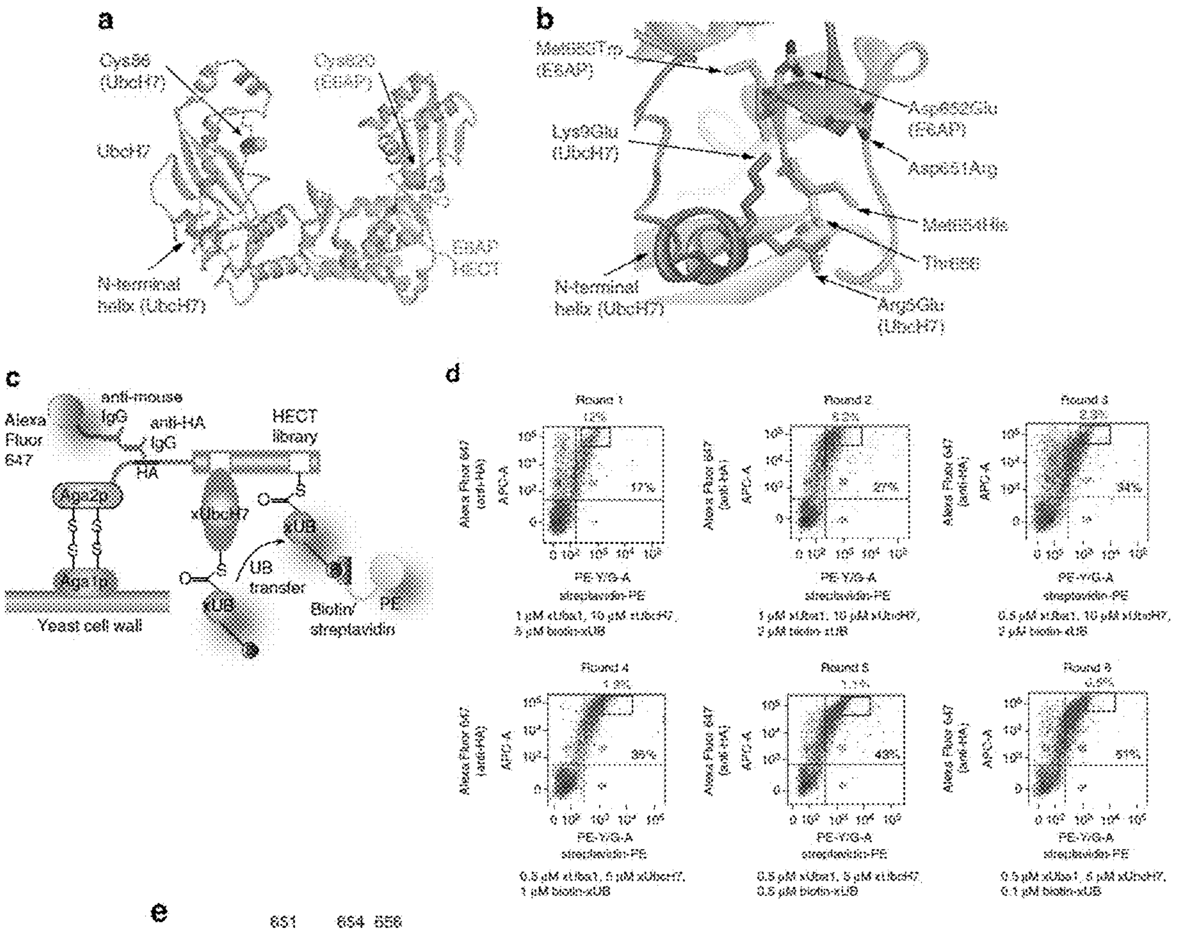

e

| | 651 | | | 654 | | 656 | | Number of times selected among 40 sequenced clones | |
|---|---|---|---|---|---|---|---|---|---|
| Wt E6AP | E D | D | M | M | I | T | F | | SEQ ID NO:14 |
| YW1 | E G | G | S | A | I | R | F | 3 | SEQ ID NO:15 |
| YW2 | E R | D | W | M | I | R | F | 3 | SEQ ID NO:16 |
| YW3 | E M | V | Y | G | I | R | F | 1 | SEQ ID NO:17 |
| YW4 | E S | L | C | H | I | V | F | 3 | SEQ ID NO:18 |
| YW5 | E R | D | I | R | I | R | F | 3 | SEQ ID NO:19 |
| YW6 | E R | E | W | H | I | T | F | 3 | SEQ ID NO:20 |
| YW7 | E M | N | Y | H | I | M | F | 1 | SEQ ID NO:21 |
| YW8 | E L | A | F | M | I | L | F | 1 | SEQ ID NO:22 |
| YW9 | E Q | A | Y | R | I | R | F | 1 | SEQ ID NO:23 |
| YW10 | E R | D | G | L | I | G | F | 1 | SEQ ID NO:24 |
| YW11 | E N | L | S | W | I | M | F | 1 | SEQ ID NO:25 |
| YW12 | E R | V | W | R | I | R | F | 1 | SEQ ID NO:26 |
| YW13 | E R | S | V | E | I | S | F | 1 | SEQ ID NO:27 |
| YW14 | E Q | S | Q | N | I | G | F | 1 | SEQ ID NO:28 |
| YW15 | E L | N | T | A | I | V | F | 1 | SEQ ID NO:29 |
| YW16 | I V | N | W | G | I | C | F | 1 | SEQ ID NO:30 |
| YW17 | E M | N | Y | R | I | R | F | 1 | SEQ ID NO:31 |
| YW18 | E S | K | W | S | I | M | F | 1 | SEQ ID NO:32 |
| YW19 | E V | E | Y | S | I | T | F | 1 | SEQ ID NO:33 |
| YW20 | E D | R | S | H | I | L | F | 1 | SEQ ID NO:34 |

*Fig. 2*

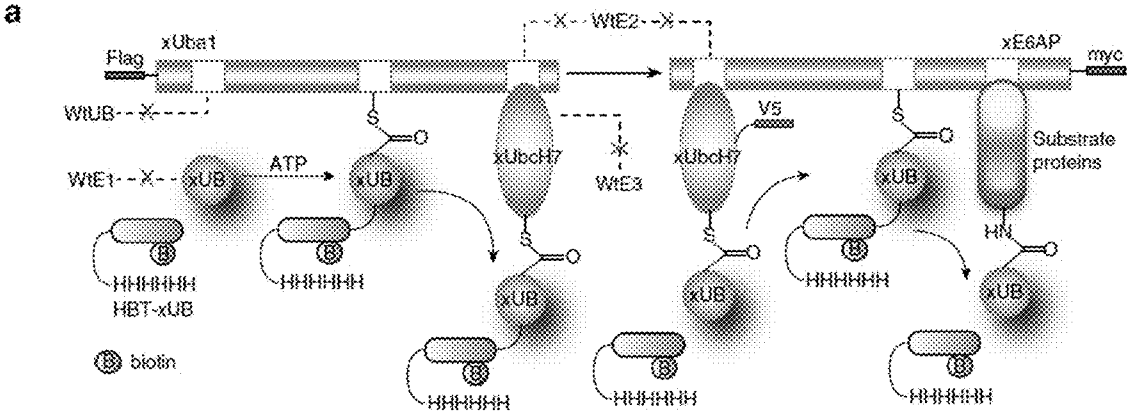
-HHHHHH (SEQ ID NO:35)
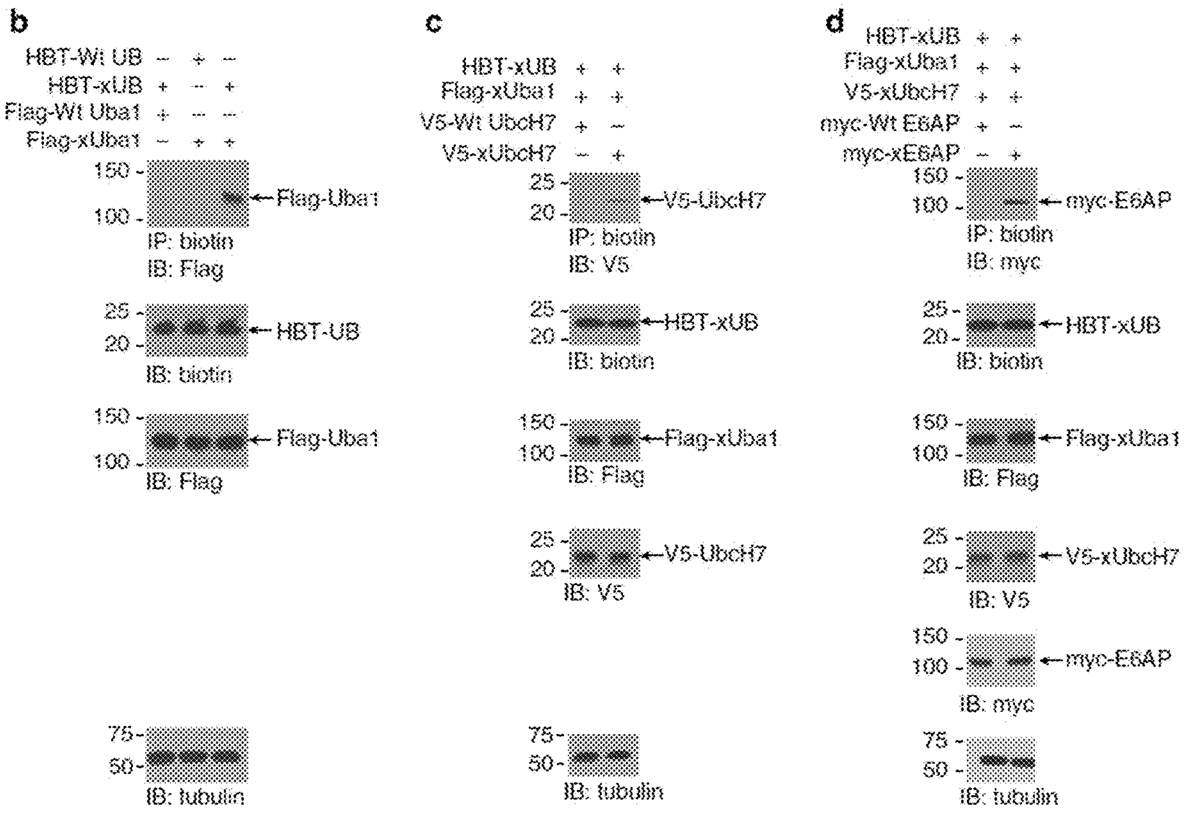
*Fig. 4*

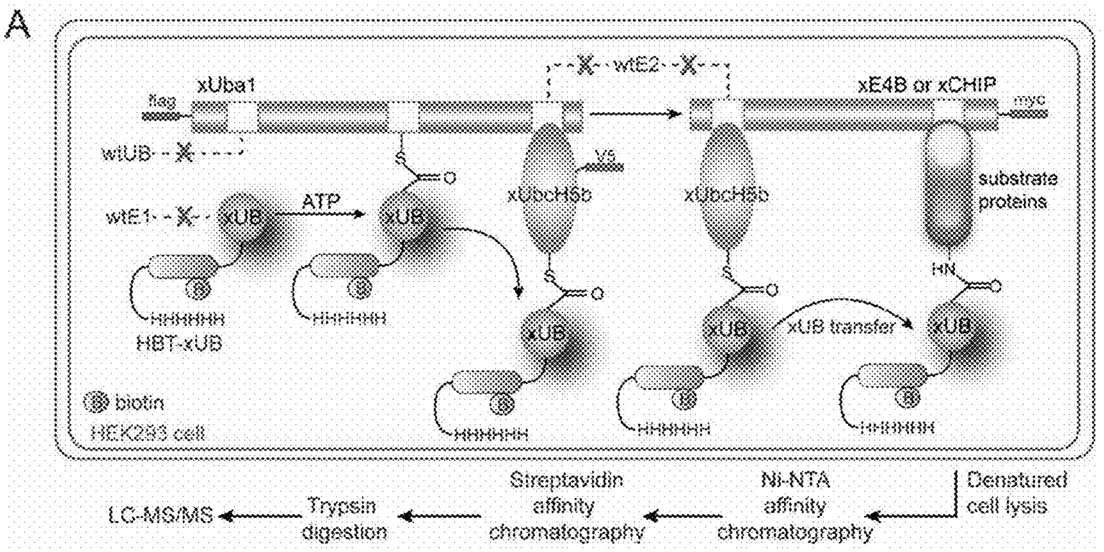
-HHHHHH (SEQ ID NO:35)
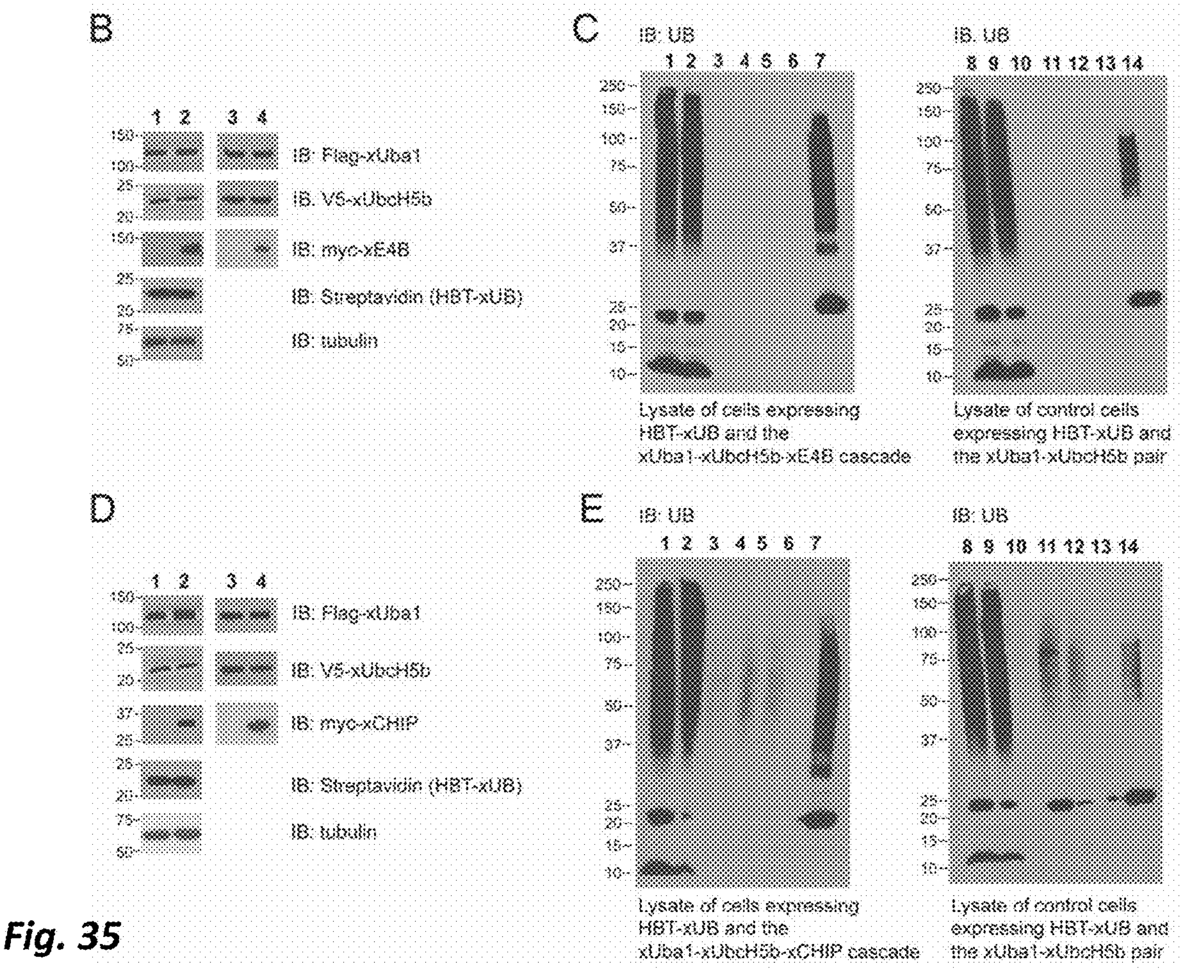
*Fig. 35*

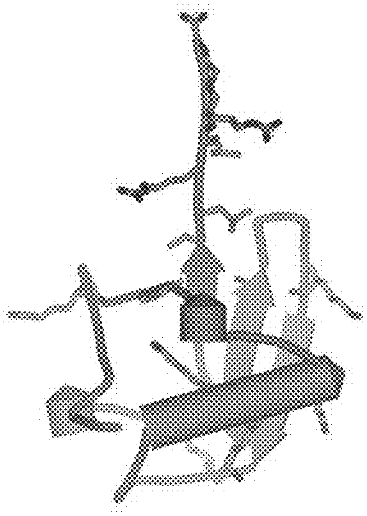
Ubiquitin (UB)
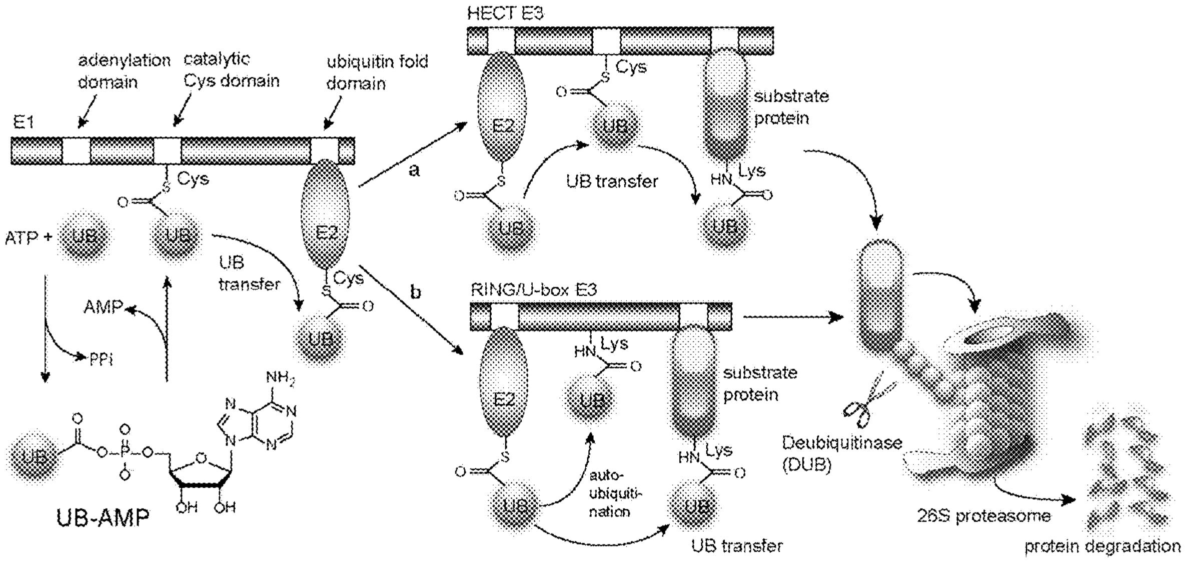
*Fig. 36*

ATP-PPi exchange

| | $K_m$ (μM) | $k_{cat}$ ($min^{-1}$) | $k_{cat}/K_m$ ($\mu M^{-1}\ min^{-1}$) |
|---|---|---|---|
| wtUB - wtE1(Uba1) | 1.44 | 50.8 | 35.3 |
| wtUB - xE1(Uba1-A5) | | | 0.011 |
| xUB(UB10) - xE1(Uba1-A5) | 4.45 | 70.8 | 15.9 |
| xUB(UB10) - wtE1(Uba1) | | | 0.012 |

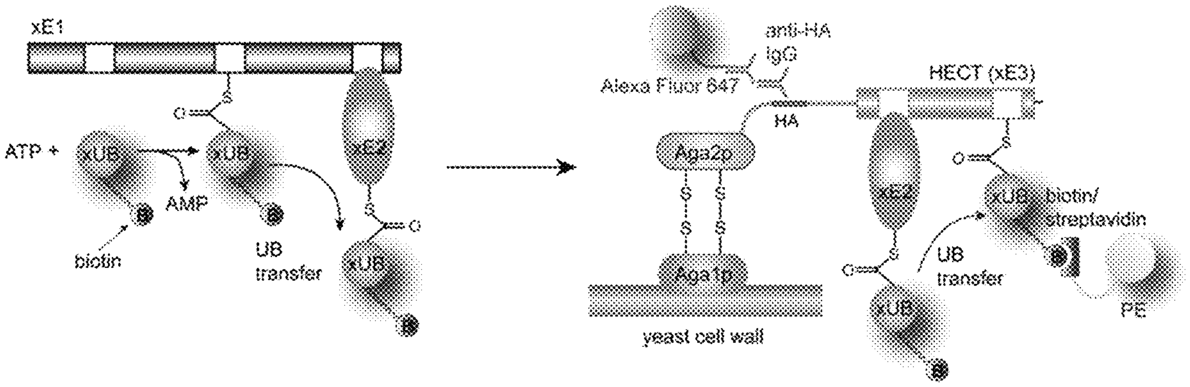

| | 661 * * * 664 * 666 * | Numbers of times selected among 40 sequenced clones | |
|---|---|---|---|
| wt E6AP | E D D M M I T F | | SEQ ID NO:96 |
| YW1 | E G G S A I R F | 3 | SEQ ID NO:97 |
| YW2 | E R D W M I R F | 3 | SEQ ID NO:98 |
| YW3 | E M V Y G I R F | 1 | SEQ ID NO:99 |
| YW4 | E S L C H I V F | 3 | SEQ ID NO:100 |
| YW5 | E R D I R I R F | 3 | SEQ ID NO:101 |
| YW6 | E R E W H I T F | 3 | SEQ ID NO:102 |
| YW7 | E M N Y H I M F | 1 | SEQ ID NO:103 |
| YW8 | E L A F M I L F | 1 | SEQ ID NO:104 |
| YW9 | E Q A Y R I R F | 1 | SEQ ID NO:105 |
| YW10 | E R D G L I G F | 1 | SEQ ID NO:106 |
| YW11 | E N L S W I M F | 1 | SEQ ID NO:107 |
| YW12 | E R V W R I R F | 1 | SEQ ID NO:108 |
| YW13 | E R S V K I S F | 1 | SEQ ID NO:109 |
| YW14 | E Q S Q N I G F | 1 | SEQ ID NO:110 |
| YW15 | E L N T A I V F | 1 | SEQ ID NO:111 |
| YW16 | I V N W G I C F | 1 | SEQ ID NO:112 |
| YW17 | E M N Y R I R F | 1 | SEQ ID NO:113 |
| YW18 | E S K W S I M F | 1 | SEQ ID NO:114 |
| YW19 | E V E Y S I T F | 1 | SEQ ID NO:115 |
| YW20 | E D R S H I L F | 1 | SEQ ID NO:116 |

*Fig. 41* p53 ubiquitination by wt E6AP and fYW4 and fYW6 in the presence of E6
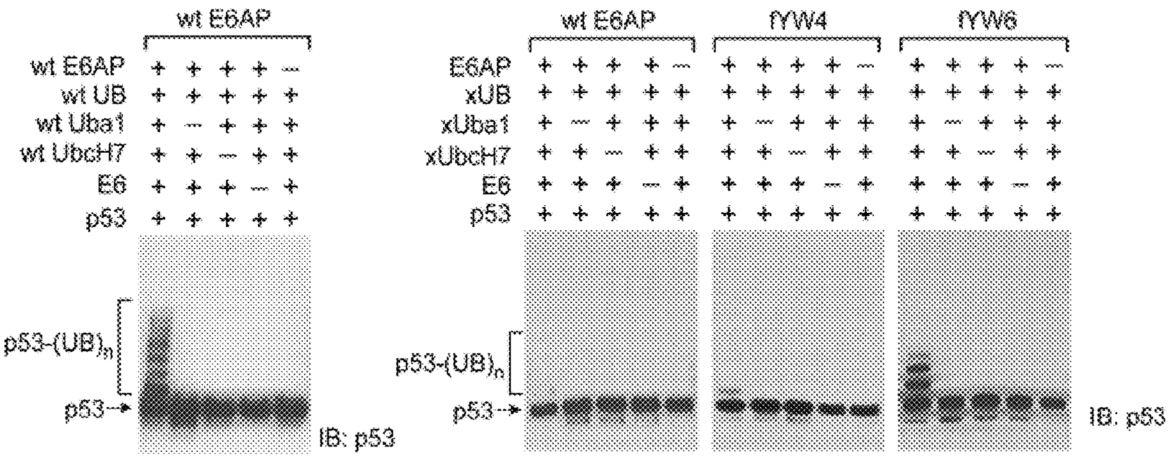
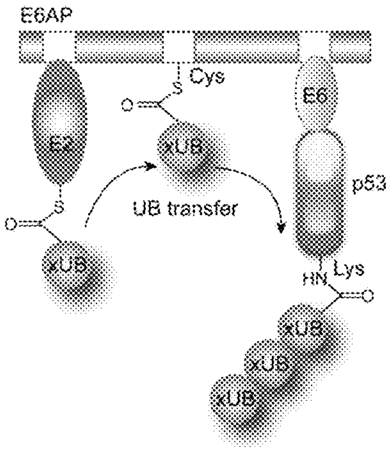
| E6AP(DDMMT) |
| --- |
| 1.GGSAR (SEQ ID NO:117) |
| 2.RDWMR (SEQ ID NO:118) |
| 3.MVYGR (SEQ ID NO:119) |
| 4.SLCHV (SEQ ID NO:120) |
| 5.RDIRR (SEQ ID NO:121) |
| 6.REWHT (SEQ ID NO:122) |
*Fig. 42*

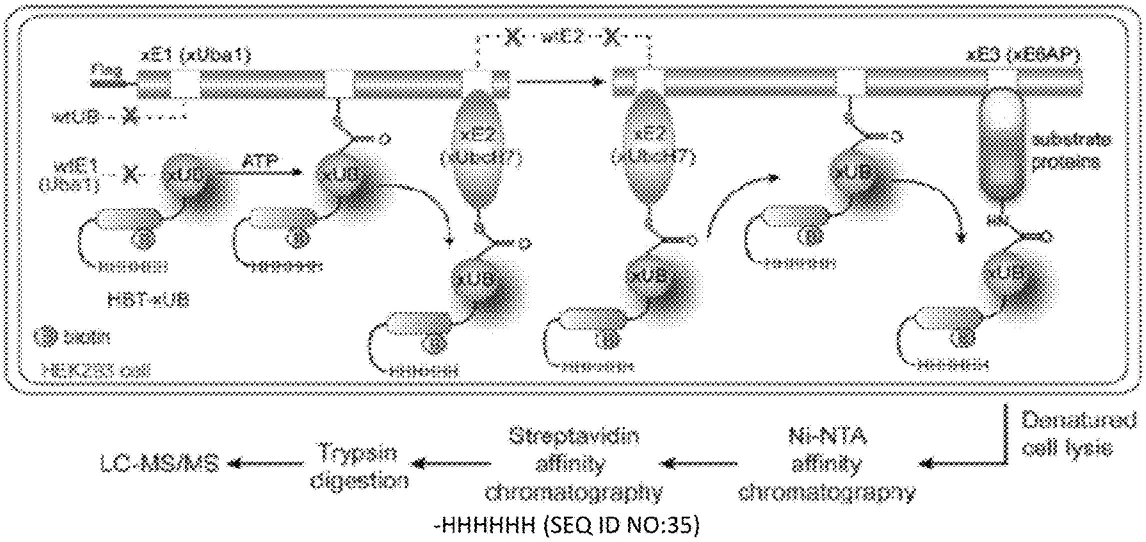
-HHHHHH (SEQ ID NO:35)
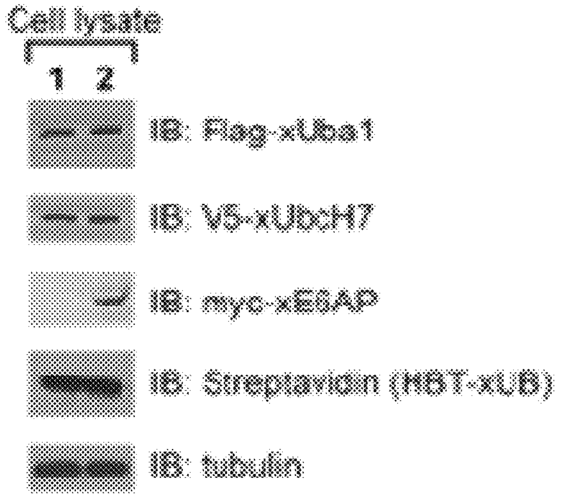
| Known substrates of E6AP | RAD23 B | RAD23 A | RNF2 | ADRM1 | PSMD4 | PSMC 3 |
|---|---|---|---|---|---|---|
| -E6AP (PSMs) | 0 | 0 | 0 | 0 | 4 | 2 |
| +E6AP (PSMs) | 39 | 6 | 4 | 5 | 19 | 10 |
*Fig. 43*

ORTHOGONAL UBIQUITIN TRANSFER AS A METHOD TO IDENTIFY CELLULAR SUBSTRATES OF E3 UBIQUITIN LIGASES

CROSS-REFERENCE TO RELATED PATENT APPLICATIONS

The present application claims the benefit of priority under 35 U.S.C. 119(e) to U.S. Provisional Application No. 62/782,111, filed on Dec. 19, 2018, the content of which is incorporated herein by reference in its entirety.

STATEMENT REGARDING FEDERALLY SPONSORED RESEARCH OR DEVELOPMENT

This invention was made with government support under GM104498 awarded by the National Institutes of Health. The government has certain rights in the invention.

REFERENCE TO A SEQUENCE LISTING SUBMITTED VIA EFS-WEB

The content of the ASCII text file of the sequence listing named "702581_01689_ST25.txt" which is 66.4 kb in size was created on Dec. 18, 2019 and electronically submitted via EFS-Web herewith the application is incorporated herein by reference in its entirety.

BACKGROUND

The field of the invention relates to proteins, vectors for expressing proteins, compositions, and methods for identifying substrates of E3 ubiquitin ligases. In particular, the field of the invention relates to components and methods for performing orthogonal ubiquitin transfer in order to identify substrates of E3 ubiquitin ligases.

The E1-E2-E3 enzymatic cascades are known in the art to mediate ubiquitin (UB) transfer and they constitute a key part of cell signaling networks. (See, e.g., Hershko, et al., *Annu. Rev. Biochem.,* 1998 67, 425, the content of which is incorporated herein by reference in its entirety). In E1-E2-E3 cascades, E1 first activates UB to form a UB~E1 thioester conjugate with the C-terminal carboxylate of UB bonded to a catalytic Cys residue of E1. (See, e.g., Lee et al., *Cell,* 2008, 134, 268, the content of which is incorporated herein by reference in its entirety). Next, UB is transferred to a catalytic Cys residue on E2 to form a UB~E2 conjugate. Subsequently, E2 carries UB to an E3 that recruits substrate proteins and catalyzes isopeptide bond formation between the C-terminal Gly of UB and Lys residues on the substrates. (See, e.g., Wenzel et al., *Biochem. J.* 2011, 433, 31; the content of which is incorporated by reference in its entirety). Several hundred E3s are known, and E3s are classified into 28 HECT, 7 U-box, 12 RBR, and more than 600 Ring types based on the domain structures to engage the UB~E2 conjugate. (See, e.g., Deshaies, et al., *Annu. Rev. Biochem.,* 2009, 78, 399; Hatakeyama et al., *Biochem. Biophyx. Res. Commun.* 2003, 302, 635; and Rotin et al., *Nat. Rev. Mol. Cell Biol.* 2009, 10, 398; the contents of which are incorporated by reference in their entireties). HECT and RBR E3s rely on a catalytic Cys residue to uptake UB from an E2 before transferring UB to the substrates. U-box and Ring E3s directly transfer UB from E2 to the substrates.

The large number of E3s and their transient interactions with substrates ($K_d$~10-100 μM) present a significant challenge to identifying the direct and specific substrates of an E3. (See, e.g., Pierce et al., Nature. 2009, 462, 615, the content of which is incorporated by reference in its entirety). Previous methods to identify E3 substrates fall into three categories of approaches: (i) affinity binding to E3, (ii) monitoring changes in protein stability or ubiquitination upon E3 perturbation, and (iii) generating E3 fusions as substrate traps. However, each of these categories of approaches has its drawback. Affinity-based approaches such as co-immunoprecipitation, yeast two-hybrid system, and protein microarray do not differentiate substrates from other E3 partners such as adaptors or regulators. Activity-based approaches follow the change of protein stability or ubiquitination level (abundance of diGly peptide after trypsin digestion) as a read-out of E3-substrate relationship. However, because a majority of UB chains are in linkages encoding non-degradation signals, following protein stability misses a significant portion of E3 substrates. E3s also cross-regulate each other, so changing the activity of one E3 may affect the ubiquitination of the substrates of other E3s. Because of this, it would be hard to assign the direct substrate an E3 based on the change in global protein ubiquitination levels. E3 fusion proteins also have been utilized as substrate traps. For example, substrate traps that fuse E3 with UB (UB-activated interaction traps, UBAIT), UB associated domain (UBA), or Nedd8 E2 (Neddylator) have been created. These E3 fusion proteins enable substrates to bind to E3s after UB transfer or to be conjugated to UB-like protein Nedd8. However, these E3 fusions may distort the substrate profile of the E3s since UB and UBA are common motifs for protein-protein interactions.

As such, better components and methods for identifying substrates of E3 ubiquitin ligases are desirable. Here, the inventors disclosed a method known as "orthogonal UB transfer (OUT)" to identify the direct substrates of an E3. In the inventors' OUT method, a UB variant (xUB) is confined to a single track of engineered xE1, xE2 and xE3 which deliver xUB exclusively to the substrates of an E3 (wherein "x" designates engineered UB or enzyme variants orthogonal to their native partners). By expressing xUB and the OUT cascade of xE1-xE2-xE3 in a cell and purifying xUB-conjugated proteins, the inventors can identify the direct substrates of the E3. The OUT cascade eliminates the complex cross-reactions among various E2s and E3s and assigns E3 substrates by directly following xUB transfer from the E3 to its target proteins.

SUMMARY

Disclosed herein are proteins, vectors expressing the proteins, compositions, and methods for identifying substrates of E3 ubiquitin ligases. The proteins, vectors, compositions, and may be utilized in methods for orthogonal ubiquitin transfer (OUT) between variant components of the ubiquitin cascade such as a variant ubiquitin (UB), a variant ubiquitin activating enzyme (E1), a variant ubiquitin-conjugating enzyme (E2), and a variant ubiquitin ligase (E3), which may include, but is not limited to a variant HECT type, U-box type, RBR type, and/or Ring type E3 ligase.

The variant components of the ubiquitin cascade utilized in the disclosed methods typically include one or more mutations relative to their wild-type counterparts, such as amino acid substitutions, such that the variant components interact specifically and orthogonally with each of their variant components and do not interact with the wild-type counterpart of their variant components. As such, the disclosed proteins, vectors, compositions, and methods may be utilized to identify specific substrates of the wild-type counterpart E3 without having to eliminate background substrates that have been ubiquitinated by other E3 ubiquitin ligases.

BRIEF DESCRIPTION OF THE FIGURES

FIG. 2. Yeast selection of E6AP library to engineer the xUbcH7-xE6AP pair. (a) Crystal structure of the E6AP HECT domain in complex with UbcH7 (PDB ID 1C4Z)[22]. The N-terminal helix of UbcH7 plays a key role in interacting with the HECT domain. The catalytic Cys residues in UbcH7 and the E6AP HECT are shown in CPK models. (b) Detailed interactions between the N-terminal helix of UbcH7 and the HECT domain of E6AP. To complement the R5E and K9E mutations in xUbcH7, D651, D652, M653, M654 and T656 in the HECT domain of E6AP were randomized for library selection by yeast cell surface display. HECT mutant YW6 with mutations D651R, D652E, M653W, and M654H was selected and used as xHECT in this study. (c) Yeast cell surface display of the HECT domain of E6AP and selection of the HECT library based on the transfer of biotin-xUB from xUbcH7 to the HECT domain. Biotin-xUB attached to HECT was labeled with streptavidin-PE, and the HA tag fused to the N-terminus of the HECT domain was labeled with a mouse anti-HA antibody and an anti-mouse IgG conjugated with Alexa 647. (d) FACS sorting of the HECT library of E6AP to select for yeast cells (EBY100) doubly labeled with PE and Alexa 647 as indicators of biotin-xUB conjugation and display of HECT on the cell surface, respectively. The HECT library underwent six rounds of xUB loading, streptavidin and antibody labeling, and cell sorting. Percentages in black designate fraction of yeast cells doubly labeled with PE and Alexa 647. The frames and percentages in blue designate the fraction of yeast cells collected by FACS in each round of selection. (e) Sequence alignment of the E6AP HECT clones selected by yeast cell surface display. Residues denoted by red stars were randomized in the HECT library.

FIG. 4. Orthogonality of the E6AP OUT cascade with wt Uba1-UbcH7-E6AP cascade in HEK293 cells. (a) Scheme showing exclusive transfer of xUB through the OUT cascade of E6AP. xUba1, xUbcH7 and xE6AP are tagged with Flag, V5 and myc tags, respectively. Dotted lines with a red "X" designate no interactions between OUT components and the native E1, E2, and E3 enzymes. xUB is tagged with biotin and 6×His tags (HBT-xUB). (b) xUB and xUba1 formed xUB~xUba1 conjugate in HEK293 cells. As a result of conjugate formation, flag-xUba1 could be copurified with HBT-xUB by binding to streptavidin beads. In contrast, flag-wt Uba1 could not be copurified with HBT-xUB, neither could flag-xUba1 be copurified with HBT-wt UB in the cells co-expressing the UB-E1 pairs. This suggests that the crossover xUB-wt Uba1 or wt UB-xUba1 pairs are not active in the cell. (c) xUB could be transferred through xUba1-xUbcH7 pair to form xUB~xUbcH7 conjugate in the cell. Due to the conjugate formation, V5-xUbcH7 could be copurified with HBT-xUB from cells expressing HBT-xUB, flag-xUba1 and V5-xUbcH7. In contrast, the expression of HBT-xUB and the crossover pair of xUba1-wt UbcH7 would not generate xUB~wt UbcH7 conjugate, so V5-wt UbcH7 could not be co-purified with HBT-xUB. (d) xUB could be transferred through xUba1-xUbcH7-xE6AP cascade to form xUB~xE6AP conjugate in the cell. As a result, myc-xE6AP could be co-purified with HBT-xUB in cells expressing HBT-xUB and the xUba1-xUbcH7-xE6AP cascade. In contrast, coexpression of HBT-xUB with the crossover cascade of xUba1-xUbcH7-wt E6AP would not generate xUB~wt E6AP conjugate, so myc-wt E6AP could not be co-purified with HBT-xUB.

FIG. 35. Affinity purification of xUB modified proteins to identify the substrates of E4B and CHIP. (A) Scheme to show cells expressing the OUT cascade of E4B and CHIP, tandem affinity purification of xUB-conjugated proteins from the cell lysate, and identification of purified proteins by LC-MS/MS. (B) Expressing the OUT cascade of E4B and HBT-xUB in cells. Expression of the components of the xUba1-xUbcH5b-xE4B cascade was confirmed in HEK293 cells (lane 2). In control cells, the xUba1-xUbcH5b pair was expressed without xE4B (lane 1). To confirm xUB transfer through the OUT cascade, lysates of the cells expressing the OUT cascade of E4B and HBT-xUB were purified by tandem affinity columns of Ni-NTA and streptavidin, and the co-purification of xUba1, xUbcH5b, and xE4B in the xUB-conjugated fraction was confirmed by Western blot (lane 4). Similar purification was done on lysate from cells expressing xUba1-xUbcH5b pair without xE4B. xUba1 and xUbcH5b were co-purified as xUB conjugated proteins (lane 3). (C) Purification of xUB conjugated proteins from lysates of cells expressing the full OUT cascade of E4B (lanes 1-7). The Western blots of the gels were probed with an anti-UB antibody. Lane 1, cell lysate; lane 2, flow-through from the Ni-NTA column; lane 3, wash solution of the Ni-NTA column; lane 4, elution from the Ni-NTA column; lane 5, flow-through from the streptavidin column; lane 6, wash solution of the streptavidin column; lane 7, protein bound to the streptavidin beads after washing. Lanes 8-14 were the same as lanes 1-7 respectively, except that xUB-conjugated proteins were purified from control cells with the expression of xUba1-xUbcH5b but without xE4B expression. xUB-conjugated proteins eluted from the Ni-NTA column (lanes 4 and 11) were much diluted comparing to the xUB-conjugated proteins bound to the streptavidin beads (lanes 7 and 14). (D) Same as (B) to confirm the expressing of OUT cascades of CHIP in cells expressing xUba1-xUbcH5b-xCHIP (lane 2) and in the control cells missing xCHIP expression (lane 1). xUba1, xUbcH5b and xCHIP were purified as xUB-conjugated proteins from lysates of the cell expressing the OUT cascade of CHIP (lane 4). xUba1 and xUbcH5b were purified as xUB-conjugated proteins from control cells without xCHIP expression (lane 3). (E) Same as (C) except that the purification was performed on cells expressing the OUT cascade of CHIP and on control cells without xCHIP expression.

FIG. 36. Model of UB transfer cascade.

FIG. 41. Model for selecting an orthogonal xUbcH7-xE6AP pair and selection results.

FIG. 42. Illustration of xUB transfer through an orthogonal UB transfer (OUT) cascade of E6AP.

FIG. 43. Model and results of profiling E6AP substrates using orthogonal UB transfer (OUT).

DETAILED DESCRIPTION

Figure 1:
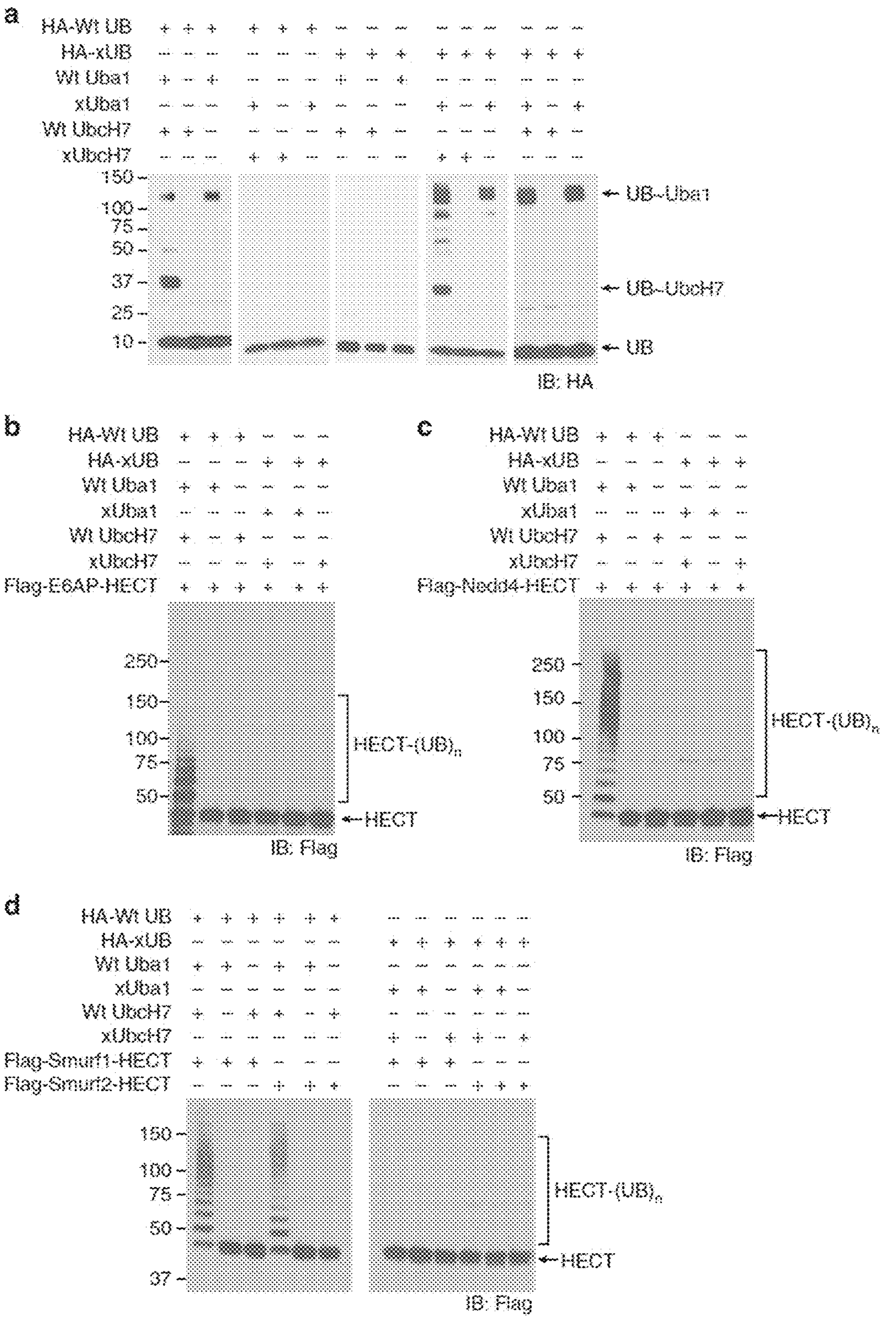
FIG. 1. Orthogonality of the xUba1-xUbcH7 pair with the wt UB transferring enzymes. (a) wt UB can be transferred to wt UbcH7 by wt human Uba1, but it cannot be activated by human xUba1 for transferring to xUbcH7. Vice versa, xUB can be activated by xUba1 for transferring to xUbcH7, but it cannot be activated by wt Uba1 for transferring to wt UbcH7, nor can it be transferred to wt UbcH7 by xUba1. The protein gels were run under non-reducing conditions to preserve the thioester conjugates of UB~E1 and UB~E2. (b, c, and d) HECT domains of wt E6AP, Nedd4, Smurf1 and Smurf2 can be loaded with wt UB through the wt Uba1-UbcH7 pair. Yet they are not reactive with xUB though the xUba1-xUbcH7 pair. The protein gels were run under reducing conditions to probe the auto-ubiquitination of the HECT enzymes.

The present invention is described herein using several definitions, as set forth below and throughout the application.

Definitions and Terminology

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a component" should be interpreted to mean "one or more components" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into subranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

Polynucleotides and Uses Thereof

The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

The terms "nucleic acid" and "oligonucleotide," as used herein, may refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

Regarding polynucleotide sequences, the terms "percent identity" and "% identity" refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized for expression in a particular host. In the art, codon usage frequency tables have been prepared for a number of host organisms including humans, mouse, rat, pig, *E. coli*, plants, and other host cells.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target," "target sequence," "target region," and "target nucleic acid," as used herein, are synonymous and may refer to a region or sequence of a nucleic acid which is to be hybridized and/or bound by another nucleic acid (e.g., a target sequence that is bound by a STAR RNA and/or a target sequence that is bound by a trigger RNA for a Toehold switch).

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, *Biochemistry,* 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)—sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Therms aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, RNA polymerases of bacteriophages (e.g. T3 RNA polymerase, T7 RNA polymerase, SP6 RNA polymerase, Syn5 RNA polymerase), and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, "expression template" refers to a nucleic acid that serves as substrate for transcribing at least one RNA. Expression templates include nucleic acids composed of DNA or RNA. Suitable sources of DNA for use in a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

"Transformation" or "transfection" describes a process by which exogenous nucleic acid (e.g., DNA or RNA) is introduced into a recipient cell. Transformation or transfection may occur under natural or artificial conditions according to various methods well known in the art, and may rely on any known method for the insertion of foreign nucleic acid sequences into a prokaryotic or eukaryotic host cell. The method for transformation or transfection is selected based on the type of host cell being transformed and may include, but is not limited to, bacteriophage or viral infection or non-viral delivery. Methods of non-viral delivery of nucleic acids include lipofection, nucleofection, microinjection, electroporation, heat shock, particle bombardment, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam.™. and Lipofectin.™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The term "transformed cells" or "transfected cells" includes stably transformed or transfected cells in which the inserted DNA is capable of replication either as an autonomously replicating plasmid or as part of the host chromosome, as well as transiently transformed or transfected cells which express the inserted DNA or RNA for limited periods of time.

The polynucleotide sequences contemplated herein may be present in expression vectors. For example, the vectors may comprise a polynucleotide encoding an ORF of a protein operably linked to a promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter operably linked to a polynucleotide that encodes a protein. A "heterologous promoter" refers to a promoter that is not the native or endogenous promoter for the protein or RNA that is being expressed.

As used herein, "expression" refers to the process by which a polynucleotide is transcribed from a DNA template (such as into mRNA or another RNA transcript) and/or the process by which a transcribed mRNA is subsequently translated into peptides, polypeptides, or proteins. Transcripts and encoded polypeptides may be collectively referred to as "gene product."

The term "vector" refers to some means by which nucleic acid (e.g., DNA) can be introduced into a host organism or host tissue. There are various types of vectors including plasmid vector, bacteriophage vectors, cosmid vectors, bacterial vectors, and viral vectors. As used herein, a "vector" may refer to a recombinant nucleic acid that has been engineered to express a heterologous polypeptide (e.g., the fusion proteins disclosed herein). The recombinant nucleic acid typically includes cis-acting elements for expression of the heterologous polypeptide.

In the methods contemplated herein, a host cell may be transiently or non-transiently transfected (i.e., stably transfected) with one or more vectors described herein. A cell transfected with one or more vectors described herein may be used to establish a new cell line comprising one or more vector-derived sequences. In the methods contemplated herein, a cell may be transiently transfected with the components of a system as described herein (such as by transient transfection of one or more vectors), and modified through the activity of a complex, in order to establish a new cell line comprising cells containing the modification but lacking any other exogenous sequence.

Peptides, Polypeptides, and Proteins

As used herein, the terms "protein" or "polypeptide" or "peptide" may be used interchangeable to refer to a polymer of amino acids. Typically, a "polypeptide" or "protein" is defined as a longer polymer of amino acids, of a length typically of greater than 50, 60, 70, 80, 90, or 100 amino acids. A "peptide" is defined as a short polymer of amino acids, of a length typically of 50, 40, 30, 20 or less amino acids.

A "protein" as contemplated herein typically comprises a polymer of naturally or non-naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). The proteins contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a non-enzymatic attachment of sugars, polysialylation (e.g., the addition of polysialic acid), glypiation (e.g., glycosylphosphatidylinositol (GPI) anchor formation), hydroxylation, iodination (e.g., of thyroid hormones), and phosphorylation (e.g., the addition of a phosphate group, usually to serine, tyrosine, threonine or histidine).

The proteins disclosed herein may include "wild type" proteins and variants, mutants, and derivatives thereof. As used herein the term "wild type" is a term of the art understood by skilled persons and means the typical form of an organism, strain, gene or characteristic as it occurs in nature as distinguished from mutant or variant forms. As used herein, a "variant, "mutant," or "derivative" refers to a protein molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a mutant or variant molecule may have one or more insertions, deletions, or substitution of at least one amino acid residue relative to a reference polypeptide.

Regarding proteins, a "deletion" refers to a change in the amino acid sequence that results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide). A "variant," "mutant," or "derivative" of a reference polypeptide sequence may include a deletion relative to the reference polypeptide sequence.

Regarding proteins, "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full-length polypeptide. A fragment may include an N-terminal truncation, a C-terminal truncation, or both truncations relative to the full-length protein. A "variant," "mutant," or "derivative" of a reference polypeptide sequence may include a fragment of the reference polypeptide sequence.

Regarding proteins, the words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A "variant," "mutant," or "derivative" of a reference polypeptide sequence may include an insertion or addition relative to the reference polypeptide sequence. A variant of a protein may have N-terminal insertions, C-terminal insertions, internal insertions, or any combination of N-terminal insertions, C-terminal insertions, and internal insertions.

Regarding proteins, the phrases "percent identity" and "% identity," refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Regarding proteins, percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Regarding proteins, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acids typically disrupt (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed proteins, mutants, variants, or described herein may have one or more functional or biological activities exhibited by a reference polypeptide (e.g., one or more functional or biological activities exhibited by wild-type protein).

In some embodiments of the disclosed compositions, systems, kits, and methods, the components may be substantially isolated or purified. The term "substantially isolated or purified" refers to components that are removed from their natural environment, and are at least 60% free, preferably at least 75% free, and more preferably at least 90% free, even more preferably at least 95% free from other components with which they are naturally associated.

Orthogonal Ubiquitin Transfer as a Method to Identify Cellular Substrates of E3 Ligases The present inventors have disclosed proteins, compositions, platforms comprising the disclosed proteins and compositions, and methods for identifying substrates of E3 ubiquitin ligases using the disclosed proteins, compositions, and platforms. The proteins, compositions, platforms, and methods include and/or utilize orthogonal ubiquitin transfer between variant components of the ubiquitin cascade such as variant ubiquitin (UB), a variant ubiquitin activating enzyme (E1), a variant ubiquitin-conjugating enzyme (E2), and a variant ubiquitin ligase (E3), which may include, but is not limited to, a variant HECT type, U-box type, RBR type, and/or Ring type E3 ligase. The variant components of the ubiquitin cascade typically include one or more mutations relative to their wild-type counterparts, such as amino acid substitutions, such that the variant components interact specifically and orthogonally with each of their variant components and do not interact with the wild-type counterpart of their variant components. As such, the disclosed proteins, compositions, platforms, and methods may be utilized to identify specific substrates of the wild-type counterpart E3 of the variant E3 ubiquitin ligase without having to eliminate background substrates that have been ubiquitinated by other E3 ubiquitin ligases.

In some embodiments, the disclosed subject matter may relate to proteins and/or platforms comprising the disclosed proteins or vectors that express the disclosed proteins. The disclosed proteins, vectors, and platforms may be utilized for identifying a substrate of an ubiquitin ligase (E3).

The disclosed platforms typically comprise or consist of one or more of the following proteins or vectors that express one or more of the following proteins: (a) a mutant (or variant) ubiquitin (UB) that comprises one or more amino acid substitutions relative to a wild-type UB; (b) a mutant (or variant) E1 protein (E1) that comprises one or more amino acid substitutions relative to a wild-type E1 protein; (c) a mutant (or variant) E2 protein (E2) that comprises one or more amino acid substitutions relative to a wild-type E2; and/or (d) a mutant (or variant) E3 ubiquitin ligase (E3) that comprises one or more amino acid substitutions relative to a wild-type E3.

In the disclosed platforms, preferably one or more of the following conditions are met: (i) the mutant E1 interacts with the mutant UB and forms a conjugate with the mutant E1, namely a mutant UB/E1 conjugate, via a thioester linkage between a catalytic Cys of the mutant E1 and the C-terminal carboxylate of the mutant UB; (ii) the mutant E1 does not interact with the wild-type UB and does not form a conjugate via a thioester linkage between a catalytic Cys of the mutant E1 and the C-terminal carboxylate of the wild-type UB; and/or (iii) the wild-type E1 does not interact with the mutant UB and does not form a conjugate via thioester linkage between with a catalytic Cys of the wild-type E1 and the C-terminal carboxylate of the mutant UB. Even more preferably, each of conditions (i), (ii), and (iii) are met.

In the disclosed platforms, preferably one or more of the following conditions are met: (i) the mutant E2 interacts with the mutant UB/E1 conjugate and the mutant UB is transferred to the mutant E2 and forms a conjugate with the mutant E2, namely a mutant UB-E2 conjugate, via formation of a thioester linkage between a catalytic Cys of the mutant E2 and the C-terminal carboxylate of the mutant UB; (ii) the mutant E2 does not interact with a wild-type UB/E1 conjugate and the wild-type UB is not transferred to the mutant E2 and does not form a conjugate with the mutant E2; and/or (iii) the wild-type E2 does not interact with the mutant UB/E1 conjugate and the mutant UB is not transferred to the wild-type E2 and does not form a conjugate with the wild-type E2. Even more preferably, each of conditions (i), (ii), and (iii) are met.

In the disclosed platforms, preferably one or more of the following conditions are met: (i) the mutant E3 interacts with the mutant UB/E2 conjugate and the mutant UB is transferred to the mutant E3 and forms a conjugate with the mutant E3, namely a mutant UB-E3 conjugate, via formation of a thioester linkage or an amide linkage between a catalytic Cys of the mutant E3 or a catalytic Lys of the mutant E3 and the C-terminal carboxylate of the mutant UB; and the mutant UB-E3 conjugate transfers the mutant UB to the substrate of E3 via formation of an amid linkage between a Lys of the substrate of E3 and the C-terminal carboxylate of the mutant UB; (ii) the mutant E3 does not interact with a wild-type UB/E2 conjugate and the wild-type UB is not transferred to the mutant E3 and does not form a conjugate with the mutant E3; and (iii) the wild-type E3 does not interact with the mutant UB/E2 conjugate and the mutant UB is not transferred to the wild-type E3 and does not form a conjugate with the wild-type E3. Even more preferably, each of conditions (i), (ii), and (iii) are met.

In the disclosed platforms, preferably one or more of the mutant UB, the mutant E1, the mutant E2, and the mutant E3 are derived from a wild-type mammalian UB, a wild-type mammalian E1, a wild-type mammalian E2, and a wild-type mammalian E3, respectively. In some embodiments of the disclosed platforms, one or more of the mutant UB, the mutant E1, the mutant E2, and the mutant E3 are derived from a wild-type human UB, a wild-type human E1, a wild-type human E2, and a wild-type human E3, respectively.

The ubiquitin protein is known in the art. (See, e.g., Herschko et al., The ubiquitin system. *Annu. Rev. Biochem.* 67, 425-479 (1998), the content of which is incorporated herein by reference in its entirety). In some embodiments of the disclosed platforms, the wild-type UB comprises the amino acid sequence of SEQ ID NO:1. In further embodiments of the disclosed platforms, the wild-type UB comprises the amino acid sequence of SEQ ID NO:1, and optionally the mutant UB comprises one or more mutations selected from R42E, R72E, and a combination thereof.

The ubiquitin-activating enzymes (E1) are known in the art. (See, e.g., Schulman et al., Ubiquitin-like protein activation by E1 enzymes: the apex for downstream signaling pathways. *Nat. Rev. Mol. Cell Biol.* 10, 319-331 (2009), the content of which is incorporated herein by reference in its entirety). In some embodiments of the disclosed platforms, the wild-type E1 comprises the amino acid sequence of SEQ ID NO:2. In further embodiments of the disclosed platforms, the wild-type E1 comprises the amino acid sequence of SEQ ID NO:2, and optionally the mutant E1 comprises one or more mutations selected from Q608R, S621R, D623R, E1037K, D1047K, E1049K, and combinations thereof.

In some embodiments of the disclosed platforms, the wild-type E1 comprises the amino acid sequence of SEQ ID NO:3. In further embodiments of the disclosed platforms the wild-type E1 comprises the amino acid sequence of SEQ ID NO:3, and optionally the mutant E1 comprises one or more mutations selected from Q568R, S581R, D583R, E997K, D1007K, E1009K, and combinations thereof.

The ubiquitin-conjugating enzymes (E2) are known in the art. (See, e.g., Wenzel, et al., E2s: structurally economical and functional replete. *Biochem. J.* 433, 31-42 (2011), the content of which is incorporated herein by reference in its entirety). In some embodiments of the disclosed platforms, the wild-type E2 comprises the amino acid sequence of SEQ ID NO:4. In further embodiments of the disclosed platforms, the wild-type E2 comprises the amino acid sequence of SEQ ID NO:4, and optionally the mutant E2 comprises one or more mutations selected from R5E, K9E, and a combination thereof.

In some embodiments of the disclosed platforms, the wild-type E2 comprises the amino acid sequence of SEQ ID NO:5. In further embodiments of the disclosed platforms, the wild-type E2 comprises the amino acid sequence of SEQ ID NO:5, and optionally the mutant E2 comprises one or more mutations selected from K5E, K8E, and a combination thereof.

In even further embodiments of the disclosed platforms, the wild-type E2 is selected from UBE2A, UBE2B, UBE2C, UBE2D1, UBE2D2 (UBCH5B), UBE2D3, UBE2D4, UBE2E1, UBE2E2, UBE2E3, UBE2F, UBE2G1, UBE2G2, UBE2H, UBE2I, UBE2J1, UBE2J2, UBE2K, UBE2L3 (UBCH7), UBE2L6, UBE2M UBE2N, UBE2O, UBE2Q1, UBE2Q2, UBE2R1 (CDC34), UBE2R2, UBE2S, UBE2T, UBE2U, UBE2V1, UBE2V2, UBE2W, UBE2Z, ATG3, BIRC6, and UFC1.

The ubiquitin ligase enzymes (E3) are known in the art. (See, e.g., Deshaies, et al., RING domain E3 ubiquitin ligases. *Annu. Rev. Biochem.* 78, 399-434 (2009); and Jin et al., Dual E1 activation systems for ubiquitin differentially regulate E2 enzyme charging. *Nature.* 447, 1135-1138

(2007); the contents of which are incorporated by reference in their entireties). Several hundred E3 ligases have been identified in the human genome. (See, e.g., Medvar et al., Comprehensive database of human E3 ubiquitin ligases: application to aquaporin-2 regulation. *Physiol Genomics* 2016; 48(7)502-512, the content of which is incorporated herein by reference in its entirety). E3 ligases consist predominantly of types referred to as HECT types, U-box types, RBR types, and/or Ring types and a comprehensive library of E3 ligases exists. (See id. citing to (hpcwebapps.cit.nih-.gov/ESBL/Database/E3-ligases/). As contemplated herein, an E3 ligase may include any of a HECT type, U-box type, RBR type, and/or Ring type E3 ligase (or a variant or mutant thereof as disclosed herein).

In some embodiments of the disclosed platforms, the wild-type E3 comprises the amino acid sequence of SEQ ID NO:6. In further embodiments of the disclosed platforms, the wild-type E3 comprises the amino acid sequence of SEQ ID NO:6, and optionally the mutant E3 comprises one or more mutations selected from D651R, D652E, M653W, M654H, and combinations thereof.

In some embodiments of the disclosed platforms, the wild-type E3 comprises the amino acid sequence of SEQ ID NO:7. In further embodiments of the disclosed platforms, the wild-type E3 comprises the amino acid sequence of SEQ ID NO:7, and optionally the mutant E3 comprises one or more mutations selected from R1233K, L12361, D1238H, D1238R, and combinations thereof.

In some embodiments of the disclosed platforms, the wild-type E3 comprises the amino acid sequence of SEQ ID NO:8. In further embodiments of the disclosed platforms, the wild-type E3 comprises the amino acid sequence of SEQ ID NO:8, and optionally the mutant E3 comprises one or more mutations selected from C213K, G214D, K215P, S217M, F218H, F218R, E219T, and combinations thereof.

In even further embodiments of the disclosed platforms, the wild-type E3 is selected from AFF4, AMFR, ANAPC11, ANKIB1, AREL1, ARIH1, ARIH2, BARD1, BFAR, BIRC2, BIRC3, BIRC7, BIRC8, BMI1, BRAP, BRCA1, CBL, CBLB, CBLC, CBLL1, CCDC36, CCNB1IP1, CGRRF1, CHFR, CNOT4, CUL9, CYHR1, DCST1, DTX1, DTX2, DTX3, DTX3L, DTX4, DZIP3, E4F1, FANCL, G2E3, HACE1, HECTD1, HECTD2, HECTD3, HECTD4, HECW1, HECW2, HERC1, HERC2, HERC3, HERC4, HERC5, HERC6, HLTF, HUWE1, IRF2BP1, IRF2BP2, IRF2BPL, Itch, KCMF1, KMT2C, KMT2D, LNX1, LNX2, LONRF1, LONRF2, LONRF3, LRSAM1, LTN1, MAEA, MAP3K1, MARCH1, MARCH10, MARCH11, MARCH2, MARCH3, MARCH4, MARCH5, MARCH6, MARCH7, MARCH8, MARCH9, Mdm2, MDM4, MECOM, MEX3A, MEX3B, MEX3C, MEX3D, MGRN1, MIB1, MIB2, MID1, MID2, MKRN1, MKRN2, MKRN3, MKRN4P, MNAT1, MSL2, MUL1, MYCBP2, MYLIP, NEDD4, NEDD4L, NEURL1, NEURL1B, NEURL3, NFX1, NFXL1, NHLRC1, NOSIP, NSMCE1, PARK2, PCGF1, PCGF2, PCGF3, PCGF5, PCGF6, PDZRN3, PDZRN4, PELI1, PELI2, PELI3, PEX10, PEX12, PEX2, PHF7, PHRF1, PJA1, PJA2, PLAG1, PLAGL1, PML, PPIL2, PRPF19, RAD18, RAG1, RAPSN, RBBP6, RBCK1, RBX1, RC3H1, RC3H2, RCHY1, RFFL, RFPL1, RFPL2, RFPL3, RFPL4A, RFPL4AL1, RFPL4B, RFWD2, RFWD3, RING1, RLF, RLIM, RMND5A, RMND5B, RNF10, RNF103, RNF11, RNF111, RNF112, RNF113A, RNF113B, RNF114, RNF115, RNF121, RNF122, RNF123, RNF125, RNF126, RNF128, RNF13, RNF130, RNF133, RNF135, RNF138, RNF139, RNF14, RNF141, RNF144A, RNF144B, RNF145, RNF146, RNF148, RNF149, RNF150, RNF151, RNF152, RNF157, RNF165, RNF166, RNF167, RNF168, RNF169, RNF17, RNF170, RNF175, RNF180, RNF181, RNF182, RNF183, RNF185, RNF186, RNF187, RNF19A, RNF19B, RNF2, RNF20, RNF207, RNF208, RNF212, RNF212B, RNF213, RNF214, RNF215, RNF216, RNF217, RNF219, RNF220, RNF222, RNF223, RNF224, RNF225, RNF24, RNF25, RNF26, RNF31, RNF32, RNF34, RNF38, RNF39, RNF4, RNF40, RNF41, RNF43, RNF44, RNF5, RNF6, RNF7, RNF8, RNFT1, RNFT2, RSPRY1, SCAF11, SH3RF1, SH3RF2, SH3RF3, SHPRH, SIAH1, SIAH2, SIAH3, SMURF1, SMURF2, STUB1 (CHIP), SYVN1, TMEM129, Topors, TRAF2, TRAF3, TRAF4, TRAF5, TRAF6, TRAF7, TRAIP, TRIM10, TRIM11, TRIM13, TRIM15, TRIM17, TRIM2, TRIM21, TRIM22, TRIM23, TRIM24, TRIM25, TRIM26, TRIM27, TRIM28, TRIM3, TRIM31, TRIM32, TRIM33, TRIM34, TRIM35, TRIM36, TRIM37, TRIM38, TRIM39, TRIM4, TRIM40, TRIM41, TRIM42, TRIM43, TRIM43B, TRIM45, TRIM46, TRIM47, TRIM48, TRIM49, TRIM49B, TRIM49C, TRIM49D1, TRIM5, TRIM50, TRIM51, TRIM52, TRIM54, TRIM55, TRIM56, TRIM58, TRIM59, TRIM6, TRIM60, TRIM61, TRIM62, TRIM63, TRIM64, TRIM64B, TRIM64C, TRIM65, TRIM67, TRIM68, TRIM69, TRIM7, TRIM71, TRIM72, TRIM73, TRIM74, TRIM75P, TRIM77, TRIM8, TRIM9, TRIML1, TRIML2, TRIP12, TTC3, UBE3A, UBE3B, UBE3C, UBE3D, UBE4A, UBE4B, UBOX5, UBR1, UBR2, UBR3, UBR4, UBR5, UBR7, UHRF1, UHRF2, UNK, UNKL, VPS11, VPS18, VPS41, VPS8, WDR59, WDSUB1, WWP1, WWP2, XIAP, ZBTB12, ZFP91, ZFPL1, ZNF280A, ZNF341, ZNF511, ZNF521, ZNF598, ZNF645, ZNRF1, ZNRF2, ZNRF3, ZNRF4, Zswim2, and ZXDC.

In some embodiments, the mutant (or variant) UB disclosed herein may include a tag as known in the art. For example, the mutant UB disclosed herein may include a tag for identifying and/or isolating a substrate to which the mutant UB has been transferred via a E3 ligase. Suitable tags may include, but are not limited to biotin or a hemagglutinin epitope (HA).

The disclosed proteins, vectors, and compositions may be utilized in methods for identifying a substrate of an E3 ubiquitin ligase (E3). In some embodiments, the disclosed methods comprise: (a) expressing one or more of the proteins of any of the foregoing platforms (e.g., a mutant UB, a mutant E1, a mutant E2, and/or a mutant E3, preferably all of the mutant UB, the mutant E1, the mutant E2, and the mutant E3) in a cell under conditions in which the mutant E3 transfers the mutant UB to the substrate to ubiquitinate the substrate; and (b) identifying the ubiquitinated substrate. The ubiquitinated substrate may be identifying (or detected) by methods known in the art. In some embodiments of the disclosed methods, the mutant UB comprises a tag for identifying and/or isolating a substrate to which the mutant UB has been transferred by the mutant E2 and the ubiquitinated substrate is identified and/or isolated via the tag. Suitable tags may include, but are not limited to biotin and a hemagglutinin epitope (HA), where the ubiquitinated substrate is identified and/or isolated via contacting the ubiquitinated substrate with the cognate partner for the tag (e.g., streptavidin or an anti-HA antibody or antigen binding fragment thereof).

Also disclosed herein are methods for preparing proteins and/or platforms comprising proteins for identifying a substrate of a ubiquitin ligase (E3). The methods may include: (a) expressing in a display system one or more libraries selected from: (i) a library of mutants of a wild-type ubiquitin (UB) that comprise one or more amino acid substitutions relative to the wild-type UB (e.g., a randomized library); (ii) a library of mutants of a wild-type E1 protein (E1) that comprise one or more amino acid substitutions relative to the wild-type E1 (e.g., a randomized library); (iii) a library of mutants of a wild-type E2 protein (E2) that comprises one or more amino acid substitutions relative to the wild-type E2 (e.g., a randomized library); (iv) a library of mutants of a wild-type E3 ubiquitin ligase (E3) that comprises one or more amino acid substitutions relative to the wild-type E3 (e.g., a randomized library); and (b) selecting from the display system one or more of mutant proteins selected from: (i) a mutant UB; (ii) a mutant E1; (iii) a mutant E2; and/or (iv) a mutant E3. The methods may include selected all of: (i) a mutant UB, (ii) a mutant E1, (iii) a mutant E2, and (iv), a mutant E3. Suitable display systems for the methods may include, but are not limited to, bacteriophage display systems and/or yeast display systems.

Preferably, in the disclosed methods for preparing proteins and platforms, one or more of the following conditions are met: (i) the mutant E1 interacts with the mutant UB and forms a conjugate with the mutant E1, namely a mutant UB/E1 conjugate, via a thioester linkage between a catalytic Cys of the mutant E1 and the C-terminal carboxylate of the mutant UB; (ii) the mutant E1 does not interact with the wild-type UB and does not form a conjugate via a thioester linkage between a catalytic Cys of the mutant E1 and the C-terminal carboxylate of the wild-type UB; and/or (iii) the wild-type E1 does not interact with the mutant UB and does not form a conjugate via thioester linkage between with a catalytic Cys of the wild-type E1 and the C-terminal carboxylate of the mutant UB. Even more preferably, each of conditions (i), (ii), and (iii) are met.

Preferably, in the disclosed methods for preparing proteins and platforms, one or more of the following conditions are met: (i) the mutant E2 interacts with the mutant UB/E1 conjugate and the mutant UB is transferred to the mutant E2 and forms a conjugate with the mutant E2, namely a mutant UB-E2 conjugate, via formation of a thioester linkage between a catalytic Cys of the mutant E2 and the C-terminal carboxylate of the mutant UB; (ii) the mutant E2 does not interact with a wild-type UB/E1 conjugate and the wild-type UB is not transferred to the mutant E2 and does not form a conjugate with the mutant E2; and/or (iii) the wild-type E2 does not interact with the mutant UB/E1 conjugate and the mutant UB is not transferred to the wild-type E2 and does not form a conjugate with the wild-type E2. Even more preferably, each of conditions (i), (ii), and (iii) are met.

Preferably, in the disclosed methods for preparing proteins and platforms, one or more of the following conditions are met: (i) the mutant E3 interacts with the mutant UB/E2 conjugate and the mutant UB is transferred to the mutant E3 and forms a conjugate with the mutant E3, namely a mutant UB-E3 conjugate, via formation of a thioester linkage or an amide linkage between a catalytic Cys of the mutant E3 or a catalytic Lys of the mutant E3 and the C-terminal carboxylate of the mutant UB; and the mutant UB-E3 conjugate transfers the mutant UB to the substrate of E3 via formation of an amid linkage between a Lys of the substrate of E3 and the C-terminal carboxylate of the mutant UB; (ii) the mutant E3 does not interact with a wild-type UB/E2 conjugate and the wild-type UB is not transferred to the mutant E3 and does not form a conjugate with the mutant E3; and (iii) the wild-type E3 does not interact with the mutant UB/E2 conjugate and the mutant UB is not transferred to the wild-type E3 and does not form a conjugate with the wild-type E3. Even more preferably, each of conditions (i), (ii), and (iii) are met.

ILLUSTRATIVE EMBODIMENTS

The following embodiments are illustrative and should not be interpreted to limit the scope of the claimed subject matter.

1. A platform for identifying a substrate of an E3 ubiquitin ligase (E3), the platform comprising as components one or more of the following proteins or vectors that express one or more of the following proteins: (a) a mutant ubiquitin (UB) that comprises one or more amino acid substitutions relative to a wild-type UB; (b) a mutant E1 protein (E1) that comprises one or more amino acid substitutions relative to a wild-type E1 protein, wherein: (i) the mutant E1 interacts with the mutant UB and forms a conjugate with the mutant E1, namely a mutant UB/E1 conjugate, via a thioester linkage between a catalytic Cys of the mutant E1 and the C-terminal carboxylate of the mutant UB; (ii) the mutant E1 does not interact with the wild-type UB and does not form a conjugate via a thioester linkage between a catalytic Cys of the mutant E1 and the C-terminal carboxylate of the wild-type UB; and (iii) the wild-type E1 does not interact with the mutant UB and does not form a conjugate via thioester linkage between with a catalytic Cys of the wild-type E1 and the C-terminal carboxylate of the mutant UB; (c) a mutant E2 protein (E2) that comprises one or more amino acid substitutions relative to a wild-type E2, wherein: (i) the mutant E2 interacts with the mutant UB/E1 conjugate and the mutant UB is transferred to the mutant E2 and forms a conjugate with the mutant E2, namely a mutant UB-E2 conjugate, via formation of a thioester linkage between a catalytic Cys of the mutant E2 and the C-terminal carboxylate of the mutant UB; (ii) the mutant E2 does not interact with a wild-type UB/E1 conjugate and the wild-type UB is not transferred to the mutant E2 and does not form a conjugate with the mutant E2; and (iii) the wild-type E2 does not interact with the mutant UB/E1 conjugate and the mutant UB is not transferred to the wild-type E2 and does not form a conjugate with the wild-type E2; and (d) a mutant E3 ubiquitin ligase (E3) that comprises one or more amino acid substitutions relative to a wild-type E3, wherein: (i) the mutant E3 interacts with the mutant UB/E2 conjugate and the mutant UB is transferred to the mutant E3 and forms a conjugate with the mutant E3, namely a mutant UB-E3 conjugate, via formation of a thioester linkage or an amide linkage between a catalytic Cys of the mutant E3 or a catalytic Lys of the mutant E3 and the C-terminal carboxylate of the mutant UB; and the mutant UB-E3 conjugate transfers the mutant UB to the substrate of E3 via formation of an amid linkage between a Lys of the substrate of E3 and the C-terminal carboxylate of the mutant UB; (ii) the mutant E3 does not interact with a wild-type UB/E2 conjugate and the wild-type UB is not transferred to the mutant E3 and does not form a conjugate with the mutant E3; and (iii) the wild-type E3 does not interact with the mutant UB/E2 conjugate and the mutant UB is not transferred to the wild-type E3 and does not form a conjugate with the wild-type E3.
2. The platform of embodiment 1, wherein the mutant UB, the mutant E1, the mutant E2, and the mutant E3 are derived from a wild-type mammalian UB, a wild-type mammalian E1, a wild-type mammalian E2, and a wild-type mammalian E3, respectively.

3. The platform of embodiment 1 or embodiment 2, wherein the mutant UB, the mutant E1, the mutant E2, and the mutant E3 are derived from a wild-type human UB, a wild-type human E1, a wild-type human E2, and a wild-type human E3, respectively.
4. The platform of any of the foregoing embodiments, wherein the wild-type UB comprises the amino acid sequence of SEQ ID NO:1, and optionally the mutant UB comprises one or more mutations selected from R42E, R72E, and a combination thereof.
5. The platform of any of the foregoing embodiments, wherein the wild-type E1 comprises the amino acid sequence of SEQ ID NO:2, and optionally the mutant E1 comprises one or more mutations selected from Q608R, S621R, D623R, E1037K, D1047K, E1049K, and combinations thereof.
6. The platform of any of the foregoing embodiments, wherein the wild-type E1 comprises the amino acid sequence of SEQ ID NO:3, and optionally the mutant E1 comprises one or more mutations selected from Q568R, S581R, D583R, E997K, D1007K, E1009K, and combinations thereof.
7. The platform of any of the foregoing embodiments, wherein the wild-type E2 comprises the amino acid sequence of SEQ ID NO:4, and optionally the mutant E2 comprises one or more mutations selected from R5E, K9E, and a combination thereof.
8. The platform of any of the foregoing embodiments, wherein the wild-type E2 comprises the amino acid sequence of SEQ ID NO:5, and optionally the mutant E2 comprises one or more mutations selected from K5E, K8E, and a combination thereof.
9. The platform of any of the foregoing embodiments, wherein the wild-type E2 is selected from UBE2A, UBE2B, UBE2C, UBE2D1, UBE2D2 (UBCH5B), UBE2D3, UBE2D4, UBE2E1, UBE2E2, UBE2E3, UBE2F, UBE2G1, UBE2G2, UBE2H, UBE2I, UBE2J1, UBE2J2, UBE2K, UBE2L3 (UBCH7), UBE2L6, UBE2M UBE2N, UBE2O, UBE2Q1, UBE2Q2, UBE2R1 (CDC34), UBE2R2, UBE2S, UBE2T, UBE2U, UBE2V1, UBE2V2, UBE2W, UBE2Z, ATG3, BIRC6, and UFC1.
10. The platform of any of the foregoing embodiments, wherein the wild-type E3 is selected from a HECT type, a U-box type, a RBR type, and/or Ring type E3 ligase, optionally wherein the wild-type E3 is selected from AFF4, AMFR, ANAPC11, ANKIB1, AREL1, ARIH1, ARIH2, BARD1, BFAR, BIRC2, BIRC3, BIRC7, BIRC8, BMI1, BRAP, BRCA1, CBL, CBLB, CBLC, CBLL1, CCDC36, CCNB1IP1, CGRRF1, CHFR, CNOT4, CUL9, CYHR1, DCST1, DTX1, DTX2, DTX3, DTX3L, DTX4, DZIP3, E4F1, FANCL, G2E3, HACE1, HECTD1, HECTD2, HECTD3, HECTD4, HECW1, HECW2, HERC1, HERC2, HERC3, HERC4, HERC5, HERC6, HLTF, HUWE1, IRF2BP1, IRF2BP2, IRF2BPL, Itch, KCMF1, KMT2C, KMT2D, LNX1, LNX2, LONRF1, LONRF2, LONRF3, LRSAM1, LTN1, MAEA, MAP3K1, MARCH1, MARCH10, MARCH11, MARCH2, MARCH3, MARCH4, MARCH5, MARCH6, MARCH7, MARCH8, MARCH9, Mdm2, MDM4, MECOM, MEX3A, MEX3B, MEX3C, MEX3D, MGRN1, MIB1, MIB2, MID1, MID2, MKRN1, MKRN2, MKRN3, MKRN4P, MNAT1, MSL2, MUL1, MYCBP2, MYLIP, NEDD4, NEDD4L, NEURL1, NEURL1B, NEURL3, NFX1, NFXL1, NHLRC1, NOSIP, NSMCE1, PARK2, PCGF1, PCGF2, PCGF3, PCGF5, PCGF6, PDZRN3, PDZRN4, PELI1, PELI2, PELI3, PEX10, PEX12, PEX2, PHF7, PHRF1, PJA1, PJA2, PLAG1, PLAGL1, PML, PPIL2, PRPF19, RAD18, RAG1, RAPSN, RBBP6, RBCK1, RBX1, RC3H1, RC3H2, RCHY1, RFFL, RFPL1, RFPL2, RFPL3, RFPL4A, RFPL4AL1, RFPL4B, RFWD2, RFWD3, RING1, RLF, RLIM, RMND5A, RMND5B, RNF10, RNF103, RNF11, RNF111, RNF112, RNF113A, RNF113B, RNF114, RNF115, RNF121, RNF122, RNF123, RNF125, RNF126, RNF128, RNF13, RNF130, RNF133, RNF135, RNF138, RNF139, RNF14, RNF141, RNF144A, RNF144B, RNF145, RNF146, RNF148, RNF149, RNF150, RNF151, RNF152, RNF157, RNF165, RNF166, RNF167, RNF168, RNF169, RNF17, RNF170, RNF175, RNF180, RNF181, RNF182, RNF183, RNF185, RNF186, RNF187, RNF19A, RNF19B, RNF2, RNF20, RNF207, RNF208, RNF212, RNF212B, RNF213, RNF214, RNF215, RNF216, RNF217, RNF219, RNF220, RNF222, RNF223, RNF224, RNF225, RNF24, RNF25, RNF26, RNF31, RNF32, RNF34, RNF38, RNF39, RNF4, RNF40, RNF41, RNF43, RNF44, RNF5, RNF6, RNF7, RNF8, RNFT1, RNFT2, RSPRY1, SCAF11, SH3RF1, SH3RF2, SH3RF3, SHPRH, SIAH1, SIAH2, SIAH3, SMURF1, SMURF2, STUB1 (CHIP), SYVN1, TMEM129, Topors, TRAF2, TRAF3, TRAF4, TRAF5, TRAF6, TRAF7, TRAIP, TRIM10, TRIM11, TRIM13, TRIM15, TRIM17, TRIM2, TRIM21, TRIM22, TRIM23, TRIM24, TRIM25, TRIM26, TRIM27, TRIM28, TRIM3, TRIM31, TRIM32, TRIM33, TRIM34, TRIM35, TRIM36, TRIM37, TRIM38, TRIM39, TRIM4, TRIM40, TRIM41, TRIM42, TRIM43, TRIM43B, TRIM45, TRIM46, TRIM47, TRIM48, TRIM49, TRIM49B, TRIM49C, TRIM49D1, TRIM5, TRIM50, TRIM51, TRIM52, TRIM54, TRIM55, TRIM56, TRIM58, TRIM59, TRIM6, TRIM60, TRIM61, TRIM62, TRIM63, TRIM64, TRIM64B, TRIM64C, TRIM65, TRIM67, TRIM68, TRIM69, TRIM7, TRIM71, TRIM72, TRIM73, TRIM74, TRIM75P, TRIM77, TRIM8, TRIM9, TRIML1, TRIML2, TRIP12, TTC3, UBE3A, UBE3B, UBE3C, UBE3D, UBE4A, UBE4B, UBOX5, UBR1, UBR2, UBR3, UBR4, UBR5, UBR7, UHRF1, UHRF2, UNK, UNKL, VPS11, VPS18, VPS41, VPS8, WDR59, WDSUB1, WWP1, WWP2, XIAP, ZBTB12, ZFP91, ZFPL1, ZNF280A, ZNF341, ZNF511, ZNF521, ZNF598, ZNF645, ZNRF1, ZNRF2, ZNRF3, ZNRF4, Zswim2, and ZXDC.
11. The platform of any of the foregoing embodiments, wherein the wild-type E3 comprises the amino acid sequence of SEQ ID NO:6, and optionally the mutant E3 comprises one or more mutations selected from D651R, D652E, M653W, M654H, and combinations thereof.
12. The platform of any of the foregoing embodiments, wherein the wild-type E3 comprises the amino acid sequence of SEQ ID NO:7, and optionally the mutant E3 comprises one or more mutations selected from R1233K, L1236I, D1238H, D1238R, and combinations thereof.
13. The platform of any of the foregoing embodiments, wherein the wild-type E3 comprises the amino acid sequence of SEQ ID NO:8, and optionally the mutant E3 comprises one or more mutations selected from C213K, G214D, K215P, S217M, F218H, F218R, E219T, and combinations thereof.

14. The platform of any of the foregoing embodiments, wherein the mutant UB comprises a tag for identifying and/or isolating a substrate to which the mutant UB has been transferred, optionally wherein the tag is selected from biotin or a hemagglutinin epitope (HA).

15. A method for identifying a substrate of an E3 ubiquitin ligase (E3), the method comprising: (a) expressing one or more of the proteins of any of the foregoing platforms in a cell under conditions in which the mutant E3 transfers the mutant UB to the substrate to ubiquitinate the substrate; and (b) identifying the ubiquitinated substrate.

16. The method of embodiment 15, wherein the mutant UB comprises a tag for identifying and/or isolating a substrate to which the mutant UB has been transferred and the ubiquitinated substrate is identified and/or isolated via the tag.

17. The method of embodiment 16, wherein the tag is selected from biotin or a hemagglutinin epitope (HA) and the ubiquitinated substrate is identified and/or isolated via contacting the ubiquitinated substrate with the cognate partner for the tag (e.g., streptavidin or an anti-HA antibody or antigen binding fragment thereof).

18. A method for preparing the platform of any of embodiments 1-14 or any component thereof, the method comprising: (a) expressing in a display system one or more libraries selected from: (i) a library of mutants of a wild-type ubiquitin (UB) that comprise one or more amino acid substitutions relative to the wild-type UB; (ii) a library of mutants of a wild-type E1 protein (E1) that comprise one or more amino acid substitutions relative to the wild-type E1; (iii) a library of mutants of a wild-type E2 protein (E2) that comprises one or more amino acid substitutions relative to the wild-type E2; (iv) a library of mutants of a wild-type E3 ubiquitin ligase (E3) that comprises one or more amino acid substitutions relative to the wild-type E3; and (b) selecting from the display system one or more mutant proteins selected from: (i) a mutant UB; (ii) a mutant E1 that interacts with the mutant UB and forms a conjugate with the mutant E1, namely a mutant UB/E1 conjugate, via a thioester linkage between a catalytic Cys of the mutant E1 and the C-terminal carboxylate of the mutant UB, wherein the mutant E1 does not interact with the wild-type UB and does not form a conjugate via a thioester linkage between a catalytic Cys of the mutant E1 and the C-terminal carboxylate of the wild-type UB; and wherein the wild-type E1 does not interact with the mutant UB and does not form a conjugate via thioester linkage between with a catalytic Cys of the wild-type E1 and the C-terminal carboxylate of the mutant UB; (iii) a mutant E2 that interacts with the mutant UB/E1 conjugate and the mutant UB is transferred to the mutant E2 and forms a conjugate with the mutant E2, namely a mutant UB-E2 conjugate, via formation of a thioester linkage between a catalytic Cys of the mutant E2 and the C-terminal carboxylate of the mutant UB; wherein the mutant E2 does not interact with a wild-type UB/E1 conjugate and the wild-type UB is not transferred to the mutant E2 and does not form a conjugate with the mutant E2; and wherein the wild-type E2 does not interact with the mutant UB/E1 conjugate and the mutant UB is not transferred to the wild-type E2 and does not form a conjugate with the wild-type E2; and/or (iv) a mutant E3 that interacts with the mutant UB/E2 conjugate and the mutant UB is transferred to the mutant E3 and forms a conjugate with the mutant E3, namely a mutant UB-E3 conjugate, via formation of a thioester linkage or an amide linkage between a catalytic Cys of the mutant E3 or a catalytic Lys of the mutant E3 and the C-terminal carboxylate of the mutant UB; and the mutant UB-E3 conjugate transfers the mutant UB to the substrate of E3 via formation of an amid linkage between a Lys of the substrate of E3 and the C-terminal carboxylate of the mutant UB; wherein the mutant E3 does not interact with a wild-type UB/E2 conjugate and the wild-type UB is not transferred to the mutant E3 and does not form a conjugate with the mutant E3; and wherein the wild-type E3 does not interact with the mutant UB/E2 conjugate and the mutant UB is not transferred to the wild-type E3 and does not form a conjugate with the wild-type E3.

19. The method of embodiment 18, wherein the display system is a bacteriophage display system or a yeast display system.

20. The method of embodiment 18 or 19, comprising selecting each of (i) a mutant UB, (ii) a mutant E1, (iii) a mutant E2, and (iv), a mutant E3.

EXAMPLES

The following Examples are illustrative and are not intended to limit the scope of the claimed subject matter.

Example I—Identifying the Ubiquitination Targets of E6AP by Orthogonal Ubiquitin Transfer Reference is made to Wang et al., "Identifying the ubiquitination targets of E6AP by orthogonal ubiquitin transfer," Nature Communications, 8:2232, pages 1-14, Dec. 20, 2017 (hereinafter Wang et al. 2017), the content of which is incorporated herein by reference in its entirety.

Abstract

E3 ubiquitin (UB) ligases are the ending modules of the E1-E2-E3 cascades that transfer UB to cellular proteins and regulate their biological functions. Identifying the substrates of an E3 holds the key to elucidate its role in cell regulation. Here, we construct an orthogonal UB transfer (OUT) cascade to identify the substrates of E6AP, a HECT E3 also known as Ube3a that is implicated in cancer and neurodevelopmental disorders. We use yeast cell surface display to engineer E6AP to exclusively transfer an affinity-tagged UB variant (xUB) to its substrate proteins. Proteomic identification of xUB-conjugated proteins in HEK293 cells affords 130 potential E6AP targets. Among them, we verify that MAPK1, CDK1, CDK4, PRMT5, β-catenin, and UbxD8 are directly ubiquitinated by E6AP in vitro and in the cell. Our work establishes OUT as an efficient platform to profile E3 substrates and reveal the cellular circuits mediated by the E3 enzymes.

Introduction

E3 ubiquitin ligases regulate biological functions by ubiquitinating defined substrate proteins but overlapping specificities complicate the identification of E3-substrate relationships. Here, the authors construct an orthogonal UB transfer cascade to identify specific substrates of the E3 enzyme E6AP.

Ubiquitin (UB), a 76-residue protein riding on a E1-E2-E3 enzymatic cascade, is a key messenger in cell signaling[1]. UB attachment to cellular proteins regulates many key processes such as protein degradation, subcellular trafficking, enzymatic turnover, and complex formation. E1 activates UB with the formation of a thioester linkage between a catalytic Cys of E1 and the C-terminal Gly of UB[2]. UB bound to E1 is loaded on an E2 in a thioester exchange reaction to form a UB~E2 conjugate ("~" designates the thioester bond)[3]. E2 then carries UB to an E3 that recruits target proteins for UB conjugation[4-6]. The human genome encodes 2 E1s, at least 40 E2s and more than 600 E3s[3,7,8]. Since E3s recognize protein ubiquitination targets, they often play key regulatory roles, and their malfunction drives the development of many diseases including cancer, neurodegeneration, and inflammation[9,10]. For example, E6AP, also known as Ube3a, is a E3 with a signature HECT domain for E2 binding[11]. E6AP is a critical regulator of neuron development; loss of its activity results in Angelman syndrome (AS), and duplications of chromosomal region 15q11-13 including its encoding gene Ube3a are associated with autism spectrum disorders (ASD)[12-15]. E6AP promotes tumorigenesis upon infection of high-risk human papillomavirus—it forms a complex with the viral oncoprotein E6 to ubiquitinate p53 and induce its degradation[11,16]. Other non-HECT E3s may bind the E2~UB conjugate through a Ring, Ring-between-Ring (RBR) or U-box motif[4,6,7]. Regardless of the type of interactions with E2s, an E3 may uptake UB from multiple E2s, and various E3s transfer UB to an overlapping pool of substrates. The complex cross-reactivities among E2, E3 and substrates make it a significant challenge to profile the substrate of a specific E3 to map it on the cell signaling network.

We envision an "orthogonal UB transfer (OUT)" pathway in which a UB variant (xUB) is confined to a single track of engineered xE1, xE2 and xE3 would guide the transfer of xUB exclusively to the substrate of a specific E3 ("x" designates engineered UB or enzyme variants orthogonal to their native partners)[17]. By expressing xUB and the OUT cascade of xE1-xE2-xE3 in the cell and purifying cellular proteins conjugated to xUB, we would be able to identify the direct substrates of an E3. The development of the OUT cascade removes the cross-reacting paths among various E2s and E3s. It enables the assignment of E3 substrates by directly following xUB transfer through the E3 instead of reading some indirect indicators of protein ubiquitination such as affinity binding with E3, or change of protein stability or ubiquitination levels upon E3 expression.

To implement OUT, we need to engineer orthogonal pairs of xUB-xE1, xE1-xE2, and xE2-xE3 that are free of cross-reactivities with native E1, E2 and E3 to secure the exclusive transfer of xUB to the substrates of an E3 in the cell. We previously reported engineering orthogonal xUB-xE1 and xE1-xE2 pairs by phage display[17]. We also generated the xUB-xE1 pairs with the two human E1, Uba1 and Uba6, respectively, to differentiate their targets of UB transfer in the cell[18]. Here we report that we have accomplished the last leg of OUT engineering: we used yeast cell surface display to engineer an orthogonal xE2-xE3 pair with the HECT E3 E6AP; we expressed the OUT cascade in HEK293 cells to profile E6AP substrates; and we identified a number of key signaling proteins as E6AP substrates and established regulatory circuits mediated by UB transfer through E6AP.

Results

Figure 8:
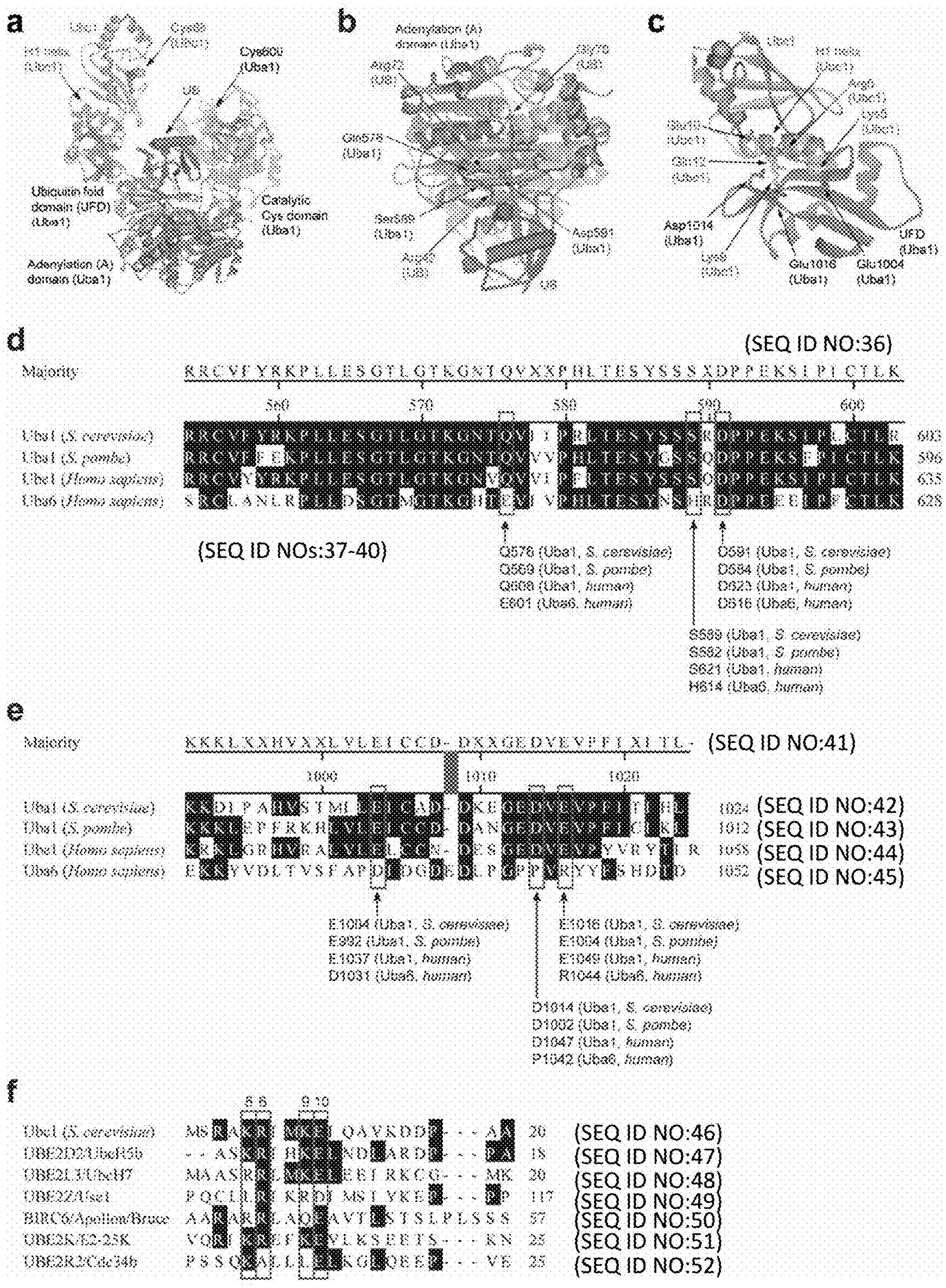
FIG. 8. Structure and sequence analysis of the UB-E1 and E1-E2 interfaces. (a) Modeled structures of *S cerevisiae* Uba1 (E1) in complex with UB and Ubc1 (E2). Ubc1 was modeled into the Uba1-UB complex (PDB ID 3CMM)[26]. (b) The binding interface between Uba1 and UB. R42E and R72E mutations were incorporated into UB to generate xUB. Mutations Q576R, S589R and D591R were incorporated into the adenylation domain of yeast Uba1 to complement the mutations in xUB and restore xUB transfer to xUba1[24]. (c) The binding interface between Uba1 and Ubc1. Mutations E1004K, D1014K and E1016K were incorporated into the UFD domain of yeast Uba1 with matching mutations in the Ubc1 (K5D, R6E, K9E, E10Q, Q12L) to generate the xUba1-xUbc1 pair[24]. (d) Regions of adenylation domains of E1s from yeast and human important for UB binding. (e) Regions of UFD domains of E1s important for binding to the N-terminal helices of E2s. (f) Sequence alignment of the N-terminal helices of the E2s from yeast and human.

Constructing the xUB-xUba1 and the xUba1-xUbcH7 pair. We previously generated an xUB-xE1 pair with the E1 enzyme Uba1 from *S. cerevisiae*[17]. Using phage selection, we found that the two mutations in xUB (R42E and R72E) would block xUB recognition by wt Uba1, yet by incorporating mutations Q576R, S589R and D591R into the adenylation domain of yeast Uba1, we could restore the activity of xUB with E1 to form xUB~E1 thioester conjugates (FIGS. 8*a* and 8*b*). We also introduced mutations E1004K, D1014K and E1016K into the UFD domain of the yeast Uba1 to block its interaction with the wt E2s (FIG. 8*c*). We then used phage display to identify mutations in the N-terminal helix of the Ubc1, a yeast E2, to restore E1-E2 interaction and enable UB transfer to the E2 enzyme. By combining the mutations in the adenylation and the UFD domains of yeast Uba1, we generated the E1 mutant xUba1 that can specifically transfer xUB to xUbc1, the E2 mutant from phage selection (Table 1). In contrast, xUB cannot be activated by wt Uba1 for its transfer to wt E2s. xUba1 cannot activate wt UB, neither can it transfer xUB to wtE2. Thus, the xUB-xE1 and xE1-xE2 pairs are orthogonal to their native partners, and they can assemble a two-step cascade to transfer xUB to a designated E2.

TABLE 1

Mutants of UB, E1, E2 and E3 for the assembly of the OUT cascade with E6AP.

| | |
|---|---|
| xUB (human) | R42E, R72E |
| xE1 | |
| xUba1 (yeast) | Q576R, S589R, D591R, E1004K, D1014K, E1016K |
| xUba1 (human) | Q608R, S621R and D623R, E1037K, D1047K and E1049K |
| xE2 | |
| xUbc1 (yeast) | K5D, R6E, K9E, E10Q, Q12L |
| xUbcH7 (human) | R5E, K9E |
| xE3 | |
| xE6AP (YW6) | D651R, D652E, M653W, M654H |

Our success in engineering the xUB-xE1 and xE1-xE2 pairs with the yeast system is instrumental for constructing the OUT cascade in the human cell. We found xUB is not catalytically active with either of the human E1s, Uba1 (also known as Ube1) or Uba6[18]. Since Uba1 plays a major role in supporting protein ubiquitination in the human cells[8], we decided to engineer human Uba1 as the xE1 for the OUT cascade. Based on the sequence homology between the human and yeast Uba1, we identified residues Q608, S621 and D623 in the adenylation domain and E1037, D1047 and E1049 in the UFD domain of human Uba1 matching the sites of mutations in the yeast Uba1 (FIGS. 8*d* and 8*e*). We mutated these residues to R or K of the opposite charge to generate human xUba1 (Table 1). As expected, we found human xUba1 is reactive with xUB by forming xUB~xUba1 conjugate, yet it rejects wt UB in the activation reaction (FIG. 1*a*). Moreover, xUba1 cannot transfer xUB to wt human E2s such as UbcH7 due to the mutations in the UFD domain of Uba1.

To restore xUB transfer to E2s, we generated orthogonal xE1-xE2 pairs based on the sequence homology between the yeast and human E2s. The N-terminal helix of E2 plays a key role in binding the UFD domain of the E1 as shown in the crystal structures of yeast *S. pombe* Uba1 in complex with E2 Ubc4, and the modeled structure of *S. cerevisiae* Uba1 bound with Ubc1 (FIGS. 8*a* and 8*c*)[19,20]. The sequences of the N-terminal helices of E2s from yeast and human align well with highly conserved K or R residues at positions 5, 6, and 9 (UbcH7 numbering) (FIG. 8*f*). Based on the sequence alignment, we mutated R5 and K9 in UbcH7 to Glu following the mutations in yeast xUbc1 and found the newly constructed xUbcH7 can pair with xUba1 to accept xUB transfer (FIG. 1*a* and Table 1). We have thus constructed an xUba1-xUbcH7 pair for xUB transfer through the OUT cascade. Since UbcH7 partners with HECT E3 in the cell, the exclusive delivery of xUB by xUba1 to xUbcH7 paved the way for transferring xUB to a specific HECT E3 to profile its substrate proteins.

Figure 9:
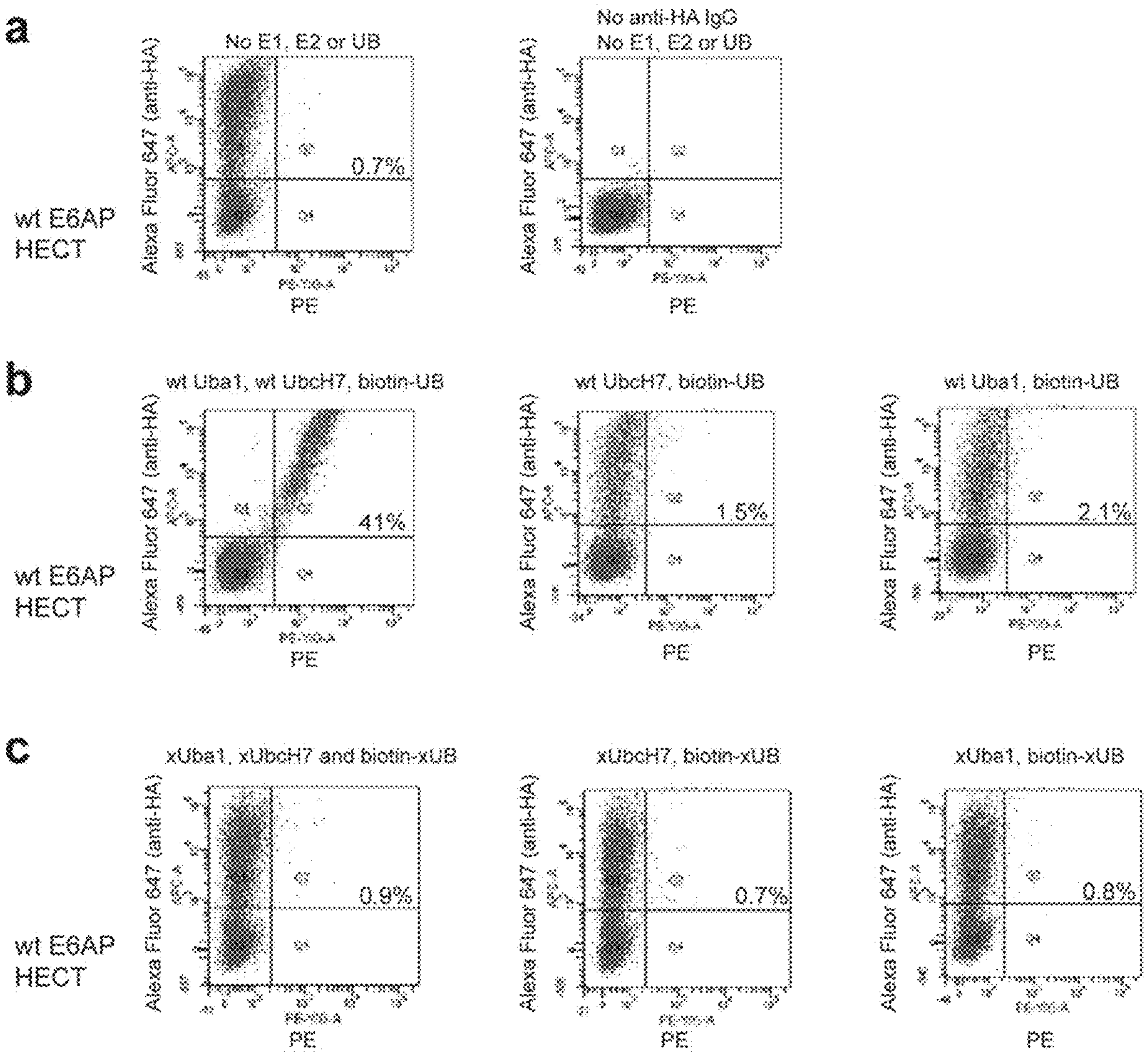
FIG. 9. Model selection of yeast cells displaying wt HECT domain of E6AP and analysis by flow cytometry. Numbers in the figure denote the percentages of cells doubly labeled with Alexa Fluor 488 and PE. (a) Yeast cells displaying the wt HECT were labeled with anti-HA antibody and subsequently with anti-IgG-Alexa Fluor 488 and streptavidin-PE. In the control labeling reaction (right panel), yeast cells displaying the wt E6AP HECT were directly labeled with streptavidin-PE and anti-IgG-Alexa Fluor 488 conjugates. (b) Yeast cells displaying the wt E6AP HECT were reacted with wt Uba1, UbcH7 and biotin-UB and bound to anti-HA antibody. Cells were labeled with anti-IgG-Alexa Fluor 488 and streptavidin-PE as secondary reagents. In the control reactions (right two panels), either wt Uba1 or wt UbcH7 was excluded in the UB transfer reaction. FACS analysis showed that a significant portion of cells (>40%) were double labeled with PE and Alexa 647 when both Uba1 and UbcH7 were added to the reaction. In contrast, when either Uba1 or UbcH7 was missing from the reaction, the cells were no longer labeled with PE, but still, a major portion of the cell (~50%) were singly labeled with Alexa 647. These results suggest that E6AP HECT displayed well on the yeast cell and was reactive with the Uba1-UbcH7 pair for UB transfer. (c) Yeast cells displaying the wt HECT domain were reacted with xUba1, xUbcH7 and biotin-xUB and bound to anti-HA antibody. Cells were labeled with streptavidin-PE and anti-IgG-Alexa Fluor 488 conjugates. In the control reactions (right two panels), either xUba1 or xUbcH7 was excluded in the xUB transfer reaction. Here, the cells were no longer labeled with PE demonstrating that wt HECT could not relay with the xUba1-xUbcH7 pair for xUB loading.

Constructing the xUbcH7-xHECT pair with E6AP. The N-terminal helix of UbcH7 is a key element not only for interaction with E1s but also for interaction with E3s (FIGS. 2*a* and 2*b*). We found the R5E and K9E mutants in the N-terminal helix of xUbcH7 interfered with the transfer of xUB to wt HECT E3s such as E6AP, Nedd4, Smurf1, and Smurf2 (FIGS. 1*b*, 1*c* and 1*d*). This is advantageous for the construction of the OUT cascade since it is preferred that xE2 would not pair with wt E3s to randomly transfer xUB to any E3 substrates in the cell. Our goal was to bridge xUB transfer through the last step of the OUT cascade by engineering an orthogonal xUbcH7-xE6AP pair. For this purpose, we used yeast cell surface display to select for HECT mutants of E6AP that would restore binding with xUbcH7 to enable xUB loading on the HECT domain (FIG. 2*c*). For yeast selection, a HECT library of E6AP was expressed as fusions to the yeast cell surface protein Aga2P with each yeast cell displaying a specific member of the HECT library[21]. The yeast library was then reacted with biotin-labeled xUB, xUba1, and xUbcH7. HECT mutants catalytically active with xUbcH7 were loaded with xUB through the formation of xUB~HECT thioester conjugate. The catalytically active HECT mutants were further auto-ubiquitinated by xUB through Lys modification. As a result, the corresponding yeast cells were labeled with biotin that would bind to streptavidin conjugated with phycoerythrin (PE). For selection of yeast cells displaying the HECT domain, a mouse anti-HA antibody was used to bind to the HA tag at the N-terminus of the HECT and it was subsequently labeled with an anti-mouse IgG conjugated with Alexa 647. Fluorescence-activated cell sorting (FACS) was used to enrich the cells that were double labeled with the PE and Alexa 647. In this way, the sorting was to enrich cells that displayed catalytically active HECT domains capable of bridging xUB transfer from xUbcH7. We validated the selection protocol by displaying the wt HECT domain of E6AP on the yeast cell surface, and demonstrating the efficient labeling of the yeast cells by biotin-wt UB transferred through the wt Uba1-UbcH7 pair (FIG. 9).

We constructed a HECT library of E6AP based on the crystal structure of the HECT domain with UbcH7 (FIGS. 2*a* and 2*b*)[22]. Residues R5 and K9 in the N-terminal helix of UbcH7 were mutated to Glu in xUbcH7 and the crystal structure shows that these residues mainly interact with a helical turn in the HECT domain of E6AP. R5 of UbcH7 is in close distance (4.6 Å) with the hydroxyl group of T656 of HECT. It also packs on the side chain of M654 that is 3.2 Å away. K9 of UbcH7 may form salt bridges with HECT D651 and D652 that are a short distance apart (4.5 Å). We thus decided to randomize E6AP residues D651, D652, M653, M654 and T656 to generate the HECT library.

We expressed the library on the yeast cell surface and carried out the selection by transferring biotin-xUB to the HECT mutants through the xUba1-xUbcH7 pair. Cells were labeled with streptavidin and antibody conjugates with fluorophores as in the model selection, and FACS was performed to harvest cells that were double labeled with PE and Alexa 647. Cells collected were cultured for next round of biotin-xUB loading, fluorescent labeling, and FACS. After 6 rounds of sorting, 51% of the cells were double labeled with both fluorophores suggesting a population of HECT mutants with efficient xUB transfer activity from xUbcH7 were selected (FIG. 2*d*). DNA sequencing of the 40 clones from the 6th round of sorting showed a clear pattern of convergence (FIG. 2*e*). Clones appearing multiple times tend to have D651 in HECT replaced with an Arg (YW2, YW5 and YW6). This change matches the charge reverse mutation of K9E in xUbcH7 (FIG. 2*b*). D652 of HECT, although randomized in the library, was most often unchanged or replaced with a similar Glu in the selected clones (YW2, YW5 and YW6). M653 is often replaced by aromatic residues such as Tyr and Trp in the selected clones (YW2, YW3 and YW6). M654 is replaced by positively charged Arg or His residues (YW4, YW5 and YW6), and residues selected at T656 is also quite converged showing a preference for positively charged Arg (YW1-3 and YW5). These changes match well with the charge reversal of R5E mutation in xUbcH7. We thus assayed if the individual HECT mutants from FACS could mediate xUB transfer with the xUba1-xUbcH7 pair.

Figure 3:
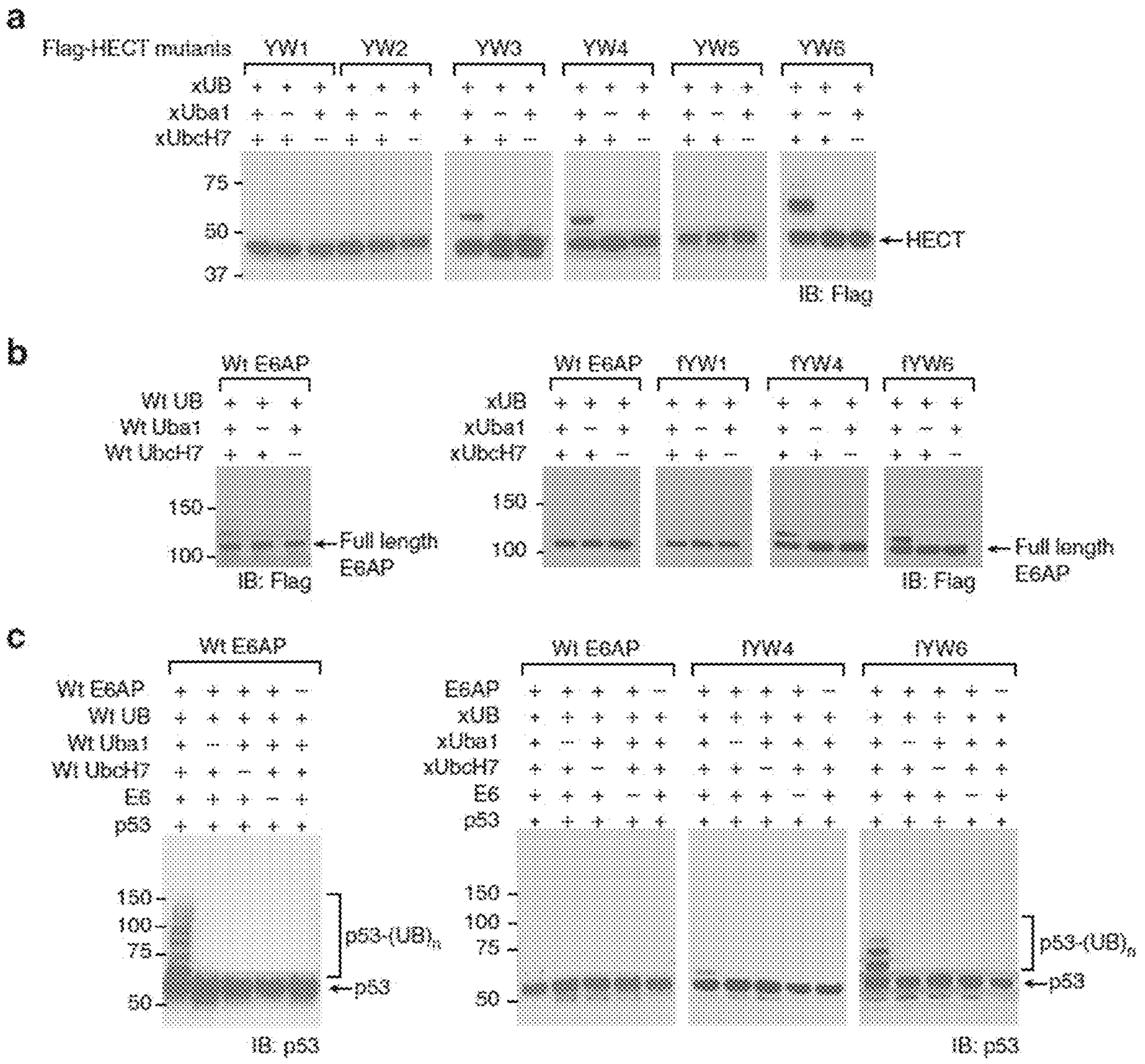
FIG. 3. Activity in xUB transfer by the E6AP mutants identified from yeast cell selection. (a) Activity of the HECT mutants YW1-6 in auto-ubiquitination by xUB through the xUba1-xUbcH7 pair. (b) Activity of the full-length E6AP mutants fYW1, fYW4 and fYW6 in auto-ubiquitination by the xUba1-xUbcH7 pair (right panel). While wt E6AP can be auto-ubiquitinated by the wt Uba1-UbcH7 pair (left panel), it cannot be conjugated to xUB by the xUba1-xUbcH7 pair (right panel). (c) p53 ubiquitination by wt E6AP and fYW4 and fYW6 in the presence of E6. p53 can be efficiently ubiquitinated by wt UB through the wt Uba1-UbcH7-E6AP cascade in the presence of E6 (left panel). p53 can also be efficiently modified by xUB through the engineered cascade of xUba1-xUbcH7-fYW6 in the presence of E6 (right panels). In contrast, xUB has very low activity in ubiquitinating p53 through the crossover cascade of xUba1-xUbcH7-wt E6AP in the presence of E6. All blots are representative of at least three independent experiments.
Figure 10:
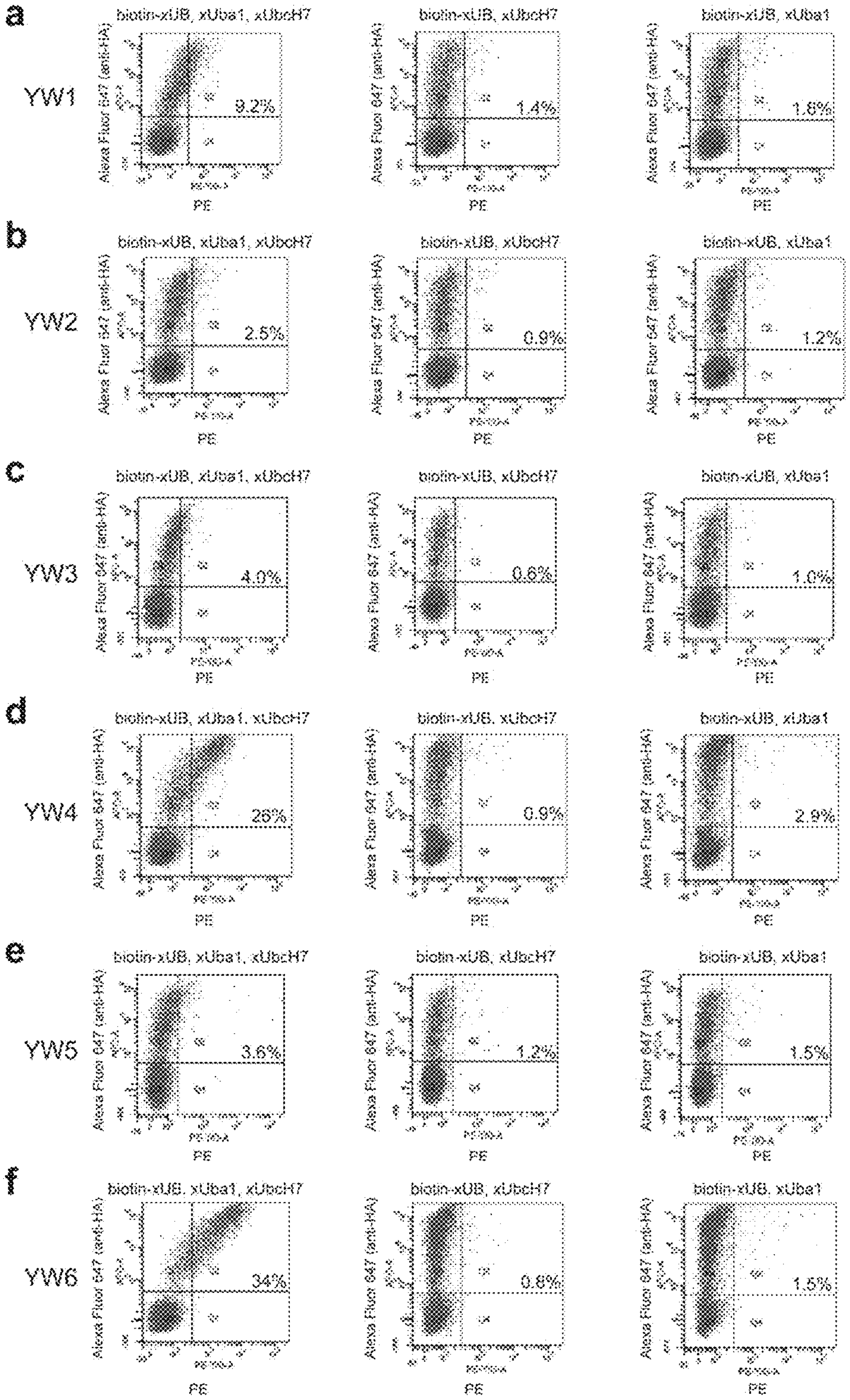
FIG. 10. Verifying the activity of the selected yeast clones in HECT modification with biotin-xUB through the xUba1-xUbcH7 pair. Clones (a) YW1, (b) YW2, (c) YW3, (d) YW4, (e) YW5, and (f) YW6 were reacted with biotin-xUB in the presence of xUba1 and xUbcH7. Biotin-xUB conjugated to HECT was detected by binding to streptavidin-PE and the display of HECT domain on cell surface was detected with a mouse anti-HA IgG and an anti-mouse IgG-Alexa 488 conjugate. In the control reaction (the panels on the right), either xUba1 or xUbcH7 was missing from the reaction. The percentage in each panel designates the fraction of doubly labeled yeast cells counted by flow cytometry.

Verifying xUB transfer through E6AP mutants. We separately cultured yeast clones YW1-6 and reacted the yeast cells with the xUba1-xUbcH7 pair for biotin-xUB loading (FIG. 10). We found yeast clones YW4 and YW6 had the strongest loading of biotin-xUB with 25% and 34% of the cells doubly labeled. To check the activities of individual HECT domains, we expressed mutants YW1-6 in *E. coli* and found YW3, YW4 and YW6 could be efficiently auto-ubiquitinated with xUB through the xUba1-xUbcH7 pair while YW1, YW2 and YW5 were not active for xUB transfer (FIG. 3*a*). We suspect the difference in activities of the HECT domains anchored on yeast cell surface and free in solution may be due to the change in their folding status in different environments. We replaced the wt HECT domain in E6AP with the mutant HECT of YW1, YW4 and YW6 to generate the full-length E6AP mutants fYW1, fYW4 and fYW6. We found fYW4 and fYW6 can be auto-ubiquitinated by xUB through the xUba1-xUbcH7 cascade (FIG. 3*b*). However, wt E6AP and fYW1 were not active in auto-ubiquitination by xUB in combination with the xUba1-xUbcH7 pair. We then tested the transfer of xUB from the E6AP mutants to p53, a key ubiquitination target recruited by E6[11,16]. We found fYW6 could efficiently ubiquitinate p53 with xUB through the xUba1-xUbcH7-fYW6 cascade and the ubiquitination was dependent on the E6 protein (FIG. 3*c*). The activity of xUB transfer to p53 through fYW6 was approaching the activity of wt UB transfer through wt E6AP. In contrast, when the xUba1-xUbcH7 pair was reacted with wt E6AP, we only observed very low activity in transferring xUB to p53 suggesting the minimal cross-reactivity of xUB with native UB transfer pathways (FIG. 3*c*). Comparing to fYW6, fYW4 was less active in transferring xUB to p53. We thus decided to use fYW6 as xE6AP in the OUT cascade to identify E6AP substrates in the cell (Table 1).

Verifying the orthogonality of OUT cascade in cells. We next tested if xUB could be exclusively transferred through the OUT cascade of xUba1-xUbcH7-xE6AP in the cells without crossing over to the wt UB transfer cascades (FIG. 4*a*). We constructed a lentiviral vector to express wt UB or xUB with tandem 6×His and biotin tags at the N-terminus of UB (HBT-wt UB and HBT-xUB)[23]. We also screened HEK293 cells that stably expressed wt Uba1 or xUba1 with an N-terminal Flag tag. Transient expression of HBT-wt UB and HBT-xUB in these cells followed by affinity pull-down with streptavidin beads showed that xUba1 was co-precipitated with HBT-xUB, but wt Uba1 could not be co-precipitated with HBT-xUB, neither xUba1 could be co-precipitated with HBT-wt UB (FIG. 4*b*). This suggests that xUB was exclusively reactive with xUba1 in the cell, and there is no cross activities between xUB and wt Uba1, or between wt UB and xUba1. To probe the orthogonality at the E1-E2 interface, we co-expressed HBT-xUB with either wt UbcH7 or xUbcH7 in cells stably expressing xUba1. We found V5-tagged xUbcH7 could be purified with the streptavidin beads suggesting the formation of HBT-xUB~xUbcH7 conjugate, yet V5-tagged wt UbcH7 could not be co-purified with HBT-xUB (FIG. 4*c*). This proves that xUba1-xUbcH7 was a functional relay for xUB in the cell, but xUba1-wt UbcH7 pair could not mediate xUB transfer to a wt E2. To verify the orthogonality at the E2-E3 interface, we co-expressed HBT-xUB with either wt E6AP or xE6AP in HEK293 cells stably expressing the xUba1-xUbcH7 pair, and purified the xUB-conjugated proteins by streptavidin beads. Myc-tagged xE6AP was co-purified with xUB suggesting the formation of xUB-xE6AP conjugate, yet no wt E6AP was conjugated with xUB (FIG. 4*d*). These results prove that xUba1-xUbcH7-xE6AP is an orthogonal cascade for the transfer of xUB, and the crossover of xUB to wt cascades was eliminated.

Figure 11:
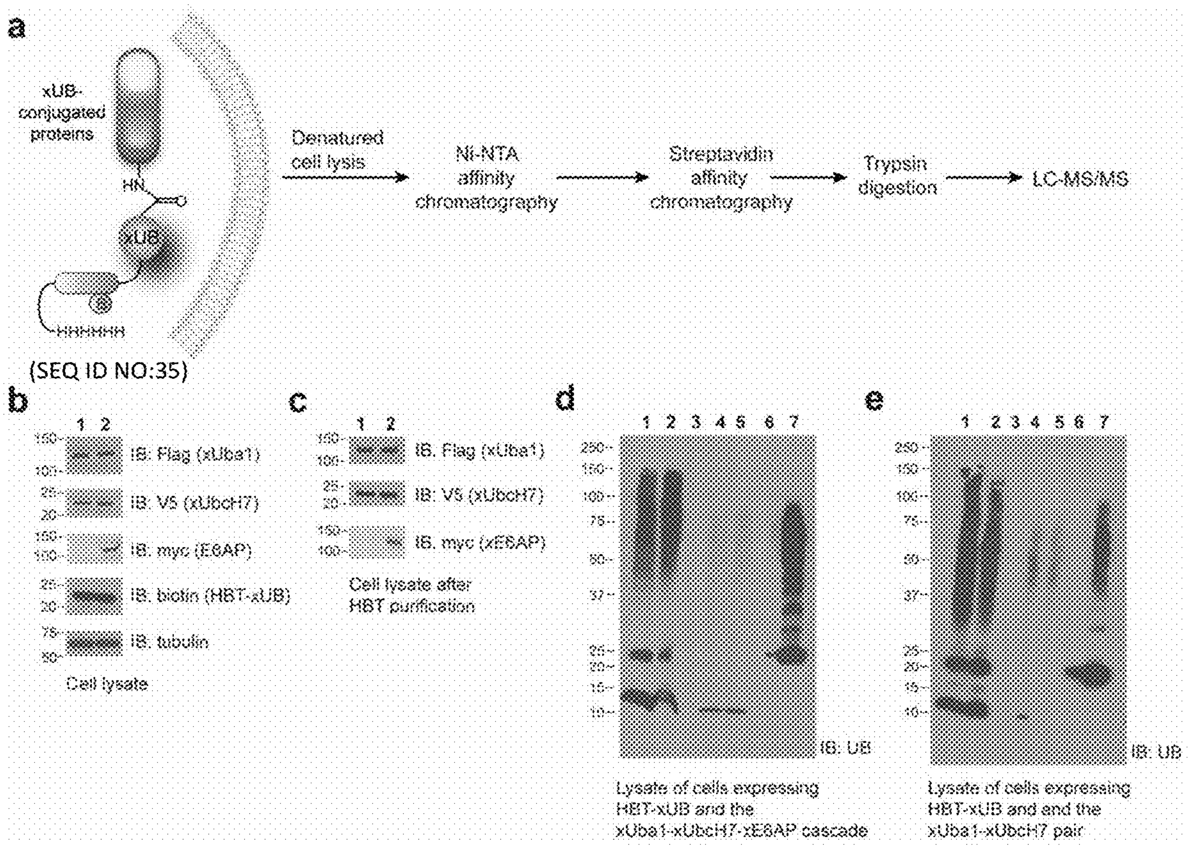
FIG. 11. Using OUT cascade to identify E6AP substrates. (a) HBT-xUB and the OUT cascade of xUba1-xUbcH7-xE6AP were expressed in the HEK293 cells. xUB-conjugated proteins in the cell were purified by sequential affinity chromatography to bind to the 6×His tag and the biotin tag on xUB. The identities of purified proteins were then revealed by tandem mass spectrometry. (b) Verification of the expression of HBT-xUB and the xUba1-xUbcH7-xE6AP cascade in HEK293 cells stably transfected with lentiviruses (lane 2). Expression levels of various OUT components were assayed with antibodies against the Flag, V5 and myc tags fused to xUba1, xUbcH7 and xE6AP, respectively. Expression of HBT-xUB was revealed by probing the Western blot with streptavidin-HRP. A control cell line was used for the expression of HBT-xUB and the xUba1-xUbcH7 pair (lane 1). (c) Verification of xUB transfer to xUba1, xUbcH7 and xE6AP in the stable cell line expressing the OUT cascade (lane 2). Proteins conjugated to HBT-xUB were purified by tandem affinity chromatography from the stable cell line. The presence of xUba1, xUbcH7 and xE6AP among the purified proteins were verified by Western blots. Stable cell line for the expression of xUba1-xUbcH7 pair was also assayed for xUB conjugation. (d and e) Progress of purification of xUB conjugated proteins through sequential affinity columns of Ni-NTA and streptavidin. Stable cell lines expressing the full-length OUT cascade xUba1-xUbcH7-xE6AP was used in (d) and stable cell lines expressing truncated OUT cascade with the xUba1-xUbcH7 pair was used in (e). Lane 1, cell lysate; lane 2, flow-through from the Ni-NTA column; lane 3, wash of the Ni-NTA column; lane 4, elution from the Ni-NTA column; lane 5, flow-through from the streptavidin column; lane 6, wash of the streptavidin column; lane 7, protein bound to the streptavidin beads after washing. All blots are representative of at least three independent experiments.

Profiling the substrates of E6AP in HEK293 cells by OUT. To express the OUT cascade of E6AP in the cell, we screened cell lines stably expressing xUba1, xUbcH7 and xE6AP by lentiviral infection. Western blots of the cell lysate probed with antibodies against each OUT component suggested their adequate expression (FIG. 11*b*). We also generated a stable cell line expressing the xUba1-xUbcH7 cascade without xE6AP as a control for the proteomic screen. To initiate xUB transfer through the OUT cascade, we transduced the two stable cell lines with lentivirus carrying the vector to express HBT-xUB. We then purified cellular proteins conjugated with HBT-xUB sequentially by Ni-NTA and streptavidin affinity columns under strong denaturing conditions (FIG. 11*a*). We found xUba1, xUbc1 and xE6AP are among the proteins retained by tandem purification suggesting the loading of HBT-xUB to the engineered E1, E2 and E3 enzymes of the OUT cascade (FIG. 11*c*). We then digested the proteins on the streptavidin beads by trypsin and analyzed the peptide fragments by LC-MS/MS to identify xUB-conjugated proteins. In parallel, we performed tandem purification and proteomic analysis on control cells expressing the xUba1-xUbcH7 pair without xE6AP (FIGS. 11*d* and 11*e*). By comparing the two proteomic profiles, we identified proteins that had ratios of peptide-spectrum match (PSM) 2-fold or higher between cells expressing the full E6AP OUT cascade and the control cells. We carried out affinity purification and proteomic screen three times. We found 130 proteins repeatedly appearing in all three screens with PSM ratio 2 (data not shown, see Wang et al. 2017). These proteins are likely the direct ubiquitination targets of E6AP.

Among the E6AP targets identified, we found previously identified substrates such as the UV excision repair protein HHR23A (RAD23A) and HHr23B (RAD23B), proteasomal ubiquitin receptor ADRM1, 26S proteasome non-ATPase regulatory subunit 4 (PSMD4 or Rpn10), 26 proteasome AAA-ATPase subunit Rpt5 (PSMC3), and E3 ligase RING2 (RNF2 or Ring1B)[24-27]. Ingenuity Pathway Analysis (IPA) of the proteins from the OUT screen showed that E6AP targets have a significant association with a variety of canonical pathways (data not shown, see Wang et al. 2017). It is intriguing that several associated pathways mediate cell cycle control and chromosome replication, matching the role of E6AP in viral oncogenesis. IPA also identified 8 protein networks that are significantly associated with E6AP substrates (data not shown, see Wang et al. 2017). The identified networks are related to cell death and survival, DNA replication, recombination, and repair, cellular growth and proliferation, and nervous system development and function.

We used the CRAPome database to evaluate whether proteins non-specifically bound to the affinity resins were among the targets identified by OUT. CRAPome selects non-specific binders in proteomic experiments based on the frequency of their appearance in pull-down experiments with various bait proteins under non-denaturing conditions. 28 In contrast, we used strong denaturing condition to purify xUB-conjugated proteins in the OUT screen. Nevertheless, we found 2 of the 130 E6AP targets identified by OUT have a frequency higher than 34% in the CRAPome database (data not shown, see Wang et al. 2018). We verified that one of them, PRMT5, is a E6AP target (see below). We also repeatedly identified 35 proteins in control cells without expression of xE6AP, and they were not present among xUB-conjugated proteins purified from cells expressing the full OUT cascade of E6AP (data not shown, see Wang et al. 2018).

Figure 5:
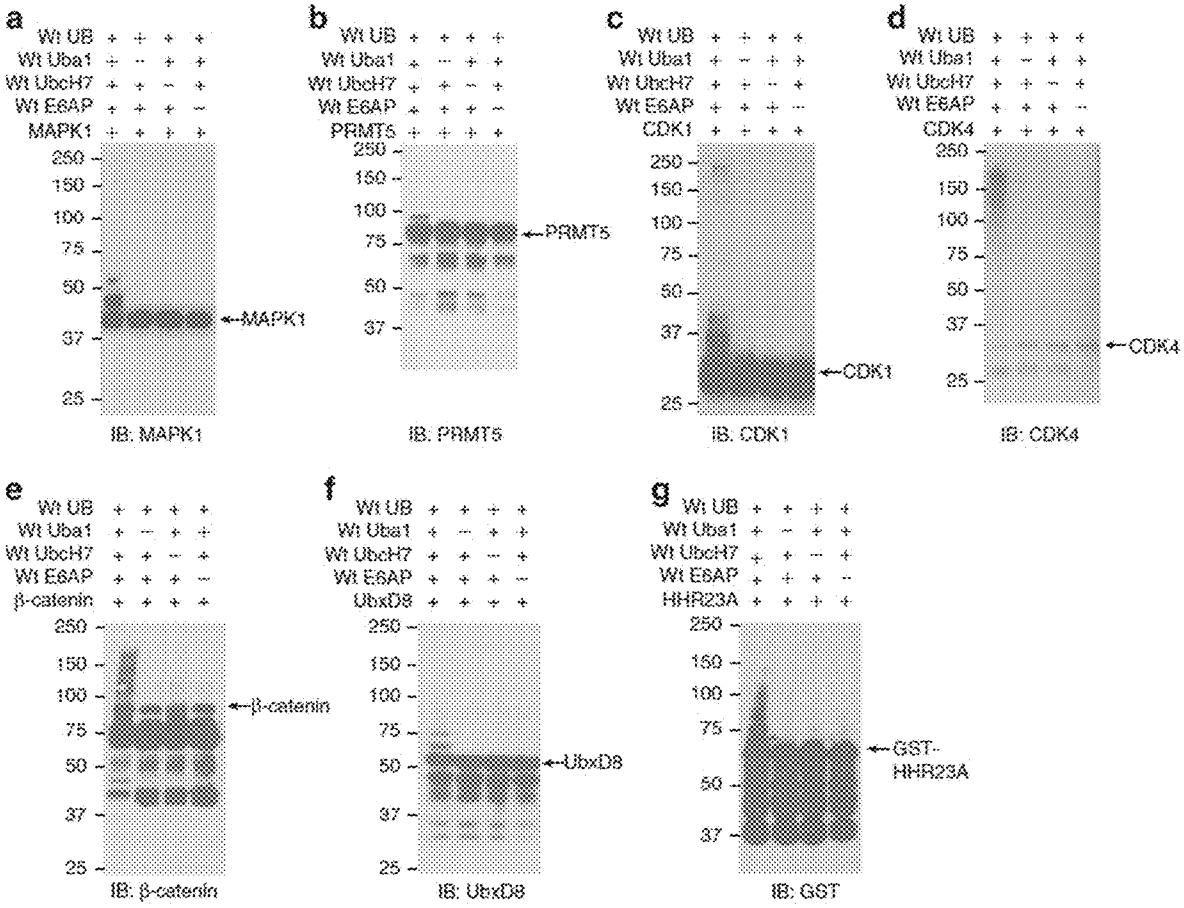
FIG. 5. In vitro assays to test ubiquitination of E6AP substrates identified by OUT. wt UB was transferred through wt Uba1-UbcH7-E6AP cascade to the potential substrate proteins expressed from *E. coli* cells. E6AP ubiquitination of MAPK1 (a), PRMT5 (b), CDK1(c), CDK4 (d), β-catenin (e), and UbxD8 (f) were confirmed. E6AP-catalyzed ubiquitination of HHR23A, a previously reported E6AP substrate, was also assayed (g). All blots are representative of at least three independent experiments.

In vitro and in vivo validation of the E6AP substrates. We found some key signaling enzymes such as kinases MAPK1, CDK1, CDK4, protein Arg methyltransferase 5 (PRMT5), transcription factor β-catenin, and FAS-associated factor UbxD8 are likely substrates of E6AP (data not shown, see Wang et al. 2018). We thus assayed if E6AP targets them for ubiquitination and regulates their stabilities in the cell. We first used the wt UB transfer cascade Uba1-UbcH7-E6AP to test if the potential substrate proteins could be modified by wt UB in vitro. We expressed and purified the potential substrates from *E. coli* cells, and found that they were ubiquitinated by E6AP to different extents: CDK1, CDK4 and β-catenin were strongly ubiquitinated by E6AP with the formation of high molecular weight bands, while MAPK1, PRMT5, and UbxD8 mainly generated species with one or two conjugated UBs (FIG. 5). As a positive control, E6AP-catalyzed ubiquitination of HHR23A, a previously identified E6AP substrate, was confirmed (FIG. 5*g*)[26]. Protein expressed in *E. coli* cells may not bear the proper posttranslational modifications for E6AP recognition, so the in vitro assays may not reflect the real activity of E6AP with the substrate proteins. We thus tested if the potential substrates are targeted for ubiquitination by E6AP in the cell.

Figure 6:
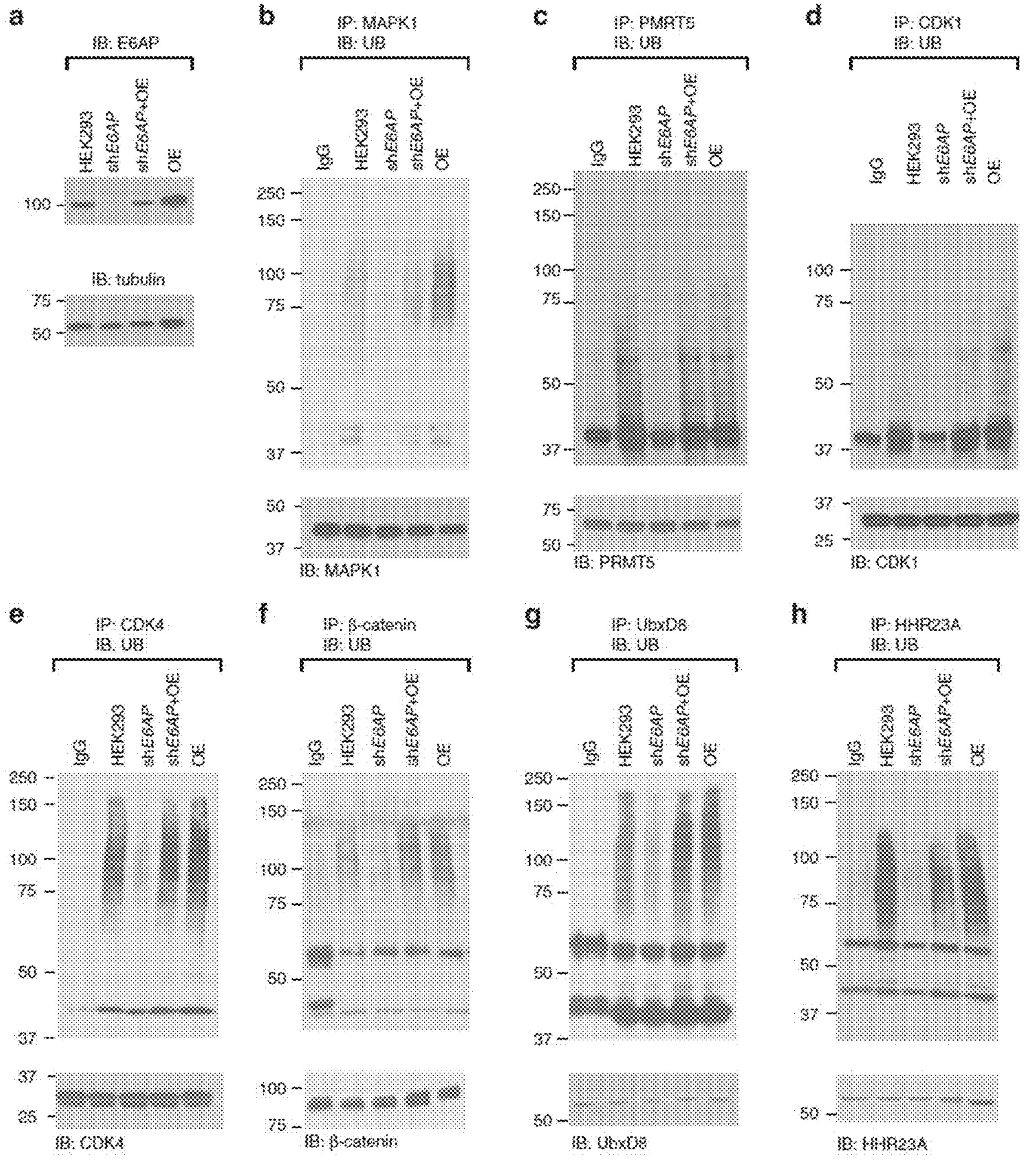
FIG. 6. Cellular assays to test the ubiquitination of E6AP substrates identified by OUT. (a) Inhibition of E6AP expression in HEK293 cells by shE6AP was confirmed with Western blot probed with an antibody against E6AP. (b-g) Ubiquitination of MAPK1 (b), PRMT5 (c), CDK1 (d), CDK4 (e), β-catenin (f) and UbxD8 (g) in HECK293 cells was assayed by immunoprecipitation with antibodies against each substrate proteins and probing the ubiquitination levels of the proteins with an anti-UB antibody on the Western blots. After 1.5-hour treatment of cells with MG132, ubiquitination of each target protein was compared among the blank HEK293 cell (HEK293), HEK293 expressing shE6AP (shE6AP), HEK293 expressing both shE6AP and recombinant E6AP (shE6AP+OE), and HEK293 expressing recombinant E6AP (OE). (h) Ubiquitination of HHR23A, a known E6AP substrate, was assayed as a control. Rabbit IgG was used as a control for immunoprecipitation in (b) and (e). Mouse IgG was used as a control for immunoprecipitation in (c), (d), (f), (g) and (h). All blots are representative of at least three independent experiments.

We inhibited E6AP expression in HEK293 cells with lentivirus delivering the anti-E6AP shRNA. We also overexpressed E6AP in blank HEK293 cells and cells harboring the anti-E6AP shRNA. Cells were treated with proteasome inhibitor MG132 before harvesting to inhibit protein degradation. Ubiquitination levels of various substrates in different cell populations were revealed by immunoprecipitation with substrate-specific antibodies and immunoblotting with an anti-UB antibody. Comparing to the parental HEK293 cells, cells expressing anti-E6AP shRNA had significantly lower levels of poly-ubiquitinated forms of MAPK1, CDK1, CDK4, PRMT5, β-catenin, and UbxD8 (FIG. 6). The poly-ubiquitination of each target protein in the HEK293 cells harboring the anti-E6AP shRNA can be restored by overexpressing E6AP in the cell. Furthermore, HEK293 cells with over-expression of E6AP gave rise to more intense poly-ubiquitination of MAPK1, CDK1, CDK4, β-catenin, and UbxD8 comparing to the parental HEK293 cells. The known E6AP substrate HHR23A showed similar dependence on E6AP for its ubiquitination in the HEK293 cell. These results prove that the potential E6AP substrates identified by the OUT screen are indeed E6AP targets in the cell.

Figure 7:
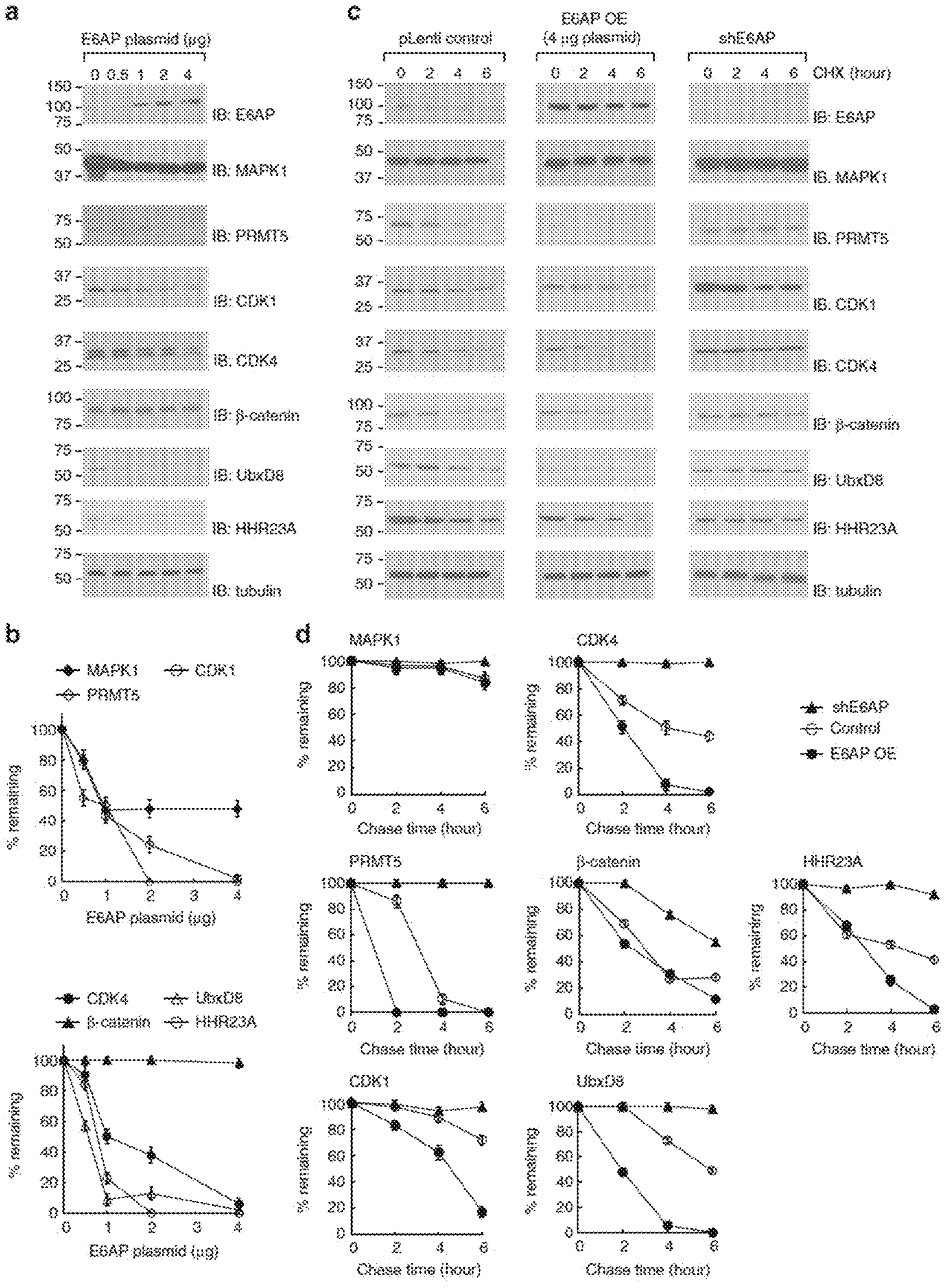
FIG. 7. Effect of E6AP expression on the stability of the substrate proteins. (a) E6AP decreases the steady state levels of the substrate proteins in the HEK293 cells. Cells were transfected with increasing amount of E6AP plasmid. Levels of the E6AP substrates were assayed with immunoblots of the cell lysate probed with substrate-specific antibodies. Approximately $5\times10^6$ cells were used for each transfection of the E6AP plasmid. (b) Quantitative analysis of substrate levels in correlation with E6AP expression. Intensity of the bands in (a) were plotted against the amount of pLenti E6AP plasmid used for transfection assuming 100% of substrate protein when an empty plasmid was used for mock transfection. Results were the average of three repeats. (c) E6AP-dependent degradation of substrate proteins assayed by cycloheximide (CHX) chase. HEK293 cells ($5\times10^6$ cells) were transfected with 4 μg of pLenti E6AP plasmid with the same amount of empty pLenti plasmid used in the controls. The cells were treated with 100 mg/ml CHX 48 hours after transfection. Cell extracts were collected at 0, 2, 4, and 6 hours after incubation with CHX, followed by immunoblotting with substrate-specific antibodies. (d) Quantitative analysis of the levels of the substrate proteins in the cell in the CHX chase experiment. Data are representative of three independent experiments. Besides the new substrates identified by OUT, HHR23A, a known E6AP substrate, was assayed for its degradation regulated by E6AP. The vertical bars in (b) and (d) represent s.e.m. from three independent experiments.

To probe if E6AP mediated ubiquitination would signal protein degradation, we transiently transfected HEK293 cells with varying amounts of wt E6AP plasmid. Western blot of the cell lysates with an anti-E6AP antibody showed an increased E6AP expression in the cells receiving more plasmid DNA. In parallel, the levels of CDK1, CDK4, PRMT5, and UbxD8 were significantly reduced in comparison to the control cells without transfection of the E6AP plasmid (FIGS. 7*a* and 7*b*). We also measured the half-lives of the target proteins with the cycloheximide (CHX) chase assay. Cells expressing E6AP were treated with CHX to inhibit protein synthesis and the substrate levels in the cell were measured by immunoblotting with anti-substrate antibodies at different time points. We found that the turnover of PRMT5, CDK1, CDK4, and UbxD8 was significantly faster in cells overexpressing E6AP compared to control cells transfected with the same amount of empty plasmid (FIGS. 7*c* and 7*d*). The level of MAPK1 remained stable despite overexpression of E6AP. MAPK1 is among the 400 most expressed proteins in the cell and its half-life is longer than 68 hours[29,30]. This may explain why E6AP expression had little effect on the level of MAPK1 in the cell. On the other hand, inhibiting endogenous E6AP expression in HEK293 cells by shRNA stabilized PRMT5, CDK1, CDK4, β-catenin, UbxD8 (FIGS. 7*c* and 7*d*). The known E6AP substrate HHR23A was also stabilized with the decreased expression of E6AP.

Discussion

Figure 12:
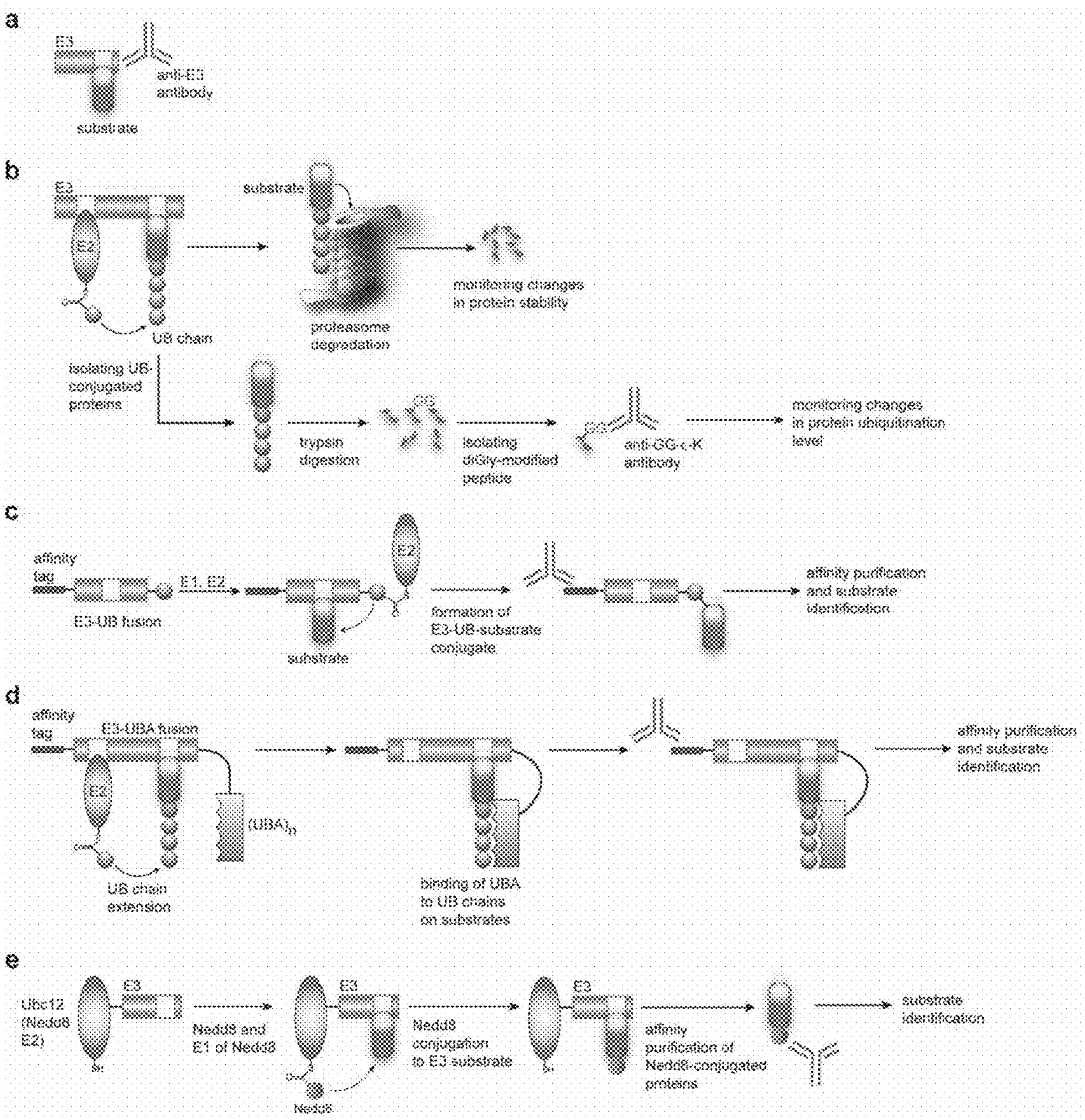
FIG. 12. Methods for identifying E3 substrates. (a) Identifying E3 substrates based on affinity binding between E3 and substrate proteins. (b) Identifying E3 substrates by monitoring changes in protein stability upon perturbation of E3 activity with a small molecule inhibitor, shRNA, or by overexpression of an E3. Alternatively, ubiquitinated proteins could be isolated from the cell and trypsin digestion would generate peptide fragments with diGly modification at Lys residues as reminiscent of UB conjugation to the substrate proteins. These fragment could be purified by an anti-GG-ε-K antibody and their levels be monitored by MS to correlate changes in protein ubiquitination level with the up or down regulation of E3 activity. (c) For "UBAIT", an E3-UB fusion was used to form conjugates with E3 substrates due to the in cis transfer of UB to substrates bound to E3. (d) An E3-UBA fusion was used to bind to polyubiquitnated proteins synthesized by the same E3 enzymes. (e) To generate "Neddylator" for E3 substrate identification, Ubc12, the E2 for the Nedd8 protein, was fused with E3. The fusion would transfer Nedd8 to E3 substrates to facilitate their identification in the pool of Nedd8-modified proteins in the cell.
Figure 13:
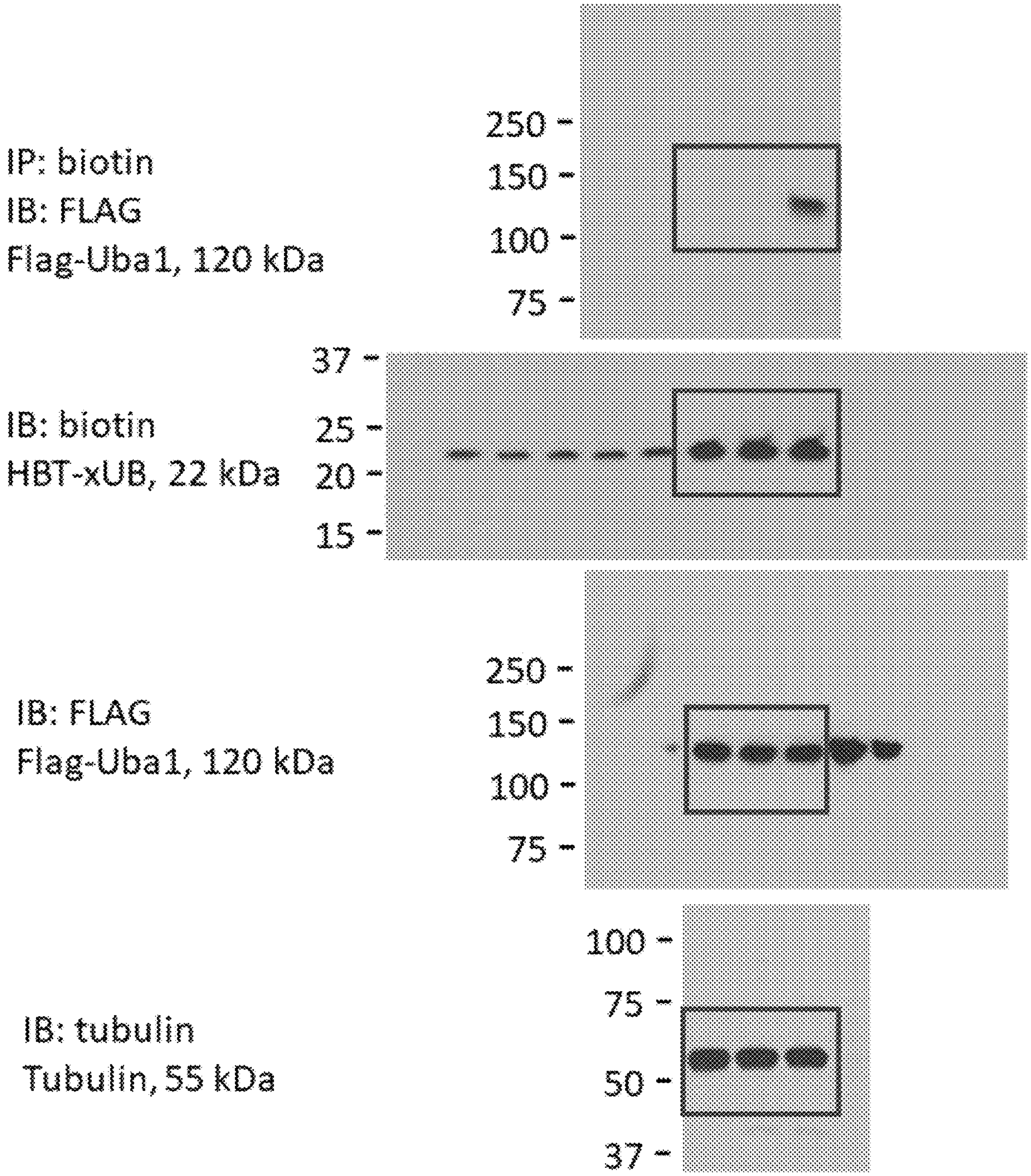
FIG. 13. Uncropped Western blots in FIG. 4*b*.
Figure 14:
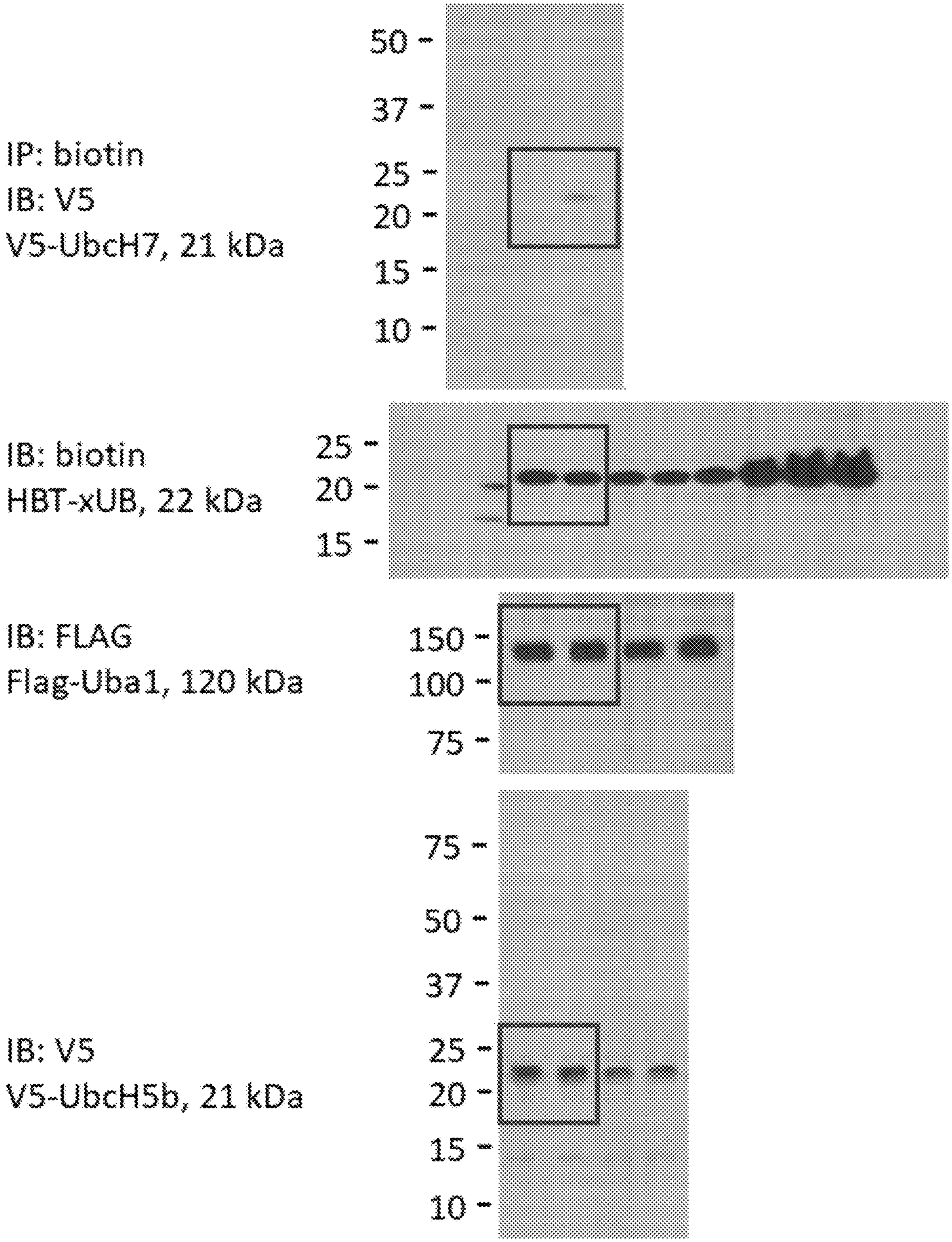
FIG. 14. Uncropped Western blots in FIG. 4*c*.
Figure 15:
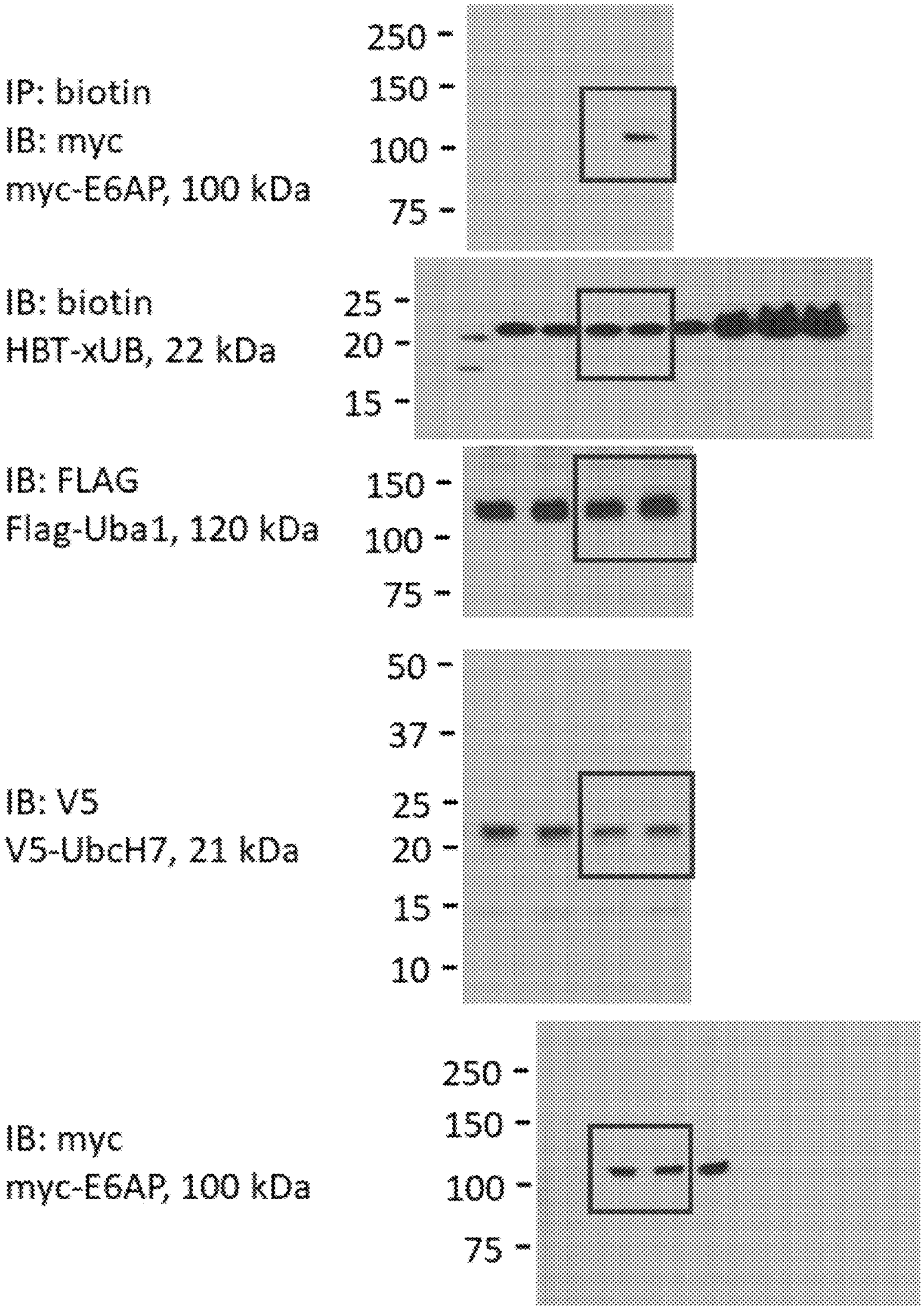
FIG. 15. Uncropped Western blots in FIG. 4*d*.
Figure 16:
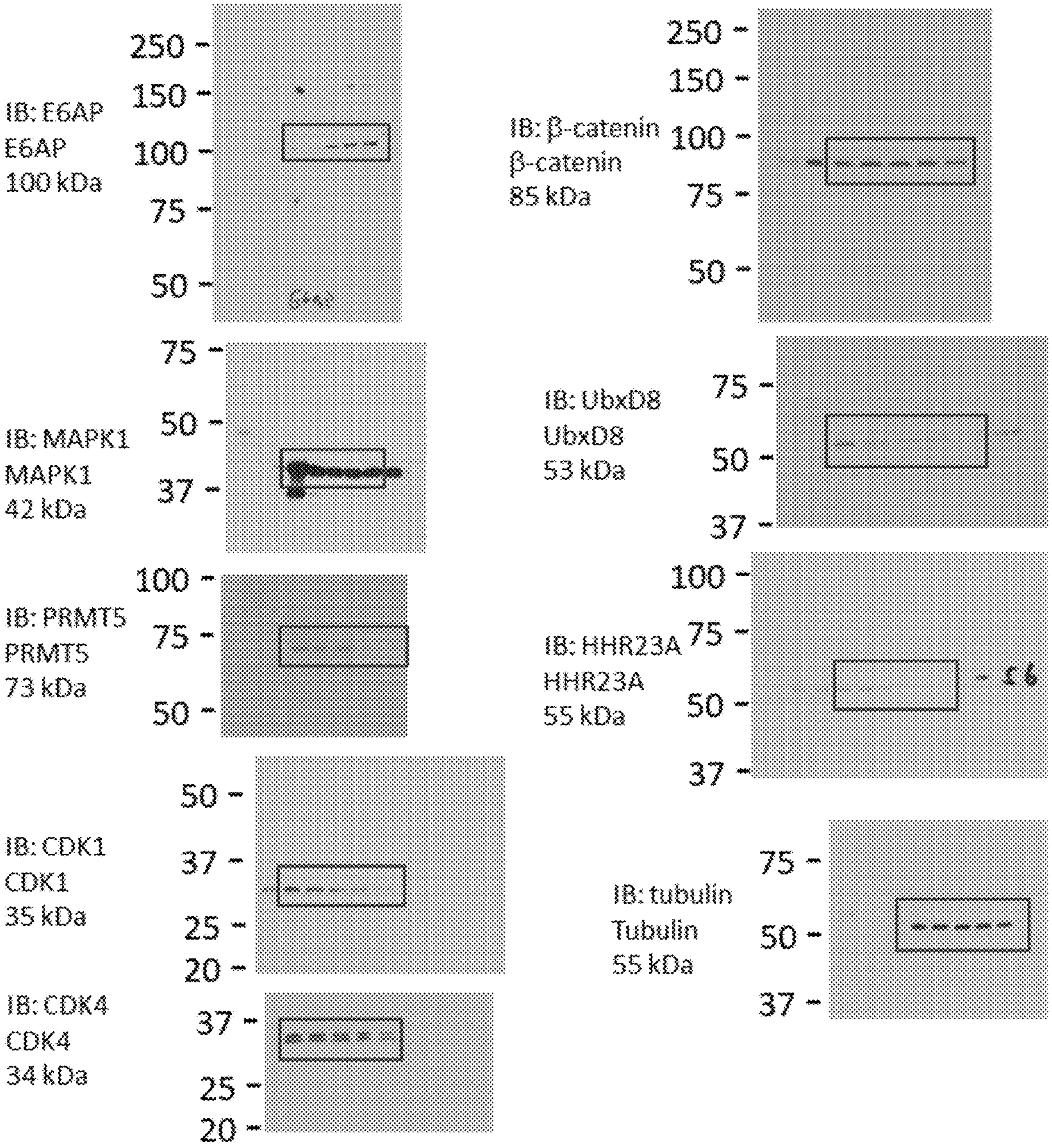
FIG. 16. Uncropped Western blots in FIG. 7*a*.
Figure 17:
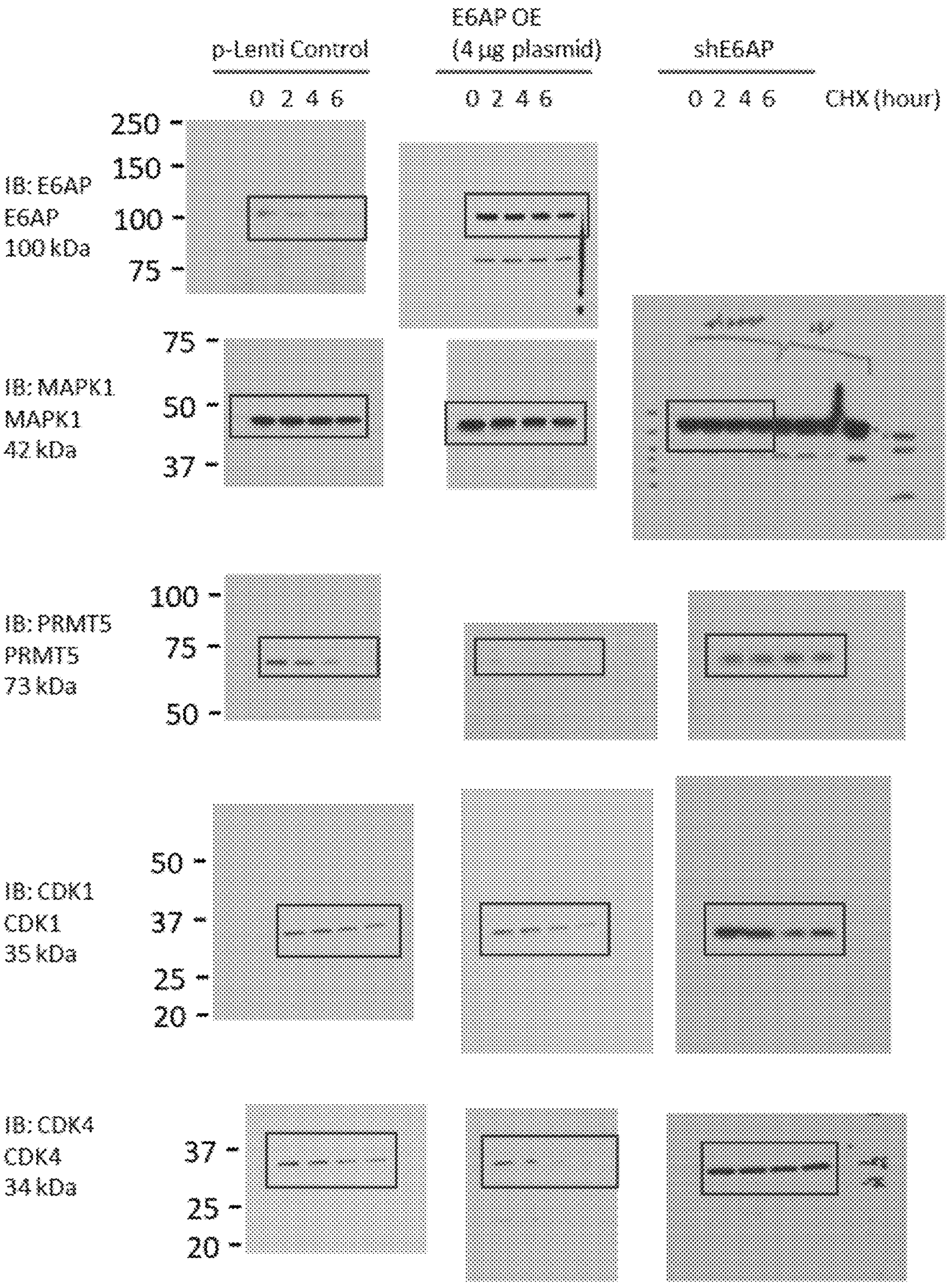
FIG. 17. Uncropped Western blots in FIG. 7*c* (part 1).
Figure 18:
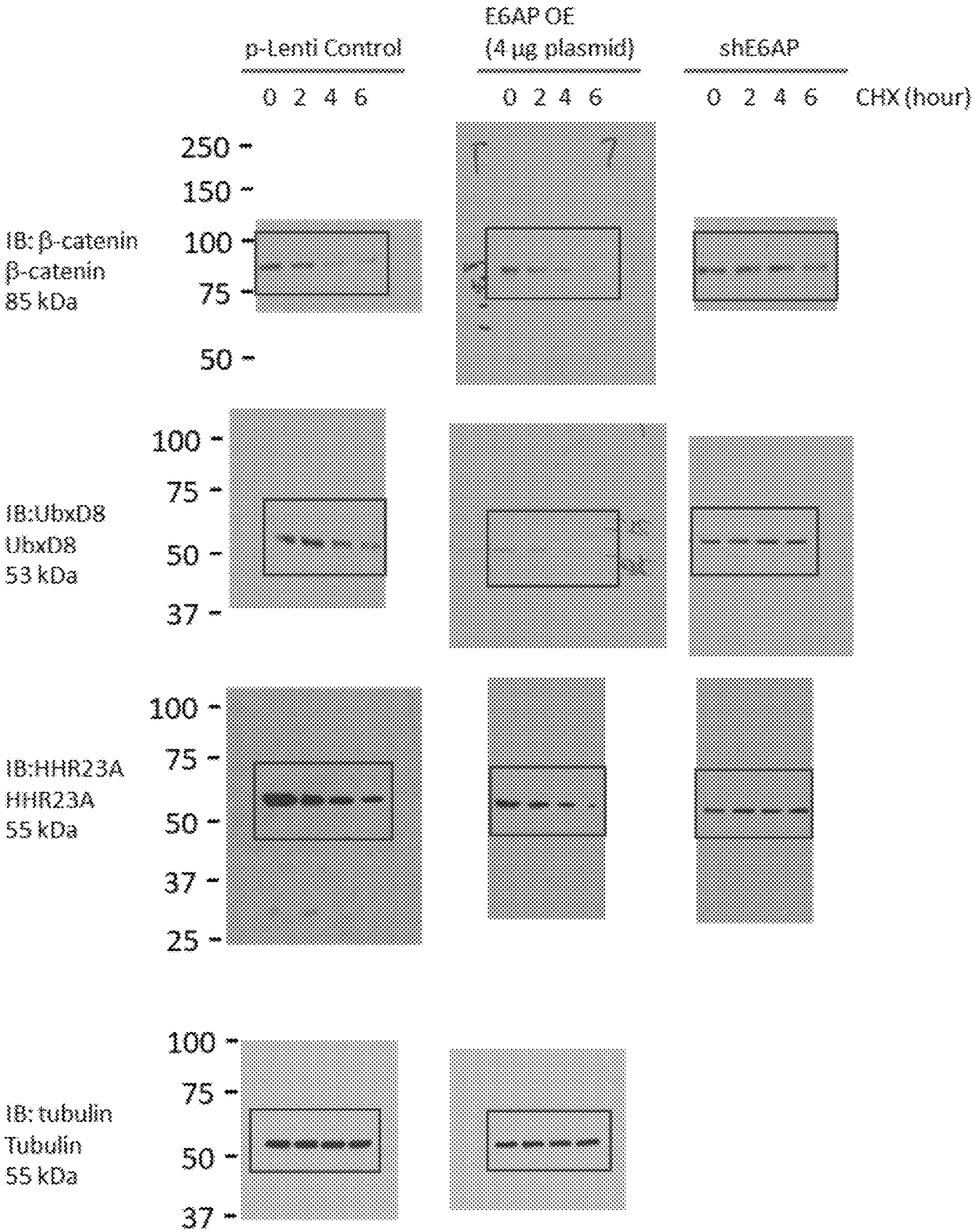
FIG. 18. Uncropped Western blots in FIG. 7*c* (part 2).

The large number of E3s (>600) encoded in the human genome reflects the key roles they play in cell regulation. On the other hand, their diversity makes it a significant challenge to identify the direct substrates of individual E3s. Current methods screening E3 substrates fall into three categories—affinity binding to E3, monitoring changes in protein stability or ubiquitination levels in response to E3 perturbation, or trapping E3 substrates by covalent or non-covalent interactions (FIG. 12). Affinity-based approaches such as co-immunoprecipitation, yeast two-hybrid system, and protein microarray have been used to screen E3 substrates based on the binding between E3 and substrates (FIG. 12*a*)[31-33]. They are less specific since the Ku's of the E3-substrate complexes are around hundreds of μM, and the complexes are transient[34]. Also, proteins other than substrates can bind to E3s to function as adaptors or regulators. Still, these methods yielded important substrate profiles of HECT E3 E6AP, Ring E3 anaphase-promoting complex (APC), and the Skp1-cullin-F-box (SCF) complex[31-33]. A more direct approach to assign E3 substrates is to correlate changes in E3 activity with the changes in stability or ubiquitination level of cellular proteins (FIG. 12*b*). One method known as "global protein stability profiling (GPS)" tracks the stability of thousands of proteins with a fused fluorescence protein tag, and it has been used to screen substrates of SCF E3s[35-37]. The development of anti-diGly antibody allows affinity enrichment of substrate peptides containing the ubiquitination sites, and comparison of protein ubiquitination levels upon perturbation of E3 activity[38]. Using the quantitative diGly proteomics (QdiGly), substrate profiles of cullin-Ring and Parkin E3s were generated[39,40]. E3s are also into a substrate trap so the substrate proteins would still be bound to E3 after UB transfer. This would enable the co-purification of the substrate proteins with E3s. To create "UB-activated interaction traps (UBAIT)", UB was fused to HECT and Ring E3s and it can attack the substrates bound to the E3-UB fusion to generate covalent linkages between E3 and the substrate proteins (FIG. 12*c*)[41]. Another design is to fuse the F-box proteins with a series of UB associated domain (UBA) and use them as UB ligase traps[42,43]. As F-box proteins recruit substrates to SCF E3s, the UB chain extending from the substrate would bind to the UBA repeats with high affinity. Purification of proteins bound to F-box-UBA fusion would enrich the substrates of the F-box protein (FIG. 12*d*). E2-E3 fusions has also been used to identify E3 substrates. Ubc12, the E2 enzyme mediating Nedd8 transfer, was fused to the substrate binding domain of Ring E3 XIAP. The fusion protein, known as a "Neddylator", allows Nedd8 transfer to XIAP substrates so the ubiquitination targets of XIAP could be identified among Nedd8-modified proteins (FIG. 12*e*)[44]. The development of diverse methods to profile E3 substrates enables the interrogation of E3 function from different perspectives. The substrate profiles generated by various methods could corroborate to reveal the functions of E3s.

Here, we developed a method known as "orthogonal ubiquitin transfer (OUT)" to identify the direct substrates of HECT E3 E6AP (FIG. 4*a*). In OUT, an affinity-tagged UB variant (xUB) is exclusively transferred through an engineered xE1-xE2-xE3 cascade to the substrates of a specific E3. By purifying xUB-modified proteins from the cell and identifying them by proteomics, we would be able to identify the direct substrates of a E3. In this study, we used OUT to identify 130 potential E6AP substrates, and among them, we confirmed MAPK1, PMRT5, CDK1, CDK4, β-catenin, and UbxD8 are ubiquitinated by E6AP in the HEK293 cells. During the revision of this manuscript, β-catenin was confirmed as an E6AP substrate by another report.[45] A key advantage of OUT is that it assigns E3 substrates by directly following UB transfer from the E3 to its substrate proteins. Methods based on E3-substrate binding, or change of protein stability upon perturbation of E3 activity, use indirect readouts of substrate ubiquitination to assign E3 substrates. The substrate profiles generated by methods could be distorted by factors such as the binding of adaptor or regulatory proteins to E3, or the attachment of UB chains of non-degradation signals to the substrates. E3 may also regulate the activities of proteasome and other E3s, thus perturbing the activity of one E3 may affect the degradation or ubiquitination levels of the substrates of other E3s[24,46-48]. In this study, we used yeast cell surface display to identify mutations at the E2-binding site of the E6AP HECT domain to generate an xE2-xE3 pair for the OUT cascade. The mutations at the E2 binding site of E6AP shall have minimal disturbance to its substrate profile. In comparison with various E3 fusions as substrate traps, the engineered xE6AP would be a better reenactor of the wt E3 in transferring xUB to the substrate proteins to enable their identification by OUT.

OUT has a few limitations. First, each E3 would require its own OUT cascade for substrate identification. The xUB-xE1 pair we engineered can be used for the OUT cascade of various E3s. Due to the high sequence homology of the N-terminal helices of the E2s, mutations can be transplanted from xUbc1 to UbcH7 and UbcH5b to generate xE1-xE2 pairs[17]. The great diversity of E3s would require the engineering of individual E3s to assemble xE2-xE3 pairs. Here we used yeast cell surface display to identify HECT mutants of E6AP that can pair with xUbcH7. The helical turn we randomized in the E6AP HECT domain is a common element in many HECT enzymes[49-52]. It is possible to generate orthogonal xE2-xE3 pairs by transplanting the mutations from xE6AP to other HECTs E3s. If such strategy is not effective, the yeast selection platform for E6AP HECT could be used to engineer other HECTs such as Smurf1/2, Nedd4-1/2, and Huwel, all playing important roles in cell regulation[5]. Another limitation of OUT is that co-expression of HBT-xUB and the full xE1-xE2-xE3 cascade, although successful in HEK293 cells, maybe a challenge in other cell types. The recently developed genome editing tools such as CRISPR/Cas9 may provide an opportunity to introduce the OUT cascade into the original genetic background to identify E3 substrates[53].

We found E6AP expression did not affect the stability of MAPK1. The ubiquitination and degradation UbxD8 signaled by E6AP suggests a role for E6AP in lipid metabolism, since UbxD8, by forming a complex with p97/VCP, regulates lipid droplet size and abundance[54]. Consistently, expression of a dominant-negative E6AP mutant promotes accumulation of lipid droplets[55], which may involve stabilized UbxD8 due to decreased activity of E6AP. The biological significance of E6AP-mediated ubiquitination of CDK1, CDK4 and PRMT5 awaits further investigations. Recent studies have suggested that E6AP is required for cellular senescence, i.e., irreversible exit from the cell cycle, as a physiological response to oxidative stress or oncogene activation[56-58]. Thus, E6AP-mediated ubiquitination of CDKs in the absence of viral oncoproteins may be involved in the senescence response to various cellular stresses. Indeed, Ingenuity Pathway Analysis showed that many of the potential E6AP substrates identified by OUT are associated with pathways and networks relevant to DNA replication, cell cycle control, oncogenic signaling, cell survival/death and development (data not shown, see Wang et al. 2017). PRMT5 plays a key role in chromatin regulation by methylating Arg residues in histones[59]. Since various studies have indicated the significance of epigenetic changes in cancers and autism spectrum diseases, it would be interesting to determine how E6AP-mediated PRMT5 ubiquitination is involved in the pathobiology of those diseases[60-62].

Methods

Reagents. XL1-Blue cells were from Agilent Technologies (Santa Clara, CA, USA). pET-15b and pET-28a plasmids for protein expression were from Novagen (Madison, WI, USA). pCTCON2 plasmid and the yeast strain EBY100 were from K. Dane Wittrup of Massachusetts Institute of Technology.[21] The plasmid with the human Uba1 gene was from Wade Harper of Harvard Medical School.[8] The plasmid for E6AP expression was from Jon M. Huibregtse of the University of Texas at Austin.[63] The plasmid for Rsp5 expression was from Linda Hicke of the Northwestern University.[64] pQCXIP HBT-Ubiquitin (26865) was from Addgene (Cambridge, MA, USA).[23] pLenti-puro plasmid was from Addgene (39478). pLenti4N5-DEST-zeocin (K498000) and ViraPower™ Lentiviral Packaging Mix (K4975-00) were from Life Technology. pLenti-puro plasmid was from Addgene (39478). pET-PRMT5 plasmid was provided by Yujun Zheng of University of Georgia, Athens. The mammalian cell expression vectors for MAPK1 (39230), CDK1 (27652), and UbxD8 (53777) and pGEX-HHR23A (10864) were from Addgene. HEK293 cells were from American Tissue Culture Collection (ATCC), and cultured in high-glucose Dulbecco's modified Eagles medium (DMEM) (Life Technologies, Carlsbad, CA, USA, 11965092) with 10% (v/v) Fetal bovine serum (FBS) (Life Technologies, 11965092). Antibiotics hygromycin, blasticidin, zeocin and puromycin were from GiBCO/Invitrogen (Carlsbad, CA, USA) and RPI (Mount Prospect, IL, USA). Doxycycline was from RPI.

Anti-β-catenin antibody (sc-65480), anti-CDK1 antibody (sc-54), anti-CDK4 antibody (sc-260), anti-E6AP antibody (sc-25509), anti-HA antibody (sc-7392), anti-HHR23A antibody (sc-365669), anti-MAPK1 antibody (sc-154), anti-Myc antibody (sc-40), anti-p53 antibody (sc-126), anti-PRMT5 antibody (sc-376937), anti-α-Tubulin antibody (sc-23948), anti-V5 antibody (sc-271944), anti-UB antibody (sc-8017), anti-UbxD8 antibody (sc-374098) were from Santa Cruz Biotechnology. These antibodies were diluted between 500 and 1,000-fold to probe the Western blots. Goat anti-rabbit IgG-HRP (sc-2004) and goat anti-rabbit IgG-HRP (sc-2005) were also from Santa Cruz Biotechnology and were diluted 10,000-fold as the secondary antibody for Western blotting. Streptavidin-HRP-conjugate was from Life Technologies and was diluted 20,000-fold for Western blotting. Anti-Flag M2 antibody (F3165) was from Sigma-Aldrich and was diluted 1,000-fold for Western blotting. His6-p53 and E6 protein of human papillomavirus type 16 were from Boston Biochem (Cambridge, MA, USA). Oligonucleotides were ordered from Integrated DNA Technologies (Coralville, IA, USA). Biotin-CoA was prepared by conjugating biotin-maleimide with Coenzyme A[17]. wt UB and xUB were expressed as fusions with an N-terminal ybbR tag and were labelled with biotin by the transfer of biotin-pantetheinyl group from biotin-CoA to the ybbR tag catalyzed by Sfp phosphopantetheinyl transferase[17,65].

Construction of the protein expression plasmids. To construct human xUba1 mutant with six mutations (Q608R, S621R and D623R, E1037K, D1047K and E1049K), primers Bo184 and Bo185, and Bo 186 and Bo187 were paired to amplify Uba1 gene in pET-wt Uba1 by polymerase chain reaction (PCR). The amplified PCR fragments had mutations Q608R, S621R and D623R incorporated into the adenylation (A) domain of Uba1. The two PCR fragments were assembled by overlapping PCR and cloned into the pET-wt Uba1 vector between restriction sites FseI and EcoRI to generate pET-xUba1 (A). To incorporate the three mutations in the UFD domain of Uba1, the mutated Uba1 gene in pET-xUba1 (A) was PCR amplified with primers Bo13 and Bo73. PCR fragment was digested by restriction enzymes BamHI and EcoRI, and cloned into pET-xUba1 (A) to generate pET-xUba1 with mutations in both the adenylation and the UFD domains. pET-UbcH7 with the R5E and K9E mutations was constructed by PCR amplifying the UbcH7 gene with primers WY9 and WY10 and cloned into pET28a between restriction sites NdeI and XhoI.

HECT domains of Sumrf1, Sumrf2, Nedd4, and E6AP with an N-terminal Flag tag were expressed with the pET28 vector. The genes of the HECT domains were amplified with primers WY1-8 by PCR. The amplified fragments were digested with restriction enzymes SacII and NotI, and cloned into the pET28a plasmid. To express the mutant E6AP HECT from yeast selection, the genes of the mutant HECT domains were PCR amplified with primers WY4 and WY8 from the corresponding pCTCON2 vector, digested by SacII and NotI, and cloned into pET28a. For the expression of full-length E6AP, PCR primers WY21 and WY8 were used to amplify the full-length gene from pGEX4-wtE6AP and cloned into the pET28a-Flag vector between restriction sites SacII and NotI. For the expression of full-length xE6AP with mutated HECT domains, mutant HECT genes were amplified with primers WY4 and WY8 and cloned into the pET28-E6AP vector between restriction sites PstI and NotI. The CDK1 and CDK4 genes were PCR amplified from their mammalian cell expression plasmids with primer pairs K1-K2 and K3-K4, respectively. The PCR fragments were digested with NedI/XhoI and ScaI/NotI, respectively, and cloned into the pET-28a plasmid. The UbxD8 gene was amplified from a mammalian expression plasmid with primers LZ1 and LZ2, digested with NdeI and NotI, and cloned into pET28. The β-catenin gene was loned into pGEX plasmid. The pET or PGEX plasmids were transformed into BL21(DE3)pLysS chemical competent cells (Invitrogen) for protein expression.

Construction of the E6AP library. The gene of the E6AP HECT domain was PCR-amplified from pET-E6AP with primers WY11 and WY12. The amplified fragment was double-digested with NheI and XhoI, and cloned into pCT-CON2 plasmid to generate pCTCON2-E6AP HECT. To generate E6AP library in the pCTCON2 plasmid, the E6AP HECT domain gene was PCR amplified with WY13 and WY14 to incorporate randomized codons at residues 651, 652, 653, 654 and 656. The PCR fragment amplified with WY13 and WY14 was combined with fragment amplified with WY11 and WY12 to assemble the HECT library gene by overlapping extension with primers WY11 and WY12. The amplified library gene was digested with NheI and XhoI, and cloned into the pCTCON2 vector. Transformation of the plasmid library into XL1-blue electro-competent cells afforded a library of $2.0\times10^8$ in diversity, large enough to cover all the mutants with randomized residues replacing D651, D652, M653, M654 and T656 in the E6AP HECT domain. Transformed XL1 blue cells were plated on LB-ampicillin plates (LB agar supplemented with 100 μg $mL^{-1}$ ampicillin) and allowed to grow at 37° C. overnight. Colonies growing on the plate were scraped and the library DNA was extracted with the Plasmid Maxiprep Kit (Qiagen).

Yeast display of the E6AP library. The E6AP library in pCTCON2 was chemically transformed into EYB100 yeast cells.[66,67] Briefly, yeast cells were first cultured at 30° C. in 200 ml YPD (20 g dextrose, 20 g peptone, and 10 g yeast extract in 1 L deionized water, sterilized by filtration) to an optical density at 600 nm (OD600) around 0.5. The cells were then pelleted at 1,000×g for 5 min. Cells were washed by 20 mL TE (100 mM Tris base, 10 mM EDTA, pH 8.0) and 20 mL LiOAc-TE (100 mM LiOAc in TE), before resuspension in approximately 800 μL LiOAc-TE. A typical transformation reaction contained a mixture of 1 μg pCT-CON2 plasmid DNA, 2 μL denatured single-stranded carrier DNA from salmon testes (Sigma-Aldrich), 25 μL resuspended yeast competent cells, and 300 μL polyethylene glycol (PEG) solution (40% (w/v) PEG 3350 in LiOAc-TE). To achieve a library size of $10^6$, 30 transformations were set up in parallel. Control was also prepared in which the pCTCON2 plasmid was excluded. Both the transformation reactions and the control were incubated at 30° C. for 1 hour and then at 42° C. for 20 min. Cells in each transformation were pelleted by centrifuging at 1,000×g for 30 s and resuspended in 20 mL SDCAA medium (2% (w/v) dextrose, 6.7 g Difco yeast nitrogen base without amino acids, 5 g Bacto casamino acids, 50 mM sodium citrate, and 20 mM citric acid monohydrate in 1 L deionized water, sterilized by filtration). Yeast cells were resuspended, pooled together into 1 L SDCAA medium, and allowed to grow at 30° C. over a 2-day period to an OD600 above 5. For long-term storage of the yeast library, 20 ml of the yeast culture was aliquoted in 15% glycerol stock and stored at −80° C. To titer the transformation efficiency, 10 μL of the resuspended yeast transformants was serially diluted in SDCAA medium and plated on Trp-plates (−20 g agar, 20 g dextrose, 5 g $(NH4)_2SO_4$, 1.7 g Difco yeast nitrogen base without amino acids, 1.3 g drop-out mix excluding Trp in 1 L deionized water, and autoclaved). Yeast cells transformed with pCT-CON2 plasmids would appear within 2 days of incubation at 30° C.

Model selection of yeast cells displaying E6AP HECT domain. Yeast cell EYB100 was transformed with pCT-CON2-wt E6AP HECT and streaked on a Trp-plate. After two days of incubation at 30° C., cells were scraped from the Trp-plate to inoculate in a 5 mL SDCAA culture that was allowed to shake at 30° C. to reach an initial OD600 of 0.5. Cells were centrifuged at 1,000×g for 5 min and induced for E6AP HECT expression by resuspension in 5 mL SGCAA (2% (w/v) galactose, 6.7 g Difco yeast nitrogen base without amino acids, 5 g Bacto casamino acids, 38 mM $Na_2HPO_4$ and 62 mM $NaH_2PO_4$, in 1 L deionized water, sterilized by filtration). The yeast culture was shaken at 20° C. for 16-24 hours. For analysis of E6AP display on the surface of yeast cells, $10^6$ cells were resuspended in 0.1 mL Tris-buffered saline (TBS) (25 mM Tris, pH 7.5, 150 mM NaCl) with 0.1% bovine serum albumin (BSA). The cells were first labeled with biotin-wt UB based on UB loading on the E6AP HECT domain displayed on the cell surface. 100 μL labeling reaction was set up with 0.5 μM wt Uba1, 5 μM wt Ubch7, 0.1 μM biotin-wt UB in a buffer containing 10 mM $MgCl_2$ and 50 mM Tris-HCl (pH 7.5). The reaction was incubated for 2 hours at 30° C., and then mixed with 100 μL 3% BSA. A mouse anti-HA antibody (Santa Cruz Biotechnology, sc-7392) was added to the reaction mixture to detect the expression of E6AP tag by binding to the HA tag fused to the N-terminus of the HECT domain. The anti-HA antibody was added to a final concentration of 10 μg $mL^{-1}$ and the cells were incubated for overnight at 4° C. The cells were then washed twice with 0.1% BSA in TBS and stained with 5 μg $mL^{-1}$ goat anti-mouse antibody conjugated with Alexa Fluor 647 (Life Technologies, A21235) in 0.1 mL 0.1% BSA in TBS. 5 μg $mL^{-1}$ streptavidin conjugated with PE (Life Technologies, 5866) was also added to bind to biotin-UB conjugated to the HECT domain. The cell suspension was shielded from light and incubated at 4° C. for 1 hour. After washing twice with 0.1% BSA in TBS, cells were analyzed on a flow cytometer (BD LSRFortessa™) to count the number of cells that were labeled with fluorophore. Cells were also analyzed from control labeling reactions in which the primary anti-HA antibody was excluded from the labeling reaction, or Uba1, UbcH7 or biotin-wt UB was excluded from the UB loading reaction.

Selection of the E6AP library displayed on the yeast cell. The first round of selection of the yeast library was carried out with magnetic-activated cell sorting (MACS). For subsequent rounds of selection, fluorescence-activated cell sorting (FACS) was used. For MACS, 500 μL reactions in TBS buffer (10 mM $MgCl_2$, 50 mM TrisHCl, pH 7.5) with 0.1% BSA were set up with approximately $5\times10^7$ yeast cells displaying the E6AP library. The reaction mixture contains 5 μM xUba1, 20 μM xUbcH7 and 5 μM biotin-xUB to enable xUB transfer to HECT. After reacting for 2 hours at 30° C., cells were pelleted by centrifugation and re-suspended in fresh 0.1% BSA in TBS. This procedure was repeated twice to remove biotin-xUB that was not covalently conjugated to yeast cells. After washing, cells were mixed with 100 μL streptavidin-coated microbeads provided by the mMACS Streptavidin Starting Kit (Miltenyi Biotec, 130-091-287) in a total volume of 1 mL TBS with 0.1% BSA. Cell suspension was shielded from light and incubated at 4° C. for 1 hour. The suspension of the cells and magnetic beads were then added to 30 mL of 0.1% BSA in TBS. The cell suspension was pelleted by centrifugation at 500×g for 10 min. The supernatant was aspirated, and the cell pellet including the magnetic beads was re-suspended in 500 μL 0.1% BSA-TBS. Yeast cells bound to magnetic beads by biotin-streptavidin interaction were captured by a magnet according to manufacturer's instructions, and the beads were washed with 0.1% BSA in TBS. Cells bound to the magnetic beads were eluted into 5 ml SDCAA medium supplemented with 100 μg/mL ampicillin, and 50 μg/mL kanamycin, and were cultured at 30° C. overnight. In parallel, library cells were bound to primary and secondary antibodies to evaluate the display of HECT mutants on the yeast cell surface.

For the 2nd round of selection, the library cells amplified from the first round were incubated with 1 μM xUba1, 10 μM xUbcH7, and 5 μM biotin-xUB for 1 hour. After loading biotin-xUB to the HECT domain, the cells were labeled with 10 μg $mL^{-1}$ mouse anti-HA antibody for 1 hour. Next, the cells were washed three times, each time with 1 mL 0.1% BSA in TBS. The cells were incubated with 5 μg $mL^{-1}$ goat anti-mouse antibody conjugated with Alexa Fluor 647 and 5 μg $mL^{-1}$ streptavidin conjugated with PE as secondary reagents. After incubation for 1 hour at 4° C., the cells were pelleted, washed twice each time with 1 mL 0.1% BSA in TBS. Cells doubly labeled with both PE and Alexa Fluor 647 fluorophores were collected by FACS (BD FACSAria™ilu). The cells collected were pelleted and resuspended in SDCAA supplemented with 100 μg $mL^{-1}$ ampicillin and 50 μg $mL^{-1}$ kanamycin. The cells were allowed to grow at 30° C. to an $OD_{600}$ between 1 and 2. Glycerol stock of the cells were prepared and they were used to inoculate yeast cell culture for the next round of selection.

In subsequent rounds of selection, the concentration of xUba1, xUbcH7 and biotin-UB in the reaction were decreased in each round. For the 6th rounds of selection, 0.5 μM xUba1, 5 μM xUbcH7 and 0.1 μM xUB was used. The gate for sorting the yeast cells also became more stringent in each round with the $6^{th}$ round only collecting the top 0.5% of doubly labeled cells. After 6 rounds of cell selection, the collected cells were grown in an SDCCA medium to an $OD_{600}$ around 0.5. Zymoprep II Yeast Plasmid Miniprep Kit (Zymo Research, D2004) was used to extract the pCTCON2 plasmid DNA. The plasmid was transformed into XL1-blue competent cells. Plasmid DNA from individual colonies were minipprepped, and sequenced to reveal the mutations in the selected HECT domain clones.

Construction of lentiviral vector and stable cell lines. To generate pLenti6-V5-D-TOPO-Ascl-hygromycin-HBT-(x) UB plasmids, HBT tag was sub-cloned from pQCXIP HBT-UB and fused with DNA fragments of human wt UB or xUB by PCR. The assembled DNA fragment was cloned into the pLenti6 plasmid with a hygromycin resistant gene. Genes of xUba1, xUbcH7 and xE6AP were cloned into lentiviral vectors for the selection of stable cell lines. Flag-xUba1 gene was PCR amplified with primer WY15 and primer WY16 and cloned into pLenti6-V5-D-TOPO-Flag-Ascl-blasticdin vector between restriction sites EcoRI and Ascl. V5-xUbcH7 gene was PCR-amplified from pET-xUbcH7 with PCR primers WY17 and WY18, digested with restriction enzymes AfeI and NheI, and cloned into pLenti4-V5-D backbone with a zeocin-resistance gene. The gene of xE6AP was PCR amplified with primers WY19 and WY20 and cloned into a pLenti-puromycin vector with a myc tag between restriction sites NheI and XhoI. Virus packaging, virus infection and selection of stable cell lines were performed according to the manufacturer's protocol for the ViraPower Lentiviral Expression System. Stable HEK293 cell lines expressing Flag-xUba1 and V5-xUbcH7 were selected with 10 μg/mL blasticidin and 100 μg/mL Zeocin, respectively. Stable cell line for Myc-xE6AP was selected with 1 μg/mL puromycin. Expression of transfected genes was induced by the addition of 1 μg/mL doxycycline to the medium.

Tandem affinity purification of xUB-conjugated proteins. Tandem purification of cellular proteins conjugated to HBT-xUB was performed as following.[23] 30 dishes (10 cm in diameter) of HEK293 cells stably expressing the xUba1-xUbch7-xE6AP cascade were acutely infected with lentivirus HBT-xUB for 72 hours. To inhibit proteasome activity, cells were treated with 10 μM MG132 for 4 hours at 37° C. Cells were then washed twice with ice cold 1×PBS, pH 7.4, and harvested by cell scraper with buffer A (8 M urea, 300 mM NaCl, 50 mM Tris, 50 mM $NaH_2PO_4$, 0.5% NP-40, 1 mM PMSF and 125 U/ml Benzonase, pH 8.0). For Ni-NTA purification, cell lysates were centrifuged at 15,000 g for 30 min at room temperature. 35 μL of $Ni^{2+}$ Sepharose beads (GE Healthcare) for each 1 mg of protein lysates were added to the clarified supernatant. After incubation overnight at room temperature in buffer A with 10 mM imidazole on a rocking platform, $Ni^{2+}$ Sepharose beads were pelleted by centrifugation at 100×g for 3 min and washed sequentially with 20-bead volume of buffer A (pH 8.0), buffer A (pH 6.3), and buffer A (pH 6.3) with 10 mM imidazole. After washing the beads, proteins were eluted twice with 5-bead volume of buffer B (8 M Urea, 200 mM NaCl, 50 mM $Na2HPO_4$, 2% SDS, 10 mM EDTA, 100 mM Tris, 250 mM imidazole, pH 4.3). For streptavidin purification, the pH of the eluted fractions were adjusted to pH 8.0. 50 μL streptavidin-sepharose beads (Thermo Scientific, Rockford, IL) was added to the elution to bind ubiquitinated proteins. After incubation on a rocking platform overnight at room temperature, streptavidin beads were pelleted and washed sequentially with 1.5 mL buffer C (8 M Urea, 200 mM NaCl, 2% SDS, 100 mM Tris, pH 8.0), buffer D (8 M Urea, 1.2 M NaCl, 0.2% SDS, 100 mM Tris, 10% EtOH, 10% Isopropanol, pH 8.0) and buffer E (8 M urea, 100 $NH_4HCO_3$, pH 8).

Sample digestion. Residual buffer E was removed and 200 μL of 50 mM $NH_4HCO_3$ was added to each sample, which were then reduced with dithiothreitol (final concentration 1 mM) for 30 minutes at 25° C. This was followed by 30 minutes of alkylation with 5 mM iodoacetamide in the dark. The samples were then digested with 1 μg of lysyl endopeptidase (Wako) at room temperature for 2 hours and further digested overnight with 1:50 (w/w) trypsin (Promega) at room temperature. Resulting peptides were acidified with 25 μL of 10% (v/v) formic acid (FA) and 1% (v/v) triflouroacetic acid (TFA) and desalted with a Sep-Pak C18 column (Waters). Briefly, the Sep-Pak column was washed with 1 mL of methanol and 1 mL of 50% (v/v) acetonitrile (ACN). Equilibration was performed with 2 rounds of 1 mL of 0.1% (v/v) TFA in water. The acidified peptides were then loaded and the column washed with 2 rounds of 1 mL 0.1% (v/v) TFA. Elution was carried out by 2 rounds of 50% (v/v) ACN (400 μL each) and the resulting peptide eluent dried under vacuum.

LC-MS/MS analysis. Liquid chromatography coupled to tandem mass spectrometry (LC-MS/MS) on an Orbitrap Fusion mass spectrometer (ThermoFisher Scientific, San Jose, CA) was performed at the Emory Integrated Proteomics Core (EIPC)[68,69]. The dried samples were resuspended in 10 μL of loading buffer (0.1% (v/v) formic acid, 0.03% (v/v) trifluoroacetic acid, 1% (v/v) acetonitrile), vortexed for 5 minutes and centrifuged down at maximum speed for 2 minutes. Peptide mixtures (2 μL) were loaded onto a 25 cm×75 μm internal diameter fused silica column (New Objective, Woburn, MA) self-packed with 1.9 μm C18 resin (Dr. Maisch, Germany). Separation was carried out over a 2-hour gradient by a Dionex Ultimate 3000 RSLCnano system at a flowrate of 350 nL/min. The gradient ranged from 3% to 80% (v/v) buffer B (buffer A: 0.1% (v/v) formic acid in water, buffer B: 0.1% (v/v) formic acid in ACN). In each cycle, the mass spectrometer performed a full MS scan followed by as many tandem MS/MS scans allowed within the 3-second time window (top speed mode). Full MS scans were collected in profile mode at 120,000 resolution at m/z 200 with an automatic gain control (AGC) of 200,000 and a maximum ion injection time of 50 ms. The full mass range was set from 400-1600 m/z. Tandem MS/MS scans were collected in the ion trap after higher-energy collisional dissociation (HCD) in the ion routing multipole. The precursor ions were isolated with a 0.7 m/z window and fragmented with 30% collision energy. The product ions were collected with the AGC set for 10,000 and the maximum injection time set to 35 ms. Previously sequenced precursor ions within +/−10 ppm were excluded from sequencing for 20 s using the dynamic exclusion parameters and only precursors with charge states between 2+ and 6+ were allowed.

Database search. All raw data files were processed using the Proteome Discoverer 2.0 data analysis suite (Thermo Scientific, San Jose, CA). The database was downloaded from Uniprot and consists of 90,300 human target sequences. Peptide matches were restricted to fully tryptic cleavage and precursor mass tolerances of +/−20 ppm. Dynamic modifications were set for methionine oxidation (+15.99492 Da), asaparagine and glutamine deamidation (+0.98402 Da), lysine ubiquitination (+114.04293 Da) and protein N-terminal acetylation (+42.03670). A maximum of 3 dynamic modifications were allowed per peptide and a static modification of +57.021465 Da was set for carbamidomethyl cysteine. The Percolator node within Proteome Discoverer was used to filter the peptide spectral match (PSM) false discovery rate to 1%[70].

Bioinformatics analysis. Ingenuity Pathway Analysis (IPA) software (http:/www.ingenuity.com) was used to map and identify the biological networks and molecular pathways with a significant proportion of genes having E6AP ubiquitination targets. Fisher exact test in Ingenuity Pathway Analysis software was used to calculate p-values for pathways and networks. The level of statistical significance was set at a p-value<0.05. IPA was also used to visualize the identified biological networks. Proteins identified by the OUT screen were also analyzed by the CRAPome database (http://www.crapome.org/).[28] CRAPome is based on data from interactome studies that carried out affinity purification under denaturing conditions. In contrast, the tandem purification for OUT screens was performed under more stringent denaturing conditions.

Lentiviral silencing of E6AP. Lentiviral GPIZ plasmids encoding shRNAs against E6AP (6 different shRNAs) were obtained from GE Dharmacon (Lafayette, CO), and lentiviruses were produced using the manufacturer's lentivurus packaging system and 293FT cells. HEK293 cells were infected with each lentivirus, followed by selection with puromycin for stable cell populations. The efficiency of gene silencing in each shRNA group was determined by immunoblotting using stable cell populations. For functional restoration, HEK293 cell population stably expressing anti-E6AP shRNA #1 was infected with the lentivirus packaged with pLenti6-Myc-wt E6AP.

In vitro assay to confirm the substrates of E6AP. All assays were set up in 30 μL TBS supplemented with 10 mM $MgCl_2$ and 1.5 mM ATP. In each UB transfer reaction, 5 μM of potential substrates (MAPK1, CDK1, CDK4, PRMT5, β-catenin, and UbxD8) were incubated with 1 μM wt Uba1, 5 μM wt UbcH7, 10 μM E6AP, and 20 μM wt UB for 2 hours at 30° C. The reactions were quenched by boiling in Laemmli buffer with BME, and analyzed by Western blotting probed with substrate-specific antibodies.

Co-immunoprecipitation and to confirm E6AP substrates. Transfection of pLenti-E6AP into the HEK293 cells was conducted with the Lipofectamine® 2000 according to the manufacturer's protocol. To immunoprecipitate substrate proteins, cells were treated with 10 μM MG132 (American Peptide, Sunnyvale, CA) for 90 min at 72-hour post-transfection. HEK293 cells (80-90% confluent monolayer in 75 $cm^2$ cell culture flask) expressing control plasmid, shE6AP, shE6AP+E6AP cDNA, and E6AP cDNA were washed twice with ice-cold PBS, pH 7.4. 1 mL ice-cold RIPA buffer was added to cell monolayer and incubated with cell for at 4° C. for 10 minutes. The cells were disrupted by repeated aspiration through a 21-gauge needle. The cell lysate was transferred to a 1.5 mL tube. The cell debris was pelleted by centrifugation at 13,000 rpm for 20 minutes at 4° C. and the supernatant was transferred to a 1.5 mL centrifuge tube and precleared by adding 1.0 μg of the appropriate control IgG (normal mouse or rabbit IgG corresponding to the host species of the primary antibody). 20 μL, of re-suspended volume of Protein A/G PLUS-agarose was added to the supernatant and incubation was continued for 30 minutes at 4° C. The agarose beads were pelleted by centrifugation at 350×g for 5 minutes at 4° C. From the cleared cell lysate, volume containing 2 mg total protein was transferred to a new tube. 30 μL (i.e., 6 μg) primary antibody was then added and incubation was continued for 1 hour at 4° C. After incubation, 50 μL of re-suspended volume of Protein A/G PLUS-Agarose was added. The tubes were capped and incubate at 4° C. on a rocking platform overnight. The agarose beads were pelleted by centrifugation at 350×g for 5 minutes at 4° C. The beads were then washed 4 times each time with 1.0 mL PBS. After the final wash, the beads were re-suspended in 40 μL 1×Laemmli buffer with BME. The samples were boiled for 5 minutes and analyzed by SDS-PAGE and Western blot probed with antibodies specific for the substrate proteins.

E6AP induced protein degradation. To examine the effects of E6AP on steady-state levels of the substrates, HEK293 cells ($5\times10^6$ cells) were transiently transfected with 0.5, 1, 2 and 4 μg pLenti-wt E6AP with Lipofactamine 2000. Cells were harvested at 48-hour post-transfection and the amount of substrate proteins in the cell lysate was assayed by immunoblotting with substrate-specific antibodies. For cycloheximide (CHX) chase assays, HEK293 cells ($5\times10^6$ cells) were transiently transfected with 4 μg empty pLenti or pLenti-E6AP plasmids. After 48 hours, cells were treated with 100 μg/mL CHX to block de novo protein synthesis and the cells were harvested after variable length of incubation time with CHX. The amount of substrate proteins in the cell were assayed by immunoblotting with antibodies against each substrate proteins. Protein levels were normalized to tubulin. Alternatively, CHX chase assays were performed on HEK293 cells stably expressing anti-E6AP shRNA to measure the effect of decreased expression of E6AP on substrate stability. Uncropped scans of the Western blots are presented in FIGS. 13-18.

REFERENCES

1. Hershko, A. & Ciechanover, A. The ubiquitin system. Annu Rev Biochem 67, 425-79 (1998).
2. Schulman, B. A. & Harper, J. W. Ubiquitin-like protein activation by E1 enzymes: the apex for downstream signalling pathways. Nat Rev Mol Cell Biol 10, 319-31 (2009).

3. Wenzel, D. M., Stoll, K. E. & Klevit, R. E. E2s: structurally economical and functionally replete. The Biochemical journal 433, 31-42 (2011).
4. Hatakeyama, S. & Nakayama, K. I. U-box proteins as a new family of ubiquitin ligases. Biochem Biophys Res Commun 302, 635-45 (2003).
5. Rotin, D. & Kumar, S. Physiological functions of the HECT family of ubiquitin ligases. Nat Rev Mol Cell Biol 10, 398-409 (2009).
6. Wenzel, D. M., Lissounov, A., Brzovic, P. S. & Klevit, R. E. UBCH7 reactivity profile reveals parkin and HHARI to be RING/HECT hybrids. Nature 474, 105-8 (2011).
7. Deshaies, R. J. & Joazeiro, C. A. RING domain E3 ubiquitin ligases. Annu Rev Biochem 78, 399-434 (2009).
8. Jin, J., Li, X., Gygi, S. P. & Harper, J. W. Dual E1 activation systems for ubiquitin differentially regulate E2 enzyme charging. Nature 447, 1135-8 (2007).
9. Frescas, D. & Pagano, M. Deregulated proteolysis by the F-box proteins SKP2 and beta-TrCP: tipping the scales of cancer. Nat Rev Cancer 8, 438-49 (2008).
10. Popovic, D., Vucic, D. & Dikic, I. Ubiquitination in disease pathogenesis and treatment. Nat Med 20, 1242-53 (2014).
11. Scheffner, M., Huibregtse, J. M., Vierstra, R. D. & Howley, P. M. The HPV-16 E6 and E6-AP complex functions as a ubiquitin-protein ligase in the ubiquitination of p53. Cell 75, 495-505 (1993).
12. Glessner, J. T. et al. Autism genome-wide copy number variation reveals ubiquitin and neuronal genes. Nature 459, 569-73 (2009).
13. Hogart, A., Wu, D., LaSalle, J. M. & Schanen, N. C. The comorbidity of autism with the genomic disorders of chromosome 15q11.2-q13. Neurobiol Dis 38, 181-91 (2010).
14. Kishino, T., Lalande, M. & Wagstaff, J. UBE3A/E6-AP mutations cause Angelman syndrome. Nat Genet 15, 70-3 (1997).
15. Matsuura, T. et al. De novo truncating mutations in E6-AP ubiquitin-protein ligase gene (UBE3A) in Angelman syndrome. Nat Genet 15, 74-7 (1997).
16. Scheffner, M., Werness, B. A., Huibregtse, J. M., Levine, A. J. & Howley, P. M. The E6 oncoprotein encoded by human papillomavirus types 16 and 18 promotes the degradation of p53. Cell 63, 1129-36 (1990).
17. Zhao, B. et al. Orthogonal Ubiquitin Transfer through Engineered E1-E2 Cascades for Protein Ubiquitination. Chemistry & Biology 19, 1265-77 (2012).
18. Liu, X. et al. Orthogonal ubiquitin transfer identifies ubiquitination substrates under differential control by the two ubiquitin activating enzymes. Nat Commun 8, 14286 (2017).
19. Lee, I. & Schindelin, H. Structural insights into E1-catalyzed ubiquitin activation and transfer to conjugating enzymes. Cell 134, 268-78 (2008).
20. Olsen, S. K. & Lima, C. D. Structure of a ubiquitin E1-E2 complex: insights to E1-E2 thioester transfer. Mol Cell 49, 884-96 (2013).
21. Chao, G. et al. Isolating and engineering human antibodies using yeast surface display. Nature protocols 1, 755-68 (2006).
22. Huang, L. et al. Structure of an E6AP-UbcH7 complex: insights into ubiquitination by the E2-E3 enzyme cascade. Science 286, 1321-6 (1999).
23. Tagwerker, C. et al. A tandem affinity tag for two-step purification under fully denaturing conditions: application in ubiquitin profiling and protein complex identification combined with in vivocross-linking. Molecular & cellular proteomics: MCP 5, 737-48 (2006).
24. Jacobson, A. D., MacFadden, A., Wu, Z., Peng, J. & Liu, C. W. Autoregulation of the 26S proteasome by in situ ubiquitination. Mol Biol Cell 25, 1824-35 (2014).
25. Zaaroor-Regev, D. et al. Regulation of the polycomb protein Ring1B by self-ubiquitination or by E6-AP may have implications to the pathogenesis of Angelman syndrome. Proc Natl Acad Sci USA 107, 6788-93 (2010).
26. Kumar, S., Talis, A. L. & Howley, P. M. Identification of HHR23A as a substrate for E6-associated protein-mediated ubiquitination. J Biol Chem 274, 18785-92 (1999).
27. Lee, S. Y. et al. Ube3a, the E3 ubiquitin ligase causing Angelman syndrome and linked to autism, regulates protein homeostasis through the proteasomal shuttle Rpn10. Cell Mol Life Sci 71, 2747-58 (2014).
28. Mellacheruvu, D. et al. The CRAPome: a contaminant repository for affinity purification-mass spectrometry data. Nat Methods 10, 730-6 (2013).
29. Schwanhausser, B. et al. Global quantification of mammalian gene expression control. Nature 473, 337-42 (2011).
30. Fujioka, A. et al. Dynamics of the Ras/ERK MAPK cascade as monitored by fluorescent probes. J Biol Chem 281, 8917-26 (2006).
31. Merbl, Y. & Kirschner, M. W. Large-scale detection of ubiquitination substrates using cell extracts and protein microarrays. Proc Natl Acad Sci USA 106, 2543-8 (2009).
32. Shimoji, T. et al. Identification of annexin A1 as a novel substrate for E6AP-mediated ubiquitylation. J Cell Biochem 106, 1123-35 (2009).
33. Tan, M. K., Lim, H. J., Bennett, E. J., Shi, Y. & Harper, J. W. Parallel SCF adaptor capture proteomics reveals a role for SCFFBXL17 in NRF2 activation via BACH1 repressor turnover. Mol Cell 52, 9-24 (2013).
34. Pierce, N. W., Kleiger, G., Shan, S. O. & Deshaies, R. J. Detection of sequential polyubiquitylation on a millisecond timescale. Nature 462, 615-9 (2009).
35. Emanuele, M. J. et al. Global identification of modular cullin-RING ligase substrates. Cell 147, 459-74 (2011).
36. Yen, H. C. & Elledge, S. J. Identification of SCF ubiquitin ligase substrates by global protein stability profiling. Science 322, 923-9 (2008).
37. Yen, H. C., Xu, Q., Chou, D. M., Zhao, Z. & Elledge, S. J. Global protein stability profiling in mammalian cells. Science 322, 918-23 (2008).
38. Xu, G. & Jaffrey, S. R. The new landscape of protein ubiquitination. Nat Biotechnol 29, 1098-100 (2011).
39. Kim, W. et al. Systematic and quantitative assessment of the ubiquitin-modified proteome. Mol Cell 44, 325-40 (2011).
40. Sarraf, S. A. et al. Landscape of the PARKIN-dependent ubiquitylome in response to mitochondrial depolarization. Nature 496, 372-6 (2013).
41. O'Connor, H. F. et al. Ubiquitin-Activated Interaction Traps (UBAITs) identify E3 ligase binding partners. EMBO Rep 16, 1699-712 (2015).
42. Mark, K. G., Loveless, T. B. & Toczyski, D. P. Isolation of ubiquitinated substrates by tandem affinity purification of E3 ligase-polyubiquitin-binding domain fusions (ligase traps). Nat Protoc 11, 291-301 (2016).
43. Mark, K. G., Simonetta, M., Maiolica, A., Seller, C. A. & Toczyski, D. P. Ubiquitin ligase trapping identifies an SCF(Saf1) pathway targeting unprocessed vacuolar/lysosomal proteins. Mol Cell 53, 148-61 (2014).
44. Zhuang, M., Guan, S., Wang, H., Burlingame, A. L. & Wells, J. A. Substrates of IAP ubiquitin ligases identified with a designed orthogonal E3 ligase, the NEDDylator. Mol Cell 49, 273-82 (2013).
45. Kuslansky, Y. et al. Ubiquitin ligase E6AP mediates nonproteolytic polyubiquitylation of beta-catenin independent of the E6 oncoprotein. J Gen Virol 97, 3313-3330 (2016).
46. Jang, K. W. et al. Ubiquitin ligase CHIP induces TRAF2 proteasomal degradation and NF-kappaB inactivation to regulate breast cancer cell invasion. J Cell Biochem 112, 3612-20 (2011).
47. Zuin, A. et al. Rpn10 monoubiquitination orchestrates the association of the ubiquilin-type DSK2 receptor with the proteasome. Biochem J 472, 353-65 (2015).
48. Altun, M. et al. Muscle wasting in aged, sarcopenic rats is associated with enhanced activity of the ubiquitin proteasome pathway. J Biol Chem 285, 39597-608 (2010).
49. Kamadurai, H. B. et al. Insights into ubiquitin transfer cascades from a structure of a UbcH5B approximately ubiquitin-HECT(NEDD4L) complex. Mol Cell 36, 1095-102 (2009).
50. Kim, H. C., Steffen, A. M., Oldham, M. L., Chen, J. & Huibregtse, J. M. Structure and function of a HECT domain ubiquitin-binding site. EMBO reports 12, 334-41 (2011).
51. Maspero, E. et al. Structure of a ubiquitin-loaded HECT ligase reveals the molecular basis for catalytic priming. Nat Struct Mol Biol 20, 696-701 (2013).
52. Ogunjimi, A. A. et al. Regulation of Smurf2 ubiquitin ligase activity by anchoring the E2 to the HECT domain. Mol Cell 19, 297-308 (2005).
53. Cong, L. et al. Multiplex genome engineering using CRISPR/Cas systems. Science 339, 819-23 (2013).
54. Olzmann, J. A., Richter, C. M. & Kopito, R. R. Spatial regulation of UBXD8 and p97/VCP controls ATGL-mediated lipid droplet turnover. Proc Natl Acad Sci USA 110, 1345-50 (2013).
55. Pal, P. et al. E3 ubiquitin ligase E6AP negatively regulates adipogenesis by downregulating proadipogenic factor C/EBPalpha. PLoS One 8, e65330 (2013).
56. Wolyniec, K. et al. E6AP ubiquitin ligase regulates PML-induced senescence in Myc-driven lymphomagenesis. Blood 120, 822-32 (2012).
57. Levav-Cohen, Y. et al. E6AP is required for replicative and oncogene-induced senescence in mouse embryo fibroblasts. Oncogene 31, 2199-209 (2012).
58. Wolyniec, K., Levav-Cohen, Y., Jiang, Y. H., Haupt, S. & Haupt, Y. The E6AP E3 ubiquitin ligase regulates the cellular response to oxidative stress. Oncogene 32, 3510-9 (2013).
59. Stopa, N., Krebs, J. E. & Shechter, D. The PRMT5 arginine methyltransferase: many roles in development, cancer and beyond. Cell Mol Life Sci 72, 2041-59 (2015).
60. Rangasamy, S., D'Mello, S. R. & Narayanan, V. Epigenetics, autism spectrum, and neurodevelopmental disorders. Neurotherapeutics 10, 742-56 (2013).
61. Lv, J., Xin, Y., Zhou, W. & Qiu, Z. The epigenetic switches for neural development and psychiatric disorders. J Genet Genomics 40, 339-46 (2013).
62. Copeland, R. A. Molecular pathways: protein methyltransferases in cancer. Clin Cancer Res 19, 6344-50 (2013).
63. Beaudenon, S. & Huibregtse, J. M. High-level expression and purification of recombinant E1 enzyme. Methods Enzymol 398, 3-8 (2005).
64. French, M. E., Kretzmann, B. R. & Hicke, L. Regulation of the RSPS ubiquitin ligase by an intrinsic ubiquitin-binding site. The Journal of biological chemistry 284, 12071-9 (2009).
65. Yin, J., Lin, A. J., Golan, D. E. & Walsh, C. T. Site-specific protein labeling by Sfp phosphopantetheinyl transferase. Nature Protocols 1, 280-285 (2006).
66. Gietz, R. D. & Woods, R. A. Transformation of yeast by lithium acetate/single-stranded carrier DNA/polyethylene glycol method. Methods in enzymology 350, 87-96 (2002).
67. Gietz, R. D. & Schiestl, R. H. Applications of high efficiency lithium acetate transformation of intact yeast cells using single-stranded nucleic acids as carrier. Yeast 7, 253-63 (1991).
68. Cutler, A. A. et al. Biochemical isolation of myonuclei employed to define changes to the myonuclear proteome that occur with aging. Aging Cell 16, 738-749 (2017).
69. Comstra, H. S. et al. The interactome of the copper transporter ATP7A belongs to a network of neurodevelopmental and neurodegeneration factors. Elife 6, e24722 (2017).
70. Kall, L., Canterbury, J. D., Weston, J., Noble, W. S. & MacCoss, M. J. Semi-supervised learning for peptide identification from shotgun proteomics datasets. Nat Methods 4, 923-5 (2007).

Example II—Identifying the Substrate Proteins of U-Box E3s E4B and CHIP by Orthogonal Ubiquitin Transfer Reference is made to Bhuripanyo et al., "Identifying the substrate protein of U-box E3s E4B and CHIP by orthogonal ubiquitin transfer," Science Advances, 2018; 4:e1701393, 3 Jan. 2018, pages 1-16 (hereinafter Bhuripanyo et al. 2018), the content of which is incorporated herein by reference in its entirety.

Abstract

E3 ubiquitin (UB) ligases E4B and CHIP use a common U-box motif to transfer UB from E1 and E2 enzymes to their substrate proteins and regulate diverse cellular processes. To profile their ubiquitination targets in the cell, we used phage display to engineer E2-E4B and E2-CHIP pairs that were free of cross-reactivity with the native UB transfer cascades. We then used the engineered E2-E3 pairs to construct "orthogonal UB transfer (OUT)" cascades so that a mutant UB (xUB) could be exclusively used by the engineered E4B or CHIP to label their substrate proteins. Purification of xUB-conjugated proteins followed by proteomics analysis enabled identification of hundreds of potential substrates of E4B and CHIP in HEK293 cells. Kinase MAPK3, methyltransferase PRMT1, and phosphatase PPP3CA were identified as the shared substrates of the two E3s. Phosphatase PGAMS and deubuiqutinase OTUB1 were confirmed as E4B substrates, and β-catenin and CDK4 as CHIP substrates. Based on the CHIP-CDK4 circuit identified by OUT, we revealed that CHIP signals CDK4 degradation in response to ER stress.

Introduction

E3 ubiquitin (UB) ligases CHIP and E4B are on the front line of defense against misfolded or damaged proteins in the cell by tagging them with UB and channeling them to the proteasome for degradation (1-3). The two E3s use a signature U-box domain to mediate UB transfer from an E1-E2 relay to their target proteins (4, 5). They play a key role in protein quality control; inadequate degradation of their substrates such as tau, huntingtin, and α-synuclein triggers Alzheimer's, Huntington's and Parkinson's diseases, respectively (6, 7). Both E3s can elongate UB chains appended to cellular proteins by other E3s, a property termed E4 ligation (8, 9). For examples, the E3-E4 pair of parkin-CHIP ubiquitinates Pael receptor (Pael-R) and signals its degradation to relieve ER stress in neuronal cells, and the E3-E4 pair of Mdm2-E4B induces p53 degradation and promotes the survival of cancer cells (10, 11). The multifaceted roles of CHIP and E4B demand an investigation of their substrate profiles to reveal their roles in cell regulation.

CHIP and E4B run the last leg of the E1-E2-E3 relay in transferring UB to the cellular proteins. The large diversity of E3s (>600 in human cells) makes it a significant challenge to identify the direct substrates of a specific E3 in the cell. We developed a method termed "orthogonal UB transfer (OUT)" to profile E3 substrate specificity (12). OUT is to transfer an engineered UB (xUB) through an engineered cascade (xE1-xE2-xE3) to the substrate proteins of a specific E3 ("x" designates engineered UB or UB transferring enzymes). To implement OUT, we need to engineer xUB-xE1, xE1-xE2 and xE2-xE3 pairs that are orthogonal (free of cross-reactivity) with native UB and the E1, E2 and E3 enzymes. We previously showed that we could generate xUB-xE1 and xE1-xE2 pairs with yeast E1 and E2, Uba1 and Ubc1 (12). Here we report that we can engineer xE2-xE3 pairs with E4B and CHIP to assemble full-length OUT cascades with the two E3s. We used the OUT cascades to identify the ubiquitination targets of E4B and CHIP in HEK293 cells. Based on the substrate profiles generated by OUT, we found CHIP plays an important role in regulating CDK4 activity during ER stress.

Results

Constructing an xUba1-xUbcH5b pair for the OUT cascade. We previously reported that an engineered yeast E1 (xUba1) could activate a UB mutant (xUB), and transfer it to an engineered yeast E2 (xUbc1) (Table 2 and FIG. 30).

TABLE 2

Mutants of UB, E1, E2 and E3 for the assembly of the OUT cascade with E4B and CHIP.

| | |
|---|---|
| xUB (human) | R42E, R72E |
| xE1 | |
| xUba1 (yeast) | Q576R, S589R, D591R, E1004K, D1014K, E1016K |
| xUba1 (human) | Q608R, S621R and D623R, E1037K, D1047K, E1049K |
| xUba1 (UFD) (human) | E1037K, D1047K, E1049K |
| xE2 | |
| xUbc1 (yeast) | K5D, R6E, K9E, E10Q, Q12L |
| xUbcH5b (human) | K4E, K8E |
| xE3 | |
| xE4B (fE4B-KB2) | R1233K, L1236I, D1238H |
| xE4B (fE4B-KB12) | R1233K, L1236I, D1238R |
| xCHIP (CHIP-KB2) | C213K, G214D, K215P, S217M, F218H, E219T |
| xCHIP (CHIP-KB12) | C213K, G214D, K215P, S217M, F218R, E219T |

Figure 30:
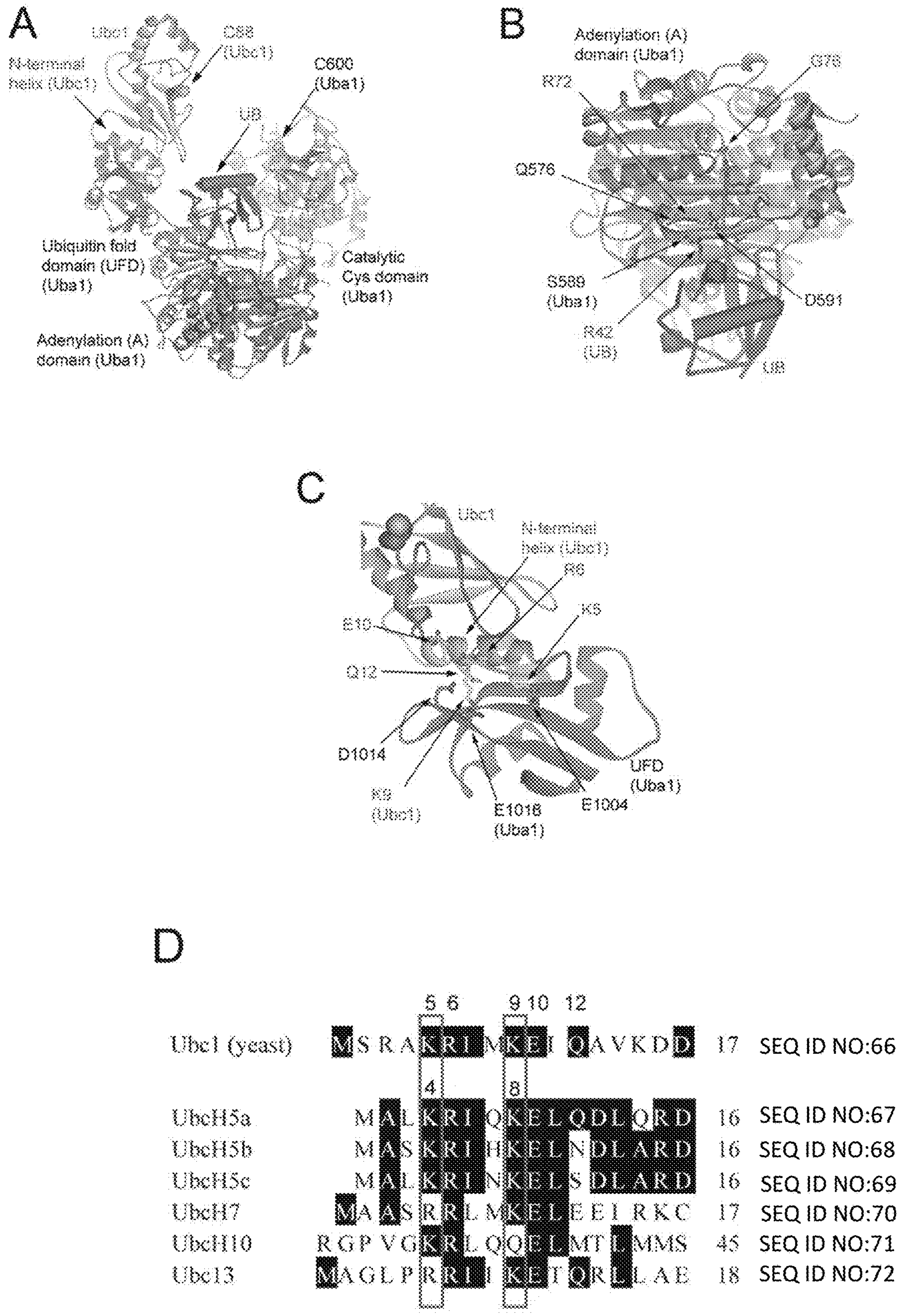
FIG. 30. Design of the xUB-xUba1 and xUba1-xUbcH5b pairs for the OUT cascade. (A) Crystal structure of the yeast E1 Uba1 in complex with UB (PDB ID 3CMM). The binding of yeast E2 Ubc1 with Uba1 was modeled in the structure (63). Cys600 and Cys88 are the catalytic Cys residues for UB conjugation in Uba1 and Ubc1, respectively. To initiate UB transfer, UB is first bound to the adenylation domain of Uba1. The energy of ATP hydrolysis is then used to form a thioester conjugate between the UB C-terminal carboxylate and the catalytic Cys residue of Uba1. UB in the UB~Uba1 conjugate ("~" designates the thioester bond) is then transferred to a catalytic Cys residue of E2 that is bound to the UB fold domain (UFD) of Uba1. (B) UB binding with key residues in the adenylation (A) domain of Uba1. R42 and R72 in UB were mutated to Glu to generate xUB, and correspondingly, Q576, Ser589 and D591 in Uba1 were mutated to Arg to generate xUba1 (A) for activation of xUB (12). xUB could react with xUba1 (A) in the presence of ATP to form xUB~xUba1 (A) thioester conjugates. In contrast, xUB could not be activated with wt Uba1, and vice versa, wt UB was not reactive with xUba1 (A). So the xUB-xUba1 (A) and wt UB-wt Uba1 pairs were orthogonal to each other. (C) Binding of the N-terminal helix of Ubc1 with the UFD domain of Uba1. To generate orthogonal xE1-xE2 pair, we introduced mutations E1004K, D1014K, E1016K into the UFD domain of yeast Uba1 to construct mutant xUba1 (UFD) (12). It could still activate wt UB to form wtUB-xUba1 (UFD) thioester conjugates but it was incapable of transferring xUB to wt Ubc1 since the UFD domain mutations blocked the binding of the N-terminal helix of the E2 enzymes. To restore E2 interaction with xUba1 (UFD), we used phage selection to screen a Ubc1 library with randomized N-terminal helix residues. We identified a Ubc1 mutant (xUbc1) with mutations K5D, R6E, K9E, E10Q, Q12L that could restore wt UB transfer from xUba1 (UFD) to xUba1 (12). By combining the mutations in xUba1 (A) and xUba1 (UFD), the newly generated xUba1 mutant could transfer xUB to xUbc1 for the formation of xUB~xUbc1 conjugate. xUB could not be transferred by xUba1 to wt E2 enzymes. So the xUba1-xUbc1 pair was orthogonal to the wt E1-E2 pairs in xUB transfer. (D) Alignment of the peptide sequences of the N-terminal helices of the E2 enzymes. K4 and K8 of UbcH5b were mutated to Glu to generate xUbcH5b for pairing with human xUba1.
Figure 31:
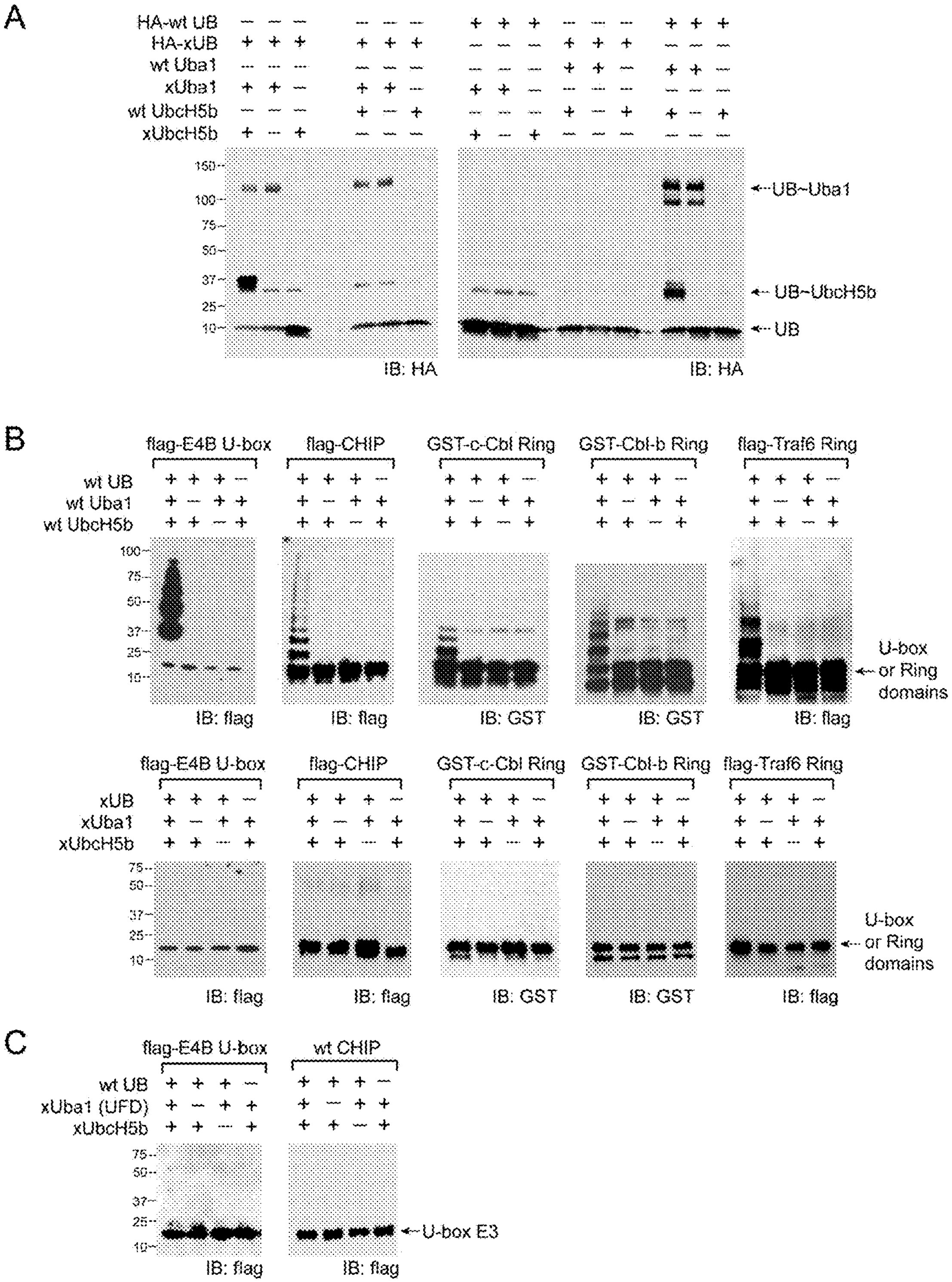
FIG. 31. xUB transfer through the human xUba1-xUbcH5b pair. (A) xUB could be activated by xUba1 to form xUB~xUba1 thioester and be further transferred to xUbcH5b to form the xUB~xUbcH5b conjugate. Crossing xUba1 with wt UbcH5b would only generate xUB~xUba1 but the transfer of xUB to wt UbcH5b was blocked. Neither could xUB be activated by wt Uba1, nor wt UB be activated by xUba1. (B) xUB transfer through xUba1-xUbcH5b to the wt U-box or Ring domains of the E3s E4B, CHIP, c-Cbl, Cbl-b, and Traf6 was blocked. In contrast, wt UB transfer through wt Uba1-UbcH5b pair to the E3s was quite efficient. (C) wt UB transfer through xUba1 (UFD)-xUbcH5b pair to the U-box domains of E4B and CHIP was also blocked suggesting a defective E2-E3 interface between xUbcH5b and wt U-box domains.

We could thus use xUba1 and xUbc1 to assemble a two-step OUT cascade for xUB transfer (12). Based on the sequence homology between the human and yeast E1s, we generated human xUba1 by incorporating mutations Q608R, S621R and D623R into the adenylation domain, and E1037K, D1047K and E1049K into the UFD domain of human Uba1 (Table 2). This human xUba1 activates xUB to form xUB~xUba1 thioester conjugates (FIG. 31A). We also introduced mutations K4E and K8E into UbcH5b based on the mutations in yeast xUbc1, and found the UbcH5b mutant (xUbcH5b) could accept xUB from xUba1 (FIGS. 30D and 31A). This human xUba1-xUbcH5b pair did not cross-react with either native protein complement—Western blots of the cross over reaction showed that xUB could not be activated by the wt human Uba1, and vice versa, wt UB could not be activated by human xUba1. Furthermore, due to the mutations in the UFD domain, xUB could not be transferred from xUba1 to wt UbcH5b (FIG. 31A). Thus, the activity of human xUba1-xUbcH5b pair is completely orthogonal to the native E1-E2 pair in xUB transfer. In a recent report, we incorporated adenylation domain mutations into the two human E1s (Uba1 and Uba6) to activate xUB. We then paired xUB with either Uba1 or Uba6 mutant to differentiate the downstream ubiquitination targets of the two E1 enzymes(13).

Figure 32:
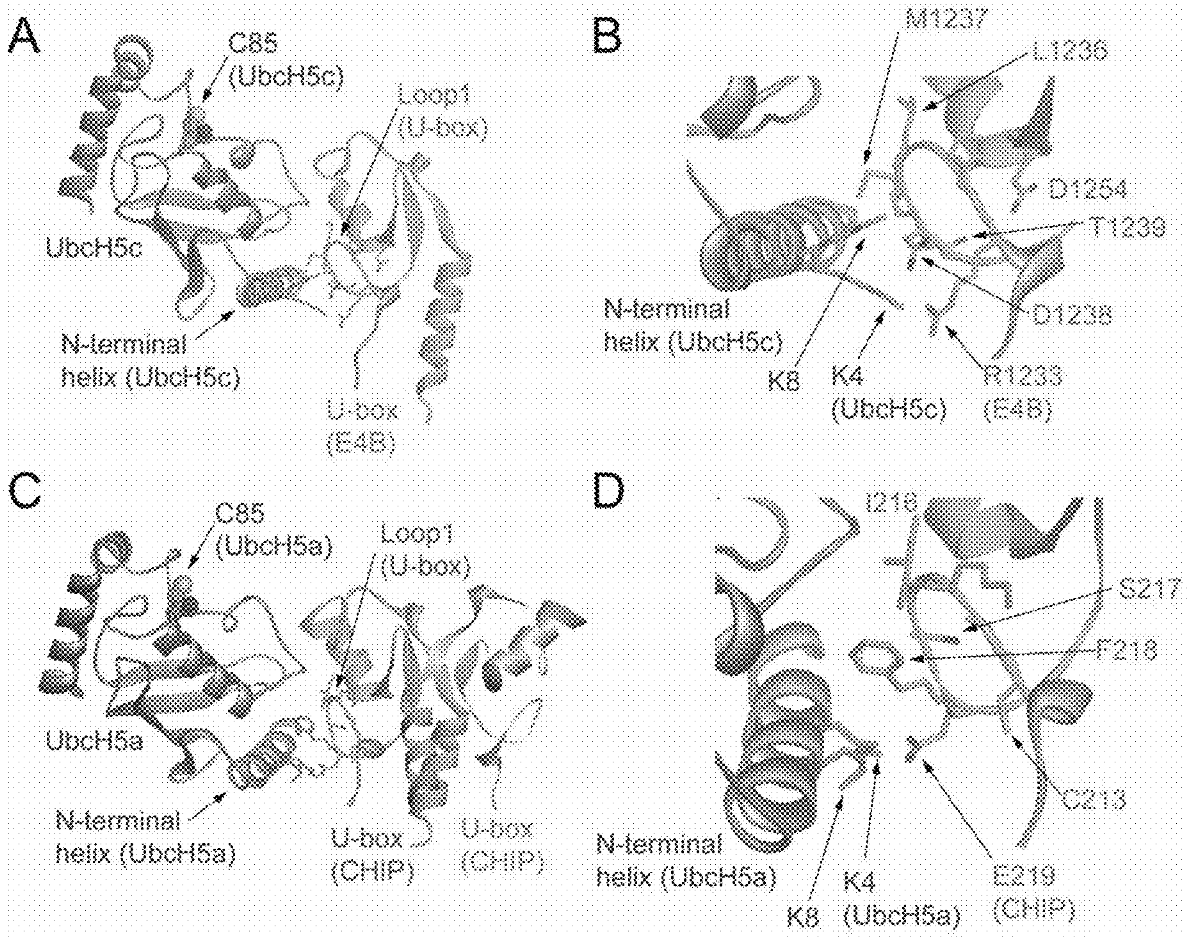
FIG. 32. Structure analysis of the U-box domains of E4B and CHIP interacting with the UbcH5c and UbcH5a, respectively. (A) Crystal structure of UbcH5c in complex with the U-box domain of E4B (PDB ID 3L1Z) (16). Cys85 is the catalytic Cys for UB conjugation in UbcH5c. N-terminal helix of UbcH5c interacts with loop1 of the U-box domain of E4B. (B) Interaction between K4 and K8 of UbcH5c with the loop1 residues in the U-box domain of E4B. K4 and K8 in UbcH5b were mutated to Glu to generate xUbcH5b and they mainly engage loop1 residues R1233, L1236, M1237, D1238, and T1239 of the U-box. The ε-$NH_2$ of K8 of UbcH5c is 3.5 Å away from the carboxylate oxygen of D1238 of the U-box; the two groups may interact by a salt bridge or a hydrogen bond. The sidechain of K8 is also close to L1236 and M1237, which are 5-6 Å away. The ε-$NH_2$ of K4 may be engaged in a salt bridge interaction with D1238 of the U-box loop1, and/or interact with nearby R1233 and T1239 (<6 Å). The hydroxyl group of the T1239 sidechain may bind to the carboxylate of D1254 with hydrogen bonding interactions to stabilized the U-box fold. Based on the structural analysis, U-box residues R1233, L1236, M1237, D1238 and T1239 were randomized to construct the U-box library for phage selection. (C) Crystal structure of UbcH5a binding to the homodimer of the U-box domain of CHIP (PDB ID 2OXQ) (18). Cys85 is the site of UB conjugation in UbcH5a. The two CHIP U-box domains in the dimer are shown in green and orange, respectively. (D) Interaction between K4 and K8 of UbcH5a with loop 1 of CHIP U-box is similar to UbcH5c interacting with the E4B U-box. E219 in CHIP is sandwiched between K4 and K8 residues of UbcH5a and may play a major role in binding to E2. Residues between Cys213 and Glu219 were replaced with the corresponding loop1 residues in the KB2 and KB12 mutants of E4B U-box to generate CHIP-KB2 and CHIP-KB12 to restore CHIP interaction with xUbcH5b.

Engineering an xUbaH5b-xE4B pair for OUT. E4B and CHIP engage UB~E2 with their C-terminal U-box domains (5). U-boxes are 70-residue domains that share a similar fold to the Ring domains found in the majority of E3s (4, 14, 15). Both Ring and U-box domains bind the N-terminal helix of the E2 with residues in loop1 (16-20) (FIG. 32). The key difference between the two is that the Ring domain relies on the chelation with two $Zn^{2+}$ atoms to stabilize its fold while the U-box domain relies on multiple hydrogen bonding and salt bridge interactions to fold properly (15). We found xUB could not be transferred to the U-box domain of E4B, full-length CHIP, or the Ring domains of E3s c-Cbl, Cbl-b, or Traf6 through the xUba1-xUbcH5b pair (FIG. 31B) (17, 19, 21). Presumably, the mutations in the N-terminal helix of xUbcH5b (K4E and K8E) block the interaction of E2 with the wt U-box. To confirm this, we generated a Uba1 mutant xUba1 (UFD) that has a wt adenylation domain to activate wt UB, but a mutated UFD domain to enable UB transfer to xUbcH5b (FIG. 30 and Table 2). We found xUba1 (UFD) could load wt UB onto xUbcH5b, but xUbcH5b could not transfer wt UB to CHIP or the U-box of E4B (FIG. 31C). This proves the K4E and K8E mutations in the N-terminal helix of xUbcH5b blocked UB transfer from xE2 to U-box E3s.

The crystal structures of E4B U-box in complex with UbcH5c, and CHIP U-box in complex with UbcH5a both suggest an important role for E2 residues K4 and K8 in binding the U-box loop1 residues (FIG. 32) (16, 18). Since the E2-E3 interface is dynamic, the crystal structures serve as guidelines for interactions that may form in the solution (22, 23). In the complex of UbcH5c with E4B U-box, K4 and K8 of E2 mainly engage loop1 residues R1233, L1236, M1237, D1238, and T1239 of the U-box (FIG. 32A and S3B) (16). We thus surmised that a U-box library of E4B with randomized residues at these sites could be used in combination with phage display to identify U-box mutants with restored UB transfer from xUbcH5b.

Figure 19:
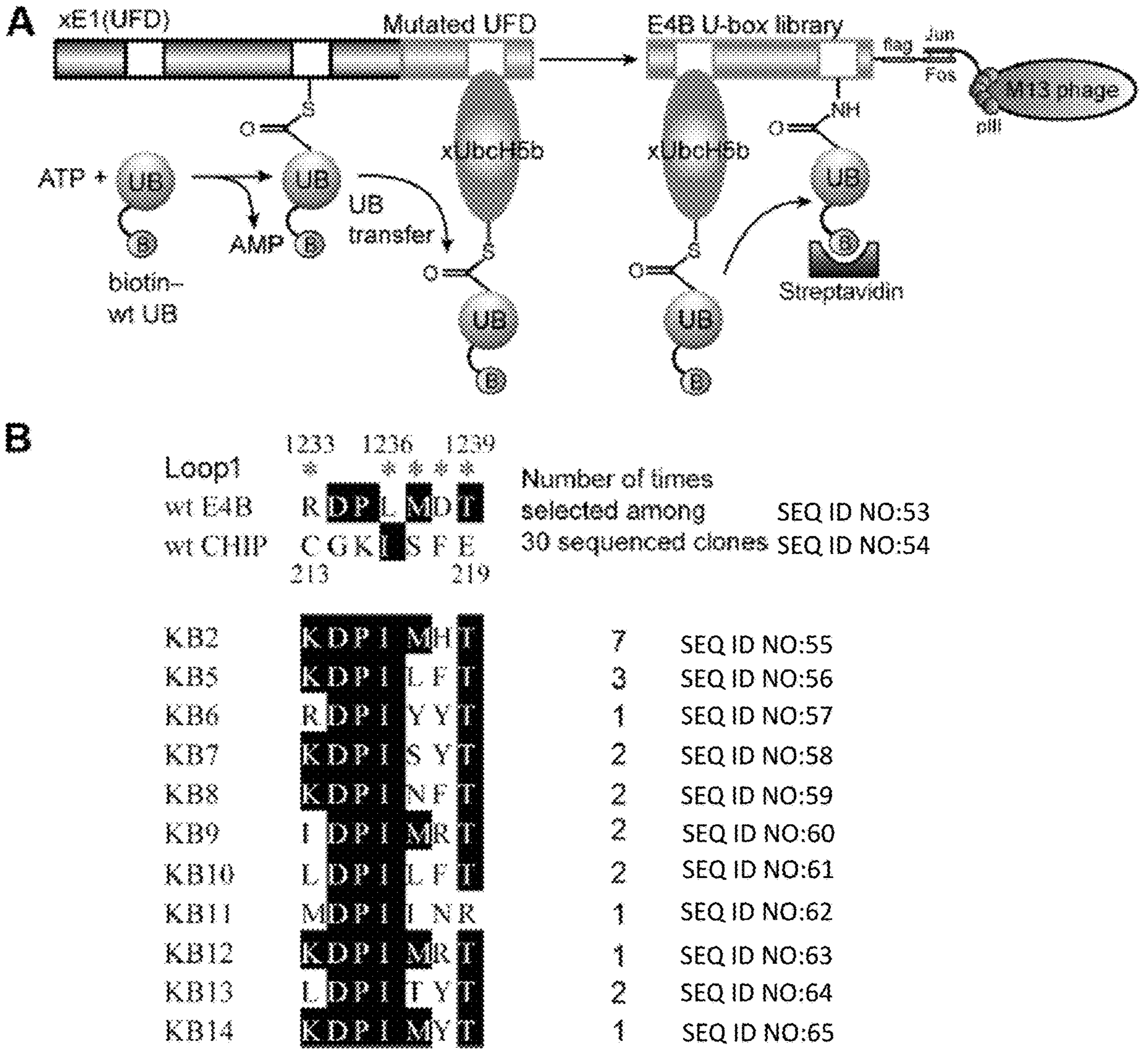
FIG. 19. Phage selection for orthogonal xUbcH5b-xU-box pair for E4B. (A) wt UB labeled with biotin (biotin-wt UB) was activated by xUba1 (UFD) and loaded on xUbcH5b. The U-box library of E4B was displayed on the surface of M13 phage. Phage displaying U-box mutants reactive with xUbcH5b were conjugated with biotin-UB and selected by binding to streptavidin. (B) Sequence alignment of U-box mutants of E4B from phage selection. Sites of randomized residues in the loop1 of the E4B U-box are marked by red asterisks. After five rounds of selection, 30 phage clones were sequenced; the alignment of the sequences showed the phage library was converged to KB2 and other highly homologous clones.
Figure 33:
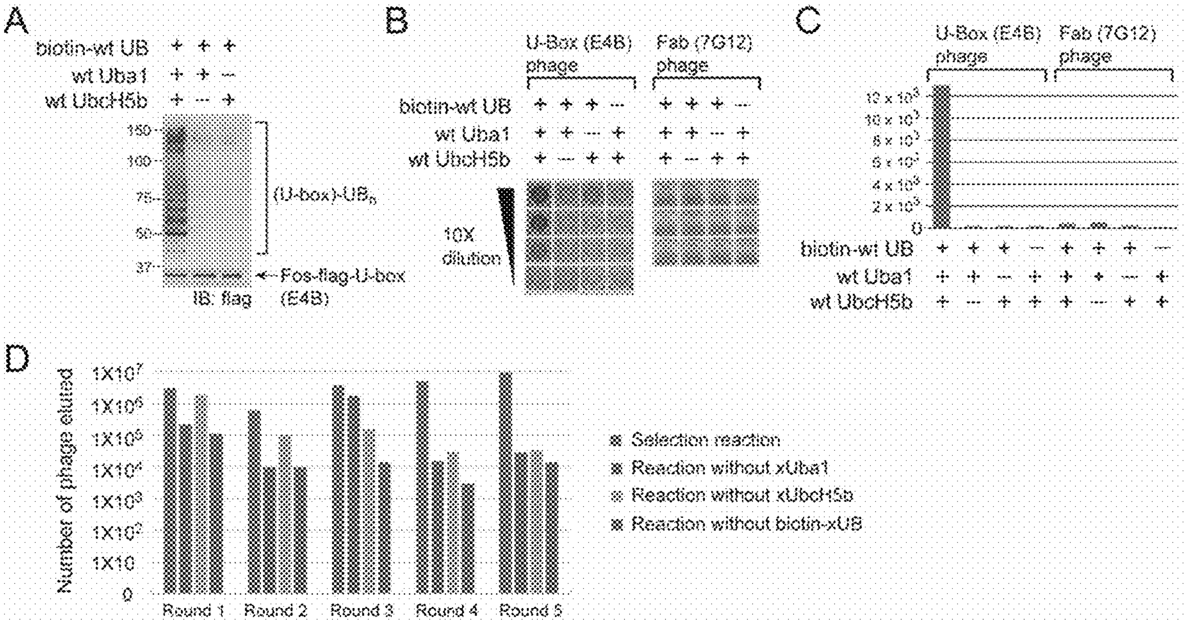
FIG. 33. Model selection of E4B U-box domain displayed on M13 phage. (A) E4B U-box retained its activity upon displaying on M13 phage surface as a fusion with the Fos peptide. wt U-box domain anchored on phage surface could be ubiquitinated by wt UB through the wt Uba1-UbcH5b pair with high efficiency. (B) Phage ELISA to measure the efficiency of phage selection based on UB transfer. M13 phage displaying wt U-box domain of E4B were added to a UB loading reaction including biotin-wt UB, wt Uba1 and UbcH5b. Control reactions were set up to exclude either Uba1 or UbcH5b from the reaction mixture. After the reaction, the phage mixture was added to the 96-well plate coated with streptavidin. Serial 10-fold dilution was carried out across the plate. The plate was washed and the amount of biotin-labeled phage bound to the streptavidin plate was revealed by binding to a mouse anti-phage antibody followed by an anti-mouse IgG antibody conjugated to horseradish peroxidase (HRP). Development of the plate with a chromogenic substrate suggested that the amount of phage bound to the streptavidin plate after biotin-UB loading was more than 100-fold higher than the controls missing wt Uba1, UbcH5b or biotin-wt UB in the reaction. In another control, phage displaying the Fab fragment of the 7G12 antibody were used (64) and ELISA showed the phage could not be loaded with biotin-UB after incubation with wt Uba1 and UbcH5b. (C) Model selection of phage displaying the U-box domain of E4B after biotin-UB transfer. Similar to (B), after the UB loading reaction, phage were bound to the streptavidin plate. The plate was washed and the phage were eluted by dithiothreitol (DTT) that would cleave the disulfide bond between the Jun and Fos peptide for U-box anchoring on phage surface. The numbers of phage eluted from the biotin-UB loading reaction and controls were determined by phage titering. Results showed that the number of phage eluted from the UB loading reaction with wt Uba1 and UbcH5b was at least 200-fold higher than the number of phage eluted from the control reactions missing either wt Uba1 or UbcH5b. Furthermore, when phage displaying the Fab fragment of the 7G12 antibody were mock reacted with biotin-UB and the wt Uba1-UbcH5b pair, no phage enrichment was found comparing to controls without wt Uba1 or UbcH5b. Such results demonstrated that phage selection based on UB transfer was targeting the U-box domains on phage. (D) Phage library of the E4B U-box underwent five round of selection based on biotin-UB transfer through the xUba1 (UFD)-xUbcH5b pair. Control reactions without xUba1 (UFD), xUbcH5b or biotin-wt UB were set up. As the selection proceeded, there was an increasing difference in the numbers of phage eluted from the selection and control reactions.

The E4B U-box functions as a monomer, hence a library of this domain could be displayed on T7 phage to select for enhanced interaction with wt UbcH5c based on UB transfer (14, 24). Encouraged by these reports, we adopted a similar strategy to select for U-box mutants based on UB transfer from xUbcH5b. In the selection scheme, we used xUba1 (UFD) to load biotin-labeled wt UB (biotin-UB) onto xUbcH5b (FIG. 19A). We then reacted the biotin-UB~xUbcH5b conjugate with the E4B U-box library displayed on the phage surface. U-box mutants that were recognized by xUbcH5b would be covalently conjugated with biotin-UB and the corresponding phage particles selected by affinity binding with streptavidin. We found the E4B U-box could be displayed well on M13 phage and it was highly active in auto-ubiquitination with wt UbcH5b (FIG. 33A). We also used model selection to confirm that wt U-box displayed on phage could be selected with high efficiency (FIGS. 33B and 33C).

Figure 20:
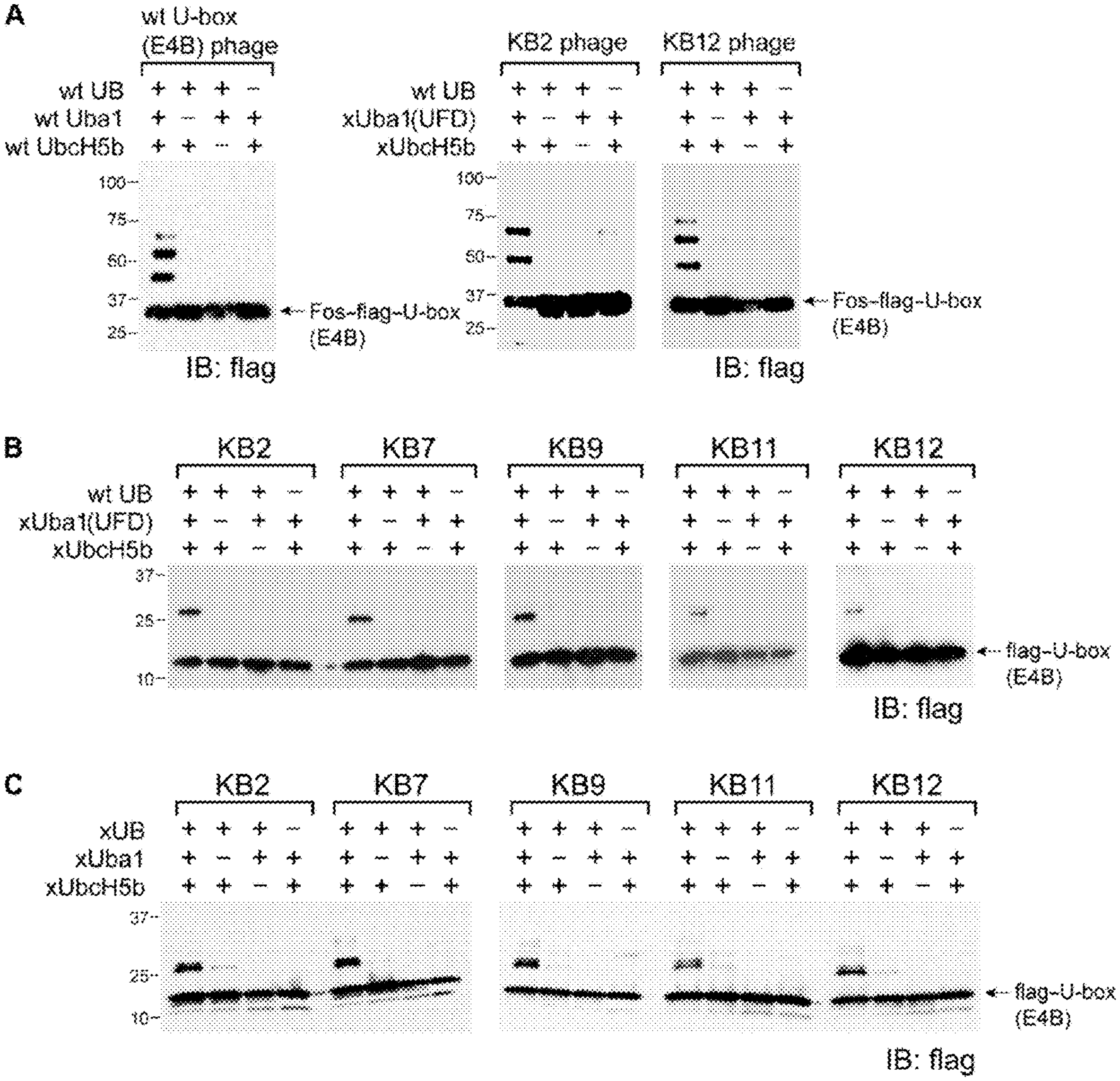
FIG. 20. Confirmation of the activity of the selected E4B U-box mutants in mediating UB transfer with xUbcH5b. (A) wt UB could be efficiently transferred through xUba1 (UFD)-xUbcH5b pair to the KB2 and KB12 mutants displayed on the phage surface. wt UB transfer through the wt Uba1-UbcH5b pair to wt U-box of E4B on phage surface was set up as a control. (B) U-box mutants KB2, KB7, KB9, KB11 and KB12 from phage selection were expressed as fusions with a flag tag, and their auto-ubiquitination with wt UB though the xUba1 (UFD)-xUbcH5b pair were analyzed by Western blots. (C) Similar to (B), U-box mutants were subjected to xUB transfer through the xUba1-xUbcH5b pair. In both cases, efficient modification of the U-box by wtUB and xUB was observed. Reactions were stopped at the stage of mono-ubiquitination to compare the reaction efficiency among various U-box mutants.

We carried out five rounds of phage selection on the E4B U-box library. As the selection proceeded, we observed a gradual increase in the number of phage eluted from the biotin-UB loading reaction compared to the controls with either xUba1 (UFD) or xUbcH5b missing from the reaction (FIG. 33D). Sequencing of the U-box clones from the 5$^{th}$ round revealed a clear pattern of convergence (FIG. 19B). Among the 30 clones sequenced, KB2 appeared 7 times and KB5, KB7 and KB8 homologous to KB2 appeared 2 or 3 times. The most significant change in the selected clones was that the negatively charged D1238 in wt U-box was replaced with positive charged His or Arg, a change that matched K4E and K8E mutations in xUbcH5b by restoring charge complementarity at the E2-U-box interface. Additionally, R1233 was frequently converted to Lys, and L1236 almost uniformly converted to Ile. The same L12361 mutation was enriched by T7 phage selection to enhance UB transfer from wt UbcH5c to E4B U-box (24). In the other two randomized positions, M1236 and T1239, wt residues dominated in the selected pool. T1239 was almost never changed, suggesting its interaction with D1254 on the opposing helix might be important for U-box structure and activity (FIG. 32B). We prepared phage with selected clones KB2 and KB12 and found the U-box mutants displayed on phage could be efficiently conjugated with biotin-UB transferred through the xUba1 (UFD)-xUbcH5b pair (FIG. 20A). This implies the U-box mutants were selected based on catalytic UB transfer to the phage library.

Figure 21:
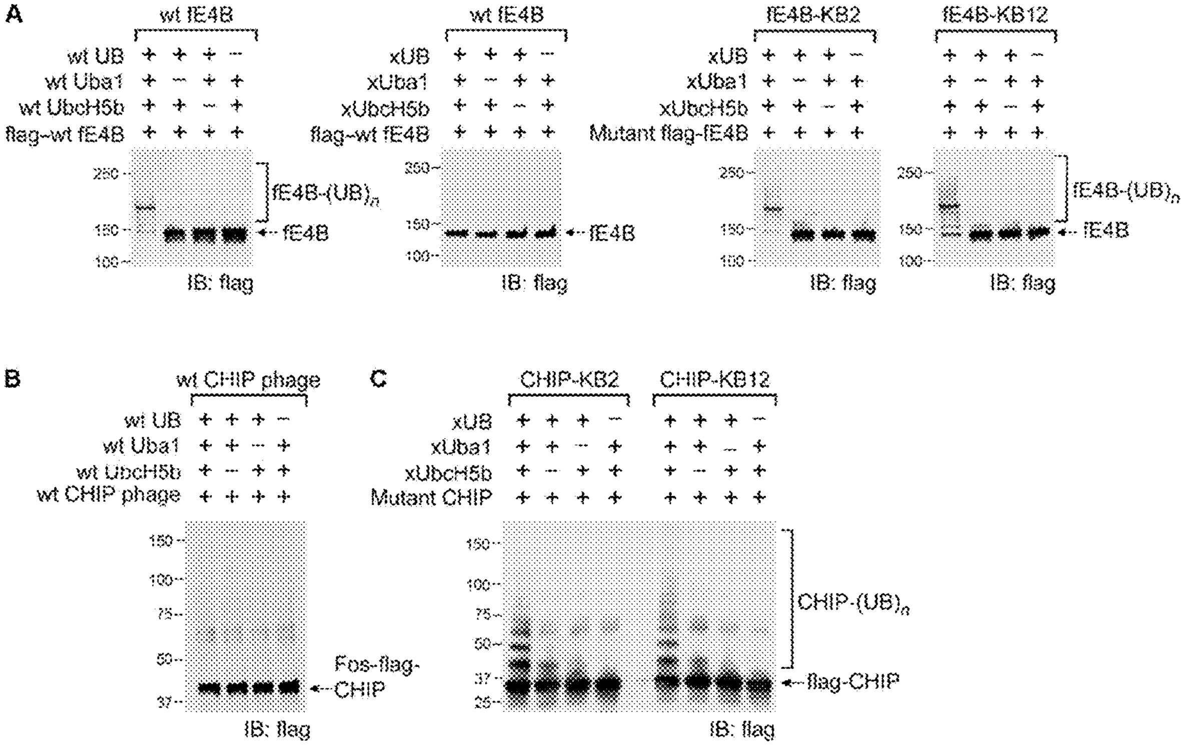
FIG. 21. Activity of engineered fE4B and CHIP mutants in auto-ubiquitination with xUB. (A) fE4B-KB2 and fE4B-KB12 are full-length E4B with mutated U-box domains KB2 and KB12. They could be auto-ubiquitinated by xUB through the xUba1-xUbcH5b pair. The activity of mutant E4B auto-ubiquitination was similar to wt fE4B auto-ubiquitination. In contrast, wt fE4B could not be ubiquitinated by xUB through the xUba1-xUbcH5b pair, suggesting the orthogonality of the OUT cascade and the native cascade of E4B. (B) wt CHIP displayed on the surface of M13 phage lost activity in auto-ubiquitination by wt UB and the wt Uba1-UbcH5b pair. (C) CHIP-KB2 and CHIP-KB12 were constructed by replacing the loop1 of CHIP U-box with corresponding sequences in the KB2 and KB12 mutants of E4B U-box. This enabled the engineered CHIP to be ubiquitinated by xUB through the xUba1-xUbcH5b pair. The efficiency of CHIP-KB2/12 auto-ubiquitination with xUB was similar to that of wt CHIP ubiquitination by wt UB through the wt Uba1-UbcH5b pair (FIG. S2B).
Figure 22:
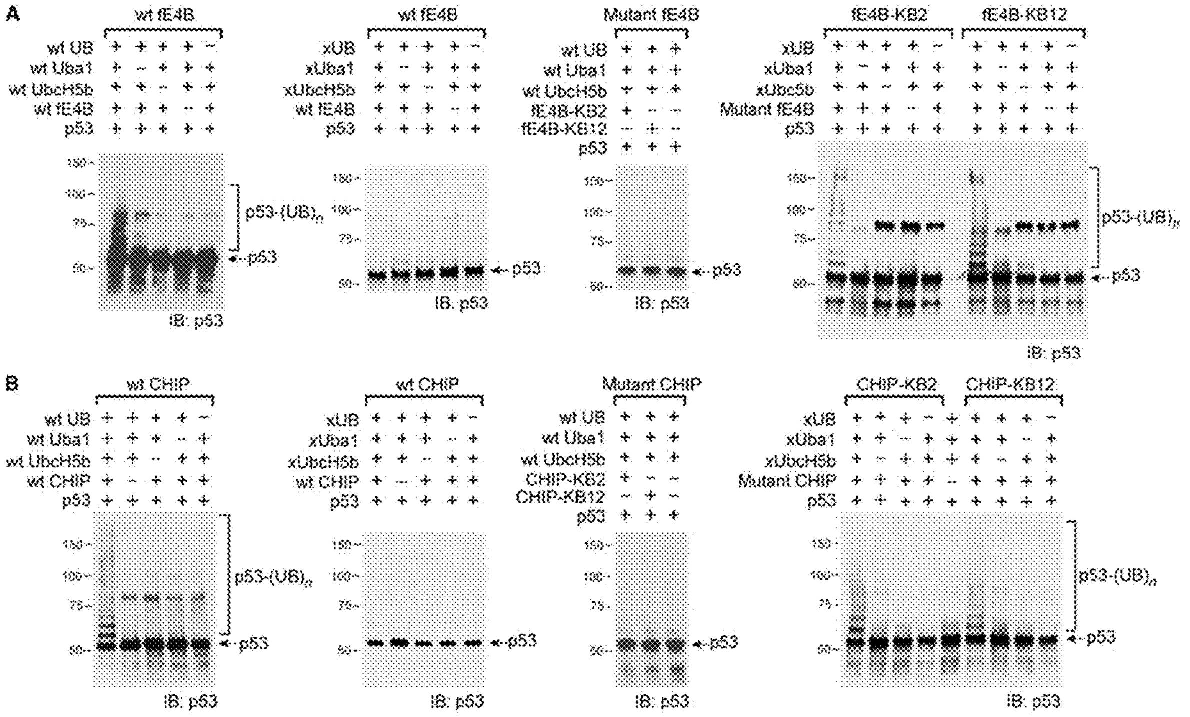
FIG. 22. xUB transfer through the OUT cascade of E4B and CHIP to p53 (A) fE4B-KB2 and fE4B-KB12 could assemble an OUT cascade with xUba1 and xUbcH5b to mediate xUB transfer to p53. The efficiency of p53 ubiquitination by xUB and the OUT cascade was similar to p53 ubiquitination with wt UB and the wt Uba1-UbcH5b-fE4B cascade. In contrast, wt E4B could not pair with xUba1-xUbcH5b to transfer xUB to p53, suggesting the orthogonality between the OUT cascade and native E3s. Mutant fE4B KB2 or KB12 could not pair with wt Uba1-wt UbcH5b to transfer wt UB to p53. (B) Similar to E4B OUT cascade, CHIP-KB2 and CHIP-KB12 could relay with xUba1-xUbcH5b to transfer xUB to p53. Efficiency of xUB modification of p53 by the CHIP OUT cascades was similar to p53 modification by wt UB going through the wt Uba1-UbcH5b-CHIP cascade. xUB could not be transferred to p53 with the crossover cascade of xUba1-xUbcH5b-wt CHIP. wt UB could not be transferred to p53 with the crossover cascade of wt Uba1-wt UbcH5b-mutant CHIP (KB2 or KB12).

Activity of the selected U-box mutants of E4B. We expressed the U-box mutants KB2, KB7, KB9, KB11 and KB12 fused to a flag tag, and reacted them with wt UB in the presence of the xUba1 (UFD)-xUbcH5b pair. We stopped the reaction at mono-ubiquitination to compare the reactivity of U-box variants (FIG. 20B). All the U-box mutants were active with the xUba1 (UFD)-xUbcH5b pair in modification with wt UB. They were also active with the xUba1-xUbcH5b pair that transferred xUB to the U-box (FIG. 20C). Next, we cloned the U-box mutants into the full-length E4B (fE4B) to assay if they could mediate xUB transfer to fE4B and then to its substrate p53 (11). We chose KB2 and KB12 for incorporation into fE4B since KB2 is the most abundant U-box clone from phage selection, and KB12 only differed from KB2 by an Arg instead of His replacing D1238. fE4B is a large protein of 1,137 residues (1). We found it could be expressed in *E. coli* with a pET vector and its activity could be enhanced by ammonium sulfate precipitation after eluting the protein from the Ni-NTA column. wt fE4B could be efficiently ubiquitinated with wt UB through the wt Uba1-UbcH5b pair, yet it could not be modified by xUB through the xUba1-xUbcH5b pair (FIG. 21A). In contrast, fE4B with U-box mutants of KB2 and KB12 (fE4B-KB2 and fE4B-KB12) could be efficiently ubiquitinated with xUB through the xUba1-xUbcH5b pair. We have thus constructed an OUT cascade for xUB transfer to fE4B-KB2 or fE4B-KB12. We also found xUB could be transferred to p53 through xUba1-xUbcH5b relaying with either fE4B-KB2 or fE4B-KB12, and with a similar efficiency, wt UB could be transferred through wt Uba1-UbcH5b-fE4B to p53 (FIG. 22A). Importantly, the crossover cascade of xUba1-xUbcH5b-wt fE4B was incapable of transferring xUB to p53, suggesting the orthogonality of the OUT cascade with the native UB transfer cascade. Hence either fE4B-KB2 or fE4B-KB12 could be used as an xE4B to construct the OUT cascade for profiling E4B substrates.

Constructing an OUT cascade with CHIP. We set out to use phage selection to identify U-box mutants of CHIP with restored UB transfer from xUbcH5b. However, although the full-length CHIP including the U-box domain could be displayed on the phage surface, it was not active in auto-ubiquitination reactions with wt UB transferred through the wt Uba1-UbcH5b pair (FIG. 21B). CHIP functions as a dimer, so the lack of activity was attributed to the inability of CHIP to form suitable dimers when displayed on phage (FIG. 32C) (20, 25). To address this challenge, we took an alternative approach by transplanting the mutated loop1 residues from the KB2 and KB12 variants of the E4B U-box into CHIP. We reasoned this might restore CHIP interaction with xUbcH5b because the U-box domains of CHIP and E4B are highly homologous in structure, even though their loop1 sequences do not align well (FIG. 19B and FIG. 32). To this end, loop 1 residues$^{213}$CGKISFE$^{219}$ (SEQ ID NO:11) in CHIP U-box were replaced with corresponding residues from the KB2 U-box ($^{1233}$KDPIMHT$^{1239}$ (SEQ ID NO:12)) and KB12 U-box ($^{1233}$KDPIMRT$^{1239}$ (SEQ ID NO:13)), generating CHIP-KB2 and CHIP-KB12 (Table 2). The success of this design was confirmed in xUB auto-ubiquitination reactions with the xUba1-xUbcH5b pair (FIG. 21C). Furthermore, both CHIP mutants could transfer xUB to p53, a known CHIP substrate (26), at an efficiency comparable to wt UB transfer by wt CHIP (FIG. 22B). Moreover, xUB could not be transferred to p53 through the crossover cascade of xUba1-xUbcH5b-wt CHIP. These results demonstrated that either CHIP-KB2 or CHIP-KB12 could be used as an xCHIP in an OUT cascade to profile its substrates.

Figure 34:
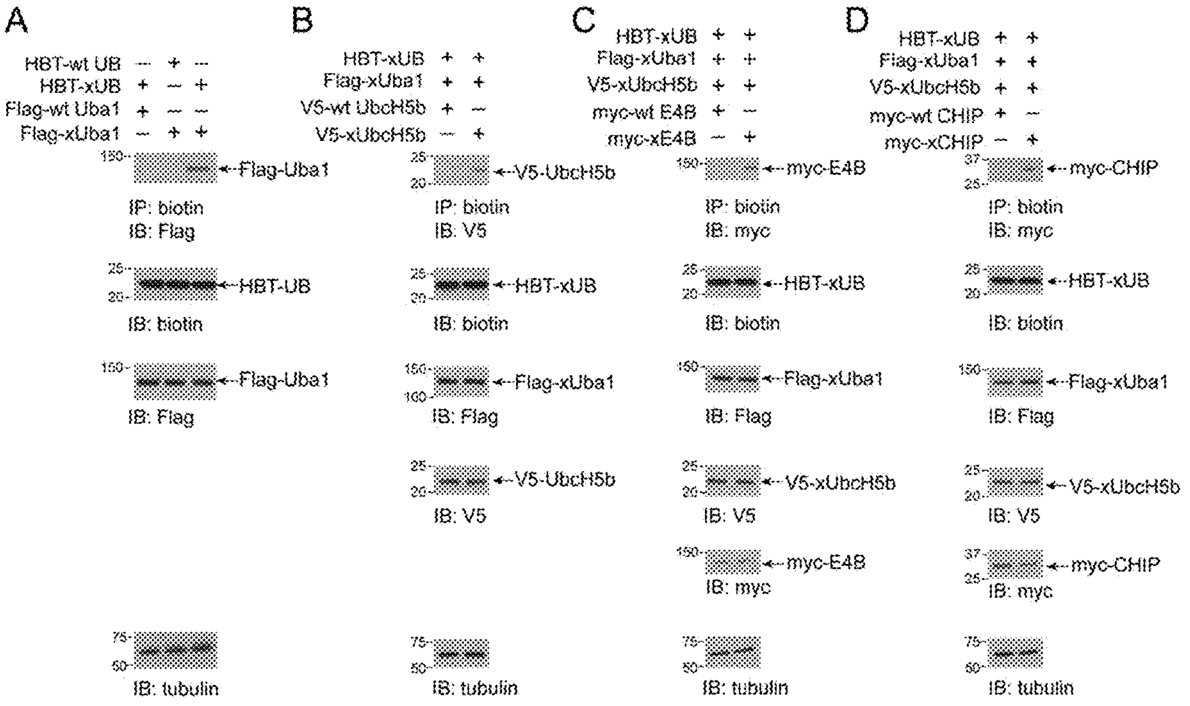
FIG. 34. Orthoganality of the OUT cascades of E4B and CHIP with the native UB tranferring enzymes. (A) xUB and xUba1 formed xUB~xUba1 conjugate in HEK293 cells. As a result of conjugate formation, flag-xUba1 could be copurified with HBT-xUB by binding to streptavidin beads. In contrast, flag-wt Uba1 could not be copurified with HBT-xUB, neither could flag-xUba1 be copurified with HBT-wt UB in the cells co-expressing the UB-E1 pairs. This suggests that the crossover xUB-wt Uba1 or wt UB-xUba1 pairs were not active in the cell. (B) xUB could be transferred through xUba1-xUbcH5b pair to form xUB~xUbcH5b conjugate in the cell. Due to the conjugate formation, V5-xUbcH5b could be copurified with HBT-xUB from cells expressing HBT-xUB, flag-xUba1 and V5-xUbcH5b. In contrast, the expression of HBT-xUB and the crossover pair of xUba1-wt UbcH5b would not generate xUB~wt UbcH5b conjugate, so V5-wt UbcH5b could not be co-purified with HBT-xUB. (C) xUB could be transferred through xUba1-xUbcH5b-xE4B cascade to form xUB-xE4B conjugate in the cell. As a result, myc-xE4B could be co-purified with HBT-xUB in cells expressing HBT-xUB and the xUba1-xUbcH5b-xE4B cascade. In contrast, coexpression of HBT-xUB with the crossover cascade of xUba1-xUbcH5b-wt E4B would not generate xUB~wt E4B conjugate, so myc-wt E4B could not be co-purified with HBT-xUB. (D) Similarily, xUB could be transferred through xUba1-xUbcH5b-xCHIP cascade to form xUB-CHIP conjugate in the cell. However xUB could not be transferred to wt CHIP by xUba1-xUbcH5b to form xUB-wt CHIP conjugate.
Figure 37:
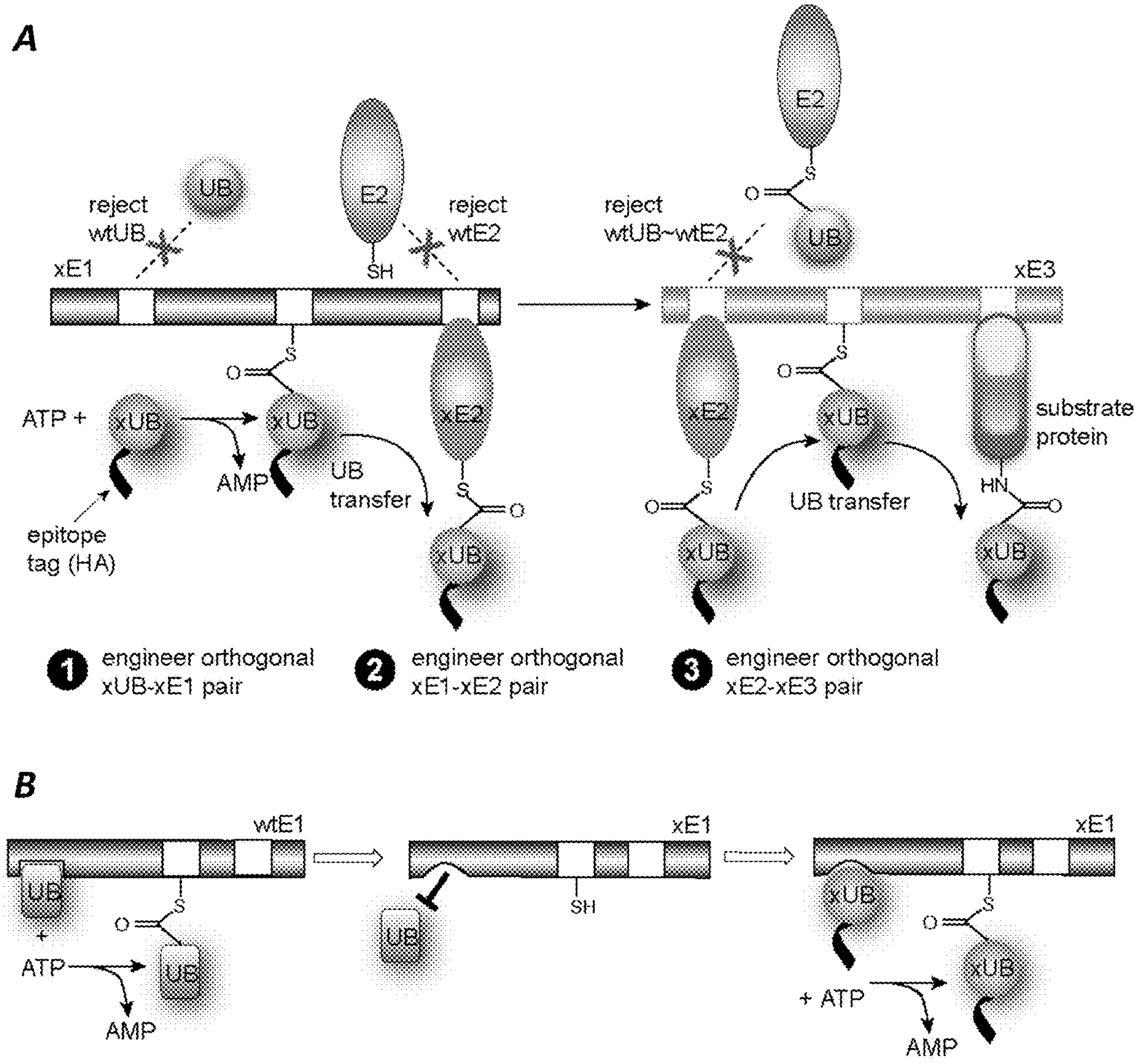
FIG. 37. Models of (A) orthogonal UB transfer (OUT) cascade and (B) the bump-and-hole strategy.
Figure 38:
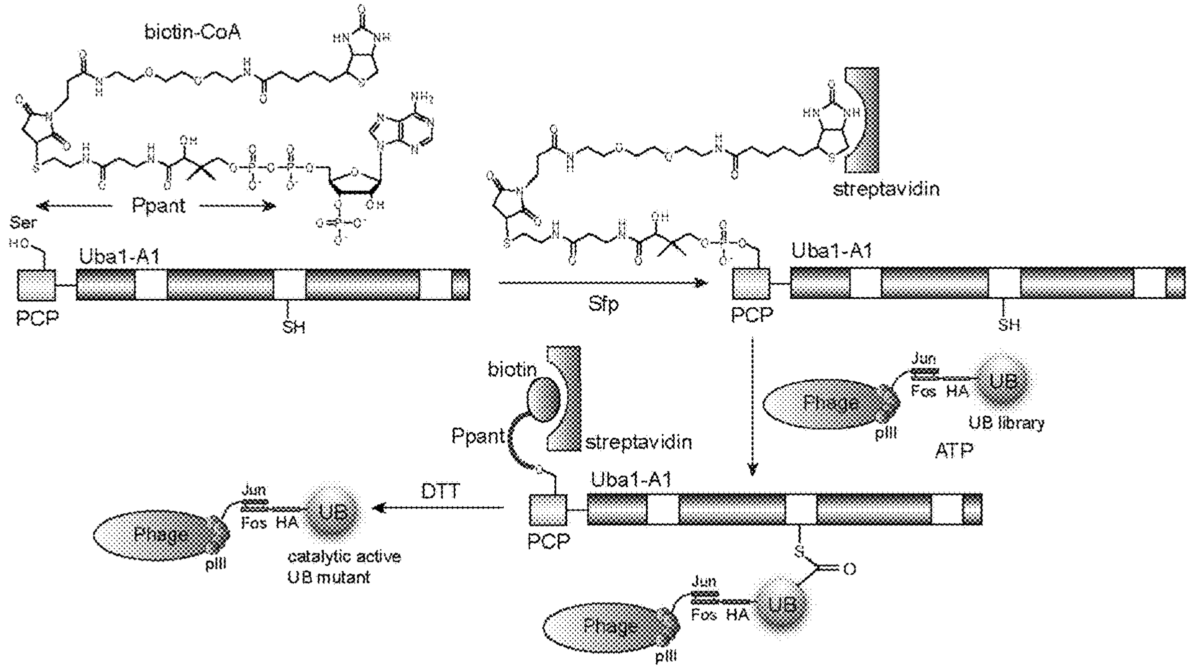
FIG. 38. Model of phage selection of a xUB-xE1 pair.
Figure 39:
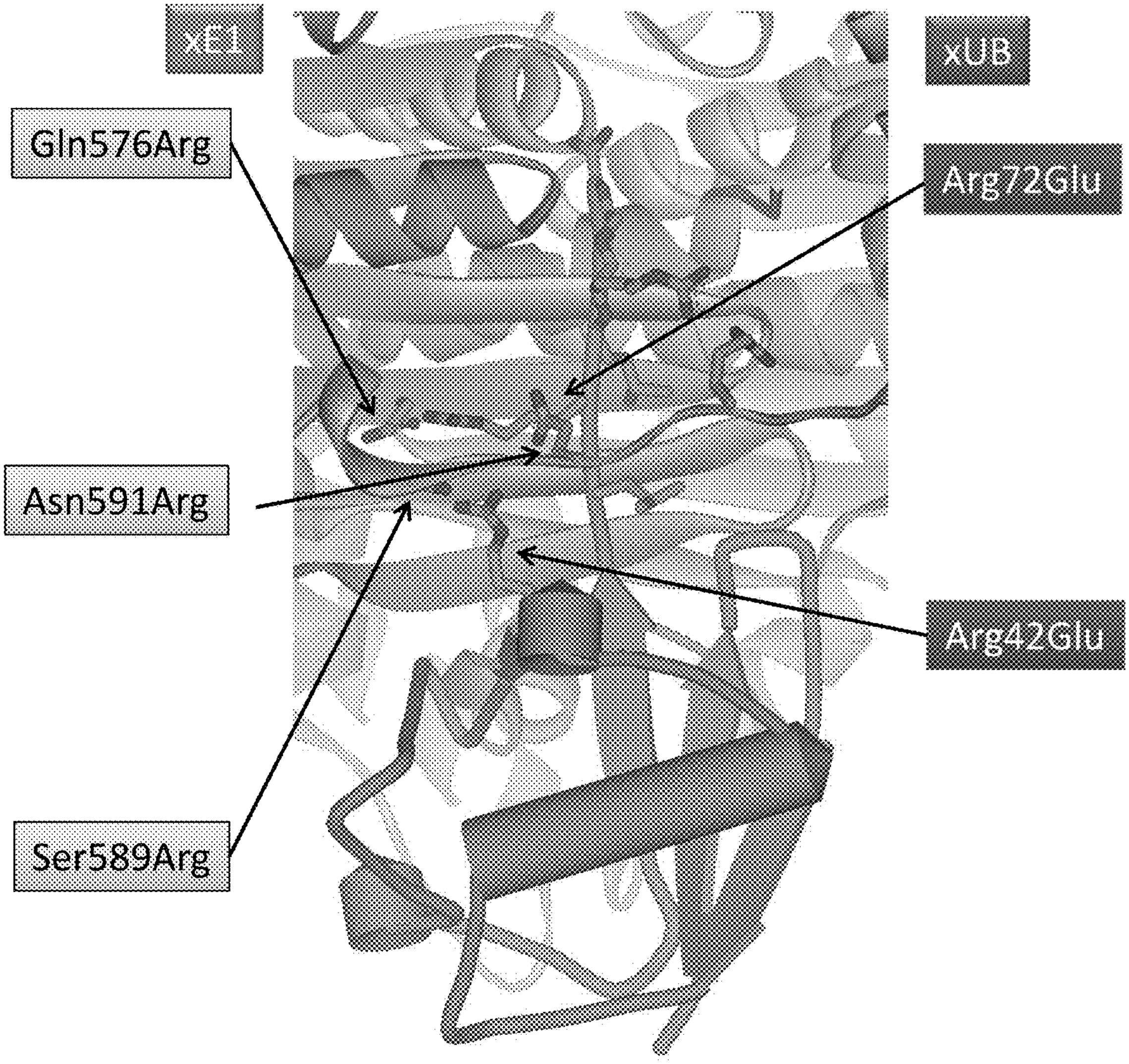
FIG. 39. Model of an orthogonal xUB-xE1 pair. ATP-PPi exchange is observed only between the orthogonal wild-type pair wtUB-wtE1(Uba1) and for the mutant pair xUB (UB10)-xE1 (Uba1-A5).
Figure 40:
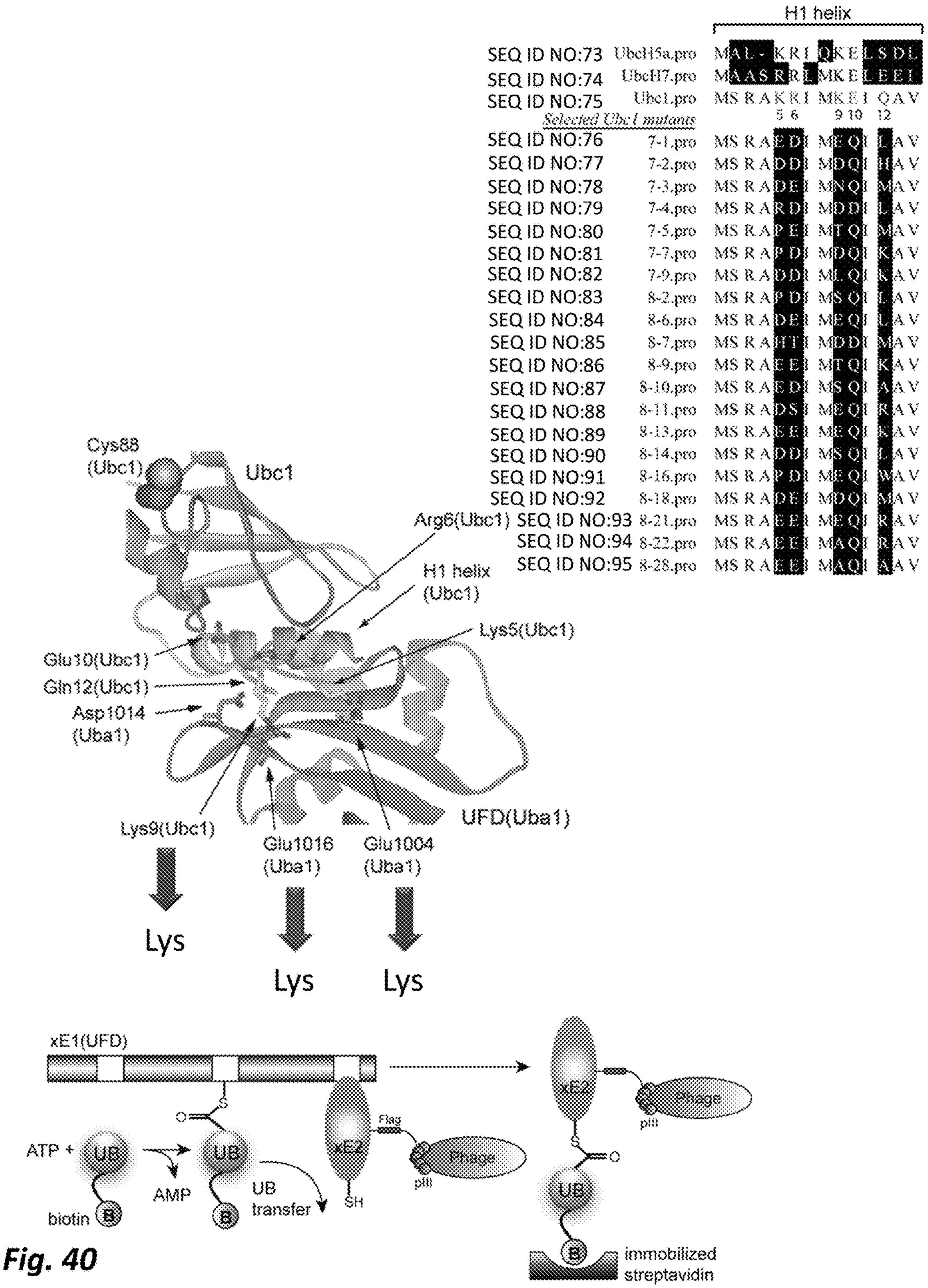
FIG. 40. Model for selecting an orthogonal xE1-xE2 pair.
Figure 44:
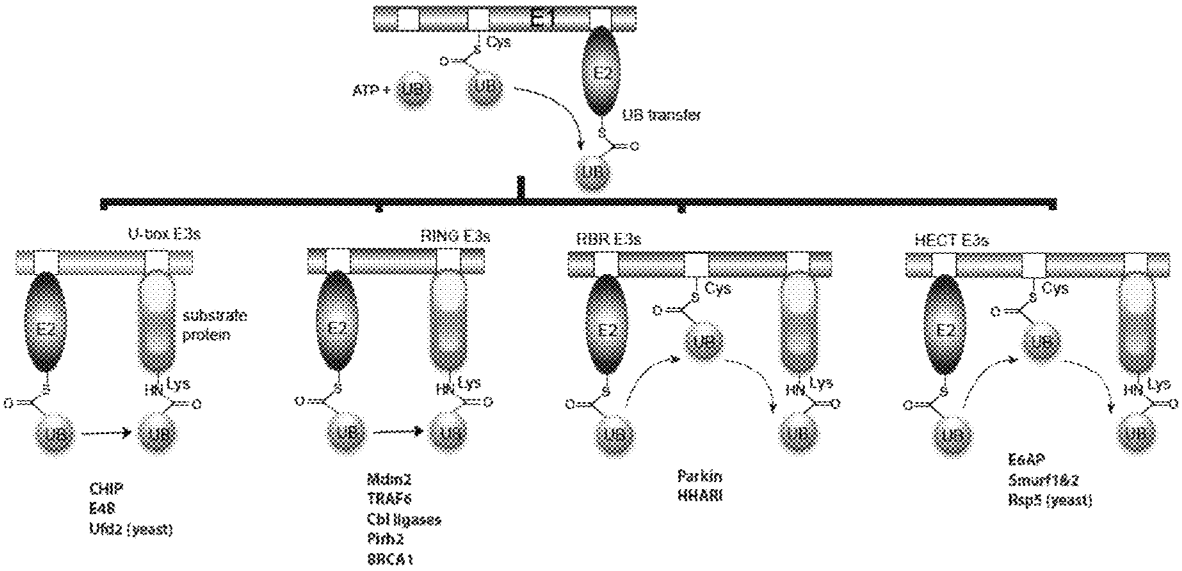
FIG. 44. Model for the expansion of orthogonal UB transfer (OUT) to additional UB ligases.

Profiling E4B and CHIP substrates by OUT. We decided to use fE4B-KB2 as xE4B and CHIP-KB12 as xCHIP to assemble the OUT cascades of the two U-box E3s and profile their substrates in the cell (Table 2). To assay the orthogonality of the OUT cascades with the native UB transferring enzymes in the cell, we expressed xUba1 or wt Uba1 in HEK293 cells with the co-expression of xUB or wt UB with a tandem 6×His tag and a biotin tag at the N-terminus (HBT-xUB or HBT-wt UB) (27). Coimmunoprecipitation proves the formation of xUB~xUba1 conjugate but not the xUB~wt Uba1 or wt UB~xUba1 conjugates in the cell (FIG. 34A). This suggests xUB is specifically transferred to xUba1 of the OUT cascade. Similarly, we found xUB was transferred to xUbcH5b or xE4B or xCHIP expressed in the cell but not the native E2 or E3 enzymes (FIG. 34B-D). This proves that the OUT cascade exclusively delivered xUB to xE3 in the cell.

We generated stable HEK293 cell lines expressing the OUT cascades of E4B and CHIP. We transiently transfected the cell lines to express HBT-xUB (FIG. 35A). To isolate the substrate proteins, cells were lysed, and xUB-conjugated proteins were purified by tandem affinity chromatography with Ni-NTA and streptavidin resin under denaturing conditions. The substrates bound to the streptavidin resin were digested by trypsin and identified by mass spectrometry (MS) proteomics. To filter away proteins bound non-specifically to the resin or conjugated to xUB independent of xE3, HBT-xUB was expressed in stable cell lines that expressed the xUba1-xUbcH5b pair without xE4B or xCHIP. xUB-conjugated proteins were purified from the control cells and identified by MS. Comparison of the profiles of xUB-conjugated proteins from cells expressing the OUT cascade and the control cells identified proteins that were dependent on xE4B or xCHIP for modification by xUB. These proteins are candidates for the direct ubiquitination targets of E4B and CHIP in the cell.

Following this protocol, we generated profiles of xUB-conjugated proteins in the cells expressing the E4B OUT cascade and in control cells expressing the xUba1-xUbcH5b pair without xE4B (FIGS. 35B and 35C). To compare the two profiles, we calculated the ratio of peptide spectrum matches (PSM) of each protein purified from cells with the OUT cascade versus the control cells. We performed tandem purification and proteomic profiling on the two cell lines three times. With the same approach, we generated a profile of CHIP substrates from the OUT screen (FIG. 35E and data not shown, see Bhuripanyo et al. 2018).

Among a few E4B substrates reported, we found p53 as an E4B target identified by OUT (data not shown, see Bhuripanyo et al. 2018). Bioinformatics analysis of the E4B substrates with the Ingenuity Pathway Analysis (IPA) revealed a protein network controlling DNA replication, recombination and repair had the most significant association with potential E4B substrates—p53 and 31 other E4B substrates from the OUT screen were associated with this network (data not shown, see Bhuripanyo et al. 2018). The CHIP substrates identified by OUT included a number of known CHIP targets such as p53, protein arginine N-methyltransferase 5 (PRMT5), filamin-A, and Hsp70 chaperones (28). IPA suggested CHIP substrates were associated most significantly with a regulatory network of cell death and survival, DNA replication, recombination and repair, which included p53, PPP3CA and 30 other substrates from the OUT screen (data not shown, see Bhuripanyo et al. 2018). We found several kinases and methyl transferases are potential targets of E4B and CHIP; their ubiquitination by the U-box E3s might underlie new mechanisms of cell regulation. For example, protein arginine methyl transferase PRMT1, kinase MAPK3, and phosphatase PPP3CA are potentially shared substrates of E4B and CHIP, deubquitinase (DUB) OTUB1 and phosphatase PGAMS could be E4B substrates, and transcription factor β-catenin and kinase CDK4 are CHIP substrate (data not shown, see Bhuripanyo et al. 2018). We carried out ubiquitination assays in vitro and in the cell to verify if these proteins were bona fide targets of E4B or CHIP.

Figure 23:
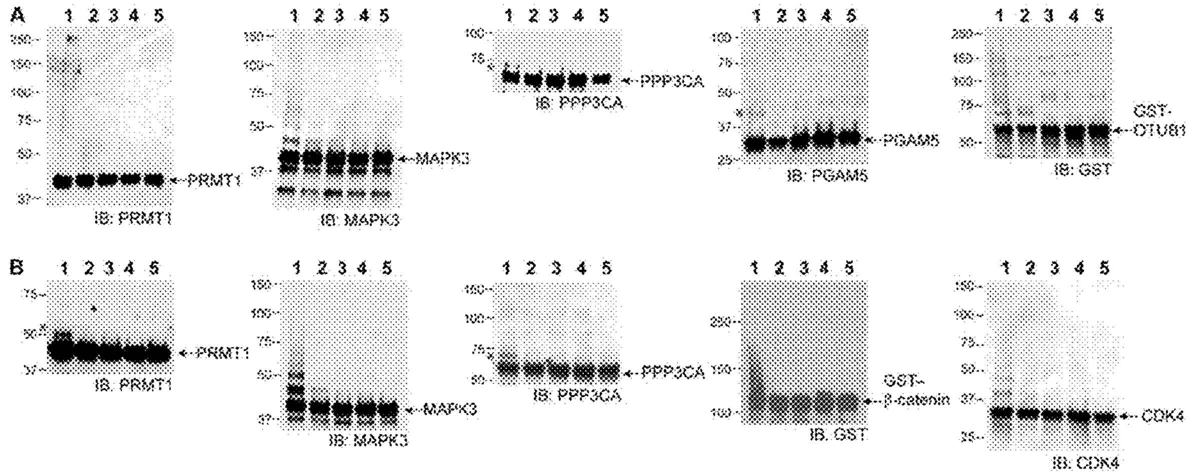
FIG. 23. In vitro assay to verify E4B and CHIP catalyzed ubiquitination of the substrates. (A) Ubiquitination of PRMT1, MAPPK3, PPP3CA, PGAMS, and OTUB1 by wt UB through the wt Uba1-UbcH5b-fE4B cascade (lane 1). In lanes 2, 3, 4 and 5, wt E4B, Uba1, UbcH5b or wt UB was missing from the reaction mixture respectively. (B) Ubiquitination of PRMT1, MAPK3, PPP3CA, β-catenin, and CDK4 by wt UB through the wt Uba1-UbcH5b-CHIP cascade (lane 1). In lanes 2, 3, 4 and 5, wt CHIP, Uba1, UbcH5b or wt UB was missing from the reaction mixture respectively. Bands marked with asterisks were likely generated by mono-ubiquitinated substrates.

Verification of E4B and CHIP substrates. We expressed PRMT1, MAPK3, PPP3CA, PGAMS, OTUB1, β-catenin and CDK4 in *E. coli* and set up in vitro ubiquitination reactions with wt fE4B and wt CHIP. Substrates expressed from the *E. coli* might not have the proper posttranslational modification such as phosphorylation to mediate recognition by an E3, or adaptor proteins could be missing to mediate UB transfer. Nevertheless, we observed poly-ubiquitination of PRMT1, MAPK3 and OTUB1 when wt UB was transferred through the wt Uba1-UbcH5b-fE4B cascade. PPP3CA and PGAMS mainly gave mono-ubiquitinated species after reaction with the UB transfer cascade of E4B (FIG. 23A). We also found CHIP could poly-ubiquitinate MAPK3, β-catenin and CDK4, and CHIP ubiquitination of PRMT1 and PPP3CA generated mono-ubiquitinated species (FIG. 23B).

To verify ubiquitination of the identified substrate proteins by E4B and CHIP in the cell, HEK293 cells were transfected with shRNA against E4B or CHIP, and screened for stable cell lines with inhibited expression of the E3s (FIGS. 24A and 24C). HEK293 cells over-expressing E4B or CHIP, or cells over-expressing an E3 and at the same time stably transfected with shRNA against the same E3 were also screened. Substrate-specific antibodies were used to immunoprecipitate each substrate proteins from the cells, and an anti-UB antibody was used to probe their ubiquitination levels. We found a decreased level of ubiquitination of PRMT1, MAPK3, and PPP3CA in the cells expressing shRNA against E4B or CHIP. Overexpression of either E4B or CHIP in cells stably transfected with shE4B or shCHIP significantly increased ubiquitination of the substrates (FIGS. 24B and 24D). These results suggest that PRMT1, MAPK3 and PPP3CA are likely shared ubiquitination targets of E4B and CHIP; inhibiting the expression of either E3 would significantly affect the ubiquitination of these substrates in the cell. Using the same assay, we confirmed that ubiquitination of PGAMS and OTUB1 was dependent on E4B—their ubiquitination was significantly decreased in shE4B cells, and the ubiquitination level was restored by overexpressing E4B in in shE4B cells (FIG. 24B). Similarly, we confirmed CHIP-dependent ubiquitination of β-catenin and CDK4 in the cell (FIG. 24D).

Figure 25:
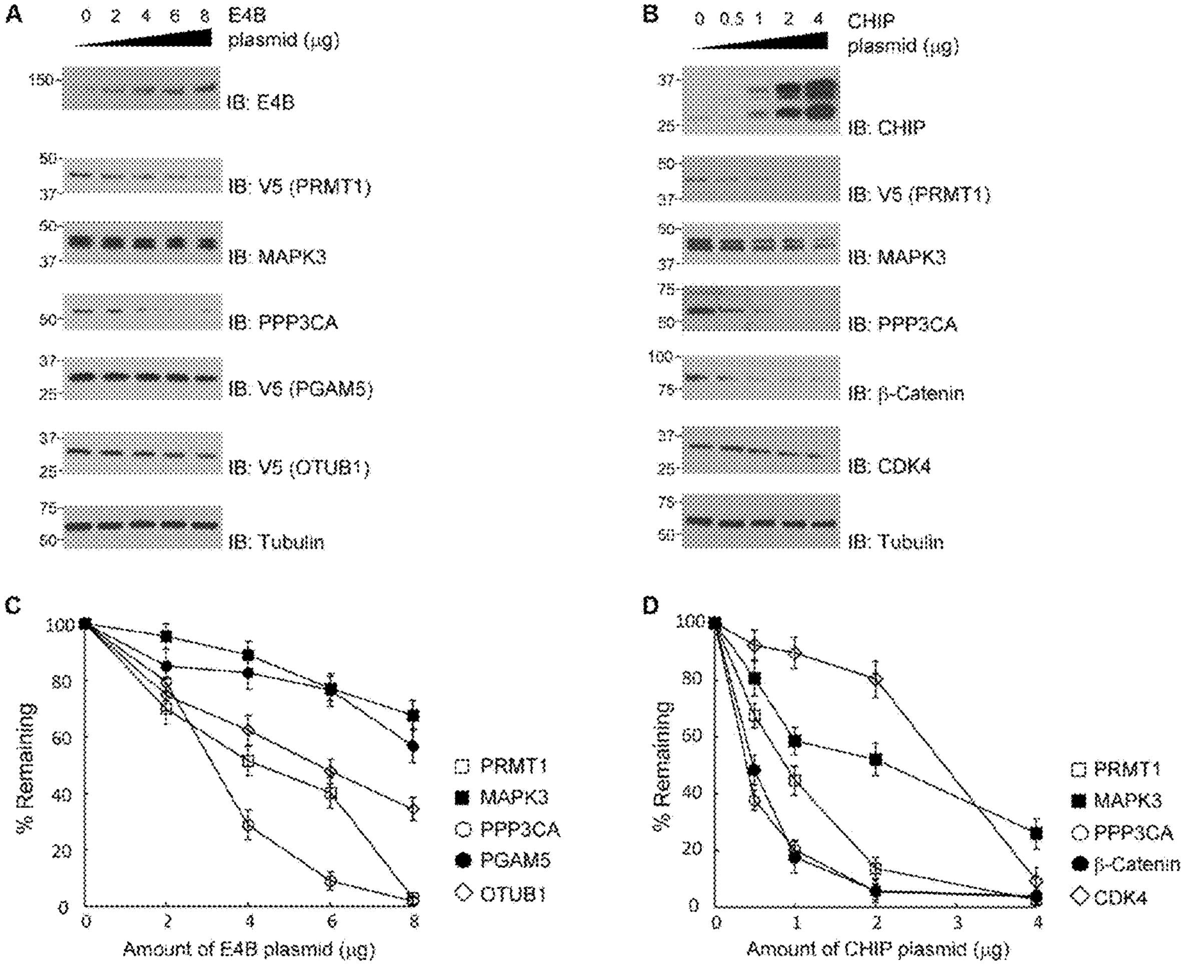
FIG. 25. Expression of E4B and CHIP accelerated the degradation of the identified substrates. (A) E4B reduced the steady-state levels of the substrate proteins in the HEK293 cells. Cells were transfected with increasing amount of E4B plasmid. Levels of the E4B substrates were assayed with immunoblots of the cell lysate probed with substrate-specific antibodies. Approximately $5\times10^6$ cells were used for each transfection of the E4B plasmid. (B) CHIP reduced the steady-state levels of the substrat proteins in the HEK293 cells. Assays were performed with a similar protocol as in (A). (C) and (D), Quantitative analysis of substrate levels in correlation with E4B and CHIP expression, respectively. Intensity of the bands in (A) and (B) was plotted against the amount of pLenti E4B or CHIP plasmid used for transfection assuming 100% of substrate protein when an empty plasmid was used for mock transfection. Results were the average of three repeats.
Figure 26:
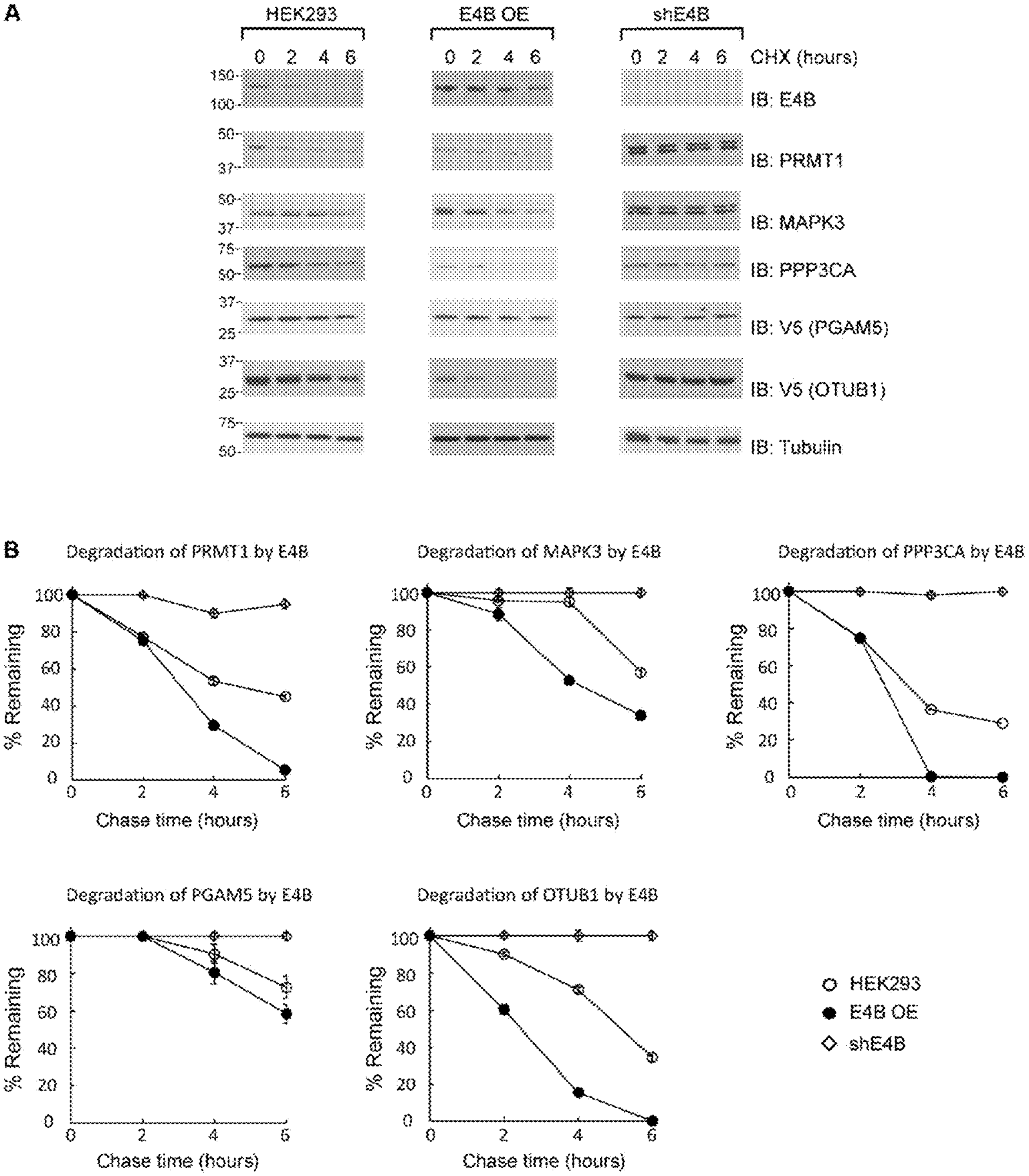
FIG. 26. Degradation of E4B substrate proteins assayed by cycloheximide (CHX) chase. (A) Comparison of the rate of substrate degradation in HEK293 cells with E4B over-expressed (E4B OE) or inhibition of E4B expression by shRNA (shE4B). $5\times10^6$ cells were transfected with various plasmids and the cells were treated with 100 mg/ml CHX 48 hours after transfection. Cell extracts were collected at 0, 2, 4, and 6 hours after incubation with CHX, followed by immunoblotting with substrate-specific antibodies. (B) Quantitative analysis of the levels of the substrate proteins in the cells after CHX chase. Data are representative of three independent trials.
Figure 27:
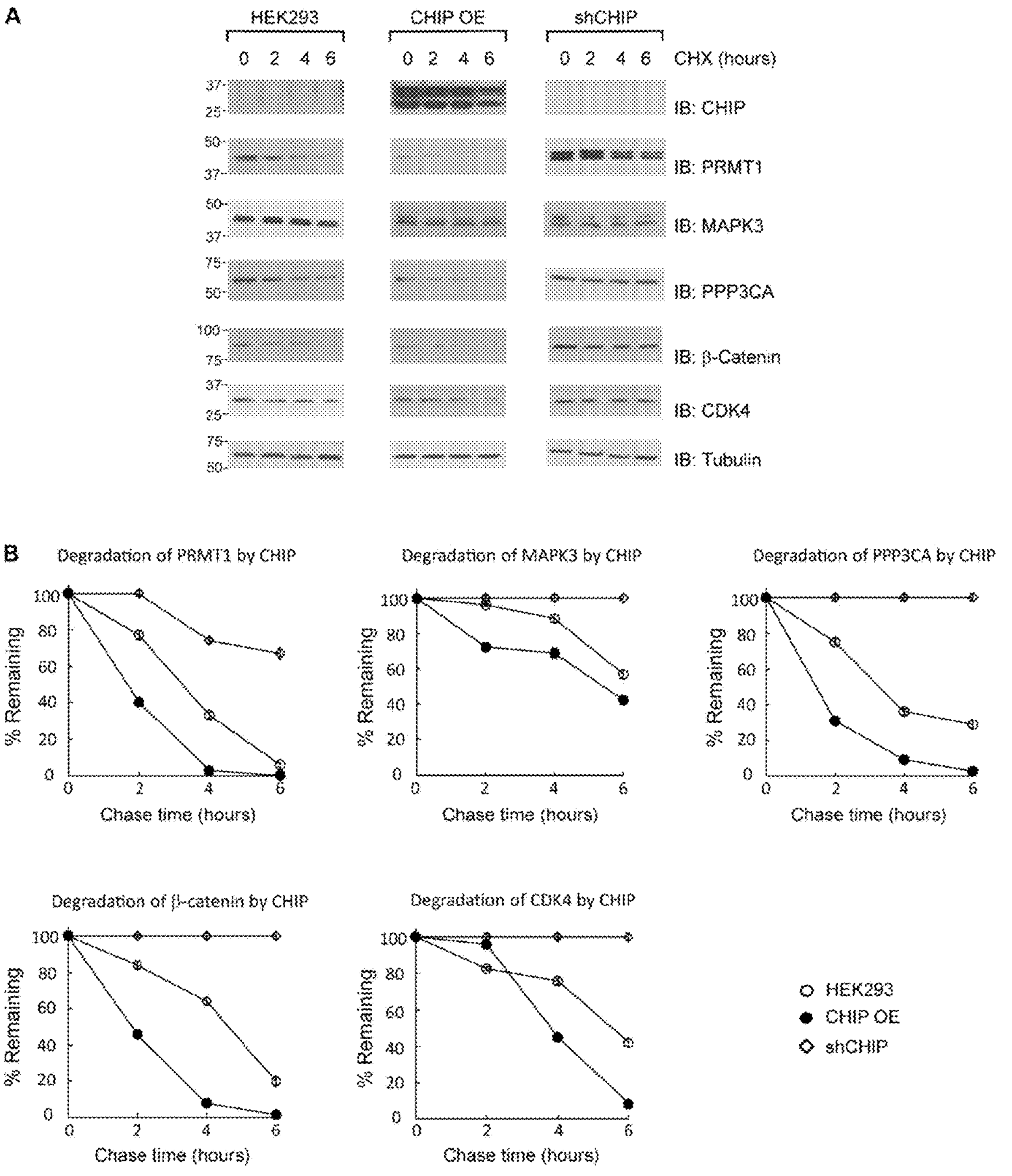
FIG. 27. Degradation of CHIP substrate proteins assayed by cycloheximide (CHX) chase. (A) Comparison of the rate of substrate degradation in HEK293 cells with CHIP over-expressed (CHIP OE) or inhibition of CHIP expression by shRNA (shCHIP). $5\times10^6$ cells were transfected with various plasmids and the cells were treated with 100 mg/ml CHX 48 hours after transfection. Cell extracts were collected at 0, 2, 4, and 6 hours after incubation with CHX, followed by immunoblotting with substrate-specific antibodies. (B) Quantitative analysis of the levels of the substrate proteins in the cells after CHX chase. Data are representative of three independent trials.

To measure the effect of E4B and CHIP expression on the stability of the identified substrate proteins, we expressed increasing amounts of the E3 enzymes in HEK293 cells and assay the level of substrate proteins by immunoblotting. We found expression of E4B significantly decreased the level of PRMT1, PGAMS and OTUB in the cell and expression of CHIP significantly decreased the level of PRMT1, MAPK3, PPP3CA, β-catenin and CDK4 in the cell (FIG. 25). We also inhibited protein expression by cycloheximide (CHX) and compared the rate of substrate degradation in HEK293 cells with the over expression of E4B and CHIP, and with the decreased expression of the two E3s by shRNAs (FIGS. 26 and 27). We found over expression of E4B accelerated the degradation of PRMT1, MAPK3, PPP3CA, and OTUB1 in HEK293 cells. Decreased E4B expression by shRNA extended the stability of PRMT1, MAPK3, PPP3CA, PGAMS and OTUB1 in the cell (FIG. 26). We also found over expression of CHIP accelerated the degradation of PRMT1, MAPK3, PPP3CA, β-catenin, and CDK4 in HEK293 cells and decreased CHIP expression by shRNA stabilized these proteins in the cell (FIG. 27). These results suggest a direct regulatory relationship between the E4B and CHIP and their ubiquitination targets in the cell.

Figure 28:
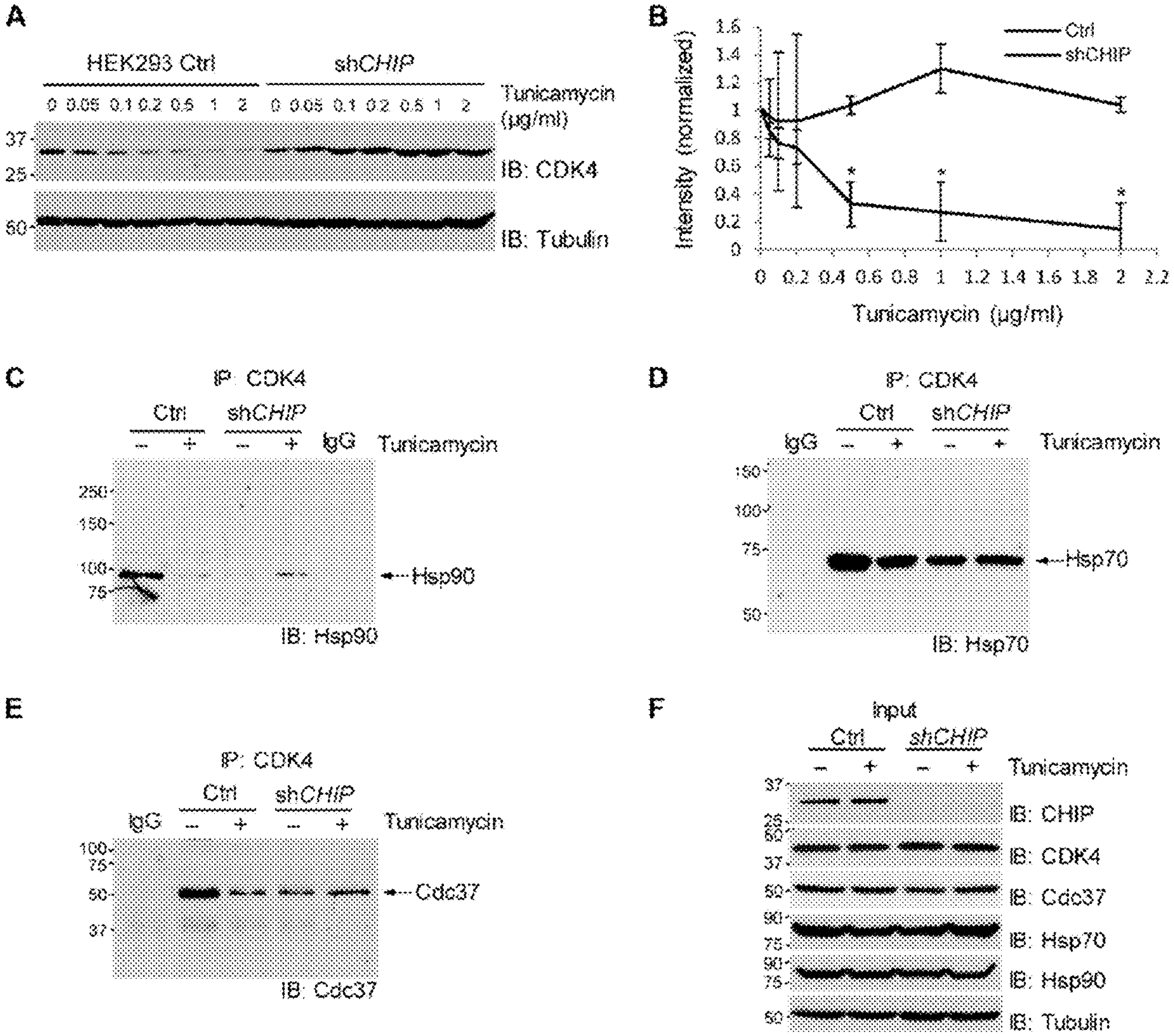
FIG. 28. ER stress-induced degradation of CDK4 is mediated by CHIP. (A) shCHIP abrogates downregulation of CDK4 protein in HEK293 cells after treatment with tunicamycin. Cells were incubated for 72 h with tunicamycin at the indicated concentrations, and harvested for immunoblotting. (B) Quantification of CDK4 protein levels after normalization by the levels of tubulin. Data are shown as mean±SEM from three biological replicates, and the asterisks indicate statistical significance ($p<0.05$). (C) ER stress decreases association of CDK4 with Hsp90 in HEK293 control cells but not in shCHIP cells. (D) ER stress does not significantly affect CDK4 association with Hsp70. (E) ER stress decreases association of CDK4 with Cdc37 in HEK293 control cells but not in shCHIP cells. (C-E) Cells were incubated with 1 μg/mL tunicamycin for 24 h, and then 10 μM MG132 was added to the medium, followed by incubation for additional 1.5 h. Cell lysates were immunoprecipitated (IP) with CDK4 antibody, followed by immunoblotting for the indicated proteins. IgG, negative control for IP with normal IgG. (F) The levels of the indicated proteins determined by direct immunoblotting using the cell lysates before IP.

The role of CHIP in ER stress-induced degradation of CDK4. We then assessed the biological significance of CHIP-mediated ubiquitination of CDK4, one of the newly identified substrates. Ubiquitination of CDK4 has not been studied previously and no E3 ligase has been identified to mediate CDK4 ubiquitination. However, CDK4 is known to associate with Hsp90 and its cochaperone, CDC37, which are thought to form a protein quality control mechanism and ensure proper folding and maintain the stability of many protein kinase clients (29, 30). CHIP has been shown to be part of the unfolded protein response (UPR) stimulated by endoplasmic reticulum (ER) stress (10, 31, 32). Thus, to determine whether CHIP-mediated polyubiquitination plays a role in the control of CDK4 under ER stress, we treated control HEK293 cells and cells stably expressing shCHIP with the ER stress inducer tunicamycin (FIG. 28A). CDK4 protein levels were decreased in control cells by tunicamycin in a concentration-dependent manner, whereas tunicamycin did not significantly alter CDK4 levels in shCHIP cells (FIG. 28B). We detected robust interaction between CDK4 and Hsp90 or CDC37 in control HEK293 cells treated with MG132, and such interactions were significantly downregulated after tunicamycin treatment even under proteasome inhibition (FIGS. 28C and 10E). Interestingly, in shCHIP cells, the levels of CDK4-Hsp90 and CDK4-CDC37 complexes were significantly lower than those in control cells, and tunicamycin minimally affected such complexes. In contrast, CDK4 interaction with Hsp70 was affected by tunicamycin or shCHIP only modestly (FIG. 28D). These observations suggest that ER stress induced by tunicamycin inhibits CDK4 association with Hsp90-CDC37 complex and targets CDK4 to CHIP-mediated polyubiquitination and proteasomal degradation.

Discussion

In this study we constructed OUT cascades for U-box E3s E4B and CHIP and used the OUT screen to identify hundreds of proteins as their potential substrates. Previously only a few E4B substrates were reported in the literature including p53, ataxin-3, fasciculation and elongation protein zeta 1 (FEZ1), and epidermal growth factor receptor (EGFR) (11, 33-35). We found p53 among the E4B substrates identified by OUT (data not shown, see Bhuripanyo et al. 2018) (36). We verified that kinase MAPK3, methyl transferase PRMT1, protein phosphatases PPP3CA and PGAMS, and deubiquitinaes OTUB1 were ubiquitinated by E4B in vitro and in HEK293 cells (37-40). The crucial roles of these enzymes in cell cycle, DNA repair and gene regulation, etc., render E4B a key position in certain cell signaling networks.

In contrast to the limited knowledge about E4B substrates, more CHIP substrates have been identified including kinases Akt, Src, and MEKK2 (MAP3K2) and ASK1 (MAP3K5) of the MAPK pathway (41-44). From the OUT screen, we identified MAPK3, another kinase in the MAPK pathway, as a CHIP substrate. Interestingly, two protein Arg methyl transferases PRMT1 and PRMT5 were found in the OUT screen as CHIP substrates. The ubiquitination of PRMT1 by CHIP was confirmed in our work, while ubiquitination of PRMT5 by CHIP was recently reported (45). We have also confirmed CHIP ubiquitination of protein phosphatase PPP3CA and β-catenin, the master transcriptional regulator in the Wnt signaling pathway. It is well established that the Skp1-Cullin-Fbox E3 complex including β-TrCP as an Fbox component polyubiquitinates cytoplasmic β-catenin under basal conditions without the Wnt signal (46-49). In addition to the canonical β-TrCP-dependent E3 activity, several other E3s have been shown to ubiquitinate β-catenin in the literature. For example, Mule/Huwel could downregulate β-catenin under hyperactive Wnt signaling, while c-Cbl and TRIM33 may target specifically nuclear β-catenin (50-52). Our identification of CHIP as another E3 for β-catenin awaits further investigations on physiological cellular contexts that require CHIP-mediated degradation of β-catenin and possible involvement of the β-catenin control in the understudied roles of CHIP in tumorigenesis (53).

The OUT screen identified a number of chaperon proteins as CHIP targets, such as Hsp70, CDC37, DNAJ (DNAJA1 and DNAJC7), and co-chaperones BAG2, and BAG6 (data not shown, see Bhuripanyo et al. 2018). It is known that CHIP is a co-chaperone of Hsp70 and Hsp90, and can ubiquitinate these proteins when they do not carry cargos (3, 54). The OUT screen with CHIP suggests an even broader association of CHIP with molecular chaperones in the protein quality control cycle, where it serves in triage between refolding and degradation. Furthermore, our study demonstrated that ER stress triggers CHIP-mediated polyubiquitination of CDK4. In the absence of proteotoxicity, the CDC37-Hsp90 complex binds to and stabilizes a substantial population of CDK4 (29, 30). Our data showed that upon ER stress induced by tunicamycin, the interaction between CDK4 and CDC37-Hsp90 is downregulated and CDK4 actively undergoes CHIP-dependent proteasomal degradation. Activation of UPR in response to ER stress leads to cell cycle arrest in the $G_1$ phase. The transient cessation of proliferation is thought to contribute to cellular adaptation and allow cells to attempt to reestablish homeostatic conditions or commit to death. Previous studies suggested the involvement of translational repression of the CDK4-regulatory subunit Cyclin D1 in the process of ER stress-induced arrest (55). Our data on the CHIP-CDK4 axis suggest that ubiquitination also plays roles in proteotoxicity-induced cell cycle arrest. Consistently, a recent study showed that parkin (PARK2) ubiquitinates and degrades Cyclins D and E (56). Thus, proteasome-mediated degradation of $G_1$-S regulators is likely to function as a translation-independent mechanism of cell cycle control in response to proteostasis. Hsp90 inhibitors have been developed and tested as anti-cancer drugs (57), and further investigations are necessary to elucidate the roles of the chaperone-associated E3s and their substrates in tumor suppression and sensitivity to anti-Hsp90 therapies.

The verification of E4B and CHIP substrates from the OUT screen proves that OUT is an effective platform for profiling the substrate specificities of the U-box E3s. Since E3s play key roles in cell regulation, many methods have been developed to identify the substrates of E3s in order to reveal their biological functions. The transient interactions between E3s and their substrates, and many auxiliary proteins associated with E3 such as adaptors or regulators make it a significant challenge to identify E3 substrates. Still conventional coimmunoprecipitation methods have been useful in defining the scope of E3 substrates based on binding affinity (58, 59). A reasonable readout of UB conjugation is the proteosomal degradation of the ubiquitinated proteins. By correlating the change in protein stability with the expression of a E3, a powerful method known as "global protein stability profiling (GPS)" has been developed to assign E3 substrates (60, 61). The recent development of anti-diGly antibody and advanced proteomic technology allows the quantitative comparison of protein ubiquitination levels in the cell (62, 63). This enables the assignment of E3 substrates by following the changes of protein ubiquitination levels upon the perturbation of E3 expression (64, 65). To identify the direct ubiquitination targets of a E3, researchers have developed ingenious methods such as "UBAIT" and "Ubiquitin Ligase Substrate Trapping" by constructing fusions of E3 with UB or with UB binding proteins to capture E3 substrates after UB transfer (66, 67). In another creative approach, E2 for Nedd8 transfer is fused with E3 to turn E3 into a "Neddylator". E3 substrates can then be identified among neddylated proteins in the cell (68). An *E. coli*-based selection system to screen E2-E3 and E3-substrate relationships has also been reported recently (69).

The advantage of OUT is that it identifies the substrate of a E3 directly based on the catalytic transfer of UB from a designated E3 to its ubiquitination targets. The OUT cascade reenacts the action of native UB transfer cascades in the cell except that it exclusively delivers an affinity tagged xUB to the substrates of a specific E3. The disadvantage of OUT is that the OUT cascade needs to be engineered with each E3 under investigation. We have shown that we can generate xUB-xE1 and xE1-xE2 pairs by mutating key residues in E1 and E2 based on sequence homology with xUba1 and xUbc1 (FIG. 30). In this study, we also generated xE2-xCHIP pair based on the homology of the loop1 residues between CHIP and E4B (FIG. 32). We expect the strategy of loop grafting to engineer xE2-xE3 pairs could be used on other U-box E3s including UIP5, CYC4, and Prp19, each of which is poorly characterized (4, 5). U-box domains share significant structural homology with the Ring domains (4). As for U-box domains, the loop1 region in the Ring is a key site to engage E2s (17, 19). So it would be of interest to test if mutations in the U-box can be transplanted to Ring domains to generate xE2-xE3 pairs. If transplantation of mutations is not effective, the phage selection platform we developed for U-box could be used to engineer xE2-xE3 pairs with Ring domains to further extend the reach of the OUT cascade.

Figure 29:
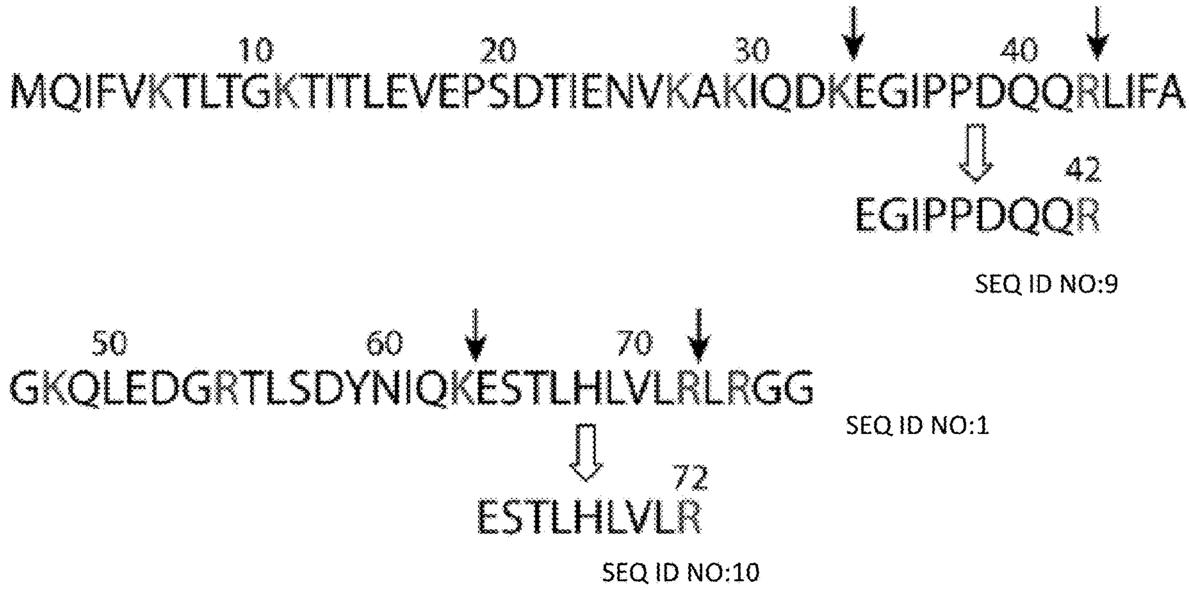
FIG. 29. Peptide sequence of wt UB and sites of trypsin digestion. Trypsin digests peptides immediately after Lys (K) or Arg (R) residues. Due to the mutations of R42E and R72E in xUB, trypsin would not cleave the xUB peptide at residues 42 and 72. Peptides with the sequence "EGIDPPDQQR" (SEQ ID NO:9) and "ESTLHLVLR" (SEQ ID NO:10) are unique to trypsin digestion of wt UB.

It should be noted that in the xUB-expressing stable cells, both xUB and wt UB are present. xUB contains all seven lysine residues that each can act as a receptor for a wt UB, resulting in the formation of wt UB-xUB chains. Also, xUB can function as a donor (with xE1-xE2-xE3) to react with the wt UB to form xUB-wt UB chains. A large body of evidence indicates that different pairs of E2-E3 can cooperate to form poly UB chains that include branched structures. Indeed, we found both xUB and wt UB were present in the sample collected by tandem affinity purification with the HBT tag on xUB (FIG. 29 and Table 3)

TABLE 3

Peptides unique to wt UB identified by proteomics.

| | Screen with the OUT cascade of E4B | | | Screen with the OUT cascade of CHIP | | |
|---|---|---|---|---|---|---|
| Peptide | #PSMs (Screen1) | #PSMs (Screen 2) | #PSMs (Screen 3) | #PSMs (Screen 1) | #PSMs (Screen 2) | #PSMs (Screen 3) |
| EGIDPPDQQR (SEQ ID NO: 9) | 11 | 1 | 7 | 19 | 20 | 9 |
| ESTLHLVLR (SEQ ID NO: 10) | 1 | 2 | 1 | 2 | 4 | 2 |

PSM, peptide spectrum match. Peptides with the sequences of “EGIDPPDQQR” (SEQ ID NO:9) and “ESTLHLVLR” (SEQ ID NO:10) would originate from wt UB but not xUB (FIG. 29). Indeed, the two peptides were present in all datasets collected with the OUT cascades of E4B and CHIP. This suggests that wt UB was conjugated to E4B or CHIP substrates that were purified by binding to HBT-xUB.

Figure 24:
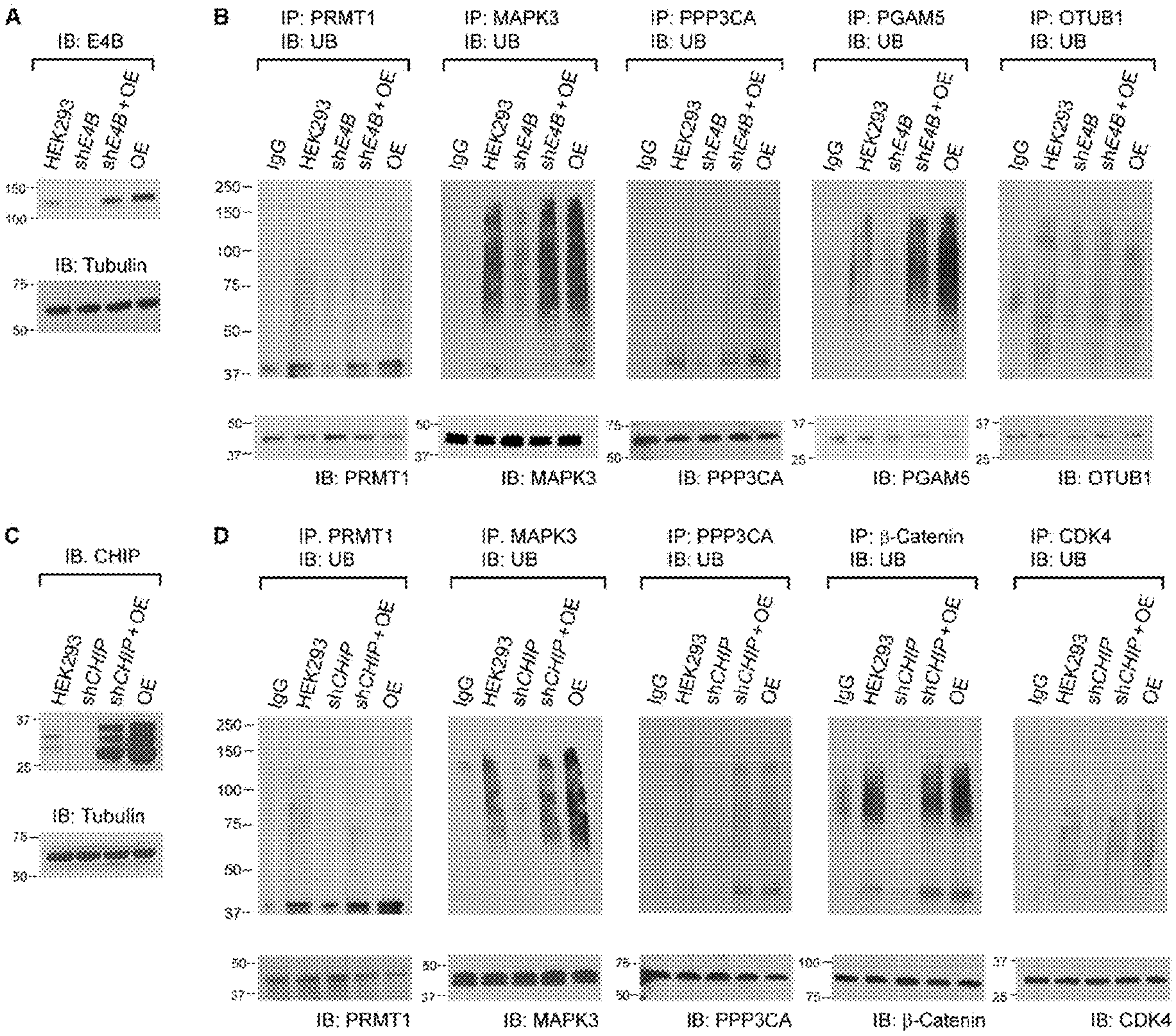
FIG. 24. E4B and CHIP-dependent ubiquitination of substrate proteins on in HEK293 cell. (A) Inhibition of E4B expression in HEK293 cells by shE4B was confirmed with Western blot probed with an antibody against E4B. (B) Ubiquitination of PRMT1, MAPPK3, PPP3CA, PGAMS, and OTUB1 in HECK293 cells was assayed by immunoprecipitation with antibodies against each substrate proteins, and probing their ubiquitination levels with an anti-UB antibody on the Western blots. The cells were treated with 10 μM MG132 for 1.5-hour before they were lysed. The ubiquitination of each substrate protein was compared among the control HEK293 cell (HEK293), HEK293 expressing shE4B (shE4B), HEK293 expressing both shE4B and recombinant E4B cDNA (shE4B+OE), and HEK293 overexpressing E4B from recombinant cDNA (OE). (C) Similar to (A) to confirm the inhibition of CHIP expression in HEK293 cells by shCHIP. (D) Similar to (B) to confirm CHIP-dependent ubiquitination of PRMT1, MAPK3, PPP3CA, β-catenin and CDK4 in HEK293 cell (HEK293), and its derivatives expressing shCHIP (shCHIP), shCHIP and recombinant CHIP (shCHIP+OE), and recombinant CHIP (OE).

Thus, among the substrates identified as xUB-conjugated proteins, the xE1-xE2-xE3 cascade may add xUB either directly to the substrate or to a wt UB pre-conjugated to the substrate. The recognition of the substrate by xE3 would be a prerequisite in either case. Nevertheless, it is important to verify the results of the OUT screen by independent approaches such as the effect of silencing the designed E3 gene (FIG. 24).

Material and Methods

Materials. The following antibodies were purchased from Santa Cruz Biotechnology: anti-β-catenin (sc-7963), anti-CHIP (sc-66830), anti-c-myc (sc-40), anti-GST (sc-138), anti-HA (sc-7392), anti-MAPK3 (sc-94), anti-OTUB1 (sc-130458), anti-p53 (sc-126), anti-PGAMS (sc-161156), anti-PP2B-A (sc-9070), anti-PRMT1 (sc-59648), anti-tubulin (sc-23948), anti-UB (sc-8017), anti-V5 (sc-271944), and goat anti-rabbit IgG (sc-2004). Goat anti-mouse IgG antibody (31438) was from Thermo Scientific. Penta-His antibody (34660) was from Qiagen. Anti-flag (M2) antibody (F3165) was from Sigma. p53 protein (SP-452-020) was from R&D Systems. Biotin-conjugated wt UB was from Boston Biochem. PCR primers were from Integrated DNA Technologies.

Constructing the expression plasmids for xUba1 and xUbcH5b. To incorporate mutations Q608R, S621R and D623R into human Uba1, primer pairs Bo184-Bo185 and Bo186-Bo187 were used to amplify the human Uba1 gene. Overlap extension of the fragments would afford the mutated Uba1 gene that was cloned into the pET vector to generate pET-xUba1(A). To incorporate mutations E1037K, D1047K and E1049K into the UFD domain of human Uba1, primer pair Bo-13-Bo73 was used to amplify the human Uba1 gene to generate pET-xUba1 (UFD). Combination of the mutations in the two plasmids afforded the plasmid pET-xUba1 for the expression of the xUba1 protein. Primers Kar64 and Kar65 were used to amplify human UbcH5b gene to incorporate the K4E and K8E mutations to generate pET-xUbcH5b.

Displaying E4B U-box domain on M13 phage and verification of the catalytic activity. Primers Kar77 and Kar78 were used to clone the U-box domain of E4B into the phagemid vector pJF3H to display the U-box on phage with a C-terminal flag tag (70). Phage preparation was following the protocol reported (12). The display of the U-box domain on phage was confirmed by Western blotting probed with an anti-flag antibody. To confirm the catalytic activity of the U-box domain displayed on phage surface, ubiquitination reactions were set up with $2\times10^{10}$ phage particles, Uba1 (0.5 μM), Ubch5b (6 μM) and HA-wt UB (14 μM) in buffer with Tris-HCl (50 mM, pH 7.5), $MgCl_2$ (10 mM), ATP (3 mM) and DTT (50 μM). After 1-hour incubation at room temperature, the reaction mixture was analyzed by SDS polyacrylamide gel electrophoresis (PAGE) and Western blotting probed with an anti-HA antibody. To analyze ubiquitination of the U-box protein on phage by enzyme-linked immunosorbent assay (ELISA), reaction was set up with similar conditions with the use of biotin-wt UB (0.2 μM) replacing HA-UB. After the reaction, phage particles were bound to a 96-well plate coated with streptavidin and the reaction was diluted 10-fold across the plate. After incubation, the plate was washed with TBST (25 mM Tris, pH 7.5, 150 mM NaCl, 0.05% Triton X-100, and 0.05% Tween 20) and TBS (25 mM Tris, pH 7.5, 150 mM NaCl). Phage bound to the plate was revealed by an anti-M13 antibody-HRP conjugate.

Selecting the E4B U-box library by phage display. Detailed procedures for library construction and selection are documented in (71). Residues to be randomized in E4B U-box (R1233, L1236, M1237, D1238 and T1239) were first mutated to Ala to generate phagemid pJF-E4B U-box 5Ala. For mutagenesis, the U-box gene was amplified by two sets of primers Kar77-Kar203 and Kar78-Kar204. The PCR fragments were assembled by overlap extension for cloning into the pJF phagemid. For randomization of the 5 residues, pJF-E4B U-box 5Ala was used as the template for PCR reactions with primer pairs of Jun13-Karlib2 and Karlib1-Kar78. The overlap extension of the amplified fragments was cloned into pJF phagemid to generate the library. The library DNA was transformed into SS320 cells (Agilent) by electroporation. The cells were plated on LB-agar plates containing 100 μg/ml ampicillin and 2% glucose, and incubated overnight at 37° C. The phagemid DNA for the library was prepared with a DNA maxi-prep kit (QIAGEN). The library phage was prepared as reported (12).

For the $1^{st}$ round phage selection, $10^{10}$ phage were reacted with xUba1 (UFD) (1 μM), xUbcH5b (10 μM), and biotin-wt UB (0.5 μM) for 1 hour. Phage were diluted 10-fold into 0.1% BSA-TBST and bound to a streptavidin plate for 1 hour at room temperature. The plate was washed with 0.1% BSA-TBST for 30 times. 100 μL TBS containing 100 mM DTT was added to each well to elute the phage particles. Phage eluted was added to a culture of XL1-Blue cells and the culture was shaken slowly for 2 hours at 37° C. After incubation, the cells were plated onto LB-agar plates containing 100 μg/ml carbenicillin and 2% glucose. After overnight incubation at 3TC, the colonies on the plates were collected, and the phagemid DNA was extracted with a DNA mini-prep kit. The library phagemid was then used for the next round of phage preparation. The concentration of enzymes and biotin-UB were decreased in each round of phage selection. For the 5th round of selection, xUba1 (UFD) (0.06 μM), xUbcH5b (5 μM), and biotin-wt UB (0.1 μM) were used, and the reaction time was shortened to 10 minutes.

Assaying the activity of the selected U-box mutants of E4B. The U-box mutants from phage selection were cloned into the pET vector to express the proteins with a C-terminal flag tag. Ubiquitination of the U-box was set up with each U-box mutant (5 xUba1 (UFD) (0.1 μM), xUbcH5b (2 μM), HA-UB (5 μM) in buffer with Tris-HCl (50 mM, pH 7.5), $MgCl_2$ (10 mM) and ATP (1.5 mM). Reaction was incubated at 37° C. for 10 minutes and was subject to SDS-PAGE and Western blot analysis with an anti-flag antibody.

The E4B full length gene was cloned into the pET30a plasmid for protein expression with an N-terminal flag tag. To incorporate mutations of KB2 into the E4B full length gene, primer set Kar239-Kar241 was used to amplify the U-box gene. The fragment was assembled with the PCR fragment generated with the Kar238-Kar242 pair and cloned into the pET30a-wt E4B plasmid for expression of the fE4B-KB2 protein. Similarly, primer set Kar240-Kar241 was used to incorporate the mutations of KB12 into the E4B gene to express the fE4B-KB12 protein. The pET30a expression vector for fE4B-KB2 and fE4B-KB12 would express fE4B mutants with an N-terminal flag.

To express the full length E4B protein and the KB2 and KB12 mutants, the pET30a plasmids were transformed into ArcticExpress(DE3) cells (Agilent). The cells were grown in terrific broth supplemented with 70 mg/ml kanamycin at 37° C. When the culture reached an optical density of 1.0, the culture was cooled down to 13° C. and IPTG was added to a concentration of 4 mM. The culture was shaken at 13° C. for 18 hours. The cells were then harvested and the proteins were purified with a Ni-NTA affinity column (Qiagene) according to the vendor's protocol. Protein eluted from the column was dialyzed overnight at 4° C. in a precipitation buffer containing Tris-HCl (50 mM, pH 7.5), ammonium sulfate (1 M), KCl (1 M), DTT (5 mM) and glycerol (10%). The protein precipitation was collected by centrifugation and was dissolved in TBS supplemented with 10 mM $MgCl_2$.

Ubiquitination reactions were set up with 5 μM of wt fE4B, fE4B-KB2, or fE4B-KB12, wt Uba1 or xUba1 (2 μM), wt UbcH5b or xUbcH5b (10 μM), and wt UB or xUB (60 μM). Reaction was allowed to proceed at 37° C. for 1.5 hours and analyzed by SDS-PAGE and Western blotting with an an-flag antibody. p53 ubiquitination was set up with wt fE4B, fE4B-KB2 or fE4B-KB12 (4 μM), p53 (0.4 μM), wt Uba1 or xUba1 (0.2 μM), wt UbcH5b or xUbcH5b (0.2 μM), and wt UB or xUB (30 μM). The reaction was incubated at 30° C. for 1 hour, and analyzed by Western blotting with an anti-p53 antibody.

Cloning and assaying the activity of xCHIP. The loop-transplanting mutants of xCHIP-KB2 and xCHIP-KB12 were constructed by PCR amplification of the CHIP gene with Kar232-Kar306 or the Kar233-Kar306 primer pair. The fragments were assembled with CHIP gene fragment amplified with the Kar234-Kar306 primer pair to generate the mutant CHIP genes. They were then cloned into the pET vector for protein expression. Ubiquitination of CHIP and CHIP-catalyzed p53 ubiquitination were set up similar to the reaction with E4B. Ubiquitination of CHIP was analyzed Western blot probed with an anti-CHIP antibody.

In vitro ubiquitination of substrate proteins. Genes of potential substrate proteins PRMT1, MAPK3, PPP3CA, and PGAMS were cloned into pET vector for protein expression. Genes of OTUB1 and β-catenin were cloned into pGEX vector. The plasmids were transformed into BL21(DE3) or ArcticExpress (DE3) cells to express the protein. To assay ubiquitination by E4B or CHIP, substrate proteins (5-10 μM) were incubated with wt Uba1 (1 μM), wt UbcH5b (2 μM), and wt UB (50 μM) in TBS supplemented with $MgCl_2$ (10 mM) and ATP (1.5 mM). After 2-hour reaction at room temperature, ubiquitination of substrates was analyzed by Western blot probed with either substrate-specific antibodies, or antibodies against the GST tag fused to the substrates.

Lentiviral vector construction and selection for stable cell lines. pLenti6-hygromycin-HBT-xUB plasmids for the expression of HBT-xUB was constructed by PCR amplifying the xUB gene and the His-biotin tag from the plasmid pQCXIP HBT-UB (27). The two fragments were overlap extended and cloned into the pLenti vector with a hygromycin resistant gene. Flag-xUba1 gene was amplified with primers WY15 and WY16, and cloned into pLenti6-blasticdin vector. V5-xUbcH5b gene was amplified with primers WY101 and WY102, and cloned into pLenti4-zeocin vector. flag-xE4B and flag-xCHIP genes were amplified with primers Kar301-Kar302 pair and Kar303-Kar304 pair, respectively, and cloned into pLenti4-puromycin plasmid. Virus packaging of the pLenti plasmids, infection, and selection of stable cell lines were performed according to the protocol for the ViraPower Lentiviral Expression System. Stable HEK293 cell lines expressing Flag-xUba1 and V5-xUbcH5a were selected with 10 μg/mL blasticidin and 100 μg/mL Zeocin, respectively. Stable cell lines for myc-xE4B and myc-xCHIP were selected with 1 μg/mL puromycin. Expression of transfected genes was induced by the addition of 1 μg/mL doxycycline to the medium.

Tandem affinity purification of xUB-conjugated proteins. Tandem purification of HBT-xUB conjugated proteins was performed as previously described (27). Briefly, 30 dishes (10 cm in diameter) of HEK293 cells stably expressing the xUba1-xUbch5b-xE4B/xCHIP cascade were acutely infected with lentivirus HBT-xUB for 72 hours. To inhibit proteasome activity, cells were treated with 10 μM MG132 for 4 hours at 37° C. Cells were then washed twice with ice cold 1×PBS, pH 7.4, and harvested by cell scraper with buffer A (8 M urea, 300 mM NaCl, 50 mM Tris, 50 mM $NaH_2PO_4$, 0.5% NP-40, 1 mM PMSF and 125 U/ml Benzonase, pH 8.0). For Ni-NTA purification, cell lysates were centrifuged at 15,000 g for 30 min at room temperature. 35 μL of $Ni^{2+}$ sepharose beads (GE Healthcare) for each 1 mg of protein lysates were added to the clarified supernatant. After incubation overnight at room temperature in buffer A with 10 mM imidazole on a rocking platform, $Ni^{2+}$ sepharose beads were pelleted by centrifugation at 100 g for 3 min and washed sequentially with 20-bead volume of buffer A (pH 8.0), buffer A (pH 6.3), and buffer A (pH 6.3) with 10 mM imidazole. After washing the beads, proteins were eluted twice with 5-bead volume of buffer B (8 M Urea, 200 mM NaCl, 50 mM $Na_2HPO_4$, 2% SDS, 10 mM EDTA, 100 mM Tris, 250 mM imidazole, pH 4.3). For streptavidin purification, the elution solution was adjusted to pH 8.0. 50 μL streptavidin sepharose beads (Thermo Scientific) was added to the elution to bind HBT-xUB conjugated proteins. After incubation on a rocking platform overnight at room temperature, streptavidin beads were pelleted and washed sequentially with 1.5 mL buffer C (8 M Urea, 200 mM NaCl, 2% SDS, 100 mM Tris, pH 8.0), buffer D (8 M Urea, 1.2 M NaCl, 0.2% SDS, 100 mM Tris, 10% EtOH, 10% Isopropanol, pH 8.0) and buffer E (8 M urea, 100 $NH_4HCO_3$, pH 8).

Sample digestion and LC-MS/MS analysis. After washing, the streptavidin beads were spun down and residual urea was removed and liquid chromatography coupled to tandem mass spectrometry (LC-MS/MS) on an Orbitrap Fusion mass spectrometer (ThermoFisher Scientific, San Jose, CA) was performed at the Emory Integrated Proteomics Core (EIPC) according to previously published methods as described (72, 73). Collected spectra were searched using Proteome Discoverer 2.0 against human Uniprot database (90,300 target sequences). Searching parameters included fully tryptic restriction and a parent ion mass tolerance (±20 ppm). Methionine oxidation (+15.99492 Da), asaparagine and glutamine deamidation (+0.98402 Da), lysine ubiquitination (+114.04293 Da) and protein N-terminal acetylation (+42.03670) were variable modifications (up to 3 allowed per peptide); cysteine was assigned a fixed carbamidomethyl modification (+57.021465 Da). Percolator was used to filter the peptide spectrum matches to a false discovery rate of 1%.

Bioinformatics analysis. Ingenuity Pathway Analysis (IPA) software (http:/www.ingenuity.com) was used to map and identify the biological networks and molecular pathways with a significant proportion of genes having E4B or CHIP ubiquitination targets. Fisher exact test in Ingenuity Pathway Analysis software was used to calculate p-values for pathways and networks. The level of statistical significance was set at a p-value<0.05. IPA was also used to visualize the identified biological networks.

Lentiviral silencing of E4B and CHIP. Lentiviral GPIZ plasmids encoding shRNAs against E4B and CHIP were obtained from GE Dharmacon (Lafayette, CO), and lentiviruses were produced using the manufacturer's lentivurus packaging system and 293FT cells. HEK293 cells were infected with each lentivirus, followed by selection with puromycin for stable cell populations. Efficiency of gene silencing in each shRNA group was determined by immunoblotting using stable cell populations. For functional restoration, HEK293 cell population stably expressing anti-E4B shRNA #2 and anti-CHIP shRNA #2 were infected with the lentivirus packaged with pLenti6-Myc-wt E4B and wtCHIP, respectively.

Co-immunoprecipitation and in vivo assay to confirm E4B and CHIP substrates. Transfection of pLenti-E4B and CHIP into the HEK293 cells was conducted with the Lipofectamine® 2000 according to the manufacturer's protocol. To immuneprecipitate the substrate proteins, cells were treated with 10 μM MG132 (American Peptide, Sunnyvale, CA) for 90 min at 72-hour post-transfection. HEK293 cells (80-90% confluent monolayer in 75 $cm^2$ cell culture flask) expressing control plasmid, shE4B/CHIP, shE4B/CHIP+E4B/CHIP cDNA, and E4B/CHIP cDNA were washed twice with ice cold PBS, pH 7.4. 1 mL ice cold RIPA buffer was added to cell monolayer and incubated with cell for at 4° C. for 10 minutes. The cells were disrupted by repeated aspiration through a 21-gauge needle. The cell lysate was transferred to a 1.5 mL tube. The cell debris was pelleted by centrifugation at 13,000 rpm for 20 minutes at 4° C. and the supernatant was transferred to a 1.5 mL centrifuge tube and precleared by adding 1.0 μg of the appropriate control IgG (normal mouse or rabbit IgG corresponding to the host species of the primary antibody). 20 μL of re-suspended volume of Protein A/G PLUS-agarose was added to the supernatant and incubation was continued for 30 minutes at 4° C. The agarose beads were pelleted by centrifugation at 2,500 rpm for 5 minutes at 4° C. From the cleared cell lysate, volume containing 2 mg total protein was transferred to a new tube. 30 μL (i.e., 6 μg) primary antibody against a specific substrate protein was then added and incubation was continued for 1 hour at 4° C. After incubation, 50 μL of re-suspended volume of Protein A/G PLUS-Agarose was added. The tubes were capped and incubate at 4° C. on a rocker platform overnight. The agarose beads were pelleted by centrifugation at 2,500 rpm for 5 minutes at 4° C. The beads were then washed 4 times each time with 1.0 mL PBS. After the final wash, the beads were re-suspended in 40 μL 1× Laemmli buffer with BME. The samples were boiled for 5 minutes and analyzed by SDS-PAGE and Western blot probed with antibodies against UB.

Protein degradation assays. To examine the effect of E4B or CHIP on steady-state levels of the substrates, HEK293 cells ($5\times10^6$ cells) were transiently transfected with varying amount of pLenti plasmid of E4B or CHIP with Lipofactamine 2000. Cells were harvested at 48-hour post-transfection and the amount of substrate proteins in the cell lysate was assayed by immunoblotting with substrate-specific antibodies. For cycloheximide (CHX) chase assays, HEK293 cells ($5\times10^6$ cells) were transiently transfected with 4 μg empty pLenti, or 8 μg pLenti-E4B or 4 μg pLenti-CHIP plasmids. After 48 hours, cells were treated with 100 μg/mL CHX to block de novo protein synthesis and the cells were harvested after variable length of incubation time with CHX. The amount of substrate proteins in the cell were assayed by immunoblotting with antibodies against each substrate proteins. Protein levels were normalized to tubulin. Alternatively, CHX chase assays were performed on HEK293 cells stably expressing anti-E4B or anti-CHIP shRNA to measure the effect of decreased expression of E4B or CHIP on substrate stability.

Assays for ER stress. Human embryonic kidney HEK293 cells were obtained from American Tissue Culture Collection (ATCC) and cultured under standard conditions recommended by ATCC. HEK293 cells were cultured on 60-mm dishes to 40-50% confluence, and treated with tunicamycin for 72 hours at the indicated concentrations to induce ER stress, and harvested for immunoblotting with anti-CDK4 antibody.

For immunoprecipitation with anti-CDK4, HEK293 Ctrl or shCHIP cells were incubated with 1 μg/mL tunicamycin for 24 h, and then treated with 10 μM MG132 for 1.5 h. The cells were lysed by sonication in RIPA lysis buffer as described previously (13). 4 mg protein lysates were incubated with 20 μL anti-cdk4 agarose (#sc-260, Santa Cruz Biotechnology) overnight at 4° C. The beads were washed with RIPA buffer three times, and 60 μL 1×SDS PAGE loading buffer was added. The sample was boiled for 5 min. Half of the immunoprecipitates or 50 μg total protein lysate were loaded for SDS-PAGE and assayed by Western blot.

The membranes were probed with anti-HSP70 (SC-24, Santa Cruz Biotechnology), anti-HSP90 (SC-13119, Santa Cruz Biotechnology), anti-CDC37 (SC-13129, Santa Cruz Biotechnology), anti-CHIP (SC-133066, Santa Cruz Biotechnology), and anti-α-Tubulin antibody (T6199, Sigma-Aldrich).

REFERENCES

1. S. Hatakeyama, M. Yada, M. Matsumoto, N. Ishida, K. I. Nakayama, U box proteins as a new family of ubiquitin-protein ligases. J Biol Chem 276, 33111-33120 (2001).
2. G. C. Meacham, C. Patterson, W. Zhang, J. M. Younger, D. M. Cyr, The Hsc70 co-chaperone CHIP targets immature CFTR for proteasomal degradation. Nat Cell Biol 3, 100-105 (2001).
3. S. B. Qian, H. McDonough, F. Boellmann, D. M. Cyr, C. Patterson, CHIP-mediated stress recovery by sequential ubiquitination of substrates and Hsp70. Nature 440, 551-555 (2006).
4. L. Aravind, E. V. Koonin, The U box is a modified RING finger—a common domain in ubiquitination. Curr Biol 10, R132-134 (2000).
5. S. Hatakeyama, K. I. Nakayama, U-box proteins as a new family of ubiquitin ligases. Biochem Biophys Res Commun 302, 635-645 (2003).
6. R. A. Zeinab, H. Wu, C. Sergi, R. Leng, UBE4B: a promising regulatory molecule in neuronal death and survival. Int J Mol Sci 13, 16865-16879 (2012).
7. W. B. Pratt, J. E. Gestwicki, Y. Osawa, A. P. Lieberman, Targeting Hsp90/Hsp70-based protein quality control for treatment of adult onset neurodegenerative diseases. Annu Rev Pharmacol Toxicol 55, 353-371 (2015).
8. T. Hoppe, Multiubiquitylation by E4 enzymes: 'one size' doesn't fit all. Trends Biochem Sci 30, 183-187 (2005).
9. M. Koegl, T. Hoppe, S. Schlenker, H. D. Ulrich, T. U. Mayer, S. Jentsch, A novel ubiquitination factor, E4, is involved in multiubiquitin chain assembly. Cell 96, 635-644 (1999).
10. Y. Imai, M. Soda, S. Hatakeyama, T. Akagi, T. Hashikawa, K. I. Nakayama, R. Takahashi, CHIP is associated with Parkin, a gene responsible for familial Parkinson's disease, and enhances its ubiquitin ligase activity. Mol Cell 10, 55-67 (2002).
11. H. Wu, S. L. Pomeroy, M. Ferreira, N. Teider, J. Mariani, K. I. Nakayama, S. Hatakeyama, V. A. Tron, L. F. Saltibus, L. Spyracopoulos, R. P. Leng, UBE4B promotes Hdm2-mediated degradation of the tumor suppressor p53. Nat Med 17, 347-355 (2011).
12. B. Zhao, K. Bhuripanyo, K. Zhang, H. Kiyokawa, H. Schindelin, J. Yin, Orthogonal Ubiquitin Transfer through Engineered E1-E2 Cascades for Protein Ubiquitination. Chem. Biol. 19, 1265-1277 (2012).
13. X. Liu, B. Zhao, L. Sun, K. Bhuripanyo, Y. Wang, Y. Bi, R. V. Davuluri, D. M. Duong, D. Nanavati, J. Yin, H. Kiyokawa, Orthogonal ubiquitin transfer identifies ubiquitination substrates under differential control by the two ubiquitin activating enzymes. Nat Commun 8, 14286 (2017).
14. K. A. Nordquist, Y. N. Dimitrova, P. S. Brzovic, W. B. Ridenour, K. A. Munro, S. E. Soss, R. M. Caprioli, R. E. Klevit, W. J. Chazin, Structural and functional characterization of the monomeric U-box domain from E4B. Biochemistry 49, 347-355 (2010).
15. M. D. Ohi, C. W. Vander Kooi, J. A. Rosenberg, W. J. Chazin, K. L. Gould, Structural insights into the U-box, a domain associated with multi-ubiquitination. Nat Struct Biol 10, 250-255 (2003).
16. R. C. Benirschke, J. R. Thompson, Y. Nomine, E. Wasielewski, N. Juranic, S. Macura, S. Hatakeyama, K. I. Nakayama, M. V. Botuyan, G. Mer, Molecular basis for the association of human E4B U box ubiquitin ligase with E2-conjugating enzymes UbcH5c and Ubc4. Structure 18, 955-965 (2010).
17. H. Dou, L. Buetow, A. Hock, G. J. Sibbet, K. H. Vousden, D. T. Huang, Structural basis for autoinhibition and phosphorylation-dependent activation of c-Cbl. Nat Struct Mol Biol 19, 184-192 (2012).
18. Z. Xu, E. Kohli, K. I. Devlin, M. Bold, J. C. Nix, S. Misra, Interactions between the quality control ubiquitin ligase CHIP and ubiquitin conjugating enzymes. BMC Struct Biol 8, 26 (2008).
19. Q. Yin, S. C. Lin, B. Lamothe, M. Lu, Y. C. Lo, G. Hura, L. Zheng, R. L. Rich, A. D. Campos, D. G. Myszka, M. J. Lenardo, B. G. Darnay, H. Wu, E2 interaction and dimerization in the crystal structure of TRAF6. Nat Struct Mol Biol 16, 658-666 (2009).
20. M. Zhang, M. Windheim, S. M. Roe, M. Peggie, P. Cohen, C. Prodromou, L. H. Pearl, Chaperoned ubiquitylation—crystal structures of the CHIP U box E3 ubiquitin ligase and a CHIP-Ubc13-Uev1a complex. Mol Cell 20, 525-538 (2005).
21. H. Dou, L. Buetow, G. J. Sibbet, K. Cameron, D. T. Huang, Essentiality of a non-RING element in priming donor ubiquitin for catalysis by a monomeric E3. Nat Struct Mol Biol 20, 982-986 (2013).
22. J. N. Pruneda, L. P. J., S. E. Soss, K. A. Nordquist, W. J. Chazin, P. S. Brzovic, R. E. Klevit, Structure of an E3:E2-Ub complex reveals an allosteric mechanism shared among RING/U-box ligases. Mol. Cell 47, 933-942 (2012).
23. S. E. Soss, R. E. Klevit, W. J. Chazin, Activation of UbcH5c~Ub is the result of a shift in interdomain motions of the conjugate bound to U-box E3 ligase E4B. Biochemistry 52, 2991-2999 (2013).
24. L. M. Starita, J. N. Pruneda, R. S. Lo, D. M. Fowler, H. J. Kim, J. B. Hiatt, J. Shendure, P. S. Brzovic, S. Fields, R. E. Klevit, Activity-enhancing mutations in an E3 ubiquitin ligase identified by high-throughput mutagenesis. Proc Natl Acad Sci USA 110, E1263-1272 (2013).
25. R. Nikolay, T. Wiederkehr, W. Rist, G. Kramer, M. P. Mayer, B. Bukau, Dimerization of the human E3 ligase CHIP via a coiled-coil domain is essential for its activity. J Biol Chem 279, 2673-2678 (2004).
26. C. Esser, M. Scheffner, J. Hohfeld, The chaperone-associated ubiquitin ligase CHIP is able to target p53 for proteasomal degradation. J Biol Chem 280, 27443-27448 (2005).
27. C. Tagwerker, K. Flick, M. Cui, C. Guerrero, Y. Dou, B. Auer, P. Baldi, L. Huang, P. Kaiser, A tandem affinity tag for two-step purification under fully denaturing conditions: application in ubiquitin profiling and protein complex identification combined with in vivocross-linking. Mol Cell Proteomics 5, 737-748 (2006).
28. I. Paul, M. K. Ghosh, A CHIPotle in physiology and disease. Int J Biochem Cell Biol 58, 37-52 (2015).
29. K. A. Verba, R. Y. Wang, A. Arakawa, Y. Liu, M. Shirouzu, S. Yokoyama, D. A. Agard, Atomic structure of Hsp90-Cdc37-Cdk4 reveals that Hsp90 traps and stabilizes an unfolded kinase. Science 352, 1542-1547 (2016).

30. L. Stepanova, X. Leng, S. B. Parker, J. W. Harper, Mammalian p50Cdc37 is a protein kinase-targeting subunit of Hsp90 that binds and stabilizes Cdk4. Genes Dev 10, 1491-1502 (1996).
31. H. McDonough, C. Patterson, CHIP: a link between the chaperone and proteasome systems. Cell Stress Chaperones 8, 303-308 (2003).
32. A. L. Edkins, CHIP: a co-chaperone for degradation by the proteasome. Subcell Biochem 78, 219-242 (2015).
33. M. Matsumoto, M. Yada, S. Hatakeyama, H. Ishimoto, T. Tanimura, S. Tsuji, A. Kakizuka, M. Kitagawa, K. I. Nakayama, Molecular clearance of ataxin-3 is regulated by a mammalian E4. Embo J 23, 659-669 (2004).
34. F. Okumura, S. Hatakeyama, M. Matsumoto, T. Kamura, K. I. Nakayama, Functional regulation of FEZ1 by the U-box-type ubiquitin ligase E4B contributes to neuritogenesis. J Biol Chem 279, 53533-53543 (2004).
35. N. Sirisaengtaksin, M. Gireud, Q. Yan, Y. Kubota, D. Meza, J. C. Waymire, P. E. Zage, A. J. Bean, UBE4B protein couples ubiquitination and sorting machineries to enable epidermal growth factor receptor (EGFR) degradation. J Biol Chem 289, 3026-3039 (2014).
36. O. A. Ross, N. J. Rutherford, M. Baker, A. I. Soto-Ortolaza, M. M. Carrasquillo, M. DeJesus-Hernandez, J. Adamson, M. Li, K. Volkening, E. Finger, W. W. Seeley, K. J. Hatanpaa, C. Lomen-Hoerth, A. Kertesz, E. H. Bigio, C. Lippa, B. K. Woodruff, D. S. Knopman, C. L. White, 3rd, J. A. Van Gerpen, J. F. Meschia, I. R. Mackenzie, K. Boylan, B. F. Boeve, B. L. Miller, M. J. Strong, R. J. Uitti, S. G. Younkin, N. R. Graff-Radford, R. C. Petersen, Z. K. Wszolek, D. W. Dickson, R. Rademakers, Ataxin-2 repeat-length variation and neurodegeneration. Hum Mol Genet 20, 3207-3212 (2011).
37. M. H. Cobb, J. E. Hepler, M. Cheng, D. Robbins, The mitogen-activated protein kinases, ERK1 and ERK2. Semin Cancer Biol 5, 261-268 (1994).
38. D. Komander, M. J. Clague, S. Urbe, Breaking the chains: structure and function of the deubiquitinases. Nat Rev Mol Cell Biol 10, 550-563 (2009).
39. Y. Shi, Serine/threonine phosphatases: mechanism through structure. Cell 139, 468-484 (2009).
40. J. Tang, A. Frankel, R. J. Cook, S. Kim, W. K. Paik, K. R. Williams, S. Clarke, H. R. Herschman, PRMT1 is the predominant type I protein arginine methyltransferase in mammalian cells. J Biol Chem 275, 7723-7730 (2000).
41. C. A. Dickey, J. Koren, Y. J. Zhang, Y. F. Xu, U. K. Jinwal, M. J. Birnbaum, B. Monks, M. Sun, J. Q. Cheng, C. Patterson, R. M. Bailey, J. Dunmore, S. Soresh, C. Leon, D. Morgan, L. Petrucelli, Akt and CHIP coregulate tau degradation through coordinated interactions. Proc Natl Acad Sci USA 105, 3622-3627 (2008).
42. J. R. Hwang, C. Zhang, C. Patterson, C-terminus of heat shock protein 70-interacting protein facilitates degradation of apoptosis signal-regulating kinase 1 and inhibits apoptosis signal-regulating kinase 1-dependent apoptosis. Cell Stress Chaperones 10, 147-156 (2005).
43. T. Maruyama, H. Kadowaki, N. Okamoto, A. Nagai, I. Naguro, A. Matsuzawa, H. Shibuya, K. Tanaka, S. Murata, K. Takeda, H. Nishitoh, H. Ichijo, CHIP-dependent termination of MEKK2 regulates temporal ERK activation required for proper hyperosmotic response. Embo J 29, 2501-2514 (2010).
44. M. Yang, C. Wang, X. Zhu, S. Tang, L. Shi, X. Cao, T. Chen, E3 ubiquitin ligase CHIP facilitates Toll-like receptor signaling by recruiting and polyubiquitinating Src and atypical PKC{zeta}. J Exp Med 208, 2099-2112 (2011).
45. H. T. Zhang, L. F. Zeng, Q. Y. He, W. A. Tao, Z. G. Zha, C. D. Hu, The E3 ubiquitin ligase CHIP mediates ubiquitination and proteasomal degradation of PRMT5. Biochim Biophys Acta 1863, 335-346 (2016).
46. M. Kitagawa, S. Hatakeyama, M. Shirane, M. Matsumoto, N. Ishida, K. Hattori, I. Nakamichi, A. Kikuchi, K. Nakayama, K. Nakayama, An F-box protein, FWD1, mediates ubiquitin-dependent proteolysis of beta-catenin. Embo J 18, 2401-2410 (1999).
47. M. Hart, J. P. Concordet, I. Lassot, I. Albert, R. del los Santos, H. Durand, C. Perret, B. Rubinfeld, F. Margottin, R. Benarous, P. Polakis, The F-box protein beta-TrCP associates with phosphorylated beta-catenin and regulates its activity in the cell. Curr Biol 9, 207-210 (1999).
48. E. Latres, D. S. Chiaur, M. Pagano, The human F box protein beta-Trcp associates with the Cul1/Skp1 complex and regulates the stability of beta-catenin. Oncogene 18, 849-854 (1999).
49. J. T. Winston, P. Strack, P. Beer-Romero, C. Y. Chu, S. J. Elledge, J. W. Harper, The SCFbeta-TRCP-ubiquitin ligase complex associates specifically with phosphorylated destruction motifs in IkappaBalpha and beta-catenin and stimulates IkappaBalpha ubiquitination in vitro. Genes Dev 13, 270-283 (1999).
50. J. Xue, Y. Chen, Y. Wu, Z. Wang, A. Zhou, S. Zhang, K. Lin, K. Aldape, S. Majumder, Z. Lu, S. Huang, Tumour suppressor TRIM33 targets nuclear beta-catenin degradation. Nat Commun 6, 6156 (2015).
51. V. Chitalia, S. Shivanna, J. Martorell, R. Meyer, E. Edelman, N. Rahimi, c-Cbl, a ubiquitin E3 ligase that targets active beta-catenin: a novel layer of Wnt signaling regulation. J Biol Chem 288, 23505-23517 (2013).
52. C. Dominguez-Brauer, R. Khatun, A. J. Elia, K. L. Thu, P. Ramachandran, S. P. Baniasadi, Z. Hao, L. D. Jones, J. Haight, Y. Sheng, T. W. Mak, E3 ubiquitin ligase Mule targets beta-catenin under conditions of hyperactive Wnt signaling. Proc Natl Acad Sci USA 114, E1148-E1157 (2017).
53. C. Sun, H. L. Li, M. L. Shi, Q. H. Liu, J. Bai, J. N. Zheng, Diverse roles of C-terminal Hsp70-interacting protein (CHIP) in tumorigenesis. J Cancer Res Clin Oncol 140, 189-197 (2014).
54. J. L. Morales, G. H. Perdew, Carboxyl terminus of hsc70-interacting protein (CHIP) can remodel mature aryl hydrocarbon receptor (AhR) complexes and mediate ubiquitination of both the AhR and the 90 kDa heat-shock protein (hsp90) in vitro. Biochemistry 46, 610-621 (2007).
55. J. W. Brewer, J. A. Diehl, PERK mediates cell-cycle exit during the mammalian unfolded protein response. Proc Natl Acad Sci USA 97, 12625-12630 (2000).
56. Y. Gong, T. I. Zack, L. G. Morris, K. Lin, E. Hukkelhoven, R. Raheja, I. L. Tan, S. Turcan, S. Veeriah, S. Meng, A. Viale, S. E. Schumacher, P. Palmedo, R. Beroukhim, T. A. Chan, Pan-cancer genetic analysis identifies PARK2 as a master regulator of G1/S cyclins. Nat Genet 46, 588-594 (2014).
57. J. J. Barrott, T. A. Haystead, Hsp90, an unlikely ally in the war on cancer. FEBS J 280, 1381-1396 (2013).
58. Y. Merbl, M. W. Kirschner, Large-scale detection of ubiquitination substrates using cell extracts and protein microarrays. Proc Natl Acad Sci USA 106, 2543-2548 (2009).
59. M. K. Tan, H. J. Lim, E. J. Bennett, Y. Shi, J. W. Harper, Parallel SCF adaptor capture proteomics reveals a role for SCFFBXL17 in NRF2 activation via BACH1 repressor turnover. Mol Cell 52, 9-24 (2013).

60. M. J. Emanuele, A. E. Elia, Q. Xu, C. R. Thoma, L. Izhar, Y. Leng, A. Guo, Y. N. Chen, J. Rush, P. W. Hsu, H. C. Yen, S. J. Elledge, Global identification of modular cullin-RING ligase substrates. Cell 147, 459-474 (2011).
61. H. C. Yen, S. J. Elledge, Identification of SCF ubiquitin ligase substrates by global protein stability profiling. Science 322, 923-929 (2008).
62. G. Xu, S. R. Jaffrey, The new landscape of protein ubiquitination. Nat Biotechnol 29, 1098-1100 (2011).
63. P. Xu, D. M. Duong, N. T. Seyfried, D. Cheng, Y. Xie, J. Robert, J. Rush, M. Hochstrasser, D. Finley, J. Peng, Quantitative proteomics reveals the function of unconventional ubiquitin chains in proteasomal degradation. Cell 137, 133-145 (2009).
64. W. Kim, E. J. Bennett, E. L. Huttlin, A. Guo, J. Li, A. Possemato, M. E. Sowa, R. Rad, J. Rush, M. J. Comb, J. W. Harper, S. P. Gygi, Systematic and quantitative assessment of the ubiquitin-modified proteome. Mol Cell 44, 325-340 (2011).
65. S. A. Sarraf, M. Raman, V. Guarani-Pereira, M. E. Sowa, E. L. Huttlin, S. P. Gygi, J. W. Harper, Landscape of the PARKIN-dependent ubiquitylome in response to mitochondrial depolarization. Nature 496, 372-376 (2013).
66. K. G. Mark, T. B. Loveless, D. P. Toczyski, Isolation of ubiquitinated substrates by tandem affinity purification of E3 ligase-polyubiquitin-binding domain fusions (ligase traps). Nat Protoc 11, 291-301 (2016).
67. H. F. O'Connor, N. Lyon, J. W. Leung, P. Agarwal, C. D. Swaim, K. M. Miller, J. M. Huibregtse, Ubiquitin-Activated Interaction Traps (UBAITs) identify E3 ligase binding partners. EMBO Rep 16, 1699-1712 (2015).
68. M. Zhuang, S. Guan, H. Wang, A. L. Burlingame, J. A. Wells, Substrates of IAP ubiquitin ligases identified with a designed orthogonal E3 ligase, the NEDDylator. Mol Cell 49, 273-282 (2013).
69. O. Levin-Kravets, N. Tanner, N. Shohat, I. Attali, T. Keren-Kaplan, A. Shusterman, S. Artzi, A. Varvak, Y. Reshef, X. Shi, O. Zucker, T. Baram, C. Katina, I. Pilzer, S. Ben-Aroya, G. Prag, A bacterial genetic selection system for ubiquitylation cascade discovery. Nat Methods 13, 945-952 (2016).
70. R. Crameri, M. Suter, Display of biologically active proteins on the surface of filamentous phages: a cDNA cloning system for selection of functional gene products linked to the genetic information responsible for their production. Gene 137, 69-75 (1993).
71. K. Bhuripanyo, Ph.D. thesis, University of Chicago, https://knowledge.uchicago.edu/handle/11417/136 (2016).
72. T. S. Wingo, D. M. Duong, M. Zhou, E. B. Dammer, H. Wu, D. J. Cutler, J. J. Lah, A. I. Levey, N. T. Seyfried, Integrating Next-Generation Genomic Sequencing and Mass Spectrometry To Estimate Allele-Specific Protein Abundance in Human Brain. J Proteome Res 16, 3336-3347 (2017).
73. H. S. Comstra, J. McArthy, S. Rudin-Rush, C. Hartwig, A. Gokhale, S. A. Zlatic, J. B. Blackburn, E. Werner, M. Petris, P. D'Souza, P. Panuwet, D. B. Barr, V. Lupashin, A. Vrailas-Mortimer, V. Faundez, The interactome of the copper transporter ATP7A belongs to a network of neurodevelopmental and neurodegeneration factors. Elife 6, (2017).

Example III—Identifying the Substrate Protein of E3 Ubiquitin Ligase by Orthogonal Ubiquitin Transfer (OUT)

Reference is made to the presentation entitled "Identifying the Substrate Protein of E3 Ubiquitin Ligase by Orthogonal Ubiquitin Transfer (OUT)," presented by Jun Yin, at the FASEB Science Research Conference Ubiquitin & Cell Regulation, Jun. 18, 2018, the content of which is incorporated herein by reference in its entirety.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A platform for identifying a substrate of an E3 ubiquitin ligase (E3), the platform comprising as components the following proteins or vectors that express the following proteins:

(a) a mutant ubiquitin (UB) protein derived from SEQ ID NO: 1, wherein the mutation is selected from the group consisting of R42E, R72E, and a combination thereof;

(b) a mutant E1 protein (E1) derived from SEQ ID NO: 2, wherein the mutation is selected from the group consisting of Q608R, S621R, D623R, E1037K, D1047K, E1049K, and combinations thereof;

(c) a mutant E2 protein (E2) derived from SEQ ID NO:4 wherein the mutation is selected from the group consisting of R5E, K9E and a combination thereof; and (d) a mutant E3 ubiquitin ligase (E3) derived from SEQ ID NO: 6 wherein the mutation is selected from the group consisting of D651R, D652E, M653W, M654H, and combinations thereof.

2. The platform of claim 1, wherein the mutant UB comprises a tag for identifying and/or isolating a substrate to which the mutant UB has been transferred.

3. The platform of claim 1, wherein the mutant UB comprises a biotin or hemagglutinin (HA) tag for identifying and/or isolating a substrate to which the mutant UB has been transferred.

4. A method for identifying a substrate of an E3 ubiquitin ligase (E3), the method comprising:

(a) expressing the proteins of the platform of claim 1 in a cell under conditions in which the mutant E3 transfers the mutant UB to the substrate to ubiquitinate the substrate; and (b) identifying the ubiquitinated substrate.

5. The method of claim 4, wherein the mutant UB comprises a tag for identifying and/or isolating a substrate to which the mutant UB has been transferred and the ubiquitinated substrate is identified and/or isolated via the tag; wherein the tag is selected from biotin or a hemagglutinin epitope (HA) and the ubiquitinated substrate is identified and/or isolated via contacting the ubiquitinated substrate with the cognate partner for the tag.

6. The platform of claim 1, wherein the mutation of the mutant UB protein consists of R42E.

7. The platform of claim 1, wherein the mutation of the mutant UB protein consists of R72E.

8. The platform of claim 1, wherein the mutation of the mutant E1 protein consists of Q608R.

9. The platform of claim 1, wherein the mutation of the mutant E1 protein consists of S621R.

10. The platform of claim 1, wherein the mutation of the mutant E1 protein consists of D623R.

11. The platform of claim 1, wherein the mutation of the mutant E1 protein consists of E1037K.

12. The platform of claim 1, wherein the mutation of the mutant E1 protein consists of D1047K.

13. The platform of claim 1, wherein the mutation of the mutant E1 protein consists of E1049K.

14. The platform of claim 1, wherein the mutation of the mutant E2 protein consists of R5E.

15. The platform of claim 1, wherein the mutation of the mutant E2 protein consists of K9E.

16. The platform of claim 1, wherein the mutation of the mutant E3 protein consists of D651R.

17. The platform of claim 1, wherein the mutation of the mutant E3 protein consists of D652E.

18. The platform of claim 1, wherein the mutation of the mutant E3 protein consists of M653W.

19. The platform of claim 1, wherein the mutation of the mutant E3 protein consists of M654H.

* * * * *

SEQUENCE LISTING

```
<160> NUMBER OF SEQ ID NOS: 122

<210> SEQ ID NO 1
<211> LENGTH: 76
<212> TYPE: PRT
<213> ORGANISM: Homo sapiens

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
```

```
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75


<210> SEQ ID NO 2
<211> LENGTH: 1058
<212> TYPE: PRT
<213> ORGANISM: Homo sapiens

<400> SEQUENCE: 2

Met Ser Ser Ser Pro Leu Ser Lys Lys Arg Arg Val Ser Gly Pro Asp
1               5                   10                  15

Pro Lys Pro Gly Ser Asn Cys Ser Pro Ala Gln Ser Val Leu Ser Glu
            20                  25                  30

Val Pro Ser Val Pro Thr Asn Gly Met Ala Lys Asn Gly Ser Glu Ala
        35                  40                  45

Asp Ile Asp Glu Gly Leu Tyr Ser Arg Gln Leu Tyr Val Leu Gly His
    50                  55                  60

Glu Ala Met Lys Arg Leu Gln Thr Ser Ser Val Leu Val Ser Gly Leu
65                  70                  75                  80

Arg Gly Leu Gly Val Glu Ile Ala Lys Asn Ile Ile Leu Gly Gly Val
                85                  90                  95

Lys Ala Val Thr Leu His Asp Gln Gly Thr Ala Gln Trp Ala Asp Leu
            100                 105                 110

Ser Ser Gln Phe Tyr Leu Arg Glu Glu Asp Ile Gly Lys Asn Arg Ala
        115                 120                 125

Glu Val Ser Gln Pro Arg Leu Ala Glu Leu Asn Ser Tyr Val Pro Val
    130                 135                 140

Thr Ala Tyr Thr Gly Pro Leu Val Glu Asp Phe Leu Ser Gly Phe Gln
145                 150                 155                 160

Val Val Val Leu Thr Asn Thr Pro Leu Glu Asp Gln Leu Arg Val Gly
                165                 170                 175

Glu Phe Cys His Asn Arg Gly Ile Lys Leu Val Val Ala Gly Thr Arg
            180                 185                 190

Gly Leu Phe Gly Gln Leu Phe Cys Asp Phe Gly Glu Glu Met Ile Leu
        195                 200                 205

Thr Asp Ser Asn Gly Glu Gln Pro Leu Ser Ala Met Val Ser Met Val
    210                 215                 220

Thr Lys Asp Asn Pro Gly Val Val Thr Cys Leu Asp Glu Ala Arg His
225                 230                 235                 240

Gly Phe Glu Ser Gly Asp Phe Val Ser Phe Ser Glu Val Gln Gly Met
                245                 250                 255

Val Glu Leu Asn Gly Asn Gln Pro Met Glu Ile Lys Val Leu Gly Pro
            260                 265                 270

Tyr Thr Phe Ser Ile Cys Asp Thr Ser Asn Phe Ser Asp Tyr Ile Arg
        275                 280                 285

Gly Gly Ile Val Ser Gln Val Lys Val Pro Lys Lys Ile Ser Phe Lys
    290                 295                 300

Ser Leu Val Ala Ser Leu Ala Glu Pro Asp Phe Val Val Thr Asp Phe
305                 310                 315                 320

Ala Lys Phe Ser Arg Pro Ala Gln Leu His Ile Gly Phe Gln Ala Leu
                325                 330                 335
```

-continued

```
His Gln Phe Cys Ala Gln His Gly Arg Pro Pro Arg Pro Arg Asn Glu
            340                 345                 350

Glu Asp Ala Ala Glu Leu Val Ala Leu Ala Gln Ala Val Asn Ala Arg
        355                 360                 365

Ala Leu Pro Ala Val Gln Gln Asn Asn Leu Asp Glu Asp Leu Ile Arg
    370                 375                 380

Lys Leu Ala Tyr Val Ala Ala Gly Asp Leu Ala Pro Ile Asn Ala Phe
385                 390                 395                 400

Ile Gly Gly Leu Ala Ala Gln Glu Val Met Lys Ala Cys Ser Gly Lys
                405                 410                 415

Phe Met Pro Ile Met Gln Trp Leu Tyr Phe Asp Ala Leu Glu Cys Leu
            420                 425                 430

Pro Gln Asp Lys Glu Val Leu Thr Glu Asp Lys Cys Leu Gln Arg Gln
        435                 440                 445

Asn Arg Tyr Asp Gly Gln Val Ala Val Phe Gly Ser Asp Leu Gln Glu
    450                 455                 460

Lys Leu Gly Lys Gln Lys Tyr Phe Leu Val Gly Ala Gly Ala Ile Gly
465                 470                 475                 480

Cys Glu Leu Leu Lys Asn Phe Ala Met Ile Gly Leu Gly Cys Gly Glu
                485                 490                 495

Gly Gly Glu Ile Ile Val Thr Asp Met Asp Thr Ile Glu Lys Ser Asn
            500                 505                 510

Leu Asn Arg Gln Phe Leu Phe Arg Pro Trp Asp Val Thr Lys Leu Lys
        515                 520                 525

Ser Asp Thr Ala Ala Ala Ala Val Arg Gln Met Asn Pro His Ile Arg
    530                 535                 540

Val Thr Ser His Gln Asn Arg Val Gly Pro Asp Thr Glu Arg Ile Tyr
545                 550                 555                 560

Asp Asp Asp Phe Phe Gln Asn Leu Asp Gly Val Ala Asn Ala Leu Asp
                565                 570                 575

Asn Val Asp Ala Arg Met Tyr Met Asp Arg Arg Cys Val Tyr Tyr Arg
            580                 585                 590

Lys Pro Leu Leu Glu Ser Gly Thr Leu Gly Thr Lys Gly Asn Val Gln
        595                 600                 605

Val Val Ile Pro Phe Leu Thr Glu Ser Tyr Ser Ser Ser Gln Asp Pro
    610                 615                 620

Pro Glu Lys Ser Ile Pro Ile Cys Thr Leu Lys Asn Phe Pro Asn Ala
625                 630                 635                 640

Ile Glu His Thr Leu Gln Trp Ala Arg Asp Glu Phe Glu Gly Leu Phe
                645                 650                 655

Lys Gln Pro Ala Glu Asn Val Asn Gln Tyr Leu Thr Asp Pro Lys Phe
            660                 665                 670

Val Glu Arg Thr Leu Arg Leu Ala Gly Thr Gln Pro Leu Glu Val Leu
        675                 680                 685

Glu Ala Val Gln Arg Ser Leu Val Leu Gln Arg Pro Gln Thr Trp Ala
    690                 695                 700

Asp Cys Val Thr Trp Ala Cys His His Trp His Thr Gln Tyr Ser Asn
705                 710                 715                 720

Asn Ile Arg Gln Leu Leu His Asn Phe Pro Pro Asp Gln Leu Thr Ser
                725                 730                 735

Ser Gly Ala Pro Phe Trp Ser Gly Pro Lys Arg Cys Pro His Pro Leu
            740                 745                 750

Thr Phe Asp Val Asn Asn Pro Leu His Leu Asp Tyr Val Met Ala Ala
```

```
        755                 760                 765

Ala Asn Leu Phe Ala Gln Thr Tyr Gly Leu Thr Gly Ser Gln Asp Arg
    770                 775                 780

Ala Ala Val Ala Thr Phe Leu Gln Ser Val Gln Val Pro Glu Phe Thr
785                 790                 795                 800

Pro Lys Ser Gly Val Lys Ile His Val Ser Asp Gln Glu Leu Gln Ser
                805                 810                 815

Ala Asn Ala Ser Val Asp Asp Ser Arg Leu Glu Glu Leu Lys Ala Thr
            820                 825                 830

Leu Pro Ser Pro Asp Lys Leu Pro Gly Phe Lys Met Tyr Pro Ile Asp
        835                 840                 845

Phe Glu Lys Asp Asp Asp Ser Asn Phe His Met Asp Phe Ile Val Ala
    850                 855                 860

Ala Ser Asn Leu Arg Ala Glu Asn Tyr Asp Ile Pro Ser Ala Asp Arg
865                 870                 875                 880

His Lys Ser Lys Leu Ile Ala Gly Lys Ile Ile Pro Ala Ile Ala Thr
                885                 890                 895

Thr Thr Ala Ala Val Val Gly Leu Val Cys Leu Glu Leu Tyr Lys Val
            900                 905                 910

Val Gln Gly His Arg Gln Leu Asp Ser Tyr Lys Asn Gly Phe Leu Asn
        915                 920                 925

Leu Ala Leu Pro Phe Phe Gly Phe Ser Glu Pro Leu Ala Ala Pro Arg
    930                 935                 940

His Gln Tyr Tyr Asn Gln Glu Trp Thr Leu Trp Asp Arg Phe Glu Val
945                 950                 955                 960

Gln Gly Leu Gln Pro Asn Gly Glu Glu Met Thr Leu Lys Gln Phe Leu
                965                 970                 975

Asp Tyr Phe Lys Thr Glu His Lys Leu Glu Ile Thr Met Leu Ser Gln
            980                 985                 990

Gly Val Ser Met Leu Tyr Ser Phe  Phe Met Pro Ala Ala  Lys Leu Lys
        995                 1000                1005

Glu Arg  Leu Asp Gln Pro Met  Thr Glu Ile Val Ser  Arg Val Ser
    1010                1015                1020

Lys Arg  Lys Leu Gly Arg His  Val Arg Ala Leu Val  Leu Glu Leu
    1025                1030                1035

Cys Cys  Asn Asp Glu Ser Gly  Glu Asp Val Glu Val  Pro Tyr Val
    1040                1045                1050

Arg Tyr  Thr Ile Arg
    1055


<210> SEQ ID NO 3
<211> LENGTH: 1018
<212> TYPE: PRT
<213> ORGANISM: Homo sapiens

<400> SEQUENCE: 3

Met Ala Lys Asn Gly Ser Glu Ala Asp Ile Asp Glu Gly Leu Tyr Ser
1               5                   10                  15

Arg Gln Leu Tyr Val Leu Gly His Glu Ala Met Lys Arg Leu Gln Thr
            20                  25                  30

Ser Ser Val Leu Val Ser Gly Leu Arg Gly Leu Gly Val Glu Ile Ala
        35                  40                  45

Lys Asn Ile Ile Leu Gly Gly Val Lys Ala Val Thr Leu His Asp Gln
    50                  55                  60
```

-continued

```
Gly Thr Ala Gln Trp Ala Asp Leu Ser Ser Gln Phe Tyr Leu Arg Glu
65                  70                  75                  80

Glu Asp Ile Gly Lys Asn Arg Ala Glu Val Ser Gln Pro Arg Leu Ala
                85                  90                  95

Glu Leu Asn Ser Tyr Val Pro Val Thr Ala Tyr Thr Gly Pro Leu Val
            100                 105                 110

Glu Asp Phe Leu Ser Gly Phe Gln Val Val Val Leu Thr Asn Thr Pro
        115                 120                 125

Leu Glu Asp Gln Leu Arg Val Gly Glu Phe Cys His Asn Arg Gly Ile
    130                 135                 140

Lys Leu Val Val Ala Gly Thr Arg Gly Leu Phe Gly Gln Leu Phe Cys
145                 150                 155                 160

Asp Phe Gly Glu Glu Met Ile Leu Thr Asp Ser Asn Gly Glu Gln Pro
                165                 170                 175

Leu Ser Ala Met Val Ser Met Val Thr Lys Asp Asn Pro Gly Val Val
            180                 185                 190

Thr Cys Leu Asp Glu Ala Arg His Gly Phe Glu Ser Gly Asp Phe Val
        195                 200                 205

Ser Phe Ser Glu Val Gln Gly Met Val Glu Leu Asn Gly Asn Gln Pro
    210                 215                 220

Met Glu Ile Lys Val Leu Gly Pro Tyr Thr Phe Ser Ile Cys Asp Thr
225                 230                 235                 240

Ser Asn Phe Ser Asp Tyr Ile Arg Gly Gly Ile Val Ser Gln Val Lys
                245                 250                 255

Val Pro Lys Lys Ile Ser Phe Lys Ser Leu Val Ala Ser Leu Ala Glu
            260                 265                 270

Pro Asp Phe Val Val Thr Asp Phe Ala Lys Phe Ser Arg Pro Ala Gln
        275                 280                 285

Leu His Ile Gly Phe Gln Ala Leu His Gln Phe Cys Ala Gln His Gly
    290                 295                 300

Arg Pro Pro Arg Pro Arg Asn Glu Glu Asp Ala Ala Glu Leu Val Ala
305                 310                 315                 320

Leu Ala Gln Ala Val Asn Ala Arg Ala Leu Pro Ala Val Gln Gln Asn
                325                 330                 335

Asn Leu Asp Glu Asp Leu Ile Arg Lys Leu Ala Tyr Val Ala Ala Gly
            340                 345                 350

Asp Leu Ala Pro Ile Asn Ala Phe Ile Gly Gly Leu Ala Ala Gln Glu
        355                 360                 365

Val Met Lys Ala Cys Ser Gly Lys Phe Met Pro Ile Met Gln Trp Leu
    370                 375                 380

Tyr Phe Asp Ala Leu Glu Cys Leu Pro Gln Asp Lys Glu Val Leu Thr
385                 390                 395                 400

Glu Asp Lys Cys Leu Gln Arg Gln Asn Arg Tyr Asp Gly Gln Val Ala
                405                 410                 415

Val Phe Gly Ser Asp Leu Gln Glu Lys Leu Gly Lys Gln Lys Tyr Phe
            420                 425                 430

Leu Val Gly Ala Gly Ala Ile Gly Cys Glu Leu Leu Lys Asn Phe Ala
        435                 440                 445

Met Ile Gly Leu Gly Cys Gly Glu Gly Gly Glu Ile Ile Val Thr Asp
    450                 455                 460

Met Asp Thr Ile Glu Lys Ser Asn Leu Asn Arg Gln Phe Leu Phe Arg
465                 470                 475                 480

Pro Trp Asp Val Thr Lys Leu Lys Ser Asp Thr Ala Ala Ala Ala Val
```

```
                485                 490                 495

Arg Gln Met Asn Pro His Ile Arg Val Thr Ser His Gln Asn Arg Val
            500                 505                 510

Gly Pro Asp Thr Glu Arg Ile Tyr Asp Asp Asp Phe Phe Gln Asn Leu
        515                 520                 525

Asp Gly Val Ala Asn Ala Leu Asp Asn Val Asp Ala Arg Met Tyr Met
    530                 535                 540

Asp Arg Arg Cys Val Tyr Tyr Arg Lys Pro Leu Leu Glu Ser Gly Thr
545                 550                 555                 560

Leu Gly Thr Lys Gly Asn Val Gln Val Val Ile Pro Phe Leu Thr Glu
                565                 570                 575

Ser Tyr Ser Ser Ser Gln Asp Pro Pro Glu Lys Ser Ile Pro Ile Cys
            580                 585                 590

Thr Leu Lys Asn Phe Pro Asn Ala Ile Glu His Thr Leu Gln Trp Ala
        595                 600                 605

Arg Asp Glu Phe Glu Gly Leu Phe Lys Gln Pro Ala Glu Asn Val Asn
    610                 615                 620

Gln Tyr Leu Thr Asp Pro Lys Phe Val Glu Arg Thr Leu Arg Leu Ala
625                 630                 635                 640

Gly Thr Gln Pro Leu Glu Val Leu Glu Ala Val Gln Arg Ser Leu Val
                645                 650                 655

Leu Gln Arg Pro Gln Thr Trp Ala Asp Cys Val Thr Trp Ala Cys His
            660                 665                 670

His Trp His Thr Gln Tyr Ser Asn Asn Ile Arg Gln Leu Leu His Asn
        675                 680                 685

Phe Pro Pro Asp Gln Leu Thr Ser Ser Gly Ala Pro Phe Trp Ser Gly
    690                 695                 700

Pro Lys Arg Cys Pro His Pro Leu Thr Phe Asp Val Asn Asn Pro Leu
705                 710                 715                 720

His Leu Asp Tyr Val Met Ala Ala Ala Asn Leu Phe Ala Gln Thr Tyr
                725                 730                 735

Gly Leu Thr Gly Ser Gln Asp Arg Ala Ala Val Ala Thr Phe Leu Gln
            740                 745                 750

Ser Val Gln Val Pro Glu Phe Thr Pro Lys Ser Gly Val Lys Ile His
        755                 760                 765

Val Ser Asp Gln Glu Leu Gln Ser Ala Asn Ala Ser Val Asp Asp Ser
    770                 775                 780

Arg Leu Glu Glu Leu Lys Ala Thr Leu Pro Ser Pro Asp Lys Leu Pro
785                 790                 795                 800

Gly Phe Lys Met Tyr Pro Ile Asp Phe Glu Lys Asp Asp Asp Ser Asn
                805                 810                 815

Phe His Met Asp Phe Ile Val Ala Ala Ser Asn Leu Arg Ala Glu Asn
            820                 825                 830

Tyr Asp Ile Pro Ser Ala Asp Arg His Lys Ser Lys Leu Ile Ala Gly
        835                 840                 845

Lys Ile Ile Pro Ala Ile Ala Thr Thr Thr Ala Ala Val Val Gly Leu
    850                 855                 860

Val Cys Leu Glu Leu Tyr Lys Val Val Gln Gly His Arg Gln Leu Asp
865                 870                 875                 880

Ser Tyr Lys Asn Gly Phe Leu Asn Leu Ala Leu Pro Phe Phe Gly Phe
                885                 890                 895

Ser Glu Pro Leu Ala Ala Pro Arg His Gln Tyr Tyr Asn Gln Glu Trp
            900                 905                 910
```

Thr Leu Trp Asp Arg Phe Glu Val Gln Gly Leu Gln Pro Asn Gly Glu
915 920 925

Glu Met Thr Leu Lys Gln Phe Leu Asp Tyr Phe Lys Thr Glu His Lys
930 935 940

Leu Glu Ile Thr Met Leu Ser Gln Gly Val Ser Met Leu Tyr Ser Phe
945 950 955 960

Phe Met Pro Ala Ala Lys Leu Lys Glu Arg Leu Asp Gln Pro Met Thr
965 970 975

Glu Ile Val Ser Arg Val Ser Lys Arg Lys Leu Gly Arg His Val Arg
980 985 990

Ala Leu Val Leu Glu Leu Cys Cys Asn Asp Glu Ser Gly Glu Asp Val
995 1000 1005

Glu Val Pro Tyr Val Arg Tyr Thr Ile Arg
1010 1015

<210> SEQ ID NO 4
<211> LENGTH: 154
<212> TYPE: PRT
<213> ORGANISM: Homo sapiens

<400> SEQUENCE: 4

Met Ala Ala Ser Arg Arg Leu Met Lys Glu Leu Glu Glu Ile Arg Lys
1 5 10 15

Cys Gly Met Lys Asn Phe Arg Asn Ile Gln Val Asp Glu Ala Asn Leu
20 25 30

Leu Thr Trp Gln Gly Leu Ile Val Pro Asp Asn Pro Pro Tyr Asp Lys
35 40 45

Gly Ala Phe Arg Ile Glu Ile Asn Phe Pro Ala Glu Tyr Pro Phe Lys
50 55 60

Pro Pro Lys Ile Thr Phe Lys Thr Lys Ile Tyr His Pro Asn Ile Asp
65 70 75 80

Glu Lys Gly Gln Val Cys Leu Pro Val Ile Ser Ala Glu Asn Trp Lys
85 90 95

Pro Ala Thr Lys Thr Asp Gln Val Ile Gln Ser Leu Ile Ala Leu Val
100 105 110

Asn Asp Pro Gln Pro Glu His Pro Leu Arg Ala Asp Leu Ala Glu Glu
115 120 125

Tyr Ser Lys Asp Arg Lys Lys Phe Cys Lys Asn Ala Glu Glu Phe Thr
130 135 140

Lys Lys Tyr Gly Glu Lys Arg Pro Val Asp
145 150

<210> SEQ ID NO 5
<211> LENGTH: 147
<212> TYPE: PRT
<213> ORGANISM: Homo sapiens

<400> SEQUENCE: 5

Met Ala Leu Lys Arg Ile His Lys Glu Leu Asn Asp Leu Ala Arg Asp
1 5 10 15

Pro Pro Ala Gln Cys Ser Ala Gly Pro Val Gly Asp Asp Met Phe His
20 25 30

Trp Gln Ala Thr Ile Met Gly Pro Asn Asp Ser Pro Tyr Gln Gly Gly
35 40 45

Val Phe Phe Leu Thr Ile His Phe Pro Thr Asp Tyr Pro Phe Lys Pro
50 55 60

Pro Lys Val Ala Phe Thr Thr Arg Ile Tyr His Pro Asn Ile Asn Ser
65 70 75 80

Asn Gly Ser Ile Cys Leu Asp Ile Leu Arg Ser Gln Trp Ser Pro Ala
85 90 95

Leu Thr Ile Ser Lys Val Leu Leu Ser Ile Cys Ser Leu Leu Cys Asp
100 105 110

Pro Asn Pro Asp Asp Pro Leu Val Pro Glu Ile Ala Arg Ile Tyr Lys
115 120 125

Thr Asp Arg Glu Lys Tyr Asn Arg Ile Ala Arg Glu Trp Thr Gln Lys
130 135 140

Tyr Ala Met
145

<210> SEQ ID NO 6
<211> LENGTH: 852
<212> TYPE: PRT
<213> ORGANISM: Homo sapiens

<400> SEQUENCE: 6

Met Lys Arg Ala Ala Ala Lys His Leu Ile Glu Arg Tyr Tyr His Gln
1 5 10 15

Leu Thr Glu Gly Cys Gly Asn Glu Ala Cys Thr Asn Glu Phe Cys Ala
20 25 30

Ser Cys Pro Thr Phe Leu Arg Met Asp Asn Asn Ala Ala Ala Ile Lys
35 40 45

Ala Leu Glu Leu Tyr Lys Ile Asn Ala Lys Leu Cys Asp Pro His Pro
50 55 60

Ser Lys Lys Gly Ala Ser Ser Ala Tyr Leu Glu Asn Ser Lys Gly Ala
65 70 75 80

Pro Asn Asn Ser Cys Ser Glu Ile Lys Met Asn Lys Lys Gly Ala Arg
85 90 95

Ile Asp Phe Lys Asp Val Thr Tyr Leu Thr Glu Glu Lys Val Tyr Glu
100 105 110

Ile Leu Glu Leu Cys Arg Glu Arg Glu Asp Tyr Ser Pro Leu Ile Arg
115 120 125

Val Ile Gly Arg Val Phe Ser Ser Ala Glu Ala Leu Val Gln Ser Phe
130 135 140

Arg Lys Val Lys Gln His Thr Lys Glu Glu Leu Lys Ser Leu Gln Ala
145 150 155 160

Lys Asp Glu Asp Lys Asp Glu Asp Glu Lys Glu Lys Ala Ala Cys Ser
165 170 175

Ala Ala Ala Met Glu Glu Asp Ser Glu Ala Ser Ser Ser Arg Ile Gly
180 185 190

Asp Ser Ser Gln Gly Asp Asn Asn Leu Gln Lys Leu Gly Pro Asp Asp
195 200 205

Val Ser Val Asp Ile Asp Ala Ile Arg Arg Val Tyr Thr Arg Leu Leu
210 215 220

Ser Asn Glu Lys Ile Glu Thr Ala Phe Leu Asn Ala Leu Val Tyr Leu
225 230 235 240

Ser Pro Asn Val Glu Cys Asp Leu Thr Tyr His Asn Val Tyr Ser Arg
245 250 255

Asp Pro Asn Tyr Leu Asn Leu Phe Ile Ile Val Met Glu Asn Arg Asn
260 265 270

Leu His Ser Pro Glu Tyr Leu Glu Met Ala Leu Pro Leu Phe Cys Lys

```
        275                 280                 285

Ala Met Ser Lys Leu Pro Leu Ala Ala Gln Gly Lys Leu Ile Arg Leu
    290                 295                 300

Trp Ser Lys Tyr Asn Ala Asp Gln Ile Arg Arg Met Met Glu Thr Phe
305                 310                 315                 320

Gln Gln Leu Ile Thr Tyr Lys Val Ile Ser Asn Glu Phe Asn Ser Arg
                325                 330                 335

Asn Leu Val Asn Asp Asp Asp Ala Ile Val Ala Ala Ser Lys Cys Leu
            340                 345                 350

Lys Met Val Tyr Tyr Ala Asn Val Val Gly Gly Glu Val Asp Thr Asn
        355                 360                 365

His Asn Glu Glu Asp Asp Glu Glu Pro Ile Pro Glu Ser Ser Glu Leu
    370                 375                 380

Thr Leu Gln Glu Leu Leu Gly Glu Glu Arg Arg Asn Lys Lys Gly Pro
385                 390                 395                 400

Arg Val Asp Pro Leu Glu Thr Glu Leu Gly Val Lys Thr Leu Asp Cys
                405                 410                 415

Arg Lys Pro Leu Ile Pro Phe Glu Glu Phe Ile Asn Glu Pro Leu Asn
            420                 425                 430

Glu Val Leu Glu Met Asp Lys Asp Tyr Thr Phe Phe Lys Val Glu Thr
        435                 440                 445

Glu Asn Lys Phe Ser Phe Met Thr Cys Pro Phe Ile Leu Asn Ala Val
    450                 455                 460

Thr Lys Asn Leu Gly Leu Tyr Tyr Asp Asn Arg Ile Arg Met Tyr Ser
465                 470                 475                 480

Glu Arg Arg Ile Thr Val Leu Tyr Ser Leu Val Gln Gly Gln Gln Leu
                485                 490                 495

Asn Pro Tyr Leu Arg Leu Lys Val Arg Arg Asp His Ile Ile Asp Asp
            500                 505                 510

Ala Leu Val Arg Leu Glu Met Ile Ala Met Glu Asn Pro Ala Asp Leu
        515                 520                 525

Lys Lys Gln Leu Tyr Val Glu Phe Glu Gly Glu Gln Gly Val Asp Glu
    530                 535                 540

Gly Gly Val Ser Lys Glu Phe Phe Gln Leu Val Val Glu Glu Ile Phe
545                 550                 555                 560

Asn Pro Asp Ile Gly Met Phe Thr Tyr Asp Glu Ser Thr Lys Leu Phe
                565                 570                 575

Trp Phe Asn Pro Ser Ser Phe Glu Thr Glu Gly Gln Phe Thr Leu Ile
            580                 585                 590

Gly Ile Val Leu Gly Leu Ala Ile Tyr Asn Asn Cys Ile Leu Asp Val
        595                 600                 605

His Phe Pro Met Val Val Tyr Arg Lys Leu Met Gly Lys Lys Gly Thr
    610                 615                 620

Phe Arg Asp Leu Gly Asp Ser His Pro Val Leu Tyr Gln Ser Leu Lys
625                 630                 635                 640

Asp Leu Leu Glu Tyr Glu Gly Asn Val Glu Asp Asp Met Met Ile Thr
                645                 650                 655

Phe Gln Ile Ser Gln Thr Asp Leu Phe Gly Asn Pro Met Met Tyr Asp
            660                 665                 670

Leu Lys Glu Asn Gly Asp Lys Ile Pro Ile Thr Asn Glu Asn Arg Lys
        675                 680                 685

Glu Phe Val Asn Leu Tyr Ser Asp Tyr Ile Leu Asn Lys Ser Val Glu
    690                 695                 700
```

Lys Gln Phe Lys Ala Phe Arg Arg Gly Phe His Met Val Thr Asn Glu
705 710 715 720

Ser Pro Leu Lys Tyr Leu Phe Arg Pro Glu Glu Ile Glu Leu Leu Ile
725 730 735

Cys Gly Ser Arg Asn Leu Asp Phe Gln Ala Leu Glu Glu Thr Thr Glu
740 745 750

Tyr Asp Gly Gly Tyr Thr Arg Asp Ser Val Leu Ile Arg Glu Phe Trp
755 760 765

Glu Ile Val His Ser Phe Thr Asp Glu Gln Lys Arg Leu Phe Leu Gln
770 775 780

Phe Thr Thr Gly Thr Asp Arg Ala Pro Val Gly Gly Leu Gly Lys Leu
785 790 795 800

Lys Met Ile Ile Ala Lys Asn Gly Pro Asp Thr Glu Arg Leu Pro Thr
805 810 815

Ser His Thr Cys Phe Asn Val Leu Leu Leu Pro Glu Tyr Ser Ser Lys
820 825 830

Glu Lys Leu Lys Glu Arg Leu Leu Lys Ala Ile Thr Tyr Ala Lys Gly
835 840 845

Phe Gly Met Leu
850

<210> SEQ ID NO 7
<211> LENGTH: 1302
<212> TYPE: PRT
<213> ORGANISM: Homo sapiens

<400> SEQUENCE: 7

Met Glu Glu Leu Ser Ala Asp Glu Ile Arg Arg Arg Arg Leu Ala Arg
1 5 10 15

Leu Ala Gly Gly Gln Thr Ser Gln Pro Thr Thr Pro Leu Thr Ser Pro
20 25 30

Gln Arg Glu Asn Pro Pro Gly Pro Pro Ile Ala Ala Ser Ala Pro Gly
35 40 45

Pro Ser Gln Ser Leu Gly Leu Asn Val His Asn Met Thr Pro Ala Thr
50 55 60

Ser Pro Ile Gly Ala Ser Gly Val Ala His Arg Ser Gln Ser Ser Glu
65 70 75 80

Gly Val Ser Ser Leu Ser Ser Ser Pro Ser Asn Ser Leu Glu Thr Gln
85 90 95

Ser Gln Ser Leu Ser Arg Ser Gln Ser Met Asp Ile Asp Gly Val Ser
100 105 110

Cys Glu Lys Ser Met Ser Gln Val Asp Val Asp Ser Gly Ile Glu Asn
115 120 125

Met Glu Val Asp Glu Asn Asp Arg Arg Glu Lys Arg Ser Leu Ser Asp
130 135 140

Lys Glu Pro Ser Ser Gly Pro Glu Val Ser Glu Glu Gln Ala Leu Gln
145 150 155 160

Leu Val Cys Lys Ile Phe Arg Val Ser Trp Lys Asp Arg Asp Arg Asp
165 170 175

Val Ile Phe Leu Ser Ser Leu Ser Ala Gln Phe Lys Gln Asn Pro Lys
180 185 190

Glu Val Phe Ser Asp Phe Lys Asp Leu Ile Gly Gln Ile Leu Met Glu
195 200 205

Val Leu Met Met Ser Thr Gln Thr Arg Asp Glu Asn Pro Phe Ala Ser

-continued

```
    210                 215                 220

Leu Thr Ala Thr Ser Gln Pro Ile Ala Ala Ala Ala Arg Ser Pro Asp
225                 230                 235                 240

Arg Asn Leu Leu Leu Asn Thr Gly Ser Asn Pro Gly Thr Ser Pro Met
                245                 250                 255

Phe Cys Ser Val Ala Ser Phe Gly Ala Ser Ser Leu Ser Ser Leu Tyr
            260                 265                 270

Glu Ser Ser Pro Ala Pro Thr Pro Ser Phe Trp Ser Ser Val Pro Val
        275                 280                 285

Met Gly Pro Ser Leu Ala Ser Pro Ser Arg Ala Ala Ser Gln Leu Ala
    290                 295                 300

Val Pro Ser Thr Pro Leu Ser Pro His Ser Ala Ala Ser Gly Thr Ala
305                 310                 315                 320

Ala Gly Ser Gln Pro Ser Ser Pro Arg Tyr Arg Pro Tyr Thr Val Thr
                325                 330                 335

His Pro Trp Ala Ser Ser Gly Val Ser Ile Leu Ser Ser Ser Pro Ser
            340                 345                 350

Pro Pro Ala Leu Ala Ser Ser Pro Gln Ala Val Pro Ala Ser Ser Ser
        355                 360                 365

Arg Gln Arg Pro Ser Ser Thr Gly Pro Pro Leu Pro Pro Ala Ser Pro
    370                 375                 380

Ser Ala Thr Ser Arg Arg Pro Ser Ser Leu Arg Ile Ser Pro Ser Leu
385                 390                 395                 400

Gly Ala Ser Gly Gly Ala Ser Asn Trp Asp Ser Tyr Ser Asp His Phe
                405                 410                 415

Thr Ile Glu Thr Cys Lys Glu Thr Asp Met Leu Asn Tyr Leu Ile Glu
            420                 425                 430

Cys Phe Asp Arg Val Gly Ile Glu Glu Lys Lys Ala Pro Lys Met Cys
        435                 440                 445

Ser Gln Pro Ala Val Ser Gln Leu Leu Ser Asn Ile Arg Ser Gln Cys
    450                 455                 460

Ile Ser His Thr Ala Leu Val Leu Gln Gly Ser Leu Thr Gln Pro Arg
465                 470                 475                 480

Ser Leu Gln Gln Pro Ser Phe Leu Val Pro Tyr Met Leu Cys Arg Asn
                485                 490                 495

Leu Pro Tyr Gly Phe Ile Gln Glu Leu Val Arg Thr Thr His Gln Asp
            500                 505                 510

Glu Glu Val Phe Lys Gln Ile Phe Ile Pro Ile Leu Gln Gly Leu Ala
        515                 520                 525

Leu Ala Ala Lys Glu Cys Ser Leu Asp Ser Asp Tyr Phe Lys Tyr Pro
    530                 535                 540

Leu Met Ala Leu Gly Glu Leu Cys Glu Thr Lys Phe Gly Lys Thr His
545                 550                 555                 560

Pro Val Cys Asn Leu Val Ala Ser Leu Arg Leu Trp Leu Pro Lys Ser
                565                 570                 575

Leu Ser Pro Gly Cys Gly Arg Glu Leu Gln Arg Leu Ser Tyr Leu Gly
            580                 585                 590

Ala Phe Phe Ser Phe Ser Val Phe Ala Glu Asp Asp Val Lys Val Val
        595                 600                 605

Glu Lys Tyr Phe Ser Gly Pro Ala Ile Thr Leu Glu Asn Thr Arg Val
    610                 615                 620

Val Ser Gln Ser Leu Gln His Tyr Leu Glu Leu Gly Arg Gln Glu Leu
625                 630                 635                 640
```

```
Phe Lys Ile Leu His Ser Ile Leu Leu Asn Gly Glu Thr Arg Glu Ala
                645                 650                 655

Ala Leu Ser Tyr Met Ala Ala Val Val Asn Ala Asn Met Lys Lys Ala
            660                 665                 670

Gln Met Gln Thr Asp Asp Arg Leu Val Ser Thr Asp Gly Phe Met Leu
        675                 680                 685

Asn Phe Leu Trp Val Leu Gln Gln Leu Ser Thr Lys Ile Lys Leu Glu
    690                 695                 700

Thr Val Asp Pro Thr Tyr Ile Phe His Pro Arg Cys Arg Ile Thr Leu
705                 710                 715                 720

Pro Asn Asp Glu Thr Arg Val Asn Ala Thr Met Glu Asp Val Asn Asp
                725                 730                 735

Trp Leu Thr Glu Leu Tyr Gly Asp Gln Pro Pro Phe Ser Glu Pro Lys
            740                 745                 750

Phe Pro Thr Glu Cys Phe Phe Leu Thr Leu His Ala His His Leu Ser
        755                 760                 765

Ile Leu Pro Ser Cys Arg Arg Tyr Ile Arg Arg Leu Arg Ala Ile Arg
    770                 775                 780

Glu Leu Asn Arg Thr Val Glu Asp Leu Lys Asn Asn Glu Ser Gln Trp
785                 790                 795                 800

Lys Asp Ser Pro Leu Ala Thr Arg His Arg Glu Met Leu Lys Arg Cys
                805                 810                 815

Lys Thr Gln Leu Lys Lys Leu Val Arg Cys Lys Ala Cys Ala Asp Ala
            820                 825                 830

Gly Leu Leu Asp Glu Ser Phe Leu Arg Arg Cys Leu Asn Phe Tyr Gly
        835                 840                 845

Leu Leu Ile Gln Leu Leu Leu Arg Ile Leu Asp Pro Ala Tyr Pro Asp
    850                 855                 860

Ile Thr Leu Pro Leu Asn Ser Asp Val Pro Lys Val Phe Ala Ala Leu
865                 870                 875                 880

Pro Glu Phe Tyr Val Glu Asp Val Ala Glu Phe Leu Phe Phe Ile Val
                885                 890                 895

Gln Tyr Ser Pro Gln Ala Leu Tyr Glu Pro Cys Thr Gln Asp Ile Val
            900                 905                 910

Met Phe Leu Val Val Met Leu Cys Asn Gln Asn Tyr Ile Arg Asn Pro
        915                 920                 925

Tyr Leu Val Ala Lys Leu Val Glu Val Met Phe Met Thr Asn Pro Ala
    930                 935                 940

Val Gln Pro Arg Thr Gln Lys Phe Phe Glu Met Ile Glu Asn His Pro
945                 950                 955                 960

Leu Ser Thr Lys Leu Leu Val Pro Ser Leu Met Lys Phe Tyr Thr Asp
                965                 970                 975

Val Glu His Thr Gly Ala Thr Ser Glu Phe Tyr Asp Lys Phe Thr Ile
            980                 985                 990

Arg Tyr His Ile Ser Thr Ile Phe  Lys Ser Leu Trp Gln  Asn Ile Ala
        995                 1000                1005

His His  Gly Thr Phe Met Glu  Glu Phe Asn Ser Gly  Lys Gln Phe
    1010                1015                1020

Val Arg  Tyr Ile Asn Met Leu  Ile Asn Asp Thr Thr  Phe Leu Leu
    1025                1030                1035

Asp Glu  Ser Leu Glu Ser Leu  Lys Arg Ile His Glu  Val Gln Glu
    1040                1045                1050
```

```
Glu Met  Lys Asn Lys Glu Gln  Trp Asp Gln Leu Pro  Arg Asp Gln
    1055                 1060                 1065

Gln Gln  Ala Arg Gln Ser Gln  Leu Ala Gln Asp Glu  Arg Val Ser
    1070                 1075                 1080

Arg Ser  Tyr Leu Ala Leu Ala  Thr Glu Thr Val Asp  Met Phe His
    1085                 1090                 1095

Ile Leu  Thr Lys Gln Val Gln  Lys Pro Phe Leu Arg  Pro Glu Leu
    1100                 1105                 1110

Gly Pro  Arg Leu Ala Ala Met  Leu Asn Phe Asn Leu  Gln Gln Leu
    1115                 1120                 1125

Cys Gly  Pro Lys Cys Arg Asp  Leu Lys Val Glu Asn  Pro Glu Lys
    1130                 1135                 1140

Tyr Gly  Phe Glu Pro Lys Lys  Leu Leu Asp Gln Leu  Thr Asp Ile
    1145                 1150                 1155

Tyr Leu  Gln Leu Asp Cys Ala  Arg Phe Ala Lys Ala  Ile Ala Asp
    1160                 1165                 1170

Asp Gln  Arg Ser Tyr Ser Lys  Glu Leu Phe Glu Glu  Val Ile Ser
    1175                 1180                 1185

Lys Met  Arg Lys Ala Gly Ile  Lys Ser Thr Ile Ala  Ile Glu Lys
    1190                 1195                 1200

Phe Lys  Leu Leu Ala Glu Lys  Val Glu Glu Ile Val  Ala Lys Asn
    1205                 1210                 1215

Ala Arg  Ala Glu Ile Asp Tyr  Ser Asp Ala Pro Asp  Glu Phe Arg
    1220                 1225                 1230

Asp Pro  Leu Met Asp Thr Leu  Met Thr Asp Pro Val  Arg Leu Pro
    1235                 1240                 1245

Ser Gly  Thr Ile Met Asp Arg  Ser Ile Ile Leu Arg  His Leu Leu
    1250                 1255                 1260

Asn Ser  Pro Thr Asp Pro Phe  Asn Arg Gln Thr Leu  Thr Glu Ser
    1265                 1270                 1275

Met Leu  Glu Pro Val Pro Glu  Leu Lys Glu Gln Ile  Gln Ala Trp
    1280                 1285                 1290

Met Arg  Glu Lys Gln Asn Ser  Asp His
    1295                 1300
```

<210> SEQ ID NO 8
<211> LENGTH: 284
<212> TYPE: PRT
<213> ORGANISM: Homo sapiens

<400> SEQUENCE: 8

```
Met Lys Gly Lys Glu Glu Lys Glu Gly Gly Ala Arg Leu Gly Ala Gly
1               5                   10                  15

Gly Gly Ser Pro Glu Lys Ser Pro Ser Ala Gln Glu Leu Lys Glu Gln
            20                  25                  30

Gly Asn Arg Leu Phe Val Gly Arg Lys Tyr Pro Glu Ala Ala Ala Cys
        35                  40                  45

Tyr Gly Arg Ala Ile Met Gln Gln His Glu Gln Ala Leu Ala Asp Cys
    50                  55                  60

Arg Arg Ala Leu Glu Leu Asp Gly Gln Ser Val Lys Ala His Phe Phe
65                  70                  75                  80

Leu Gly Gln Cys Gln Leu Glu Met Glu Ser Tyr Asp Glu Ala Ile Ala
                85                  90                  95

Asn Leu Gln Arg Ala Tyr Ser Leu Ala Lys Glu Gln Arg Leu Asn Phe
            100                 105                 110
```

```
Gly Asp Asp Ile Pro Ser Ala Leu Arg Ile Ala Lys Lys Lys Arg Trp
        115                 120                 125

Asn Ser Ile Glu Glu Arg Arg Ile His Gln Glu Ser Glu Leu His Ser
    130                 135                 140

Tyr Leu Ser Arg Leu Ile Ala Ala Glu Arg Glu Arg Glu Leu Glu Glu
145                 150                 155                 160

Cys Gln Arg Asn His Glu Gly Asp Glu Asp Asp Ser His Val Arg Ala
                165                 170                 175

Gln Gln Ala Cys Ile Glu Ala Lys His Asp Lys Tyr Met Ala Asp Met
            180                 185                 190

Asp Glu Leu Phe Ser Gln Val Asp Glu Lys Arg Lys Lys Arg Asp Ile
        195                 200                 205

Pro Asp Tyr Leu Cys Gly Lys Ile Ser Phe Glu Leu Met Arg Glu Pro
    210                 215                 220

Cys Ile Thr Pro Ser Gly Ile Thr Tyr Asp Arg Lys Asp Ile Glu Glu
225                 230                 235                 240

His Leu Gln Arg Val Gly His Phe Asp Pro Val Thr Arg Ser Pro Leu
                245                 250                 255

Thr Gln Glu Gln Leu Ile Pro Asn Leu Ala Met Lys Glu Val Ile Asp
            260                 265                 270

Ala Phe Ile Ser Glu Asn Gly Trp Val Glu Asp Tyr
        275                 280
```

<210> SEQ ID NO 9
<211> LENGTH: 10
<212> TYPE: PRT
<213> ORGANISM: Homo sapiens

<400> SEQUENCE: 9

```
Glu Gly Ile Asp Pro Pro Asp Gln Gln Arg
1               5                   10
```

<210> SEQ ID NO 10
<211> LENGTH: 9
<212> TYPE: PRT
<213> ORGANISM: Homo sapiens

<400> SEQUENCE: 10

```
Glu Ser Thr Leu His Leu Val Leu Arg
1               5
```

<210> SEQ ID NO 11
<211> LENGTH: 7
<212> TYPE: PRT
<213> ORGANISM: Homo sapiens

<400> SEQUENCE: 11

```
Cys Gly Lys Ile Ser Phe Glu
1               5
```

<210> SEQ ID NO 12
<211> LENGTH: 7
<212> TYPE: PRT
<213> ORGANISM: Homo sapiens

<400> SEQUENCE: 12

```
Lys Asp Pro Ile Met His Thr
1               5
```

<210> SEQ ID NO 13
<211> LENGTH: 7
<212> TYPE: PRT
<213> ORGANISM: Homo sapiens

<400> SEQUENCE: 13

Lys Asp Pro Ile Met Arg Thr
1               5

<210> SEQ ID NO 14
<211> LENGTH: 8
<212> TYPE: PRT
<213> ORGANISM: Homo sapiens

<400> SEQUENCE: 14

Glu Asp Asp Met Met Ile Thr Phe
1               5

<210> SEQ ID NO 15
<211> LENGTH: 8
<212> TYPE: PRT
<213> ORGANISM: Artificial Sequence
<220> FEATURE:
<223> OTHER INFORMATION: synthetic

<400> SEQUENCE: 15

Glu Gly Gly Ser Ala Ile Arg Phe
1               5

<210> SEQ ID NO 16
<211> LENGTH: 8
<212> TYPE: PRT
<213> ORGANISM: Artificial Sequence
<220> FEATURE:
<223> OTHER INFORMATION: synthetic

<400> SEQUENCE: 16

Glu Arg Asp Trp Met Ile Arg Phe
1               5

<210> SEQ ID NO 17
<211> LENGTH: 8
<212> TYPE: PRT
<213> ORGANISM: Artificial Sequence
<220> FEATURE:
<223> OTHER INFORMATION: synthetic

<400> SEQUENCE: 17

Glu Met Val Tyr Gly Ile Arg Phe
1               5

<210> SEQ ID NO 18
<211> LENGTH: 8
<212> TYPE: PRT
<213> ORGANISM: Artificial Sequence
<220> FEATURE:
<223> OTHER INFORMATION: synthetic

<400> SEQUENCE: 18

Glu Ser Leu Cys His Ile Val Phe
1               5

<210> SEQ ID NO 19
<211> LENGTH: 8
<212> TYPE: PRT
<213> ORGANISM: Artificial Sequence
<220> FEATURE:

<223> OTHER INFORMATION: synthetic

<400> SEQUENCE: 19

Glu Arg Asp Ile Arg Ile Arg Phe
1 5

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Glu Arg Glu Trp His Ile Thr Phe
1 5

<210> SEQ ID NO 21
<211> LENGTH: 8
<212> TYPE: PRT
<213> ORGANISM: Artificial Sequence
<220> FEATURE:
<223> OTHER INFORMATION: synthetic

<400> SEQUENCE: 21

Glu Met Asn Tyr His Ile Met Phe
1 5

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Glu Leu Ala Phe Met Ile Leu Phe
1 5

<210> SEQ ID NO 23
<211> LENGTH: 8
<212> TYPE: PRT
<213> ORGANISM: Artificial Sequence
<220> FEATURE:
<223> OTHER INFORMATION: synthetic

<400> SEQUENCE: 23

Glu Gln Ala Tyr Arg Ile Arg Phe
1 5

<210> SEQ ID NO 24
<211> LENGTH: 8
<212> TYPE: PRT
<213> ORGANISM: Artificial Sequence
<220> FEATURE:
<223> OTHER INFORMATION: synthetic

<400> SEQUENCE: 24

Glu Arg Asp Gly Leu Ile Gly Phe
1 5

<210> SEQ ID NO 25
<211> LENGTH: 8
<212> TYPE: PRT
<213> ORGANISM: Artificial Sequence
<220> FEATURE:
<223> OTHER INFORMATION: synthetic

<400> SEQUENCE: 25

Glu Asn Leu Ser Trp Ile Met Phe
1 5

<210> SEQ ID NO 26
<211> LENGTH: 8
<212> TYPE: PRT
<213> ORGANISM: Artificial Sequence
<220> FEATURE:
<223> OTHER INFORMATION: synthetic

<400> SEQUENCE: 26

Glu Arg Val Trp Arg Ile Arg Phe
1 5

<210> SEQ ID NO 27
<211> LENGTH: 8
<212> TYPE: PRT
<213> ORGANISM: Artificial Sequence
<220> FEATURE:
<223> OTHER INFORMATION: synthetic

<400> SEQUENCE: 27

Glu Arg Ser Val Lys Ile Ser Phe
1 5

<210> SEQ ID NO 28
<211> LENGTH: 8
<212> TYPE: PRT
<213> ORGANISM: Artificial Sequence
<220> FEATURE:
<223> OTHER INFORMATION: synthetic

<400> SEQUENCE: 28

Glu Gln Ser Gln Asn Ile Gly Phe
1 5

<210> SEQ ID NO 29
<211> LENGTH: 8
<212> TYPE: PRT
<213> ORGANISM: Artificial Sequence
<220> FEATURE:
<223> OTHER INFORMATION: synthetic

<400> SEQUENCE: 29

Glu Leu Asn Thr Ala Ile Val Phe
1 5

<210> SEQ ID NO 30
<211> LENGTH: 8
<212> TYPE: PRT
<213> ORGANISM: Artificial Sequence
<220> FEATURE:
<223> OTHER INFORMATION: synthetic

<400> SEQUENCE: 30

Ile Val Asn Trp Gly Ile Cys Phe
1 5

<210> SEQ ID NO 31
<211> LENGTH: 8
<212> TYPE: PRT
<213> ORGANISM: Artificial Sequence
<220> FEATURE:
<223> OTHER INFORMATION: synthetic

<400> SEQUENCE: 31

Glu Met Asn Tyr Arg Ile Arg Phe
1 5

<210> SEQ ID NO 32
<211> LENGTH: 8
<212> TYPE: PRT
<213> ORGANISM: Artificial Sequence
<220> FEATURE:
<223> OTHER INFORMATION: synthetic

<400> SEQUENCE: 32

Glu Ser Lys Trp Ser Ile Met Phe
1 5

<210> SEQ ID NO 33
<211> LENGTH: 8
<212> TYPE: PRT
<213> ORGANISM: Artificial Sequence
<220> FEATURE:
<223> OTHER INFORMATION: synthetic

<400> SEQUENCE: 33

Glu Val Glu Tyr Ser Ile Thr Phe
1 5

<210> SEQ ID NO 34
<211> LENGTH: 8
<212> TYPE: PRT
<213> ORGANISM: Artificial Sequence
<220> FEATURE:
<223> OTHER INFORMATION: synthetic

<400> SEQUENCE: 34

Glu Asp Arg Ser His Ile Leu Phe
1 5

<210> SEQ ID NO 35
<211> LENGTH: 6
<212> TYPE: PRT
<213> ORGANISM: Artificial Sequence
<220> FEATURE:
<223> OTHER INFORMATION: synthetic

<400> SEQUENCE: 35

His His His His His His
1 5

<210> SEQ ID NO 36
<211> LENGTH: 50
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid

<400> SEQUENCE: 36

Arg Arg Cys Val Phe Tyr Arg Lys Pro Leu Leu Glu Ser Gly Thr Leu
1 5 10 15

Gly Thr Lys Gly Asn Thr Gln Val Xaa Xaa Pro His Leu Thr Glu Ser

```
            20                  25                  30

Tyr Ser Ser Ser Xaa Asp Pro Pro Glu Lys Ser Ile Pro Ile Cys Thr
        35                  40                  45

Leu Lys
    50


<210> SEQ ID NO 37
<211> LENGTH: 50
<212> TYPE: PRT
<213> ORGANISM: Saccharomyces cerevisiae

<400> SEQUENCE: 37

Arg Arg Cys Val Phe Tyr Arg Lys Pro Leu Leu Glu Ser Gly Thr Leu
1               5                   10                  15

Gly Thr Lys Gly Asn Thr Gln Val Ile Ile Pro Arg Leu Thr Glu Ser
            20                  25                  30

Tyr Ser Ser Ser Arg Asp Pro Pro Glu Lys Ser Ile Pro Leu Cys Thr
        35                  40                  45

Leu Arg
    50


<210> SEQ ID NO 38
<211> LENGTH: 50
<212> TYPE: PRT
<213> ORGANISM: Schizosaccharomyces pombe

<400> SEQUENCE: 38

Arg Arg Cys Val Phe Phe Glu Lys Pro Leu Leu Glu Ser Gly Thr Leu
1               5                   10                  15

Gly Thr Lys Gly Asn Thr Gln Val Val Val Pro His Leu Thr Glu Ser
            20                  25                  30

Tyr Gly Ser Ser Gln Asp Pro Pro Glu Lys Ser Phe Pro Ile Cys Thr
        35                  40                  45

Leu Lys
    50


<210> SEQ ID NO 39
<211> LENGTH: 50
<212> TYPE: PRT
<213> ORGANISM: Homo sapiens

<400> SEQUENCE: 39

Arg Arg Cys Val Tyr Tyr Arg Lys Pro Leu Leu Glu Ser Gly Thr Leu
1               5                   10                  15

Gly Thr Lys Gly Asn Thr Gln Val Val Ile Pro Phe Leu Thr Glu Ser
            20                  25                  30

Tyr Ser Ser Ser Gln Asp Pro Pro Glu Lys Ser Ile Pro Ile Cys Thr
        35                  40                  45

Leu Lys
    50


<210> SEQ ID NO 40
<211> LENGTH: 50
<212> TYPE: PRT
<213> ORGANISM: Homo sapiens

<400> SEQUENCE: 40

Ser Arg Cys Leu Ala Asn Leu Arg Pro Leu Leu Asp Ser Gly Thr Met
1               5                   10                  15
```

```
Gly Thr Lys Gly His Thr Glu Val Ile Val Pro His Leu Thr Glu Ser
            20                  25                  30

Tyr Asn Ser His Arg Asp Pro Pro Glu Glu Glu Ile Pro Phe Cys Thr
        35                  40                  45

Leu Lys
    50


<210> SEQ ID NO 41
<211> LENGTH: 36
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: MISC_FEATURE
<222> LOCATION: (19)..(19)
<223> OTHER INFORMATION: X is E or absent
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: MISC_FEATURE
<222> LOCATION: (36)..(36)
<223> OTHER INFORMATION: X is R or absent

<400> SEQUENCE: 41

Lys Lys Lys Leu Xaa Xaa His Val Xaa Xaa Leu Val Leu Glu Ile Cys
1               5                   10                  15

Cys Asp Xaa Asp Xaa Xaa Gly Glu Asp Val Glu Val Pro Phe Ile Xaa
            20                  25                  30

Ile Thr Leu Xaa
        35


<210> SEQ ID NO 42
<211> LENGTH: 34
<212> TYPE: PRT
<213> ORGANISM: Saccharomyces cerevisiae

<400> SEQUENCE: 42

Lys Lys Asp Ile Pro Ala His Val Ser Thr Met Ile Leu Glu Ile Cys
1               5                   10                  15

Ala Asp Asp Lys Glu Gly Glu Asp Val Glu Val Pro Phe Ile Thr Ile
            20                  25                  30

His Leu


<210> SEQ ID NO 43
<211> LENGTH: 34
<212> TYPE: PRT
<213> ORGANISM: Schizosaccharomyces pombe

<400> SEQUENCE: 43

Lys Lys Lys Leu Glu Pro Phe Arg Lys His Leu Val Leu Glu Ile Cys
1               5                   10                  15
```

Cys Asp Asp Ala Asn Gly Glu Asp Val Glu Val Pro Phe Ile Cys Ile
20 25 30

Lys Leu

<210> SEQ ID NO 44
<211> LENGTH: 35
<212> TYPE: PRT
<213> ORGANISM: Homo sapiens

<400> SEQUENCE: 44

Lys Arg Lys Leu Gly Arg His Val Arg Ala Leu Val Leu Glu Leu Cys
1 5 10 15

Cys Asn Asp Glu Ser Gly Glu Asp Val Glu Val Pro Tyr Val Arg Tyr
20 25 30

Thr Ile Arg
35

<210> SEQ ID NO 45
<211> LENGTH: 35
<212> TYPE: PRT
<213> ORGANISM: Homo sapiens

<400> SEQUENCE: 45

Glu Lys Lys Tyr Val Asp Leu Thr Val Ser Phe Ala Pro Asp Ile Asp
1 5 10 15

Gly Asp Glu Asp Leu Pro Gly Pro Pro Val Arg Tyr Tyr Phe Ser His
20 25 30

Asp Thr Asp
35

<210> SEQ ID NO 46
<211> LENGTH: 20
<212> TYPE: PRT
<213> ORGANISM: Saccharomyces cerevisiae

<400> SEQUENCE: 46

Met Ser Arg Ala Lys Arg Ile Met Lys Glu Ile Gln Ala Val Lys Asp
1 5 10 15

Asp Pro Ala Ala
20

<210> SEQ ID NO 47
<211> LENGTH: 18
<212> TYPE: PRT
<213> ORGANISM: Artificial Sequence
<220> FEATURE:
<223> OTHER INFORMATION: synthetic

<400> SEQUENCE: 47

Ala Ser Lys Arg Ile His Lys Glu Leu Asn Asp Leu Ala Arg Asp Pro
1 5 10 15

Pro Ala

<210> SEQ ID NO 48
<211> LENGTH: 20
<212> TYPE: PRT
<213> ORGANISM: Artificial Sequence
<220> FEATURE:
<223> OTHER INFORMATION: synthetic

<400> SEQUENCE: 48

Met Ala Ala Ser Arg Arg Leu Met Lys Glu Leu Glu Glu Ile Arg Lys

```
1               5                   10                  15

Cys Gly Met Lys
            20


<210> SEQ ID NO 49
<211> LENGTH: 20
<212> TYPE: PRT
<213> ORGANISM: Artificial Sequence
<220> FEATURE:
<223> OTHER INFORMATION: synthetic

<400> SEQUENCE: 49

Pro Gln Cys Leu Leu Arg Ile Lys Arg Asp Ile Met Ser Ile Tyr Lys
1               5                   10                  15

Glu Pro Pro Pro
            20


<210> SEQ ID NO 50
<211> LENGTH: 23
<212> TYPE: PRT
<213> ORGANISM: Artificial Sequence
<220> FEATURE:
<223> OTHER INFORMATION: synthetic

<400> SEQUENCE: 50

Ala Ala Arg Ala Arg Arg Leu Ala Gln Glu Ala Val Thr Leu Ser Thr
1               5                   10                  15

Ser Leu Pro Leu Ser Ser Ser
            20


<210> SEQ ID NO 51
<211> LENGTH: 20
<212> TYPE: PRT
<213> ORGANISM: Artificial Sequence
<220> FEATURE:
<223> OTHER INFORMATION: synthetic

<400> SEQUENCE: 51

Val Gln Arg Ile Lys Arg Glu Phe Lys Glu Val Leu Lys Ser Glu Glu
1               5                   10                  15

Thr Ser Lys Asn
            20


<210> SEQ ID NO 52
<211> LENGTH: 20
<212> TYPE: PRT
<213> ORGANISM: Artificial Sequence
<220> FEATURE:
<223> OTHER INFORMATION: synthetic

<400> SEQUENCE: 52

Pro Ser Ser Gln Lys Ala Leu Leu Leu Glu Leu Lys Gly Leu Gln Glu
1               5                   10                  15

Glu Pro Val Glu
            20


<210> SEQ ID NO 53
<211> LENGTH: 7
<212> TYPE: PRT
<213> ORGANISM: Homo sapiens

<400> SEQUENCE: 53

Arg Asp Pro Leu Met Asp Thr
1               5
```

<210> SEQ ID NO 54
<211> LENGTH: 7
<212> TYPE: PRT
<213> ORGANISM: Homo sapiens

<400> SEQUENCE: 54

Cys Gly Lys Ile Ser Phe Glu
1               5

<210> SEQ ID NO 55
<211> LENGTH: 7
<212> TYPE: PRT
<213> ORGANISM: Artificial Sequence
<220> FEATURE:
<223> OTHER INFORMATION: synthetic

<400> SEQUENCE: 55

Lys Asp Pro Ile Met His Thr
1               5

<210> SEQ ID NO 56
<211> LENGTH: 7
<212> TYPE: PRT
<213> ORGANISM: Artificial Sequence
<220> FEATURE:
<223> OTHER INFORMATION: synthetic

<400> SEQUENCE: 56

Lys Asp Pro Ile Leu Phe Thr
1               5

<210> SEQ ID NO 57
<211> LENGTH: 7
<212> TYPE: PRT
<213> ORGANISM: Artificial Sequence
<220> FEATURE:
<223> OTHER INFORMATION: synthetic

<400> SEQUENCE: 57

Arg Asp Pro Ile Tyr Tyr Thr
1               5

<210> SEQ ID NO 58
<211> LENGTH: 7
<212> TYPE: PRT
<213> ORGANISM: Artificial Sequence
<220> FEATURE:
<223> OTHER INFORMATION: synthetic

<400> SEQUENCE: 58

Lys Asp Pro Ile Ser Tyr Thr
1               5

<210> SEQ ID NO 59
<211> LENGTH: 7
<212> TYPE: PRT
<213> ORGANISM: Artificial Sequence
<220> FEATURE:
<223> OTHER INFORMATION: synthetic

<400> SEQUENCE: 59

Lys Asp Pro Ile Asn Phe Thr
1               5

<210> SEQ ID NO 60

<211> LENGTH: 7
<212> TYPE: PRT
<213> ORGANISM: Artificial Sequence
<220> FEATURE:
<223> OTHER INFORMATION: synthetic

<400> SEQUENCE: 60

Ile Asp Pro Ile Met Arg Thr
1               5

<210> SEQ ID NO 61
<211> LENGTH: 7
<212> TYPE: PRT
<213> ORGANISM: Artificial Sequence
<220> FEATURE:
<223> OTHER INFORMATION: synthetic

<400> SEQUENCE: 61

Ile Asp Pro Ile Leu Phe Thr
1               5

<210> SEQ ID NO 62
<211> LENGTH: 7
<212> TYPE: PRT
<213> ORGANISM: Artificial Sequence
<220> FEATURE:
<223> OTHER INFORMATION: synthetic

<400> SEQUENCE: 62

Met Asp Pro Ile Ile Asn Arg
1               5

<210> SEQ ID NO 63
<211> LENGTH: 7
<212> TYPE: PRT
<213> ORGANISM: Artificial Sequence
<220> FEATURE:
<223> OTHER INFORMATION: synthetic

<400> SEQUENCE: 63

Lys Asp Pro Ile Met Arg Thr
1               5

<210> SEQ ID NO 64
<211> LENGTH: 7
<212> TYPE: PRT
<213> ORGANISM: Artificial Sequence
<220> FEATURE:
<223> OTHER INFORMATION: synthetic

<400> SEQUENCE: 64

Leu Asp Pro Ile Thr Tyr Thr
1               5

<210> SEQ ID NO 65
<211> LENGTH: 7
<212> TYPE: PRT
<213> ORGANISM: Artificial Sequence
<220> FEATURE:
<223> OTHER INFORMATION: synthetic

<400> SEQUENCE: 65

Lys Asp Pro Ile Met Tyr Thr
1               5

<210> SEQ ID NO 66
<211> LENGTH: 17

<212> TYPE: PRT
<213> ORGANISM: Saccharomyces cerevisiae

<400> SEQUENCE: 66

Met Ser Arg Ala Lys Arg Ile Met Lys Glu Ile Gln Ala Val Lys Asp
1 5 10 15

Asp

<210> SEQ ID NO 67
<211> LENGTH: 16
<212> TYPE: PRT
<213> ORGANISM: Artificial Sequence
<220> FEATURE:
<223> OTHER INFORMATION: synthetic

<400> SEQUENCE: 67

Met Ala Leu Lys Arg Ile Gln Lys Glu Leu Gln Asp Leu Gln Arg Asp
1 5 10 15

<210> SEQ ID NO 68
<211> LENGTH: 16
<212> TYPE: PRT
<213> ORGANISM: Artificial Sequence
<220> FEATURE:
<223> OTHER INFORMATION: synthetic

<400> SEQUENCE: 68

Met Ala Ser Lys Arg Ile His Lys Glu Leu Asn Asp Leu Ala Arg Asp
1 5 10 15

<210> SEQ ID NO 69
<211> LENGTH: 16
<212> TYPE: PRT
<213> ORGANISM: Artificial Sequence
<220> FEATURE:
<223> OTHER INFORMATION: synthetic

<400> SEQUENCE: 69

Met Ala Leu Lys Arg Ile Asn Lys Glu Leu Ser Asp Leu Ala Arg Asp
1 5 10 15

<210> SEQ ID NO 70
<211> LENGTH: 17
<212> TYPE: PRT
<213> ORGANISM: Artificial Sequence
<220> FEATURE:
<223> OTHER INFORMATION: 71

<400> SEQUENCE: 70

Met Ala Ala Ser Arg Arg Leu Met Lys Glu Leu Glu Glu Ile Arg Lys
1 5 10 15

Cys

<210> SEQ ID NO 71
<211> LENGTH: 18
<212> TYPE: PRT
<213> ORGANISM: Artificial Sequence
<220> FEATURE:
<223> OTHER INFORMATION: synthetic

<400> SEQUENCE: 71

Arg Gly Pro Val Gly Lys Arg Leu Gln Gln Glu Leu Met Thr Leu Met
1 5 10 15

Met Ser

<210> SEQ ID NO 72
<211> LENGTH: 18
<212> TYPE: PRT
<213> ORGANISM: Artificial Sequence
<220> FEATURE:
<223> OTHER INFORMATION: synthetic

<400> SEQUENCE: 72

Met Ala Gly Leu Pro Arg Arg Ile Ile Lys Glu Thr Gln Arg Leu Leu
1               5                   10                  15

Ala Glu

<210> SEQ ID NO 73
<211> LENGTH: 13
<212> TYPE: PRT
<213> ORGANISM: Artificial Sequence
<220> FEATURE:
<223> OTHER INFORMATION: synthetic

<400> SEQUENCE: 73

Met Ala Leu Lys Arg Ile Gln Lys Glu Leu Ser Asp Leu
1               5                   10

<210> SEQ ID NO 74
<211> LENGTH: 14
<212> TYPE: PRT
<213> ORGANISM: Artificial Sequence
<220> FEATURE:
<223> OTHER INFORMATION: synthetic

<400> SEQUENCE: 74

Met Ala Ala Ser Arg Arg Leu Met Lys Glu Leu Glu Glu Ile
1               5                   10

<210> SEQ ID NO 75
<211> LENGTH: 14
<212> TYPE: PRT
<213> ORGANISM: Artificial Sequence
<220> FEATURE:
<223> OTHER INFORMATION: synthetic

<400> SEQUENCE: 75

Met Ala Arg Ser Lys Arg Ile Met Lys Glu Ile Gln Ala Val
1               5                   10

<210> SEQ ID NO 76
<211> LENGTH: 14
<212> TYPE: PRT
<213> ORGANISM: Artificial Sequence
<220> FEATURE:
<223> OTHER INFORMATION: synthetic

<400> SEQUENCE: 76

Met Ser Arg Ala Glu Asp Ile Met Glu Gln Ile Leu Ala Val
1               5                   10

<210> SEQ ID NO 77
<211> LENGTH: 14
<212> TYPE: PRT
<213> ORGANISM: Artificial Sequence
<220> FEATURE:
<223> OTHER INFORMATION: synthetic

<400> SEQUENCE: 77

Met Ser Arg Ala Asp Asp Ile Met Asp Gln Ile His Ala Val
1               5                   10

<210> SEQ ID NO 78
<211> LENGTH: 14
<212> TYPE: PRT
<213> ORGANISM: Artificial Sequence
<220> FEATURE:
<223> OTHER INFORMATION: synthetic

<400> SEQUENCE: 78

Met Ser Arg Ala Asp Glu Ile Met Asn Gln Ile Met Ala Val
1               5                   10

<210> SEQ ID NO 79
<211> LENGTH: 14
<212> TYPE: PRT
<213> ORGANISM: Artificial Sequence
<220> FEATURE:
<223> OTHER INFORMATION: synthetic

<400> SEQUENCE: 79

Met Ser Arg Ala Arg Asp Ile Met Asp Asp Ile Leu Ala Val
1               5                   10

<210> SEQ ID NO 80
<211> LENGTH: 14
<212> TYPE: PRT
<213> ORGANISM: Artificial Sequence
<220> FEATURE:
<223> OTHER INFORMATION: synthetic

<400> SEQUENCE: 80

Met Ser Arg Ala Pro Glu Ile Met Thr Gln Ile Met Ala Val
1               5                   10

<210> SEQ ID NO 81
<211> LENGTH: 14
<212> TYPE: PRT
<213> ORGANISM: Artificial Sequence
<220> FEATURE:
<223> OTHER INFORMATION: synthetic

<400> SEQUENCE: 81

Met Ser Arg Ala Pro Asp Ile Met Asp Gln Ile Lys Ala Val
1               5                   10

<210> SEQ ID NO 82
<211> LENGTH: 14
<212> TYPE: PRT
<213> ORGANISM: Artificial Sequence
<220> FEATURE:
<223> OTHER INFORMATION: synthetic

<400> SEQUENCE: 82

Met Ser Arg Ala Asp Asp Ile Met Leu Gln Ile Lys Ala Val
1               5                   10

<210> SEQ ID NO 83
<211> LENGTH: 14
<212> TYPE: PRT
<213> ORGANISM: Artificial Sequence
<220> FEATURE:
<223> OTHER INFORMATION: synthetic

<400> SEQUENCE: 83

Met Ser Arg Ala Pro Asp Ile Met Ser Gln Ile Leu Ala Val
1               5                   10

<210> SEQ ID NO 84
<211> LENGTH: 14
<212> TYPE: PRT
<213> ORGANISM: Artificial Sequence
<220> FEATURE:
<223> OTHER INFORMATION: synthetic

<400> SEQUENCE: 84

Met Ser Arg Ala Asp Glu Ile Met Glu Gln Ile Leu Ala Val
1 5 10

<210> SEQ ID NO 85
<211> LENGTH: 14
<212> TYPE: PRT
<213> ORGANISM: Artificial Sequence
<220> FEATURE:
<223> OTHER INFORMATION: synthetic

<400> SEQUENCE: 85

Met Ser Arg Ala His Thr Ile Met Asp Asp Ile Met Ala Val
1 5 10

<210> SEQ ID NO 86
<211> LENGTH: 14
<212> TYPE: PRT
<213> ORGANISM: Artificial Sequence
<220> FEATURE:
<223> OTHER INFORMATION: synthetic

<400> SEQUENCE: 86

Met Ser Arg Ala Glu Glu Ile Met Thr Gln Ile Lys Ala Val
1 5 10

<210> SEQ ID NO 87
<211> LENGTH: 14
<212> TYPE: PRT
<213> ORGANISM: Artificial Sequence
<220> FEATURE:
<223> OTHER INFORMATION: synthetic

<400> SEQUENCE: 87

Met Ser Arg Ala Glu Asp Ile Met Ser Gln Ile Ala Ala Val
1 5 10

<210> SEQ ID NO 88
<211> LENGTH: 14
<212> TYPE: PRT
<213> ORGANISM: Artificial Sequence
<220> FEATURE:
<223> OTHER INFORMATION: synthetic

<400> SEQUENCE: 88

Met Ser Arg Ala Asp Ser Ile Met Glu Gln Ile Arg Ala Val
1 5 10

<210> SEQ ID NO 89
<211> LENGTH: 14
<212> TYPE: PRT
<213> ORGANISM: Artificial Sequence
<220> FEATURE:
<223> OTHER INFORMATION: synthetic

<400> SEQUENCE: 89

Met Ser Arg Ala Glu Glu Ile Met Glu Gln Ile Lys Ala Val
1 5 10

<210> SEQ ID NO 90
<211> LENGTH: 14
<212> TYPE: PRT
<213> ORGANISM: Artificial Sequence
<220> FEATURE:
<223> OTHER INFORMATION: synthetic

<400> SEQUENCE: 90

Met Ser Arg Ala Asp Asp Ile Met Ser Gln Ile Leu Ala Val
1 5 10

<210> SEQ ID NO 91
<211> LENGTH: 14
<212> TYPE: PRT
<213> ORGANISM: Artificial Sequence
<220> FEATURE:
<223> OTHER INFORMATION: synthetic

<400> SEQUENCE: 91

Met Ser Arg Ala Pro Asp Ile Met Glu Gln Ile Trp Ala Val
1 5 10

<210> SEQ ID NO 92
<211> LENGTH: 14
<212> TYPE: PRT
<213> ORGANISM: Artificial Sequence
<220> FEATURE:
<223> OTHER INFORMATION: synthetic

<400> SEQUENCE: 92

Met Ser Arg Ala Asp Glu Ile Met Asp Gln Ile Met Ala Val
1 5 10

<210> SEQ ID NO 93
<211> LENGTH: 14
<212> TYPE: PRT
<213> ORGANISM: Artificial Sequence
<220> FEATURE:
<223> OTHER INFORMATION: synthetic

<400> SEQUENCE: 93

Met Ser Arg Ala Glu Glu Ile Met Glu Gln Ile Arg Ala Val
1 5 10

<210> SEQ ID NO 94
<211> LENGTH: 14
<212> TYPE: PRT
<213> ORGANISM: Artificial Sequence
<220> FEATURE:
<223> OTHER INFORMATION: synthetic

<400> SEQUENCE: 94

Met Ser Arg Ala Glu Glu Ile Met Ala Gln Ile Arg Ala Val
1 5 10

<210> SEQ ID NO 95
<211> LENGTH: 14
<212> TYPE: PRT
<213> ORGANISM: Artificial Sequence
<220> FEATURE:
<223> OTHER INFORMATION: synthetic

<400> SEQUENCE: 95

Met Ser Arg Ala Glu Glu Ile Met Ala Gln Ile Ala Ala Val
1 5 10

<210> SEQ ID NO 96

<211> LENGTH: 8
<212> TYPE: PRT
<213> ORGANISM: Homo sapiens

<400> SEQUENCE: 96

Glu Asp Asp Met Met Ile Thr Phe
1 5

<210> SEQ ID NO 97
<211> LENGTH: 8
<212> TYPE: PRT
<213> ORGANISM: Artificial Sequence
<220> FEATURE:
<223> OTHER INFORMATION: synthetic

<400> SEQUENCE: 97

Glu Gly Gly Ser Ala Ile Arg Phe
1 5

<210> SEQ ID NO 98
<211> LENGTH: 8
<212> TYPE: PRT
<213> ORGANISM: Artificial Sequence
<220> FEATURE:
<223> OTHER INFORMATION: synthetic

<400> SEQUENCE: 98

Glu Arg Asp Trp Met Ile Arg Phe
1 5

<210> SEQ ID NO 99
<211> LENGTH: 8
<212> TYPE: PRT
<213> ORGANISM: Artificial Sequence
<220> FEATURE:
<223> OTHER INFORMATION: synthetic

<400> SEQUENCE: 99

Glu Met Val Tyr Gly Ile Arg Phe
1 5

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Glu Ser Leu Cys His Ile Val Phe
1 5

<210> SEQ ID NO 101
<211> LENGTH: 8
<212> TYPE: PRT
<213> ORGANISM: Artificial Sequence
<220> FEATURE:
<223> OTHER INFORMATION: synthetic

<400> SEQUENCE: 101

Glu Arg Asp Ile Arg Ile Arg Phe
1 5

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Glu Arg Glu Trp His Ile Thr Phe
1 5

<210> SEQ ID NO 103
<211> LENGTH: 8
<212> TYPE: PRT
<213> ORGANISM: Artificial Sequence
<220> FEATURE:
<223> OTHER INFORMATION: synthetic

<400> SEQUENCE: 103

Glu Met Asn Tyr His Ile Met Phe
1 5

<210> SEQ ID NO 104
<211> LENGTH: 8
<212> TYPE: PRT
<213> ORGANISM: Artificial Sequence
<220> FEATURE:
<223> OTHER INFORMATION: synthetic

<400> SEQUENCE: 104

Glu Leu Ala Phe Met Ile Leu Phe
1 5

<210> SEQ ID NO 105
<211> LENGTH: 8
<212> TYPE: PRT
<213> ORGANISM: Artificial Sequence
<220> FEATURE:
<223> OTHER INFORMATION: synthetic

<400> SEQUENCE: 105

Glu Gln Ala Tyr Arg Ile Arg Phe
1 5

<210> SEQ ID NO 106
<211> LENGTH: 8
<212> TYPE: PRT
<213> ORGANISM: Artificial Sequence
<220> FEATURE:
<223> OTHER INFORMATION: synthetic

<400> SEQUENCE: 106

Glu Arg Asp Gly Leu Ile Gly Phe
1 5

<210> SEQ ID NO 107
<211> LENGTH: 8
<212> TYPE: PRT
<213> ORGANISM: Artificial Sequence
<220> FEATURE:
<223> OTHER INFORMATION: synthetic

<400> SEQUENCE: 107

Glu Asn Leu Ser Trp Ile Met Phe
1 5

<210> SEQ ID NO 108
<211> LENGTH: 8
<212> TYPE: PRT
<213> ORGANISM: Artificial Sequence
<220> FEATURE:

<223> OTHER INFORMATION: synthetic

<400> SEQUENCE: 108

Glu Arg Val Trp Arg Ile Arg Phe
1 5

<210> SEQ ID NO 109
<211> LENGTH: 8
<212> TYPE: PRT
<213> ORGANISM: Artificial Sequence
<220> FEATURE:
<223> OTHER INFORMATION: synthetic

<400> SEQUENCE: 109

Glu Arg Ser Val Lys Ile Ser Phe
1 5

<210> SEQ ID NO 110
<211> LENGTH: 8
<212> TYPE: PRT
<213> ORGANISM: Artificial Sequence
<220> FEATURE:
<223> OTHER INFORMATION: synthetic

<400> SEQUENCE: 110

Glu Gln Ser Gln Asn Ile Gly Phe
1 5

<210> SEQ ID NO 111
<211> LENGTH: 8
<212> TYPE: PRT
<213> ORGANISM: Artificial Sequence
<220> FEATURE:
<223> OTHER INFORMATION: synthetic

<400> SEQUENCE: 111

Glu Leu Asn Thr Ala Ile Val Phe
1 5

<210> SEQ ID NO 112
<211> LENGTH: 8
<212> TYPE: PRT
<213> ORGANISM: Artificial Sequence
<220> FEATURE:
<223> OTHER INFORMATION: synthetic

<400> SEQUENCE: 112

Ile Val Asn Trp Gly Ile Cys Phe
1 5

<210> SEQ ID NO 113
<211> LENGTH: 8
<212> TYPE: PRT
<213> ORGANISM: Artificial Sequence
<220> FEATURE:
<223> OTHER INFORMATION: synthetic

<400> SEQUENCE: 113

Glu Met Asn Tyr Arg Ile Arg Phe
1 5

<210> SEQ ID NO 114
<211> LENGTH: 8
<212> TYPE: PRT
<213> ORGANISM: Artificial Sequence
<220> FEATURE:
<223> OTHER INFORMATION: synthetic

<400> SEQUENCE: 114

Glu Ser Lys Trp Ser Ile Met Phe
1 5

<210> SEQ ID NO 115
<211> LENGTH: 8
<212> TYPE: PRT
<213> ORGANISM: Artificial Sequence
<220> FEATURE:
<223> OTHER INFORMATION: synthetic

<400> SEQUENCE: 115

Glu Val Glu Tyr Ser Ile Thr Phe
1 5

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

Glu Asp Arg Ser His Ile Leu Phe
1 5

<210> SEQ ID NO 117
<211> LENGTH: 5
<212> TYPE: PRT
<213> ORGANISM: Artificial Sequence
<220> FEATURE:
<223> OTHER INFORMATION: synthetic

<400> SEQUENCE: 117

Gly Gly Ser Ala Arg
1 5

<210> SEQ ID NO 118
<211> LENGTH: 5
<212> TYPE: PRT
<213> ORGANISM: Artificial Sequence
<220> FEATURE:
<223> OTHER INFORMATION: synthetic

<400> SEQUENCE: 118

Arg Asp Trp Met Arg
1 5

<210> SEQ ID NO 119
<211> LENGTH: 5
<212> TYPE: PRT
<213> ORGANISM: Artificial Sequence
<220> FEATURE:
<223> OTHER INFORMATION: synthetic

<400> SEQUENCE: 119

Met Val Tyr Gly Arg
1 5

<210> SEQ ID NO 120
<211> LENGTH: 5
<212> TYPE: PRT
<213> ORGANISM: Artificial Sequence
<220> FEATURE:
<223> OTHER INFORMATION: synthetic -continued

```
<400> SEQUENCE: 120

Ser Leu Cys His Val
1               5


<210> SEQ ID NO 121
<211> LENGTH: 5
<212> TYPE: PRT
<213> ORGANISM: Artificial Sequence
<220> FEATURE:
<223> OTHER INFORMATION: synthetic

<400> SEQUENCE: 121

Arg Asp Ile Arg Arg
1               5


<210> SEQ ID NO 122
<211> LENGTH: 5
<212> TYPE: PRT
<213> ORGANISM: Artificial Sequence
<220> FEATURE:
<223> OTHER INFORMATION: synthetic

<400> SEQUENCE: 122

Arg Glu Trp His Thr
1               5
```